(12) United States Patent
Tong et al.

(10) Patent No.: US 12,152,051 B2
(45) Date of Patent: Nov. 26, 2024

(54) CYCLIC DINUCLEOTIDE ANALOGUE, PHARMACEUTICAL COMPOSITION THEREOF, AND APPLICATION

(71) Applicant: SHANGHAI DE NOVO PHARMATECH CO., LTD., Shanghai (CN)

(72) Inventors: Zhaolong Tong, Shanghai (CN); Ping Qin, Shanghai (CN); Fengtao Liu, Shanghai (CN); Jinglu Wang, Shanghai (CN); Xiaolei Deng, Shanghai (CN); Hongli Guo, Shanghai (CN); Dawei Chen, Shanghai (CN); Daxin Gao, Shanghai (CN)

(73) Assignee: SHANGHAI DE NOVO PHARMATECH CO., LTD., Shanghai (CN)

( * ) Notice: Subject to any disclaimer, the term of this patent is extended or adjusted under 35 U.S.C. 154(b) by 905 days.

(21) Appl. No.: 17/277,534

(22) PCT Filed: Sep. 18, 2019

(86) PCT No.: PCT/CN2019/106425
§ 371 (c)(1),
(2) Date: Mar. 18, 2021

(87) PCT Pub. No.: WO2020/057546
PCT Pub. Date: Mar. 26, 2020

(65) Prior Publication Data
US 2022/0041644 A1 Feb. 10, 2022

(30) Foreign Application Priority Data

Sep. 21, 2018 (CN) .......................... 201811105973.6
Oct. 30, 2018 (CN) .......................... 201811276297.9
Jan. 17, 2019 (CN) .......................... 201910042984.2
Apr. 11, 2019 (CN) .......................... 201910287528.4

(51) Int. Cl.
*C07H 21/02* (2006.01)
*A61K 39/00* (2006.01)
*A61K 45/06* (2006.01)

(52) U.S. Cl.
CPC .......... *C07H 21/02* (2013.01); *A61K 39/0011* (2013.01); *A61K 45/06* (2013.01); *A61K 2039/5152* (2013.01)

(58) Field of Classification Search
None
See application file for complete search history.

(56) References Cited

U.S. PATENT DOCUMENTS

| | | | |
|---|---|---|---|
| 10,106,574 B2 | 10/2018 | Altman et al. | |
| 10,450,341 B2 | 10/2019 | Biggadike et al. | |
| 11,001,605 B2 | 5/2021 | Genieser et al. | |
| 2016/0287623 A1 | 10/2016 | Gajewski et al. | |
| 2018/0186828 A1 | 7/2018 | Biggadike et al. | |
| 2018/0194793 A1 | 7/2018 | Dyatkina et al. | |
| 2018/0230178 A1 | 8/2018 | Altman et al. | |
| 2018/0244712 A1 | 8/2018 | Altman et al. | |
| 2020/0010501 A1 | 1/2020 | Zhong et al. | |
| 2020/0282049 A1 | 9/2020 | Dubensky, Jr. et al. | |

FOREIGN PATENT DOCUMENTS

| | | |
|---|---|---|
| CN | 105228450 A | 1/2016 |
| CN | 105408341 A | 3/2016 |
| CN | 106459131 A | 2/2017 |
| CN | 106540260 A | 3/2017 |

(Continued)

OTHER PUBLICATIONS

Lious, T. et al. "Design, Synthesis, and Biological Evaluation of Novel Cyclic Adenosine-Inosine Monophosphate (cAIMP) Analogs That Activate Stimulator of Interferon Genes (STING)", *Journal of Medicinal Chemistry*, vol. 59, Oct. 26, 2016 (Oct. 26, 2016), pp. 10253-10267.

(Continued)

*Primary Examiner* — Dale R Miller
(74) *Attorney, Agent, or Firm* — Harness, Dickey & Pierce, P.L.C.

(57) ABSTRACT

A cyclic dinucleotide analogue, a pharmaceutical composition thereof, and application. A cyclic dinucleotide analogue (I), an isomer thereof, a prodrug, a stable isotope derivative, or a pharmaceutically acceptable salt has the following structure. The cyclic dinucleotide analogue can be used as a regulator of a stimulator of interferon genes (STING) and a related signal path thereof, and can effectively treat and/or relieve multiple types of diseases, including but not limited to malignant tumors, inflammations, autoimmune diseases, and infectious diseases. In addition, the STING regulator can also be used as a vaccine adjuvant.

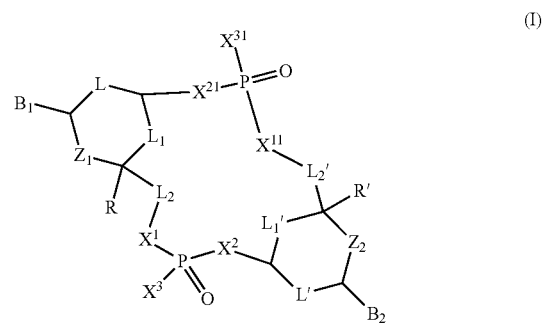

17 Claims, 1 Drawing Sheet

(56) References Cited

FOREIGN PATENT DOCUMENTS

| | | |
|---|---|---|
| CN | 108137641 A | 6/2018 |
| JP | 2016538344 A | 12/2016 |
| JP | 2017518302 A | 7/2017 |
| JP | 2018522914 A | 8/2018 |
| JP | 2019509339 A | 4/2019 |
| WO | WO-2014093936 A1 | 6/2014 |
| WO | WO-2014179760 A1 | 11/2014 |
| WO | WO-2014189805 A1 | 11/2014 |
| WO | WO-2014189806 A1 | 11/2014 |
| WO | WO-2015077354 A1 | 5/2015 |
| WO | WO-2015185565 A1 | 12/2015 |
| WO | WO-2016120305 A1 | 8/2016 |
| WO | WO-2016145102 A1 | 9/2016 |
| WO | WO-2017027645 A1 | 2/2017 |
| WO | WO-2017075477 A1 | 5/2017 |
| WO | WO-2017093933 A1 | 6/2017 |
| WO | WO-2017123657 A1 | 7/2017 |
| WO | WO-2017123669 A1 | 7/2017 |
| WO | WO-2017161349 A1 | 9/2017 |
| WO | WO-2017186711 A1 | 11/2017 |
| WO | WO-2018009466 A1 | 1/2018 |
| WO | WO-2018009648 A1 | 1/2018 |
| WO | WO-2018009652 A1 | 1/2018 |
| WO | WO-2018045204 A1 | 3/2018 |
| WO | WO-2018060323 A1 | 4/2018 |
| WO | WO-2018065360 A1 | 4/2018 |
| WO | WO-2018098203 A1 | 5/2018 |
| WO | WO-2018100558 A2 | 6/2018 |
| WO | WO-2018118665 A1 | 6/2018 |
| WO | WO-2018119117 A1 | 6/2018 |

OTHER PUBLICATIONS

Zhang, Xu et al. "Cyclic GMP-AMP Containing Mixed Phosphodiester Linkages Is An Endogenous High-Affinity Ligand for STING", *Molecular Cell*, vol. 51, Jul. 25, 2013 (Jul. 25, 2013), pp. 226-235.

Dec. 19, 2019 International Search Report issued in International Patent Application No. PCT/CN2019/106425.

Dec. 19, 2019 Written Opinion of the International Searching Authority issued in International Patent Application No. PCT/CN2019/106425.

Harlin et al, Cancer Res, 2009; 69(7):OF1.

Diamond et al, J. Exp. Med., 2011; 208(10):1989.

Fuerte et al, J. Exp. Med., 2011; 208(10):2005.

Sun et al, Science, 2013; 339(15): 786.

Berge, et al., "Pharmaceutically acceptable salts", J. Pharm. Sci., 66, 1-19(1977).

May 23, 2023 Second Office Action & Examination Search Report issued in Canadian Patent Application No. 3113425.

Apr. 26, 2023 First Office Action & Search Report issued in Taiwan Patent Application No. 108134126.

Sep. 29, 2022 First Office Action issued in Canadian Patent Application No. 3113425.

Jan. 24, 2022 the EESR issued in European Patent Application No. 19861381.2.

Sep. 28, 2023 Chinese Office Action issued in Chinese Patent Application No. 2019108815963.

Sep. 28, 2023 Chinese Search Report issued in Chinese Patent Application No. 2019108815963.

Barbara L. Gaffney et,al., "One-Flask Syntheses of c-di-GMP and the [Rp,Rp] and [Rp,Sp] Thiophosphate Analogues," Organic Letters, 12(14): 3269-3271, Jul. 16, 2010.

Oct. 30, 2023 Korean Office Action issued in Korean Patent Application No. 10-2021-7011633.

Sep. 15, 2023 New Zealand Office Action issued in New Zealand Patent Application No. 774965.

Jun. 20, 2022 Australian Office Action issued in corresponding Australian Patent Application No. 20193443981.

Jun. 7, 2022 Japanese Office Action issued in corresponding Japanese Patent Application No. 2021-515621.

Jun. 15, 2022 Eurasian Office Action issued in corresponding Eurasian Patent Application No. 202190120.

Jul. 24, 2022 Singaporean Office Action issued in corresponding Singaporean Patent Application No. 11202102742R.

Thierry Lioux,et al."Design, Synthesis, and Biological Evaluation of Novel Cyclic Adenosine-Inosine Monophosphate (cAIMP) Analogs That Activate Stimulator of Interfer", J. Med. Chem. 2016, 59, 10253-10267,DOI: 10.1021/acs.jmedchem.6b01300.

Xu Zhang,et al."Cyclic GMP-AMP Containing Mixed Phosphodiester Linkages Is An Endogenous High-Affinity Ligand for STING",Molecular Cell 51, 1-10, Jul. 25, 2013,http://dx.doi.org/10.1016/j.molcel.2013.05.022.

Jan. 16, 2024 third Office Action issued in Canadian Patent Application No. 3,113,425.

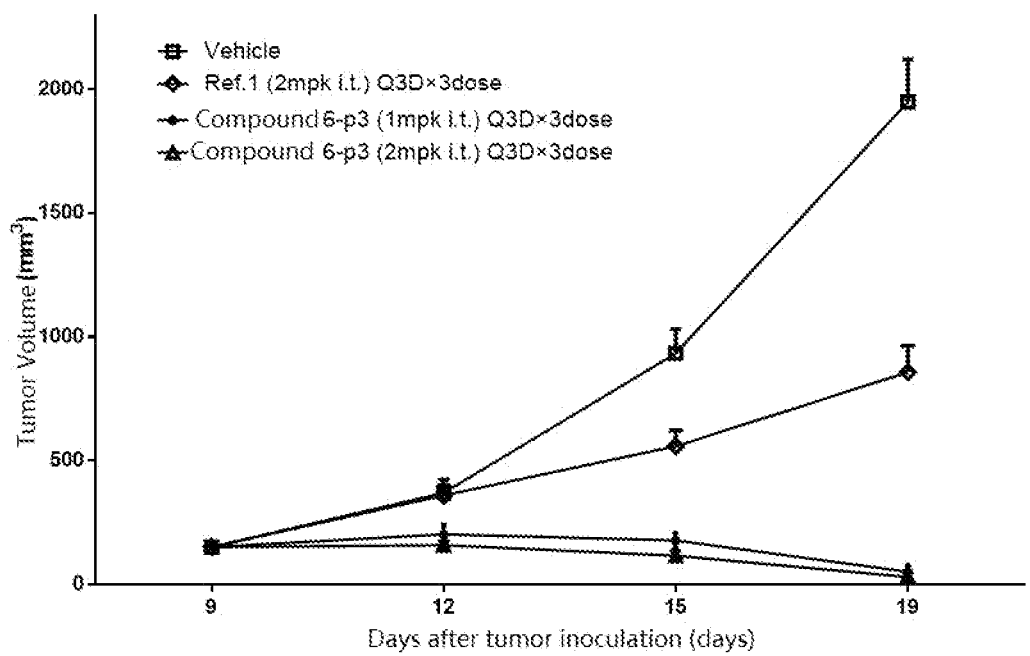

CYCLIC DINUCLEOTIDE ANALOGUE, PHARMACEUTICAL COMPOSITION THEREOF, AND APPLICATION

CROSS-REFERENCE TO RELATED APPLICATIONS

This application is a U.S. National Phase Application under 35 U.S.C. 371 of International Application No. PCT/CN2019/106425, filed on Sep. 18, 2019, which claims the benefit and priority of Chinese patent application CN201811105973.6 filed on Sep. 21, 2018, Chinese patent application CN201811276297.9 filed on Oct. 30, 2018, Chinese patent application CN201910042984.2 filed on Jan. 17, 2019 and Chinese patent application CN201910287528.4 filed on Apr. 11, 2019. The entire disclosures of the above applications are incorporated herein by reference in their entireties.

TECHNICAL FIELD

The present disclosure relates to a cyclic di-nucleotide analogue, a pharmaceutical composition thereof and a use thereof as STING agonist and for activation of the STING pathway.

BACKGROUND

Stimulator of Interferon Genes (STING), also known as T1MEM173, MITA, MPYS and ERIS, is an important signaling molecule in innate immune signaling. The protein encoded by this gene contains a 5-stranded transmembrane structure and plays an important regulatory role in the immune response associated with viral or bacterial infection. STING is a pattern recognition receptor which detects exogenous nucleic acids in the cytoplasm and activates signal transduction pathways associated with type I interferon responses. In addition, it has been shown that STING is involved in the regulation of apoptotic signaling by interacting with the type II major histocompatibility complex (MHCII). Studies performed on human tumors with spontaneous T-cell infiltration have shown that CD8+ T-cell infiltration is closely associated with the transcriptional profile of type I interferons (Harlin et al., Cancer $R^e s$, 2009; 69 (7): OF1). Mechanistic studies carried out on mouse models have shown that T cell activation processes against tumor-associated antigens show abnormalities in experimental animals with defective type I interferon signaling (Diamond et al., *J. Exp. Med.,* 2011; 208(10): 1989; Fuerte et al., *J. Exp. Med,* 2011; 208(10):2005). Further studies on tumor recognition by the innate immune system in vivo and on the signaling pathways involved in this process, such as tumor-triggered IFN expression mediated by antigen-presenting cells (APCs), have revealed that the STING signaling pathway can be activated by cytoplasmic DNA, and that these exogenous nucleic acids can be recognized by cyclic-GMP-AMP synthetase (cGAS) and then catalyzes the generation of cyclized nucleic acids such as cyclic GMP-AMP (cGMP) which can act as endogenous ligands activating STING signaling (Sun et al, *Science,* 2013; 339(15): 786). Activated STING can subsequently induce autophosphorylation of TBK1 kinase and phosphorylation of interferon regulatory factor 3 (IRF-3), and phosphorylated IRF3 can further activate the gene transcription process of type I interferon and regulate the synthesis and secretion of type I interferon, which in turn induces an immune response. In summary, it has been shown that the STING signaling pathway plays an extremely important role in the tumor recognition process by the innate immune system, and the activation of this signaling pathway on antigen-presenting cells is directly related to the activation of T cells against tumor-associated antigens. Based on its role in tumor immune recognition, it can be expected that activation of STING signaling by drugs or other pharmacological approaches can enhance IFN expression and have a positive effect on tumor therapy. Therefore, the development of STING signaling agonists for the treatment of tumor diseases has become a hot research topic.

In addition, it has been shown that the stimulation of STING signaling pathway activation also contributes to antiviral responses. Loss of functional response at the cellular or organismal level demonstrates that viral load cannot be controlled in the absence of STING. Activation of the STING signaling pathway triggers immune response leading to anti-vascular and pro-inflammatory cytokines against the virus and mobilizes the innate and acquired immune systems. Thus, small molecule compounds with agonistic effects on the STING signaling pathway have potential for the treatment of chronic viral infections and could be used, for example, to treat HBV.

Several cyclic di-nucleotide analogs with agonistic effects on the STING signaling pathway have been disclosed (WO2014/093936, WO2014/189805, WO2014/189806, WO2016/120305, WO2016/145102, WO2017/027645, WO2017/075477, WO2017/093933, WO2017/123657, WO2017/123669, WO2017/161349, WO2017/186711, WO2018/009466, WO2018/009648, WO2018/009652, WO2018/045204, WO2018/060323, WO2018/065360, WO2018/098203, WO2018/100558), but at present, no STING agonist has been approved for marketing.

Content of the Present Disclosure

The technical problem to be solved in the present disclosure is to provide a novel cyclic di-nucleotide analogue, a pharmaceutical composition thereof and a use thereof. The cyclic di-nucleotide analogue of the present disclosure has good STING modulating effect and can effectively treat, alleviate and/or prevent various diseases caused by immunosuppression, such as tumors, infectious diseases, neurodegenerative diseases, psychiatric disorders or autoimmune diseases.

The present disclosure provides a cyclic di-nucleotide analogue (I), an isomer, a prodrug, a stable isotope derivative or a pharmaceutically acceptable salt thereof;

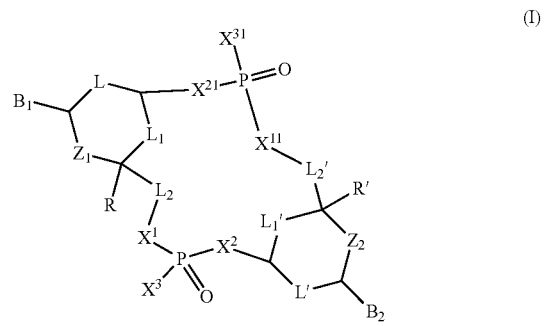

wherein, each of $Z_1$, $Z_2$ is independently O, S, $SO_2$, $CH_2$, $CF_2$ or Se;

B₁ is
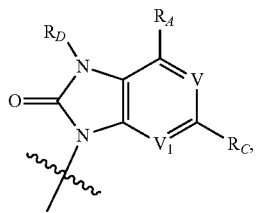
B-1
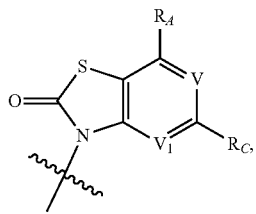
B-2
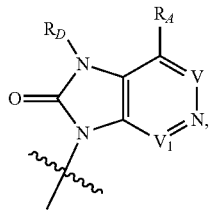
B-3
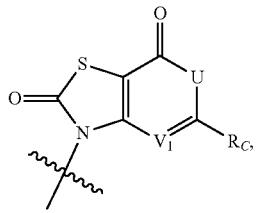
B-17
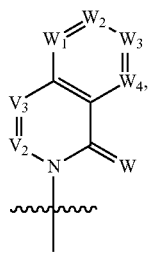
B-18
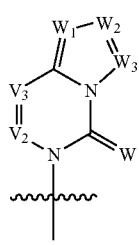
B-19
or
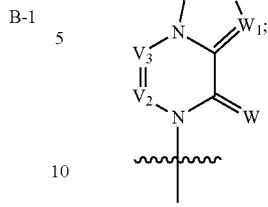
B-20
B₂ is
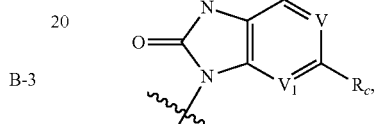
B-1
B-2
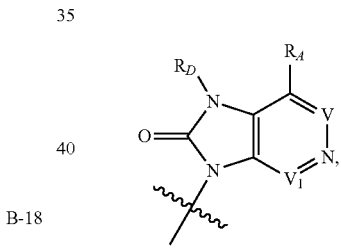
B-3
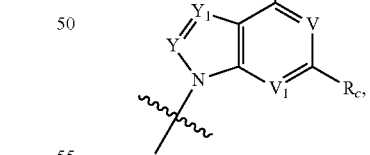
B-4
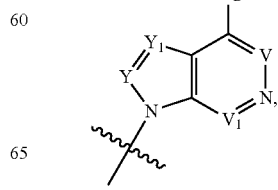
B-5

-continued
B-6
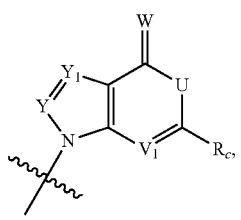
B-7
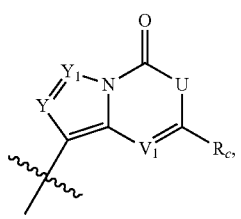
B-8
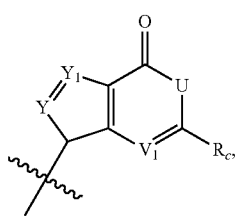
B-9
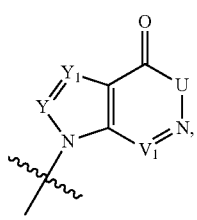
B-10
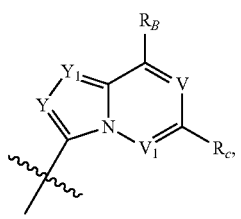
B-11
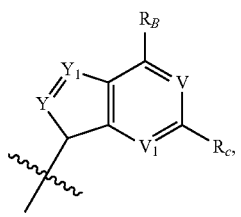
B-12
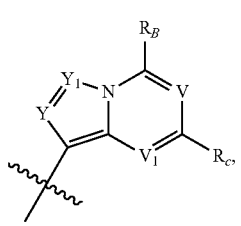
-continued
B-13
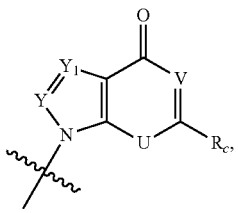
B-14
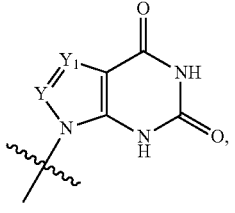
B-15
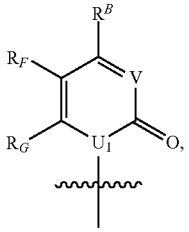
B-16
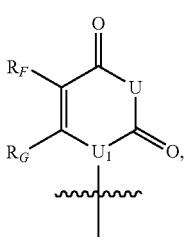
B-17
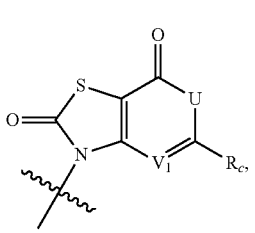
B-18
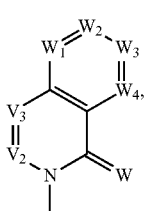
B-19
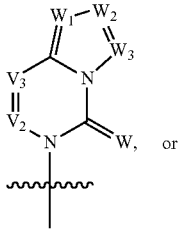 or -continued

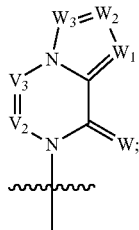

B-20

L and L₁ are each independently a connecting bond or CR¹R²;
L' and L₁' are each independently a connecting bond or CR¹¹R²¹
L₂ is O, S or CR³R⁴; L₂' is O, S or CR³¹R⁴¹;
X¹ is O, S or CR⁵R⁶; X¹¹ is O, S or CR⁵¹R⁶¹;
X² is O, S, or CR⁷R⁸; and X²¹ is O, S, or CR⁷¹R⁸¹;
X³ and X³¹ are each independently OH, SH or BH₃⁻;
R and R' are each independently hydrogen, C₂₋₆ alkenyl, C₂₋₆ alkynyl or C₁₋₆ alkyl; the C₂₋₆ alkenyl, C₂₋₆ alkynyl or C₁₋₆ alkyl is unsubstituted or selectively substituted at any position by 1 to 3 substituents selected from halogen, hydroxyl, amino, azido and cyano;
R¹ and R² are each independently hydrogen, halogen, cyano, hydroxyl, thiol, amino, azido, C₂₋₆ alkenyl, C₂₋₆ alkynyl, C₁₋₆ alkyl, halo-C₁₋₆ alkyl, halo-C₁₋₆ alkoxy, halo-C₁₋₆ alkylthio, C₁₋₆ alkylamino, OC(O)Rᵃ or ORᵃ; the C₂₋₆ alkenyl, C₂₋₆ alkynyl, or C₁₋₆ alkyl is unsubstituted or selectively substituted at any position by 1 to 3 substituents selected from halogen, hydroxyl, amino, azido, and cyano;
R¹¹ and R²¹ are each independently hydrogen, halogen, cyano, hydroxyl, thiol, amino, azido, C₂₋₆ alkenyl, C₂₋₆ alkynyl, C₁₋₆ alkyl, halo-C₁₋₆ alkyl, halo-C₁₋₆ alkoxy, halo-C₁₋₆ alkylthio, C₁₋₆ alkylamino, OC(O)Rᵃ, or ORᵃ; the C₂₋₆ alkenyl, C₂₋₆ alkynyl, or C₁₋₆ alkyl is unsubstituted or selectively substituted at any position by 1 to 3 substituents selected from halogen, hydroxyl, amino, azido, and cyano;
alternatively, R¹ and R² together form carbonyl;
alternatively, R¹¹ and R²¹ together form carbonyl;
alternatively, R is —CH₂—, R¹ is —O—, R and R¹ are interconnected to form heterocycloalkyl;
alternatively, R' is —CH₂—, R¹¹ is —O—, R' and R¹¹ are interconnected to form heterocycloalkyl;
R³ and R⁴ are each independently hydrogen, deuterium, halogen or C₁₋₆ alkyl;
R³¹ and R⁴¹ are each independently hydrogen, deuterium, halogen or C₁₋₆ alkyl;
R⁵ and R⁶ are each independently hydrogen, deuterium, halogen or C₁₋₆ alkyl;
R⁵¹ and R⁶¹ are each independently hydrogen, deuterium, halogen or C₁₋₆ alkyl;
R⁷ and R⁸ are each independently hydrogen, deuterium, halogen or C₁₋₆ alkyl;
R⁷¹ and R⁸¹ are each independently hydrogen, deuterium, halogen or C₁₋₆ alkyl;
Y and Y₁ are each independently CR_E or N;
U is CHR_E' or NR_D';
U₁ is CH or N;
V, V₁, V₂ and V₃ are each independently CR_E'' or N;
W is O or S;
W₁, W₂, W₃ and W₄ are each independently N or CR_F';
each of R_A, R_B, R_C, R_E, R_E', R_E'', R_F, R_F' and R_G is independently H, halogen, —CN, —NO₂, —N₃, Rᶜ, —SRᶜ, —ORᶜ, —OC(O)Rᶜ, —OC(O)ORᶜ, —OC(O)NRᵇRᶜ, —C(O)ORᶜ, —C(O)Rᶜ, —C(O)NRᵇRᶜ, —NRᵇRᶜ, —NRᵇC(O)Rᶜ, —N(Rᵇ)C(O)ORᶜ, —N(Rᵃ)C(O)NRᵇRᶜ, —NRᵇS(O)₂Rᶜ, —NRᵇC(=NH)Rᶜ, —NRᵇC(=NRᶜ)NH₂, —S(O)₁₋₂Rᶜ, —S(O)₂NRᵇRᶜ or —NRᵃS(O)₂NRᵇRᶜ;
each of R_D and R_D' is independently H or Rᶜ;
each of Rᵃ and Rᵇ is independently H, C₂₋₆ alkenyl, C₂₋₆ alkynyl, C₁₋₁₀ alkyl, halo-C₁₋₆ alkyl, aryl, heteroaryl, cycloalkyl, heterocycloalkyl, aryl-C₁₋₆ alkyl, heteroaryl-C₁₋₆ alkyl, cycloalkyl-C₁₋₆ alkyl, or heterocycloalkyl-C₁₋₆ alkyl;
each Rᶜ is independently H, substituted or unsubstituted C₁₋₁₀ alkyl, substituted or unsubstituted C₂₋₈ alkenyl, substituted or unsubstituted C₂₋₈ alkynyl, substituted or unsubstituted C₃₋₁₀ cycloalkyl, substituted or unsubstituted C₆₋₁₀ aryl, substituted or unsubstituted 3-10 membered heterocycloalkyl, substituted or unsubstituted 5-10 membered heteroaryl, substituted or unsubstituted C₆₋₁₀ aryl-C₁₋₆ alkyl, substituted or unsubstituted C₃₋₁₀ cycloalkyl-C₁₋₆ alkyl, substituted or unsubstituted 3-10 membered heterocycloalkyl-C₁₋₆ alkyl, substituted or unsubstituted 5-10 membered heteroaryl-C₁₋₆ alkyl; the C₁₋₁₀ alkyl, C₂₋₈ alkenyl, C₂₋₈ alkynyl, C₃₋₁₀ cycloalkyl, C₆₋₁₀ aryl, 3-10 membered heteroaryl, 5-10 membered heteroaryl, C₆₋₁₀ aryl-C₁₋₆ alkyl, C₃₋₁₀ cycloalkyl-C₁₋₆ alkyl, 3-10 membered heterocycloalkyl-C₁₋₆ alkyl, or 5-10 membered heteroaryl-C₁₋₆ alkyl is unsubstituted or selectively substituted at any position by one or more Rᵈ;
each Rᵈ is independently halogen, halo-C₁₋₆ alkyl, halo-C₁₋₆ alkoxy, C₁₋₆ alkyl, —CN, —N₃, —SRᵉ, —ORᵉ, —C(O)Rᵉ, —NRᵉRᵉ', substituted or unsubstituted C₆₋₁₀ aryl, substituted or unsubstituted 5-10 membered heteroaryl, substituted or unsubstituted C₃₋₁₀ cycloalkyl, or substituted or unsubstituted 3-10 membered heterocycloalkyl; the C₆₋₁₀ aryl, 5-10 membered heteroaryl, C₃₋₁₀ cycloalkyl or 3-10 membered heterocycloalkyl is unsubstituted or selectively substituted at any position by one or more substituents selected from halogen, hydroxyl, cyano, amino, C₁₋₄ alkyl, halo-C₁₋₄ alkyl, C₁₋₄ alkoxy, C₁₋₄ alkylamino and halo-C₁₋₄ alkoxy;
each of Rᵉ and Rₑ' is independently C₂₋₆ alkenyl, C₂₋₆ alkynyl, C₁₋₁₀ alkyl, halo-C₁₋₆ alkyl, aryl, heteroaryl, cycloalkyl, heterocycloalkyl, aryl-C₁₋₆ alkyl, heteroaryl-C₁₋₆ alkyl, cycloalkyl-C₁₋₆ alkyl, or heterocycloalkyl-C₁₋₆ alkyl.

In some embodiments, the cyclic di-nucleotide analogue (I), the isomer, prodrug, stable isotope derivative or pharmaceutically acceptable salt, having the structural general formula of

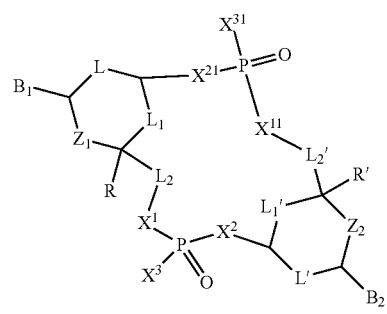

(I)

wherein, $Z_1$, $Z_2$ are each independently O, S, $SO_2$, $CH_2$, $CF_2$ or Se;
$B_1$ is
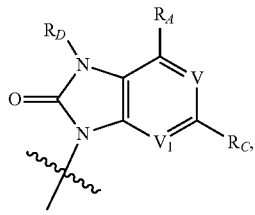
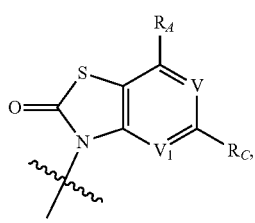
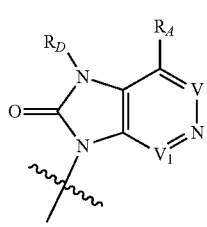
or
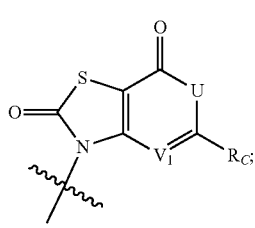
$B_2$ is
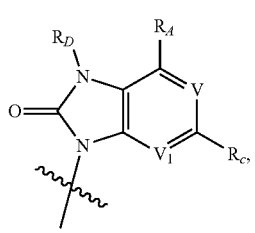
B-1
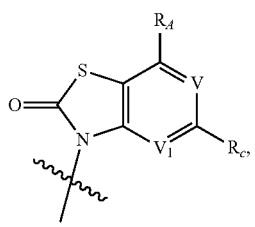
B-2
-continued
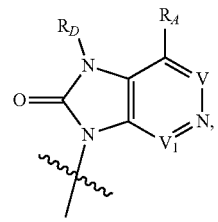
B-3
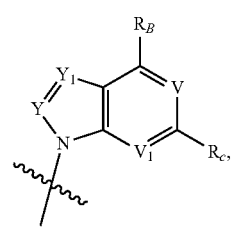
B-4
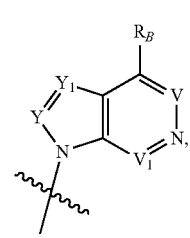
B-5
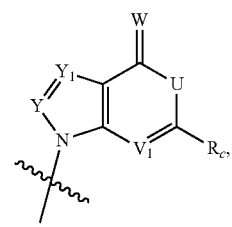
B-6
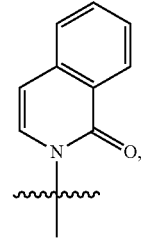
B-17
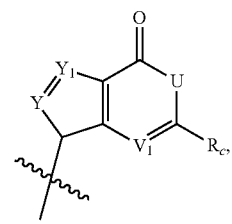
B-8
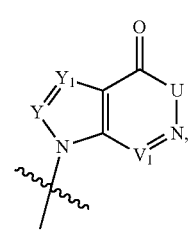
B-9

-continued

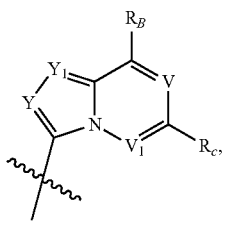
B-10

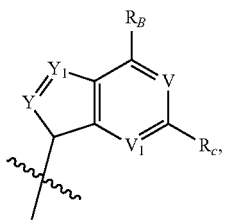
B-11

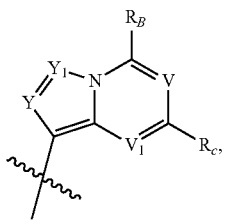
B-12

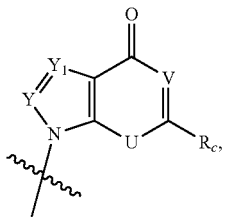
B-13

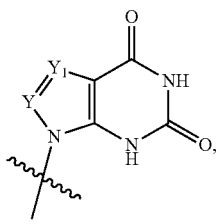
B-14

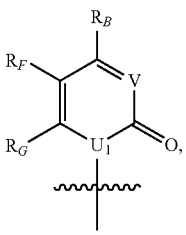
B-15

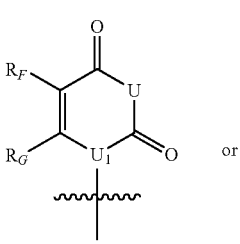
B-16

-continued

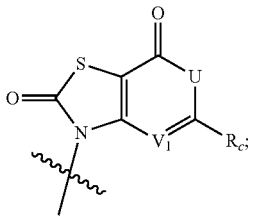
B-17

L and $L_1$ are each independently a connecting bond or $CR^1R^2$;
L' and $L_1'$ are each independently a connecting bond or $CR^{11}R^{21}$;
$L_2$ is O, S or $CR^3R^4$, $L_2'$ is O, S or $CR^{31}R^{41}$;
$X^1$ is O, S or $CR^5R^6$; $X^{11}$ is O, S or $CR^{51}R^{61}$
$X^2$ is O, S or $CR^7R^8$; and $X^{21}$ is O, S or $CR^{71}R^{81}$;
$X^3$ and $X^{31}$ are each independently OH, SH or $BH_3^-$;
R and R' are each independently hydrogen, $C_{2-6}$ alkenyl, $C_{2-6}$ alkynyl or $C_{1-6}$ alkyl; the $C_{2-6}$ alkenyl, $C_{2-6}$ alkynyl or $C_{1-6}$ alkyl is unsubstituted or selectively substituted at any position by 1 to 3 substituents selected from halogen, hydroxyl, amino, azido and cyano;
$R^1$ and $R^2$ are each independently hydrogen, halogen, cyano, hydroxyl, thiol, amino, azido, $C_{2-6}$ alkenyl, $C_{2-6}$ alkynyl, $C_{1-6}$ alkyl, halo-$C_{1-6}$ alkyl, halo-$C_{1-6}$ alkoxy, halo-$C_{1-6}$ alkylthio, $C_{1-6}$ alkylamino, $OC(O)R^a$ or $OR^a$; the $C_{2-6}$ alkenyl, $C_{2-6}$ alkynyl, or $C_{1-6}$ alkyl is unsubstituted or selectively substituted at any position by 1 to 3 substituents selected from halogen, hydroxyl, amino, azido, and cyano;
$R^{11}$ and $R^{21}$ are each independently hydrogen, halogen, cyano, hydroxyl, thiol, amino, azido, $C_{2-6}$ alkenyl, $C_{2-6}$ alkynyl, $C_{1-6}$ alkyl, halo-$C_{1-6}$ alkyl, halo-$C_{1-6}$ alkoxy, halo-$C_{1-6}$ alkylthio, $C_{1-6}$ alkylamino, $OC(O)R^a$ or $OR^a$; the $C_{2-6}$ alkenyl, $C_{2-6}$ alkynyl, or $C_{1-6}$ alkyl is unsubstituted or selectively substituted at any position by 1 to 3 substituents selected from halogen, hydroxyl, amino, azido, and cyano;
alternatively, $R^1$ and $R^2$ together form carbonyl;
alternatively, $R^{11}$ and $R^{21}$ together form carbonyl;
alternatively, R is —$CH_2$—, $R^1$ is —O—, R and $R^1$ are interconnected to form heterocycloalkyl;
alternatively, R' is —$CH_2$—, $R^{11}$ is —O—, R' and $R^{11}$ are interconnected to form heterocycloalkyl;
$R^3$ and $R^4$ are each independently hydrogen, deuterium, halogen or $C_{1-6}$ alkyl;
$R^{31}$ and $R^{41}$ are each independently hydrogen, deuterium, halogen or $C_{1-6}$ alkyl;
$R^5$ and $R^6$ are each independently hydrogen, deuterium, halogen or $C_{1-6}$ alkyl;
$R^{51}$ and $R^{61}$ are each independently hydrogen, deuterium, halogen or $C_{1-6}$ alkyl;
$R^7$ and $R^8$ are each independently hydrogen, deuterium, halogen or $C_{1-6}$ alkyl;
$R^{71}$ and $R^{81}$ are each independently hydrogen, deuterium, halogen or $C_{1-6}$ alkyl;
Y and $Y_1$ are each independently $CR_E$ or N;
U is $CHR_E'$ or $NR_D'$;
$U_1$ is CH or N;
V and $V_1$ are each independently $CR_E''$ or N;
W is O or S;
each of $R_A$, $R_B$, $R_C$, $R_E$, $R_E'$, $R_E''$, $R_F$ and $R_G$ is independently H, halogen, —CN, —$NO_2$, —$N_3$, $R^c$, —$SR^c$, —$OR^c$, —$OC(O)R^c$, —$OC(O)OR^c$, —$OC(O)NR^bR^c$, —C(O)OR$^c$, —C(O)R$^c$, —C(O)NR$^b$R$^c$, —NR$^b$R$^c$, —NR$^b$C(O)R$^c$, —N(R$^b$)C(O)OR$^c$, —N(R$^a$)C(O)NR$^b$R$^c$, —NR$^b$S(O)$_2$R$^c$, —NR$^b$C(=NH)R$^c$, —NR$^b$C(=NR$^c$)NH$_2$, —S(O)$_{1-2}$R$^c$, —S(O)$_2$NR$^b$R$^c$ or —NR$^a$S(O)$_2$NR$^b$R$^c$;

each of R$_D$ and R$_D$' is independently H or R$^c$;

each of R$^a$ and R$^b$ is independently H, C$_{2-6}$ alkenyl, C$_{2-6}$ alkynyl, C$_{1-10}$ alkyl, halo-C$_{1-6}$ alkyl, aryl, heteroaryl, cycloalkyl, heterocycloalkyl, aryl-C$_{1-6}$ alkyl, heteroaryl-C$_{1-6}$ alkyl, cycloalkyl-C$_{1-6}$ alkyl, or heterocycloalkyl-C$_{1-6}$ alkyl;

each R$^c$ is independently H, substituted or unsubstituted C$_{1-10}$ alkyl, substituted or unsubstituted C$_{2-8}$ alkenyl, substituted or unsubstituted C$_{2-8}$ alkynyl, substituted or unsubstituted C$_{3-10}$ cycloalkyl, substituted or unsubstituted C$_{6-10}$ aryl, substituted or unsubstituted 3-10 membered heterocycloalkyl, substituted or unsubstituted 5-10 membered heteroaryl, substituted or unsubstituted C$_{6-10}$ aryl-C$_{1-6}$ alkyl, substituted or unsubstituted C$_{3-10}$ cycloalkyl-C$_{1-6}$ alkyl, substituted or unsubstituted 3-10 membered heterocycloalkyl-C$_{1-6}$ alkyl, substituted or unsubstituted 5-10 membered heteroaryl-C$_{1-6}$ alkyl; the C$_{1-10}$ alkyl, C$_{2-8}$ alkenyl, C$_{2-8}$ alkynyl, C$_{3-10}$ cycloalkyl, C$_{6-10}$ aryl, 3-10 membered heterocycloalkyl, 5-10 membered heteroaryl, C$_{6-10}$ aryl-C$_{1-6}$ alkyl, C$_{3-10}$ cycloalkyl-C$_{1-6}$ alkyl, 3-10 membered heterocycloalkyl-C$_{1-6}$ alkyl, or 5-10 membered heteroaryl-C$_{1-6}$ alkyl is unsubstituted or selectively substituted at any position by one or more R$^d$;

each R$^d$ is independently halogen, halo-C$_{1-6}$ alkyl, halo-C$_{1-6}$ alkoxy, C$_{1-6}$ alkyl, —CN, —N$_3$, —SR$^e$, —OR$^e$, —C(O)R$^e$, —NR$^e$R$^{e'}$, substituted or unsubstituted C$_{6-10}$ aryl, substituted or unsubstituted 5-10 membered heteroaryl, substituted or unsubstituted C$_{3-10}$ cycloalkyl, or substituted or unsubstituted 3-10 membered heterocycloalkyl; the C$_{6-10}$ aryl, 5-10 membered heteroaryl, C$_{3-10}$ cycloalkyl or 3-10 membered heterocycloalkyl is unsubstituted or selectively substituted at any position by one or more substituents selected from halogen, hydroxyl, cyano, amino, C$_{1-4}$ alkyl, halo-C$_{1-4}$ alkyl, C$_{1-4}$ alkoxy, C$_{1-4}$ alkylamino and halo-C$_{1-4}$ alkoxy;

each of R$^e$ and R$^{e'}$ is independently C$_{2-6}$ alkenyl, C$_{2-6}$ alkynyl, C$_{1-10}$ alkyl, halo-C$_{1-6}$ alkyl, aryl, heteroaryl, cycloalkyl, heterocycloalkyl, aryl-C$_{1-6}$ alkyl, heteroaryl-C$_{1-6}$ alkyl, cycloalkyl-C$_{1-6}$ alkyl, or heterocycloalkyl-C$_{1-6}$ alkyl.

In some embodiments, the cyclic di-nucleotide analogue (I), the isomer, prodrug, stable isotope derivative or pharmaceutically acceptable salt thereof, having the structural general formula of

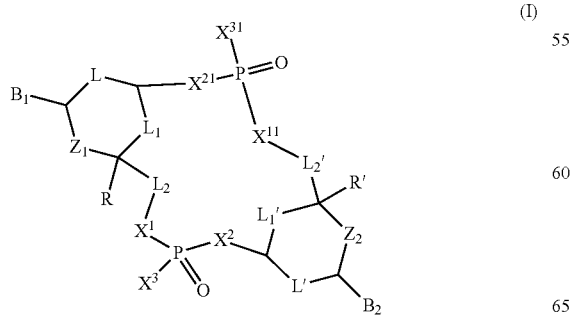
(I)

wherein, Z$_1$, Z$_2$ are each independently O, S, SO$_2$, CH$_2$, CF$_2$ or Se;

B$_1$ is

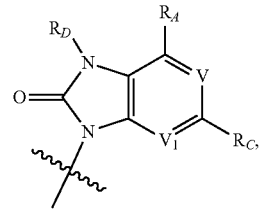
B-1

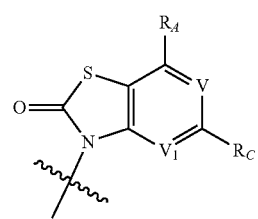
B-2 or

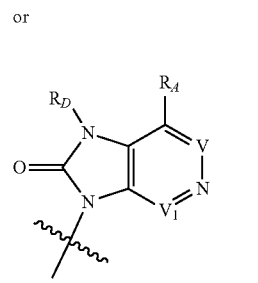
B-3

B$_2$ is

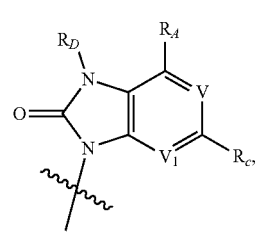
B-1

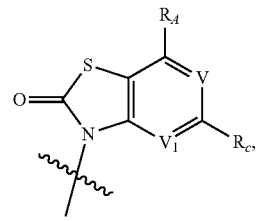
B-2

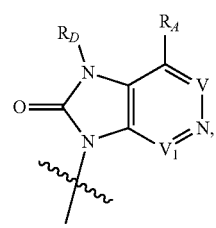
B-3

-continued

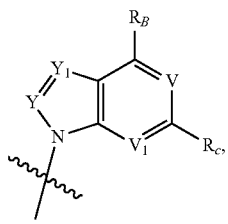
B-4

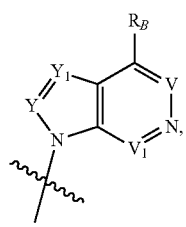
B-5

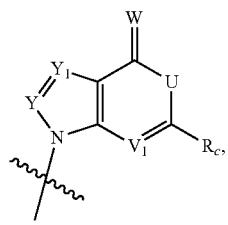
B-6

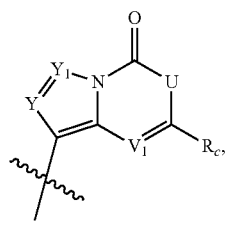
B-7

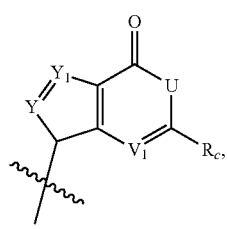
B-8

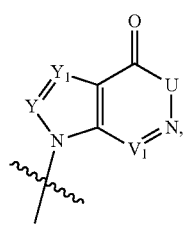
B-9

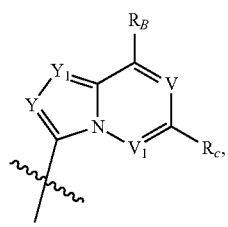
B-10

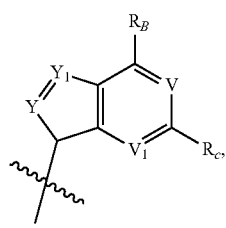
B-11

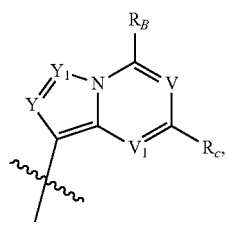
B-12

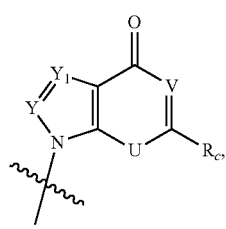
B-13

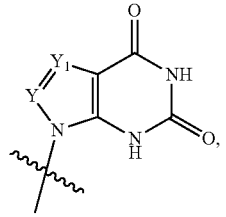
B-14

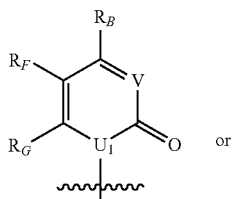
B-15 or

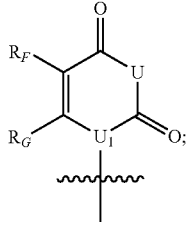
B-16

L and $L_1$ are each independently a connecting bond or $CR^1R^2$;
L' and $L_1$' are each independently a connecting bond or $CR^{11}R^{21}$;
$L_2$ is O, S or $CR^3R^4$; $L_2$' is O, S or $CR^{31}R^{41}$;
$X^1$ is O, S or $CR^5R^6$; $X^{11}$ is O, S or $CR^{51}R^{61}$;
$X^2$ is O, S or $CR^7R^8$; and $X^{21}$ is O, S or $CR^{71}R^{81}$
$X^3$ and $X^{31}$ are each independently OH, SH or $BH_3^-$;
R and R' are each independently hydrogen, $C_{2-6}$ alkenyl, $C_{2-6}$ alkynyl or $C_{1-6}$ alkyl; the $C_{2-6}$ alkenyl, $C_{2-6}$ alkynyl or $C_{1-6}$ alkyl is unsubstituted or selectively substituted at any position by 1 to 3 substituents selected from halogen, hydroxyl, amino, azido and cyano;

$R^1$ and $R^2$ are each independently hydrogen, halogen, cyano, hydroxyl, thiol, amino, azido, $C_{2-6}$ alkenyl, $C_{2-6}$ alkynyl, $C_{1-6}$ alkyl, halo-$C_{1-6}$ alkyl, halo-$C_{1-6}$ alkoxy, halo-$C_{1-6}$ alkylthio, $C_{1-6}$ alkylamino, $OC(O)R^a$, or $OR^a$; the $C_{2-6}$ alkenyl, $C_{2-6}$ alkynyl, or $C_{1-6}$ alkyl is unsubstituted or selectively substituted at any position by 1 to 3 substituents selected from halogen, hydroxyl, amino, azido, and cyano;

$R^{11}$ and $R^{21}$ are independently hydrogen, halogen, cyano, hydroxyl, thiol, amino, azido, $C_{2-6}$ alkenyl, $C_{2-6}$ alkynyl, $C_{1-6}$ alkyl, halo-$C_{1-6}$ alkyl, halo-$C_{1-6}$ alkoxy, halo-$C_{1-6}$ alkylthio, $C_{1-6}$ alkylamino, $OC(O)R^a$, or $OR^a$; the $C_{2-6}$ alkenyl, $C_{2-6}$ alkynyl, or $C_{1-6}$ alkyl is unsubstituted or selectively substituted at any position by 1 to 3 substituents selected from halogen, hydroxyl, amino, azido, and cyano;

alternatively, $R^1$ and $R^2$ together form carbonyl;

alternatively, $R^{11}$ and $R^{21}$ together form carbonyl;

alternatively, R is —$CH_2$—, $R^1$ is —O—, R and $R^1$ are interconnected to form heterocycloalkyl;

alternatively, R' is —$CH_2$—, $R^{11}$ is —O—, R' and $R^{11}$ are interconnected to form heterocycloalkyl;

$R^3$ and $R^4$ are each independently hydrogen, deuterium, halogen or $C_{1-6}$ alkyl;

$R^{31}$ and $R^{41}$ are each independently hydrogen, deuterium, halogen or $C_{1-6}$ alkyl;

$R^5$ and $R^6$ are each independently hydrogen, deuterium, halogen or $C_{1-6}$ alkyl;

$R^{51}$ and $R^{61}$ are each independently hydrogen, deuterium, halogen or $C_{1-6}$ alkyl;

$R^7$ and $R^8$ are each independently hydrogen, deuterium, halogen or $C_{1-6}$ alkyl;

$R^{71}$ and $R^{81}$ are each independently hydrogen, deuterium, halogen or $C_{1-6}$ alkyl;

Y and $Y_1$ are each independently $CR_E$ or N;

U is $CHR_E'$ or $NR_D'$;

$U_1$ is CH or N;

V and $V_1$ are each independently $CR_E''$ or N;

W is O or S;

each of $R_A$, $R_B$, $R_C$, $R_E$, $R_E'$, $R_E''$, $R_F$ and $R_G$ is independently H, halogen, —CN, —$NO_2$, —$N_3$, $R^c$, —$SR^c$, —$OR^c$, —$OC(O)R^c$, —$OC(O)OR^c$, —$OC(O)NR^bR^c$, —$C(O)OR^c$, —$C(O)R^c$, —$C(O)NR^bR^c$, —$NR^bR^c$, —$NR^bC(O)R^c$, —$N(R^b)C(O)OR^c$, —$N(R^a)C(O)NR^bR^c$, —$NR^bS(O)_2R^c$, —$NR^bC(=NH)R^c$, —$NR^bC(=NR^c)NH_2$, —$S(O)_{1-2}R^c$, —$S(O)_2NR^bR^c$ or —$NR^aS(O)_2NR^bR^c$;

each of $R_D$ and $R_D'$ is independently H or $R^c$;

each of $R^a$ and $R^b$ is independently H, $C_{2-6}$ alkenyl, $C_{2-6}$ alkynyl, $C_{1-10}$ alkyl, halo-$C_{1-6}$ alkyl, aryl, heteroaryl, cycloalkyl, heterocycloalkyl, aryl-$C_{1-6}$ alkyl, heteroaryl-$C_{1-6}$ alkyl, cycloalkyl-$C_{1-6}$ alkyl, or heterocycloalkyl-$C_{1-6}$ alkyl;

each $R^c$ is independently H, substituted or unsubstituted $C_{1-10}$ alkyl, substituted or unsubstituted $C_{2-8}$ alkenyl, substituted or unsubstituted $C_{2-8}$ alkynyl, substituted or unsubstituted $C_{3-10}$ cycloalkyl, substituted or unsubstituted $C_{6-10}$ aryl, substituted or unsubstituted 3-10 membered heterocycloalkyl, substituted or unsubstituted 5-10 membered heteroaryl, substituted or unsubstituted $C_{6-10}$ aryl-$C_{1-6}$ alkyl, substituted or unsubstituted $C_{3-10}$ cycloalkyl-$C_{1-6}$ alkyl, substituted or unsubstituted 3-10 membered heterocycloalkyl-$C_{1-6}$ alkyl, substituted or unsubstituted 5-10 membered heteroaryl-$C_{1-6}$ alkyl; the $C_{1-10}$ alkyl, $C_{2-8}$ alkenyl, $C_{2-8}$ alkynyl, $C_{3-10}$ cycloalkyl, $C_{6-10}$ aryl, 3-10 membered heterocycloalkyl, 5-10 membered heteroaryl, $C_{6-10}$ aryl-$C_{1-6}$ alkyl, $C_{3-10}$ cycloalkyl-$C_{1-6}$ alkyl, 3-10 membered heterocycloalkyl-$C_{1-6}$ alkyl, or 5-10 membered heteroaryl-$C_{1-6}$ alkyl is unsubstituted or selectively substituted at any position by one or more $R^d$;

each $R^d$ is independently halogen, halo-$C_{1-6}$ alkyl, halo-$C_{1-6}$ alkoxy, $C_{1-6}$ alkyl, —CN, —$N_3$, —$SR^e$, —$OR^e$, —$C(O)R^e$, —$NR^eR_{e'}$, substituted or unsubstituted $C_{6-10}$ aryl, substituted or unsubstituted 5-10 membered heteroaryl, substituted or unsubstituted $C_{3-10}$ cycloalkyl, or substituted or unsubstituted 3-10 membered heterocycloalkyl; the $C_{6-10}$ aryl, 5-10 membered heteroaryl, $C_{3-10}$ cycloalkyl or 3-10 membered heterocycloalkyl is unsubstituted or selectively substituted at any position by one or more substituents selected from halogen, hydroxyl, cyano, amino, $C_{1-4}$ alkyl, halo-$C_{1-4}$ alkyl, $C_{1-4}$ alkoxy, $C_{1-4}$ alkylamino and halo-$C_{1-4}$ alkoxy;

each of $R^e$ and $R^{e'}$ is independently $C_{2-6}$ alkenyl, $C_{2-6}$ alkynyl, $C_{1-10}$ alkyl, halo-$C_{1-6}$ alkyl, aryl, heteroaryl, cycloalkyl, heterocycloalkyl, aryl-$C_{1-6}$ alkyl, heteroaryl-$C_{1-6}$ alkyl, cycloalkyl-$C_{1-6}$ alkyl, or heterocycloalkyl-$C_{1-6}$ alkyl.

In some embodiments, each $R^c$ is independently H, substituted or unsubstituted $C_{1-10}$ alkyl, substituted or unsubstituted $C_{3-10}$ cycloalkyl, substituted or unsubstituted $C_{6-10}$ aryl, substituted or unsubstituted 3-10 membered heterocycloalkyl, substituted or unsubstituted 5-10 membered heteroaryl, substituted or unsubstituted $C_{6-10}$ aryl-$C_{1-6}$ alkyl, substituted or unsubstituted $C_{3-10}$ cycloalkyl-$C_{1-6}$ alkyl, substituted or unsubstituted 3-10 membered heterocycloalkyl-$C_{1-6}$ alkyl, substituted or unsubstituted 5-10 membered heteroaryl-$C_{1-6}$ alkyl; the $C_{1-10}$ alkyl, $C_{3-10}$ cycloalkyl, $C_{6-10}$ aryl, 3-10 membered heterocycloalkyl, 5-10 membered heteroaryl, $C_{6-10}$ aryl-$C_{1-6}$ alkyl, $C_{3-10}$ cycloalkyl-$C_{1-6}$ alkyl, 3-10 membered heterocycloalkyl-$C_{1-6}$ alkyl or 5-10 membered heteroaryl-$C_{1-6}$ alkyl is unsubstituted or selectively substituted at any position by one or more $R^d$; $R^d$ is as defined above.

In the definition of $R^c$, the substituted or unsubstituted $C_{1-10}$ alkyl is preferably substituted or unsubstituted $C_{1-6}$ alkyl, such as methyl, ethyl, propyl, isopropyl, tert-butyl, n-butyl; wherein the methyl, ethyl, propyl, isopropyl, tert-butyl, or n-butyl is substituted or unsubstituted;

in the definition of $R^c$, the substituted or unsubstituted $C_{3-10}$ cycloalkyl is preferably cyclopropyl, cyclobutyl, cyclopentyl, cyclohexyl, 2,3-dihydro-1H-inden-1-yl, 2,3-dihydro-1H-inden-2-yl; wherein the cyclopropyl, cyclobutyl, cyclopentyl, cyclohexyl, 2,3-dihydro-1H-inden-1-yl, or 2,3-dihydro-1H-inden-2-yl is substituted or unsubstituted;

in the definition of $R^c$, the substituted or unsubstituted $C_{6-10}$ aryl is preferably substituted or unsubstituted phenyl;

in the definition of $R^c$, the substituted or unsubstituted 3-10 membered heterocycloalkyl is preferably tetrahydrofuran-3-yl, tetrahydro-2H-pyran-3-yl, tetrahydro-2H-pyran-4-yl, pyrrolidin-3-yl, piperidin-3-yl, piperidin-4-yl; wherein the tetrahydrofuran-3-yl, tetrahydro-2H-pyran-3-yl, tetrahydro-2H-pyran-4-yl, pyrrolidin-3-yl, piperidin-3-yl, piperidin-4-yl is substituted or unsubstituted;

in the definition of $R^c$, the substituted or unsubstituted 5-10 membered heteroaryl is preferably substituted or unsubstituted 5-6-membered heteroaryl.

In some embodiments, each $R^c$ is independently H, $C_{1-4}$ alkyl or halo-$C_{1-4}$ alkyl.

In some embodiments, each $R^b$ is independently H or $C_{1-4}$ alkyl.

In some embodiments, $Z_1$ is O.

In some embodiments, $Z_2$ is O.

In some embodiments, in the definition of B-4 to B-16, Y is N.

In some embodiments, in the definition of B-4 to B-16, Y is $CR_E$, and $R_E$ is preferably H, F, Cl, —$CF_3$, —$CH_3$, —CN, —$NH_2$.

In some embodiments, in the definition of B-4 to B-16, $Y_1$ is N.

In some embodiments, in the definition of B-4 to B-16, $Y_1$ is $CR_E$, and $R_E$ is preferably H, F, Cl, —$CF_3$, —$CH_3$, —CN or —$NH_2$.

In some embodiments, in the definition of B-6 to B-9, B-13, B-16 to B-17, U is $NR_D$ and $R_D'$ is H or —$CH_3$.

In some embodiments, in the definition of B-1 to B-5, B-10 to B-13, B-15, V is N or CH.

In some embodiments, in the definition of B-1 to B-12, B-17, $V_1$ is N or CH.

In some embodiments, in the definition of B-1 to B-3, $R_A$ is H, halogen, —$OR^c$, —$NR^bR^c$; wherein $R^b$ and $R^c$ are as defined above.

In some embodiments, in the definition of B-4, B-5, B-10 to B-12, B-15, $R_B$ is H, halogen, —$OR^c$, —$NR^bR^c$; wherein $R^b$ and $R^c$ are as defined above.

In some embodiments, in the definition of B-1, B-2, B-4, B-6 to B-8, B-10 to B-13, B-17, the $R_C$ is H, F, Cl, —$OR^c$, —$SR^c$, —$NR^bR^c$ or $R^c$; wherein $R^c$ is as defined above.

In some embodiments, in the definition of B-15, B-16, $R_G$ is H.

In some embodiments, in the definition of B-15, B-16, $R_F$ is H.

In some embodiments, in the definition of B-18 to B-20, $V_3$ is N or CH.

In some embodiments, in the definition of B-18 to B-20, $V_2$ is CH.

In some embodiments, in the definition of B-18 to B-20, $W_1$ is N or CH.

In some embodiments, in the definition of B-18 to B-20, $W_2$ is $CR_F'$; wherein $R_F'$ is H or —$NH_2$.

In some embodiments, in the definition of B-18 to B-20, $W_3$ is CH.

In some embodiments, in the definition of B-18, $W_4$ is CH.

In some embodiments, $B_1$ is any of the following structures:

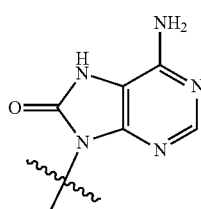 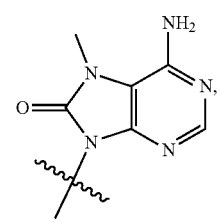

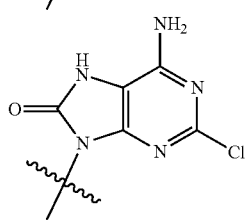 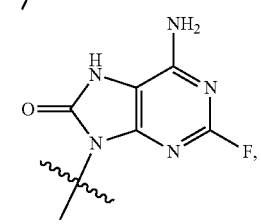

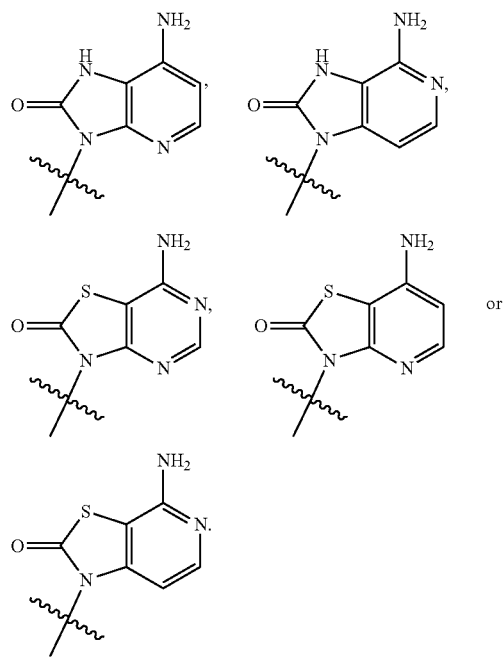

In some embodiments, $B_1$ is

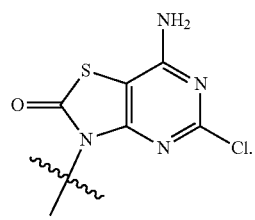 [SMILES: *n1c(=O)sc2c(N)nc(Cl)nc21]

In some embodiments, $B_1$ is

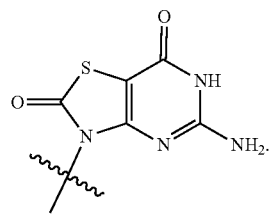 [SMILES: *n1c(=O)sc2c(=O)[nH]c(N)nc21]

In some embodiments, $B_1$ is any of the following structures:

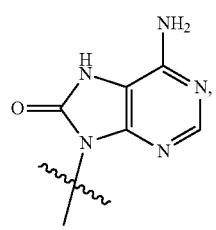 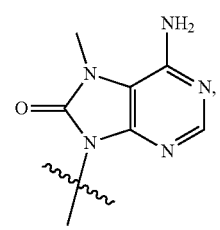

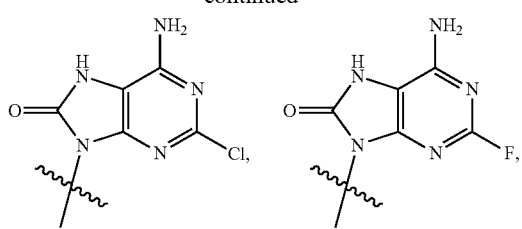
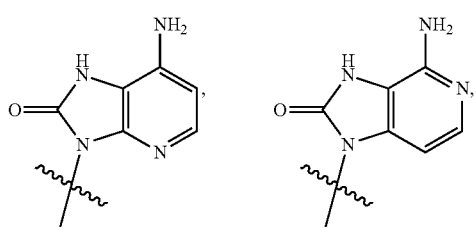
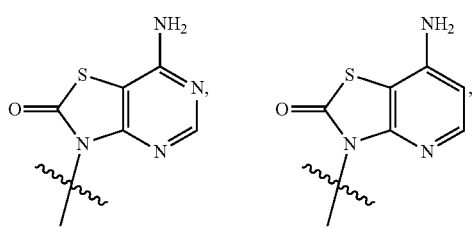
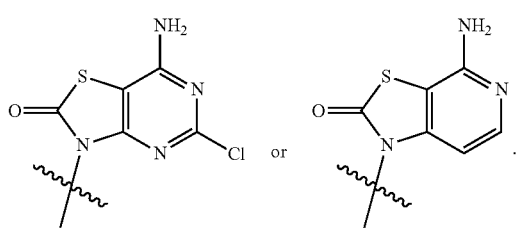
In some embodiments, B₁ is any of the following structures:
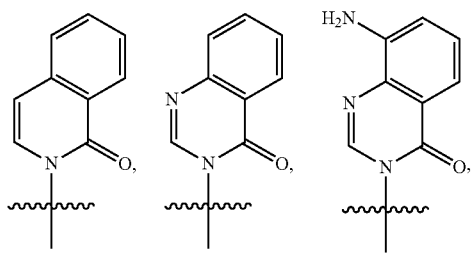
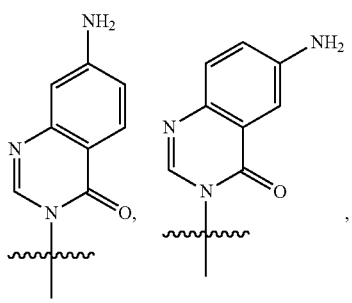
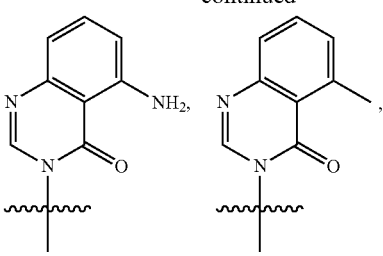
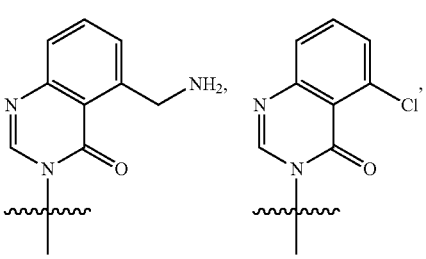
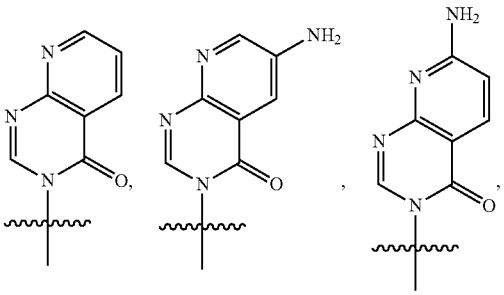
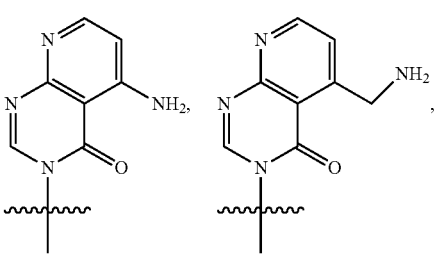
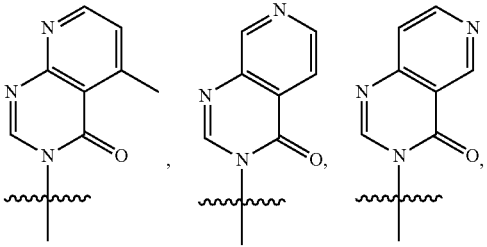
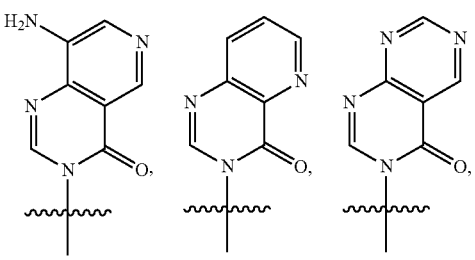

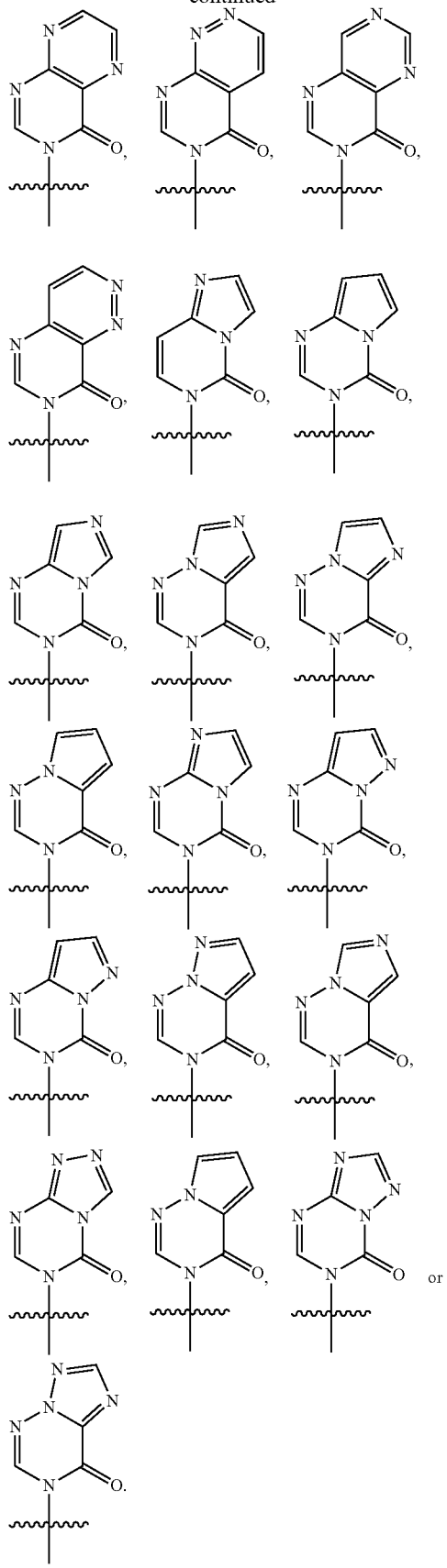
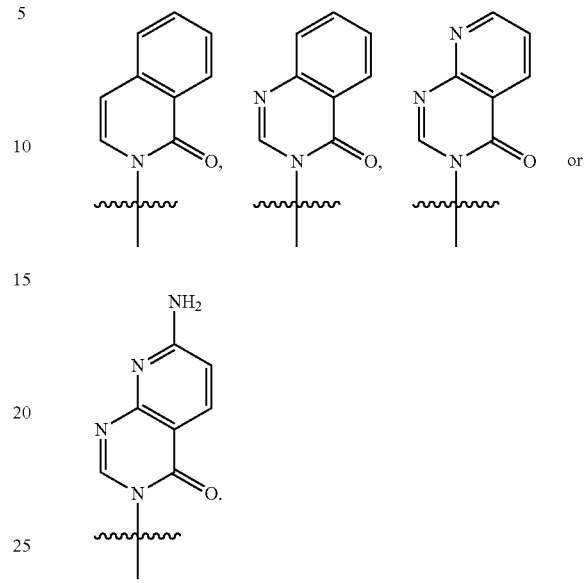
In some embodiments, $B_1$ is any of the following structures:
In some embodiments, $B_1$ is any of the following structures:
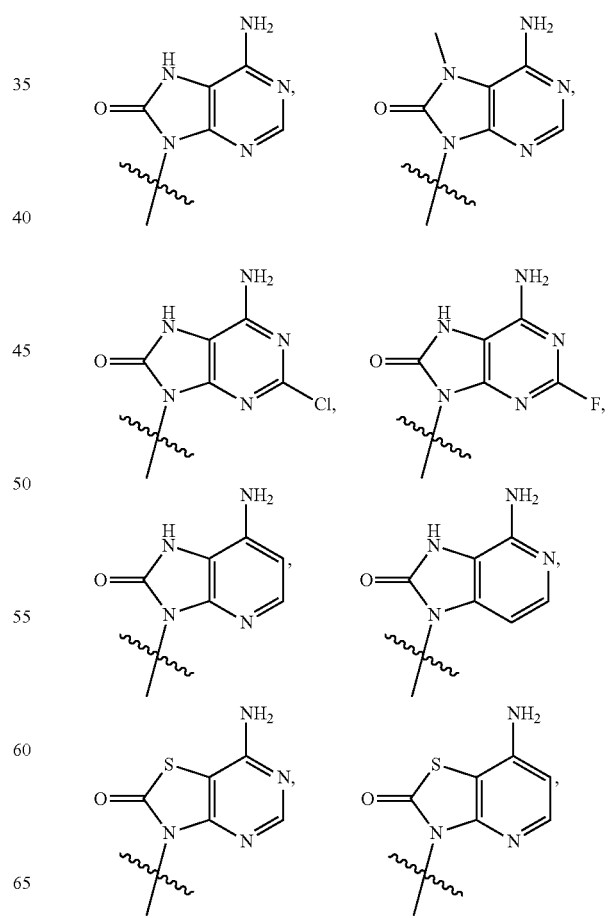

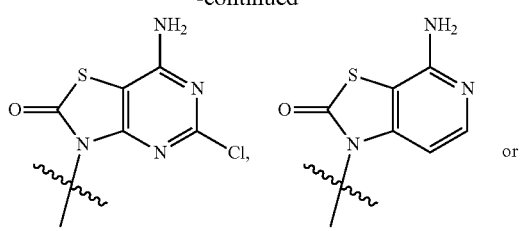
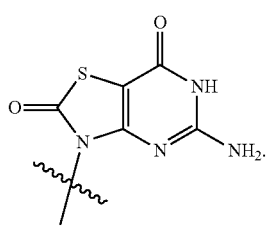
In some embodiments, $B_1$ is any of the following structures:
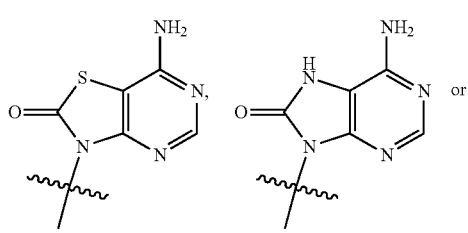
In some embodiments, $B_2$ is any of the following structures:
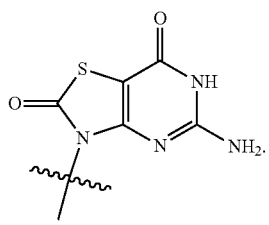
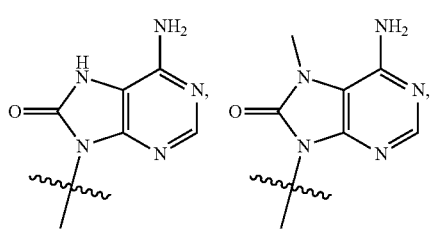
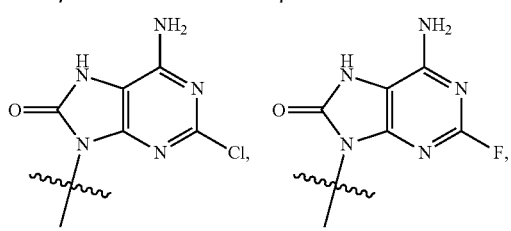
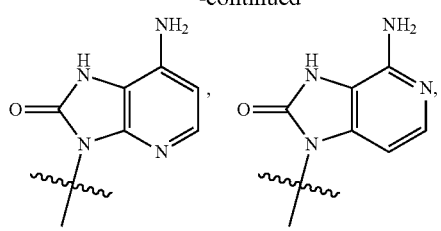
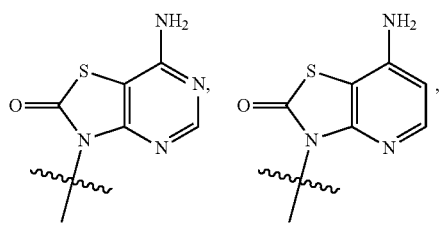
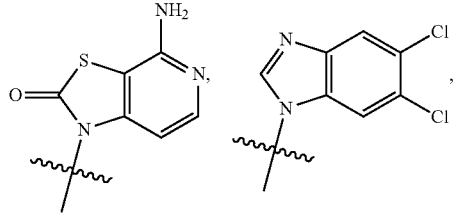
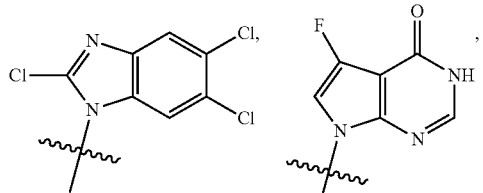
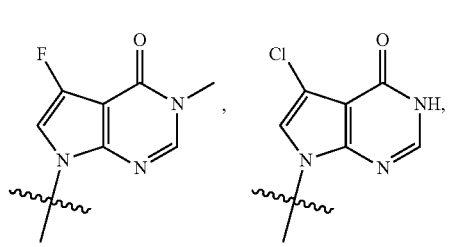
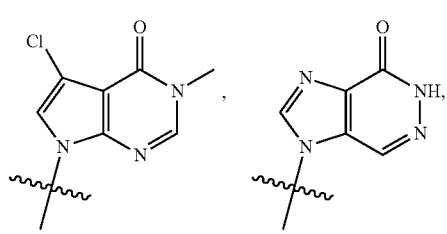
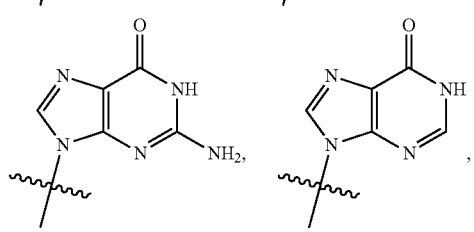

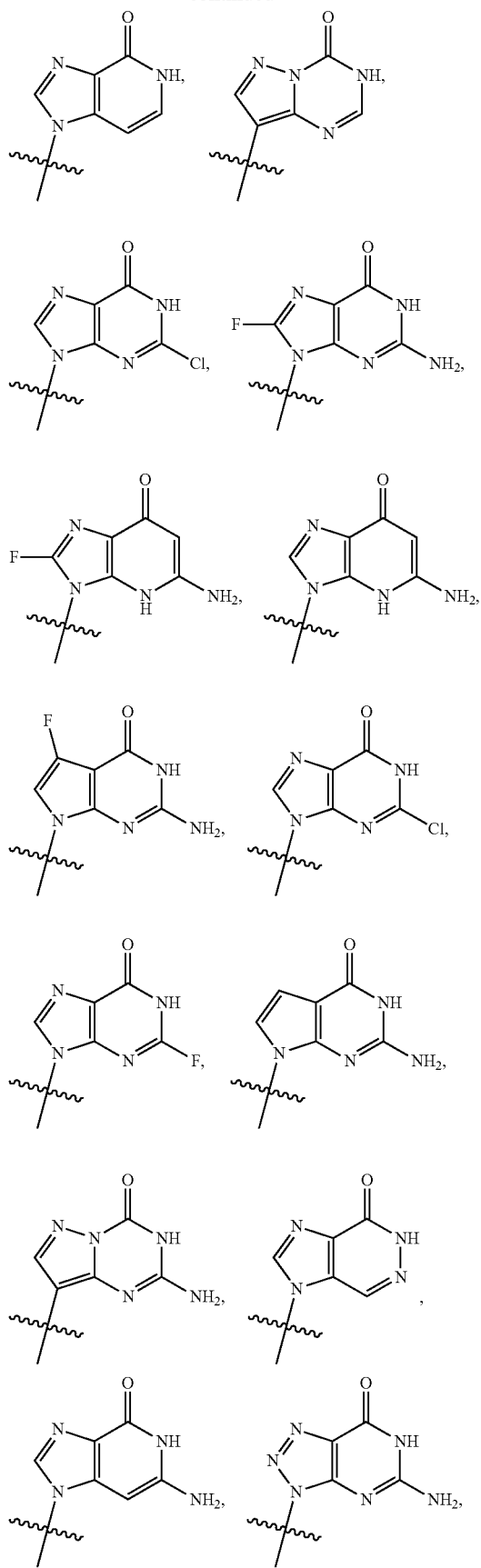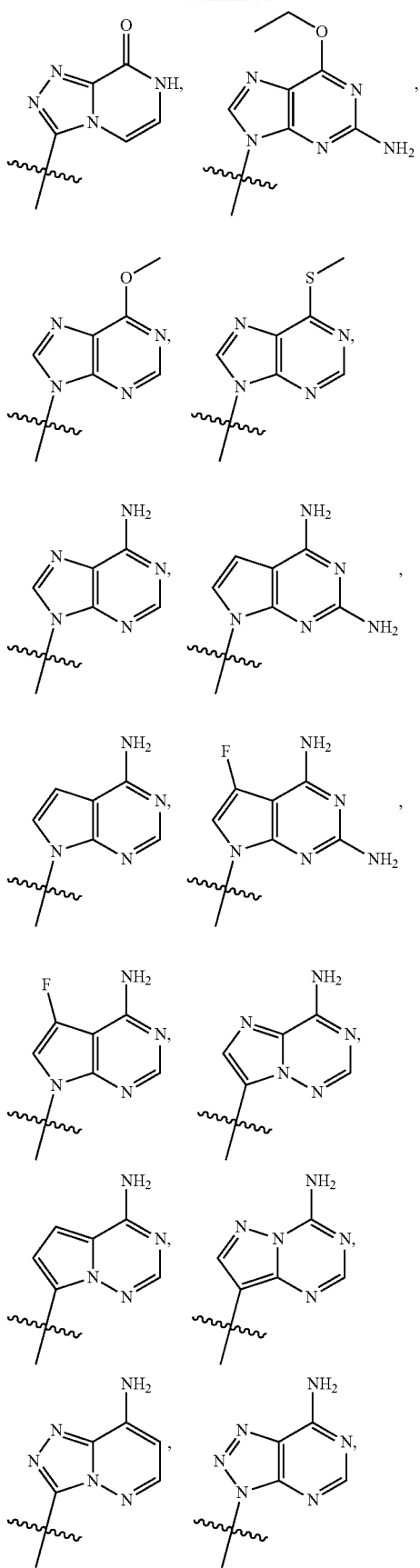

-continued
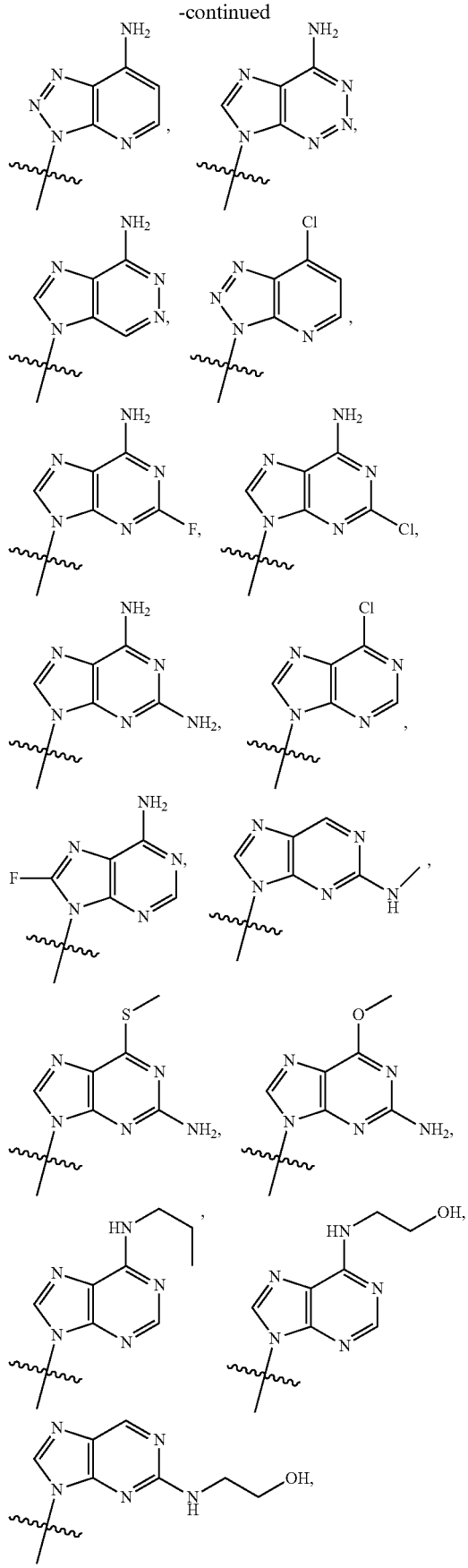
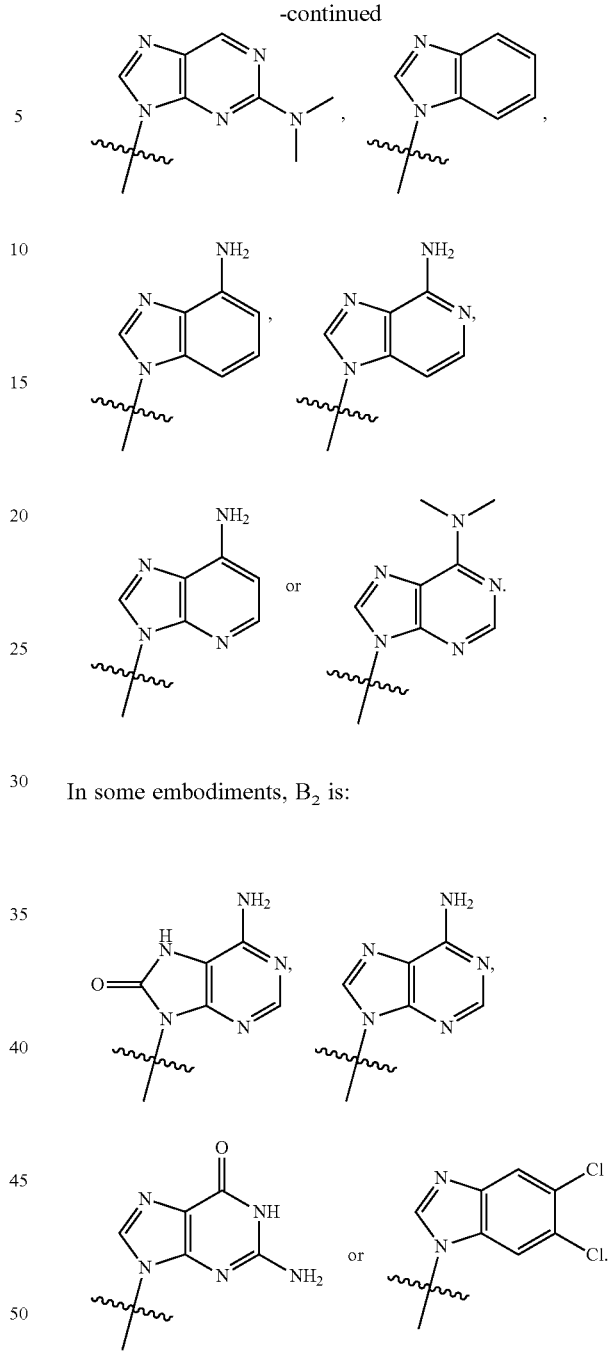
In some embodiments, $B_2$ is:
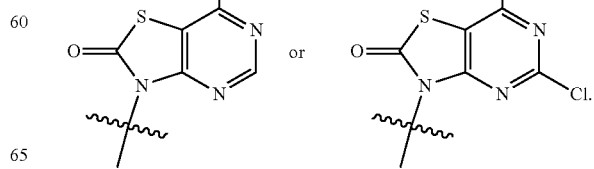
In some embodiments, $B_2$ is:

In some embodiments, $B_2$ is:

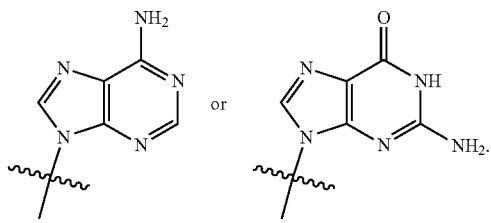 [SMILES: *n1cnc2c(N)ncnc21 ; "or" ; *n1cnc2c(=O)[nH]c(N)nc21]

or

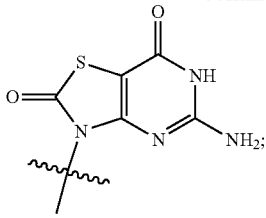

In some embodiments, when L is a connecting bond, then $L_1$ is $CR^1R^2$; $R^1$ and $R^2$ are defined as previously described.

In some embodiments, when L is $CR^1R^2$, then $L_1$ is a connecting bond; $R^1$ and $R^2$ are defined as previously described.

In some embodiments, when L' is a connecting bond, then $L_1'$ is $CR^{11}R^{21}$; $R^{11}$ and $R^{21}$ are defined as previously described.

In some embodiments, when L' is $CR^{11}R^{21}$, then $L_1'$ is a connecting bond; $R^{11}$ and $R^{21}$ are defined as previously described.

In some embodiments, $L_2$ is $CH_2$.
In some embodiments, $L_2'$ is $CH_2$.
In some embodiments, $X^1$ is O.
In some embodiments, $X^{11}$ is O.
In some embodiments, $X^2$ is O.
In some embodiments, $X^{21}$ is O.
In some embodiments, $R^a$ is $C_{1-4}$ alkyl or halo-$C_{1-4}$ alkyl.
In some embodiments, $R^a$ is $C_{1-4}$ alkyl.
In some embodiments, $R^1$ and $R^2$ are each independently hydrogen, halogen, hydroxyl, or $OR^a$; $R^a$ is defined as previously described.

In some embodiments, $R^{11}$ and $R^{21}$ are each independently hydrogen, halogen, hydroxyl, or $OR^a$; $R^a$ is defined as previously described.

In some embodiments, $R^1$ is hydrogen.
In some embodiments, $R^2$ is hydrogen, fluorine, hydroxyl or methoxy.
In some embodiments, $R^{11}$ is hydrogen.
In some embodiments, $R^{21}$ is hydrogen, fluorine, hydroxyl or methoxy.
In some embodiments, R is hydrogen.
In some embodiments, R' is hydrogen.

In some embodiments, certain groups in the compound represented by Formula I, the isomer, prodrug, stable isotope derivative or pharmaceutically acceptable salt thereof can be as defined below, and undescribed groups can be as defined in any of the above embodiments:
$Z_1$ is O;
$Z_2$ is O;
$B_1$ is

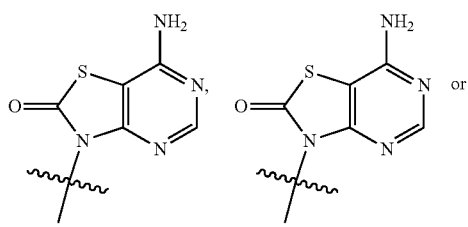

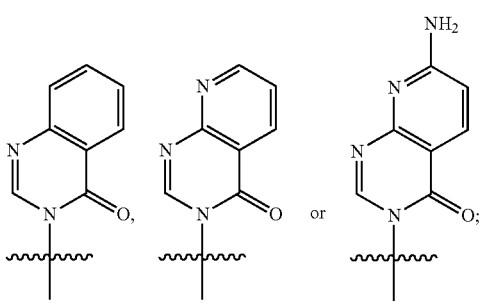

$B_2$ is

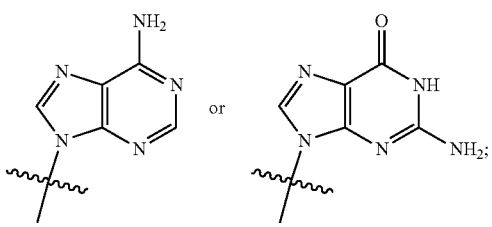 [SMILES: *n1cnc2c(N)ncnc21 ; "or" ; *n1cnc2c(=O)[nH]c(N)nc21]

L and $L_1$ are each independently a connecting bond or $CR^1R^2$;
L' and $L_1'$ are each independently a connecting bond or $CR^{11}R^{21}$; and, L, $L_1$, L' and $L_1'$ are defined in the following combinations:
1) L is a connecting bond, $L_1$ is $CR^1R^2$, L' is $CR^{11}R^{21}$, $L_1'$ is a connecting bond, or
2) L is $CR^1R^2$, $L_1$ is a connecting bond, L' is a connecting bond, $L_1'$ is $CR^{11}R^{21}$;
$L_2$ is $CH_2$;
$L_2'$ is $CH_2$;
$X^1$ is O;
$X^{11}$ is O;
$X^2$ is O;
$X^{21}$ is O;
$X^3$ and $X^{31}$ are each independently OH or SH;
R and R' are each independently hydrogen;
$R^1$ and $R^2$ are each independently hydrogen, halogen, hydroxyl or $OR^a$;
$R^{11}$ and $R^{21}$ are each independently hydrogen, halogen, hydroxyl or $OR^a$;
each $R^a$ is independently $C_{1-4}$ alkyl or halo-$C_{1-4}$ alkyl.

In some embodiments, certain groups in the compound represented by Formula I, the isomer, prodrug, stable isotope derivative or pharmaceutically acceptable salt thereof can be as defined below, and undescribed groups can be as defined in any of the above embodiments:
$Z_1$ is O;
$Z_2$ is O;
$B_1$ is B₂ is

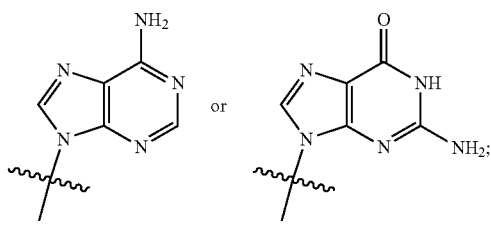 [SMILES: *n1cnc2c(N)ncnc21 ; "or" ; *n1cnc2c(=O)[nH]c(N)nc21]

L and L₁ are each independently a connecting bond or CR¹R²;
L' and L₁' are each independently a connecting bond or CR¹¹R²¹; and, L, L₁, L' and L₁' are as defined in the following combinations:
1) L is a connecting bond, L₁ is CR¹R², L' is CR¹¹R²¹, L₁' is a connecting bond, or
2) L is CR¹R², L₁ is a connecting bond, L' is a connecting bond and L₁' is CR¹¹R²¹;
L₂ is CH₂;
L₂' is CH₂;
X¹ is O;
X¹¹ is O;
X² is O;
X²¹ is O;
X³ and X³¹ are each independently OH or SH;
R and R' are each independently hydrogen;
R¹ and R² are each independently hydrogen, halogen, hydroxyl or ORᵃ;
R¹¹ and R²¹ are each independently hydrogen, halogen, hydroxyl or ORᵃ;
each Rᵃ is independently $C_{1-4}$ alkyl or halo-$C_{1-4}$ alkyl.

In some embodiments, certain groups in the compound represented by Formula I, the isomer, prodrug, stable isotope derivative or pharmaceutically acceptable salt thereof can be as defined below, and undescribed groups can be as defined in any of the above embodiments:
Z₁ is O;
Z₂ is O;
B₁ is

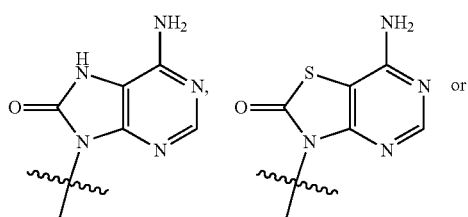

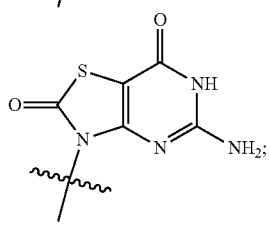

B₂ is

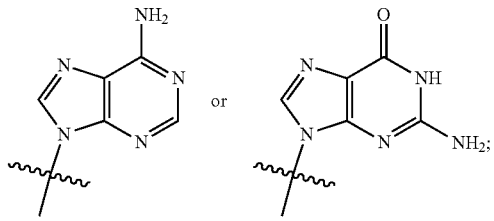

L and L₁ are each independently a connecting bond or CR¹R²;
L' and L₁' are each independently a connecting bond or CR¹¹R²¹; and, L, L₁, L' and L₁' are as defined in the following combinations:
1) L is a connecting bond, L₁ is CR¹R², L' is CR¹¹R²¹, L₁' is a connecting bond, or
2) L is CR¹R², L₁ is a connecting bond, L' is a connecting bond, L₁' is CR¹¹R²¹;
L₂ is CH₂;
L₂' is CH₂;
X¹ is O;
X¹¹ is O;
X² is O;
X²¹ is O;
X³ and X³¹ are each independently SH;
R and R' are each independently hydrogen;
R¹ is hydrogen;
R² is hydrogen, halogen, hydroxyl or ORᵃ;
R¹¹ is hydrogen;
R²¹ is hydrogen, halogen, hydroxyl or ORᵃ;
each Rᵃ is independently $C_{1-4}$ alkyl.

In some embodiments, certain groups in the compound represented by Formula I, the isomer, prodrug, stable isotope derivative or pharmaceutically acceptable salt thereof can be as defined below, and undescribed groups can be as defined in any of the above embodiments:
Z₁ is O;
Z₂ is O;
B₁ is

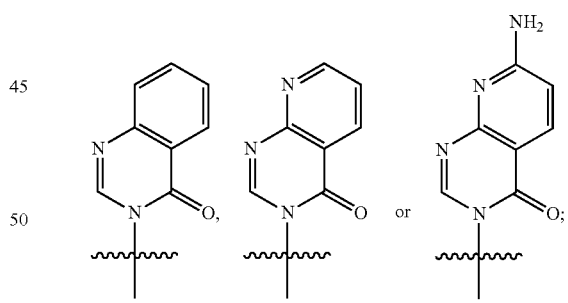

B₂ is

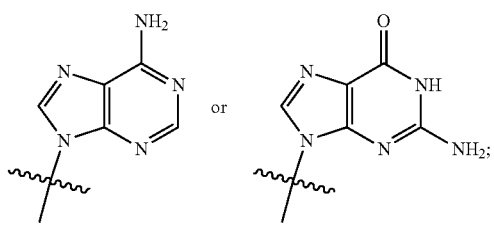 [SMILES: *n1cnc2c(N)ncnc21 ; "or" ; *n1cnc2c(=O)[nH]c(N)nc21]

L and $L_1$ are each independently a connecting bond or $CR^1R^2$;

L' and $L_1$' are each independently a connecting bond or $CR^{11}R^{21}$; and, L, $L_1$, L' and $L_1$' are as defined in the following combinations:
1) L is a connecting bond, $L_1$ is $CR^1R^2$, L' is $CR^{11}R^{21}$, $L_1$' is a connecting bond, or
2) L is $CR^1R^2$, $L_1$ is a connecting bond, L' is a connecting bond and $L_1$' is $CR^{11}R^{21}$;

$L_2$ is $CH_2$;
$L_2$' is $CH_2$;
$X^1$ is O;
$X^{11}$ is O;
$X^2$ is O;
$X^{21}$ is O;
$X^3$ and $X^{31}$ are SH;
R and R' are hydrogen;
$R^1$ is hydrogen;
$R^2$ is hydrogen, halogen, hydroxyl or $OR^a$;
$R^{11}$ is hydrogen;
$R^{21}$ is hydrogen, halogen, hydroxyl or $OR^a$;
each $R^a$ is independently $C_{1-4}$ alkyl.

In some embodiments, the compound of Formula I, the isomer, prodrug, stable isotope derivative or pharmaceutically acceptable salt thereof, is the compound of Formula II, III, IV or V, an isomer, prodrug, stable isotope derivative or pharmaceutically acceptable salt thereof:

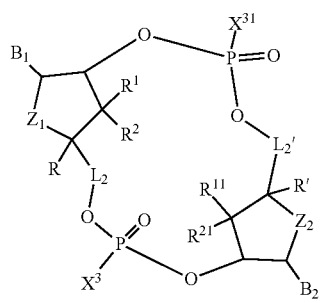

(II)

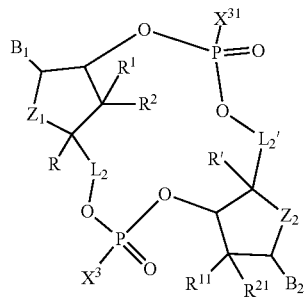

(III)

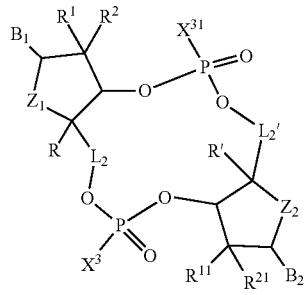

(IV)

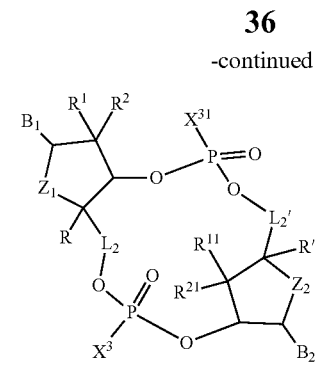

(V)

wherein, $B_1$, $B_2$, $Z_1$, $Z_2$, R, R', $R^1$, $R^2$, $R^{11}$, $R^{21}$, $X^3$, $X^{31}$, $L_2$ and $L_2$' are defined as described previously.

The combinations including any of the $B_1$, $B_2$, $Z_1$, $Z_2$, R, R', $R^1$, $R^2$, $R^{11}$, $R^{21}$, $X^3$, $X^{31}$, $L_2$ and $L_2$' embodiments as described in Formula I are included in the scope of the Formula II, III, IV or V in the present disclosure.

All embodiments of Formula II, III, IV or V described below are included in the scope of the Formula II, III, IV or V in the present disclosure.

In some preferred embodiments of Formula II, III, IV or V, $R^1$ is H; $R^2$ is —OH, F, —$N_3$, —$SCF_3$ or —$OCH_3$.

In some preferred embodiments of Formula II, III, IV or V, $R^{11}$ is H; $R^{21}$ is —OH, F, —$N_3$, —$SCF_3$ or —$OCH_3$.

In some preferred embodiments of Formula II, III, IV or V, R is —$CH_2$—, $R^1$ is —O—, R and $R^1$ are interconnected to form heterocycloalkyl.

In some preferred embodiments of Formula II, III, IV or V, R' is —$CH_2$—, $R^{11}$ is —O—, R' and $R^{11}$ are interconnected to form heterocycloalkyl.

In some preferred embodiments of Formula II, III, IV or V, $Z_1$ is O; $Z_2$ is O.

In some preferred embodiments of Formula II, III, IV or V, $L_2$ is —$CH_2$—; $L_2$' is —$CH_2$—.

In some embodiments, the compound of Formula I, the isomer thereof, prodrug, stable isotope derivative or pharmaceutically acceptable salt thereof, is preferably the compound of Formula VI or VII, an isomer, prodrug, stable isotope derivative or pharmaceutically acceptable salt thereof:

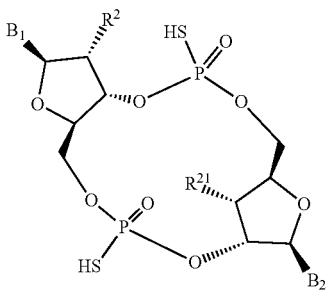

(VI)

(VII)

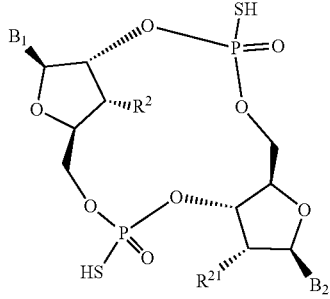

wherein, $B_1$, $B_2$, $R^2$ and $R^{21}$ are defined as previously described.

The combinations including any of the $B_1$, $B_2$, $R^2$ and $R^{21}$ embodiments as described in Formula I are included in the scope of the Formula VI or VII in the present disclosure.

All embodiments of Formula VI or VII described below are included in the scope of the Formula VI or VII in the present disclosure.

In some preferred embodiments of Formula VI or VII, $R^2$ is —OH.

In some preferred embodiments of Formula VI or VII, $R^2$ is F.

In some preferred embodiments of Formula VI or VII, $R^{21}$ is —OH.

In some preferred embodiments of Formula VI or VII, $R^{21}$ is F.

In some preferred embodiments of Formula VI or VII, $B_1$ is

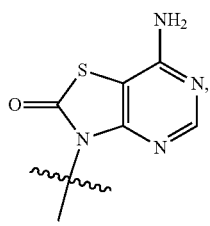

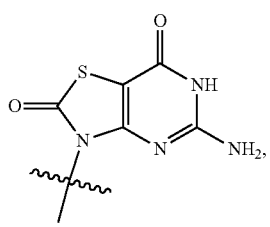

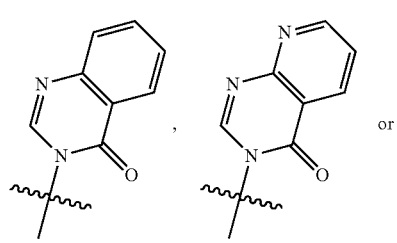

In some preferred embodiments of Formula VI or VII, $B_2$ is

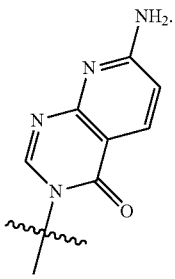

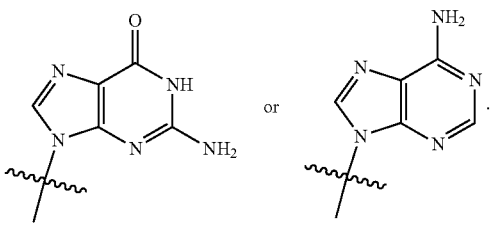 [SMILES: *n1cnc2c(=O)[nH]c(N)nc21 ; "or" ; *n1cnc2c(N)ncnc21 ; "."]

In some preferred embodiments of Formula VI or VII, the stereo configuration is (Sp, Sp), (Sp, Rp), (Rp, Rp), or (Rp, Sp).

In some preferred embodiments of Formula VI, $R^2$ is —OH; $R^{21}$ is —OH.

In some preferred embodiments of Formula VII, $R^2$ is —OH or —OCH$_3$; $R^{21}$ is —OH or F.

In some embodiments, the compound of Formula I, the isomer, prodrug, stable isotope derivative or pharmaceutically acceptable salt is any of the following structures:

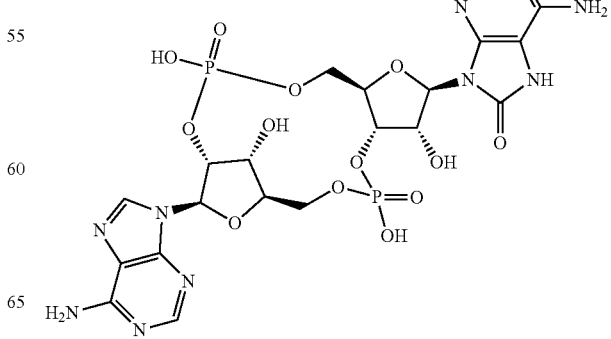

39
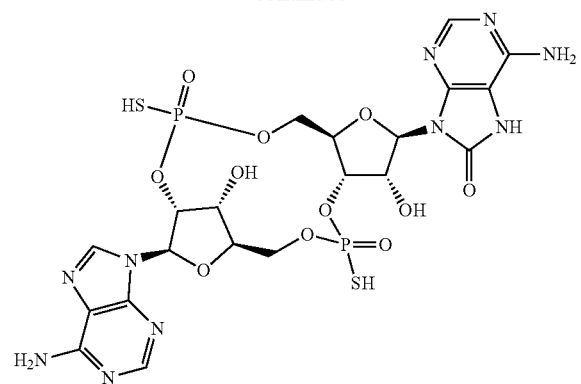
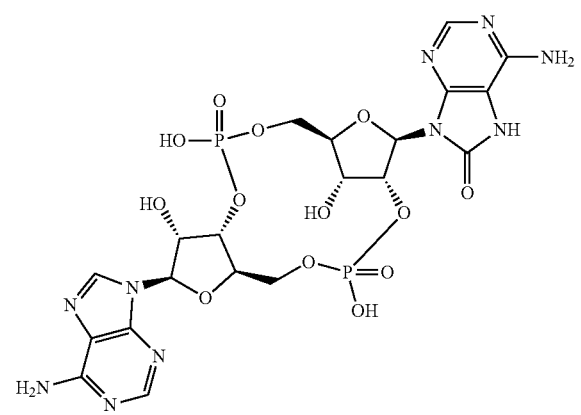
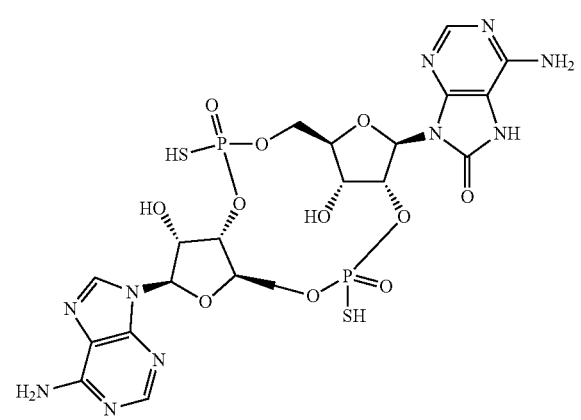
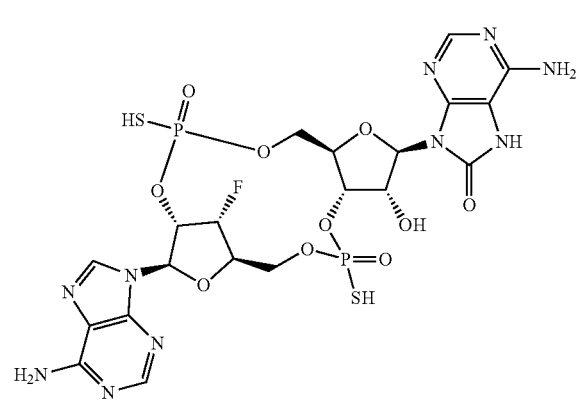
40
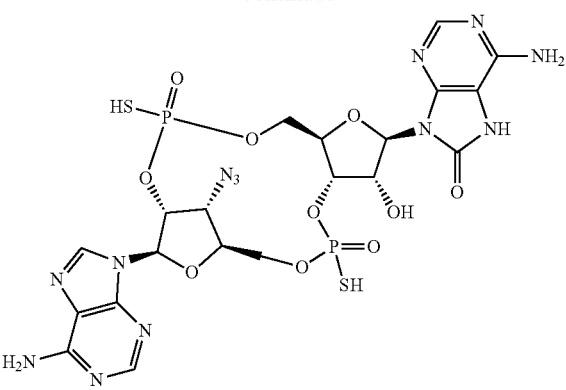
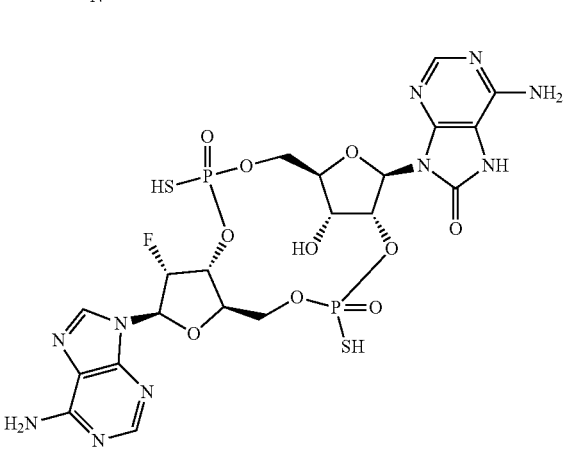
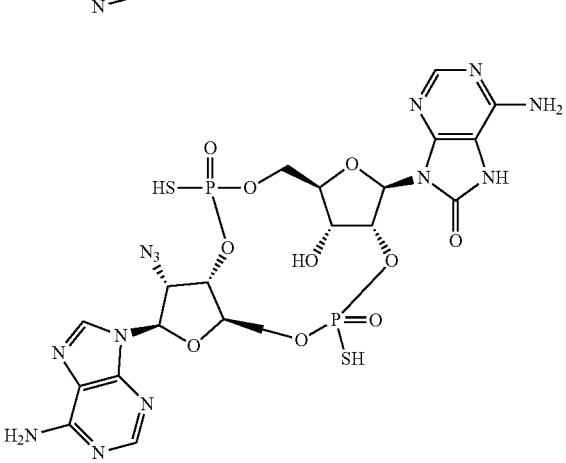
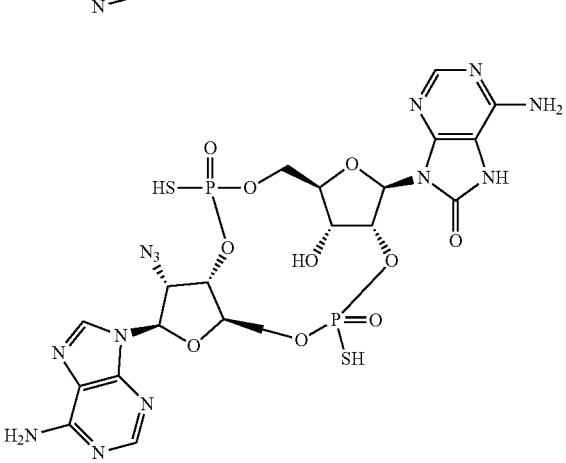

41
-continued
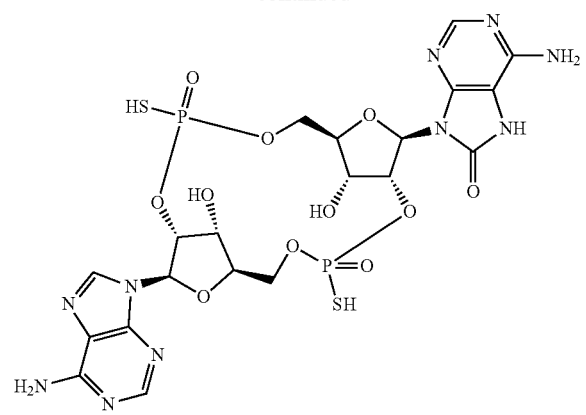
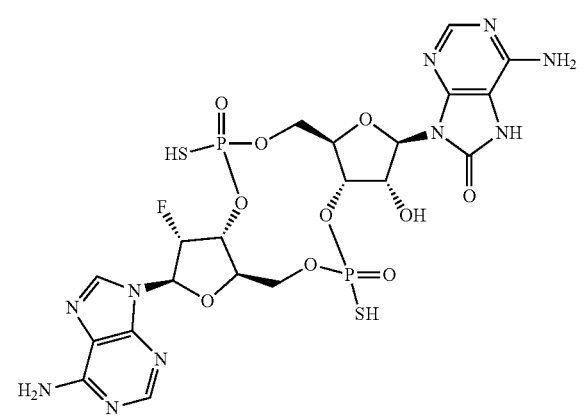
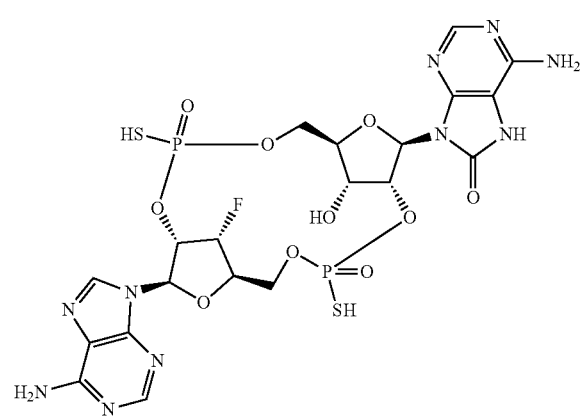
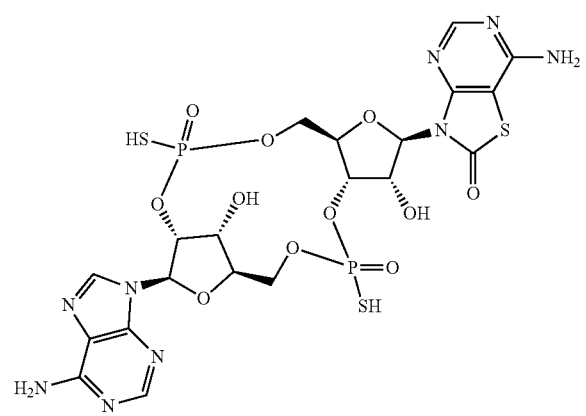
42
-continued
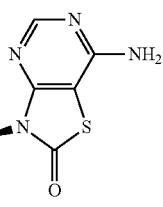
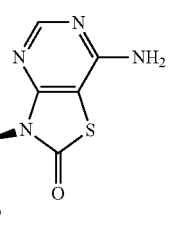
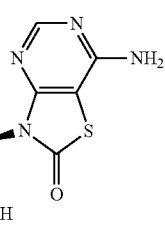
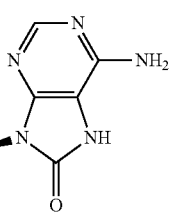

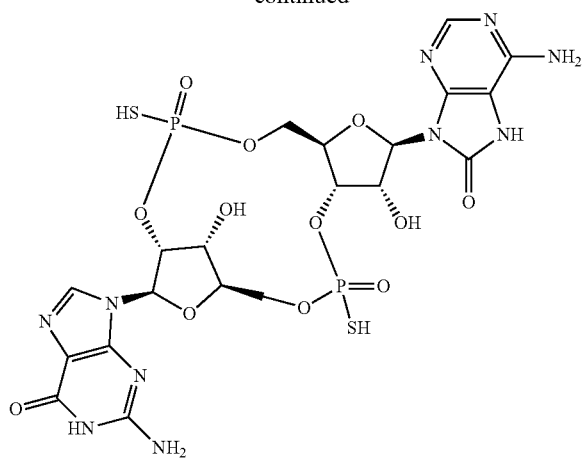
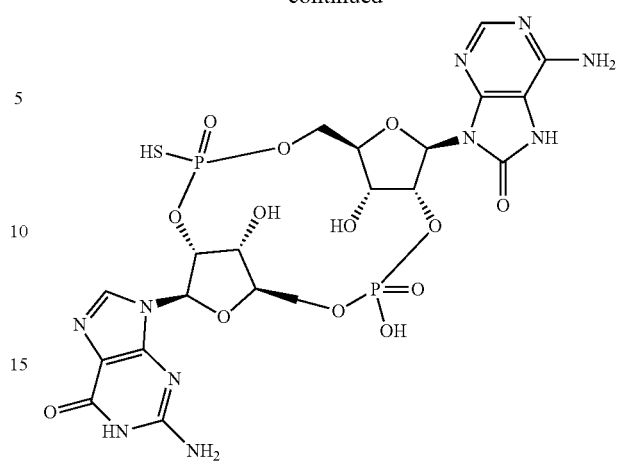

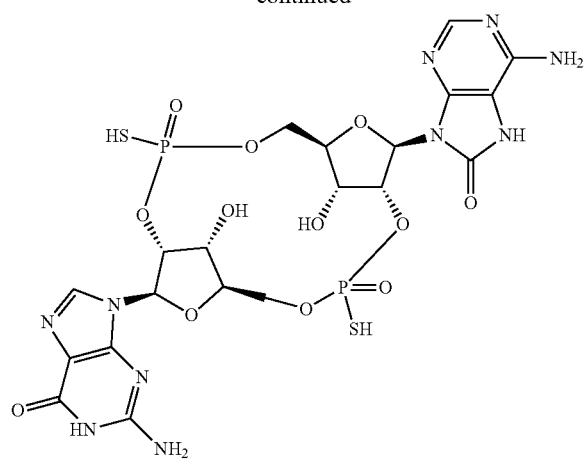
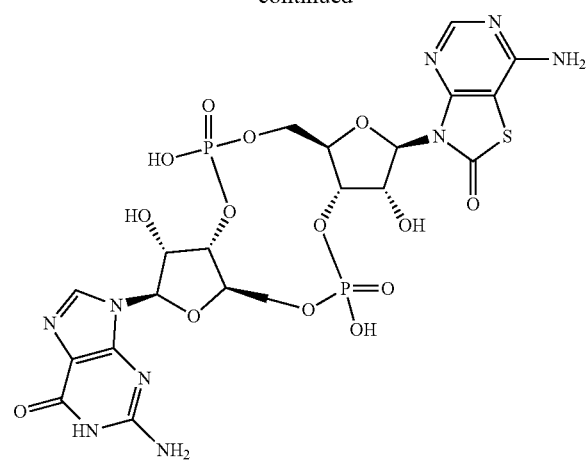
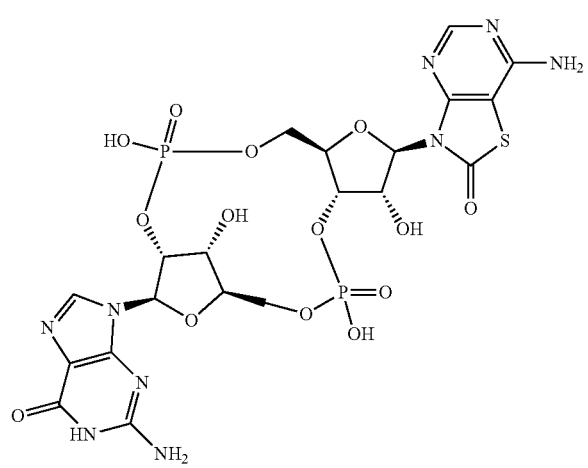
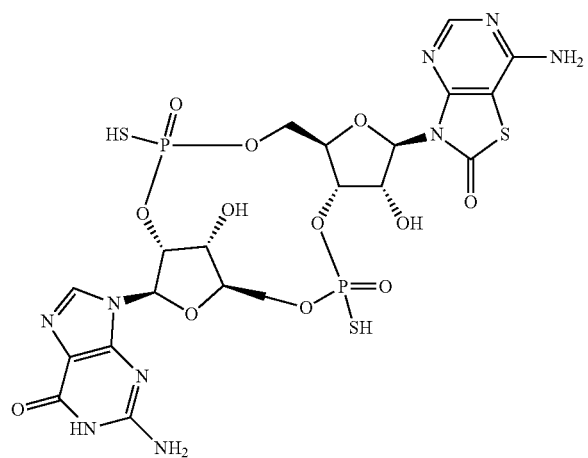
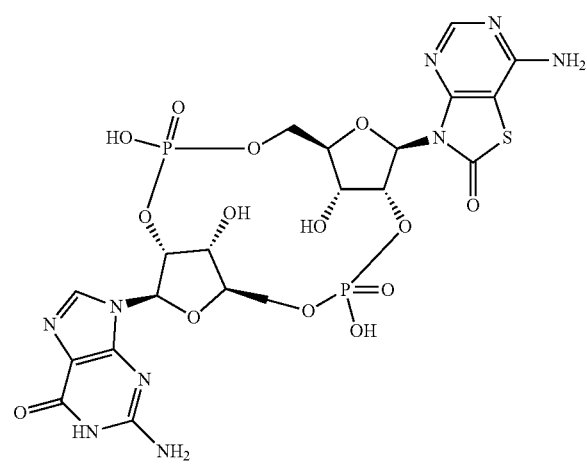

47
-continued
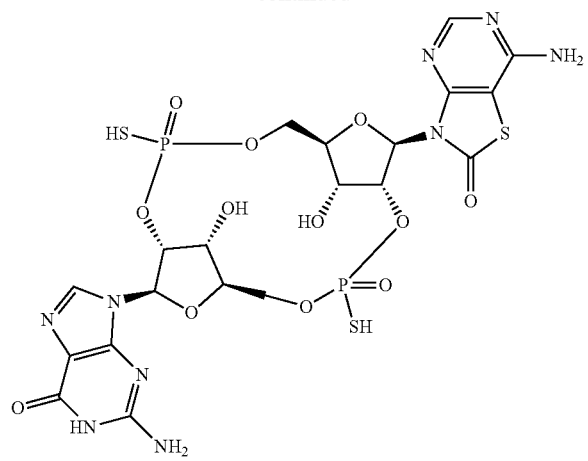
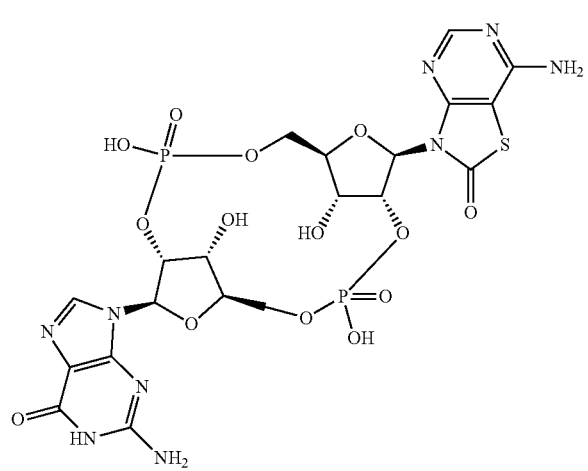
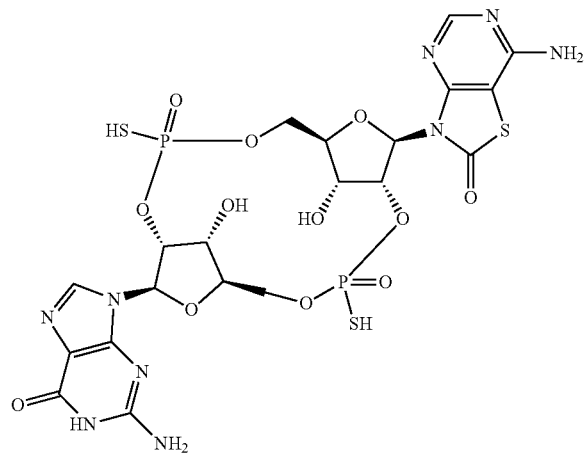
48
-continued
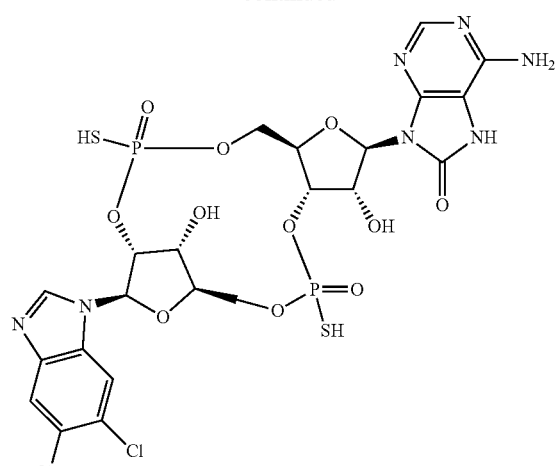
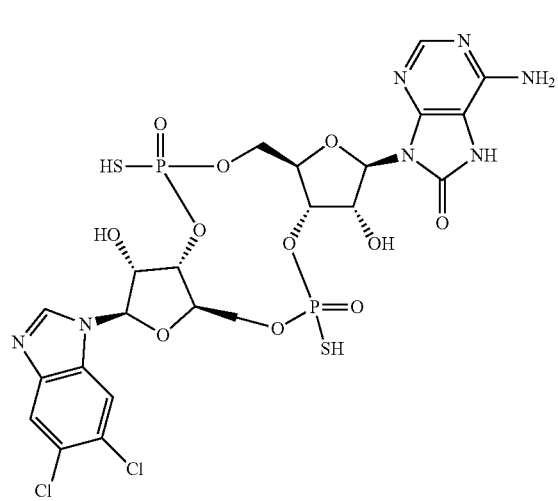
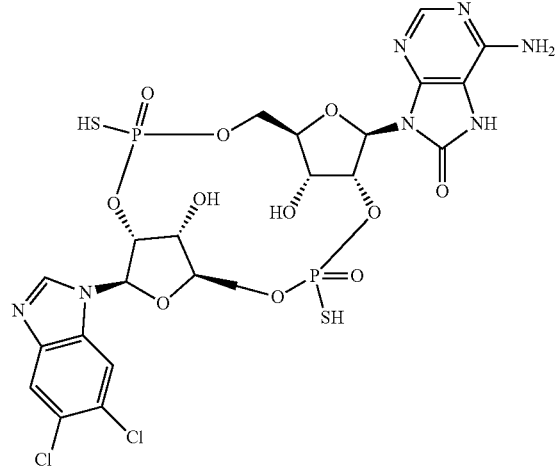 [SMILES: Nc1ncnc2c1[nH]c(=O)n2[C@@H]1O[C@@H]2COP(=O)(S)O[C@@H]3[C@H](O)[C@@H](COP(=O)(S)O[C@@H]1[C@@H]2O)O[C@H]3n1cnc2cc(Cl)c(Cl)cc21]

49
-continued
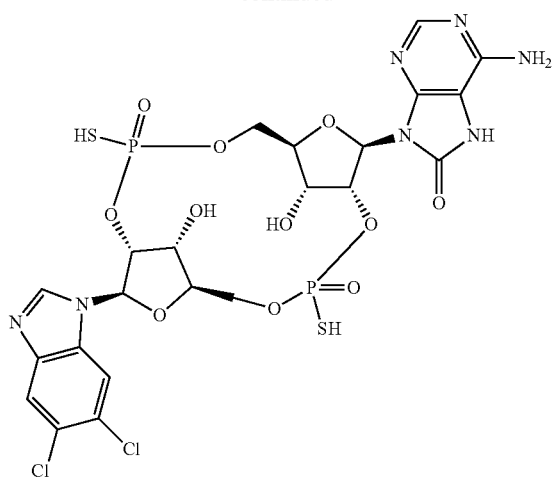 [SMILES: Nc1ncnc2c1sc(=O)n2[C@@H]1O[C@@H]2COP(=O)(S)O[C@@H]3[C@H](O)[C@@H](COP(=O)(S)O[C@@H]1[C@@H]2O)O[C@H]3n1cnc2cc(Cl)c(Cl)cc21]
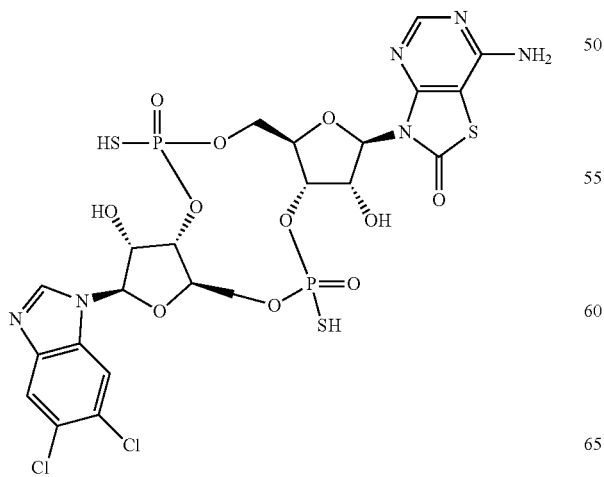
50
-continued
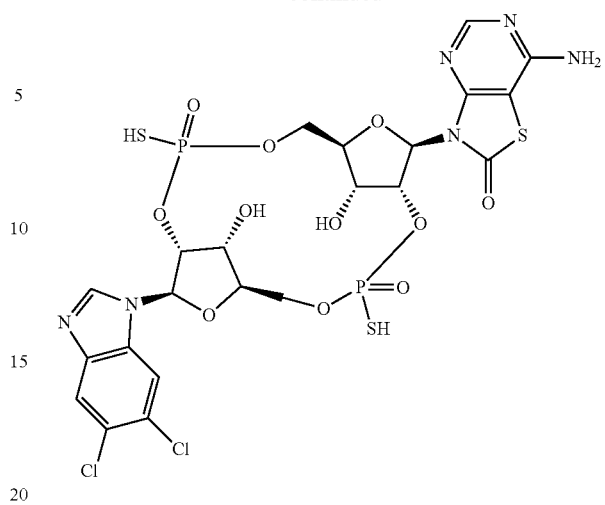
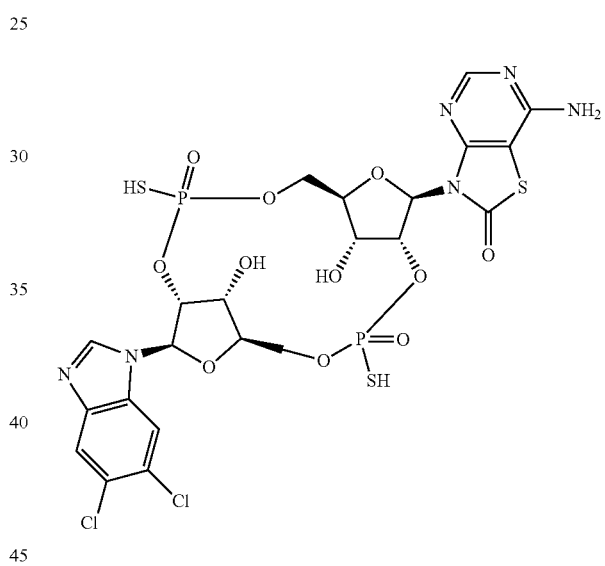
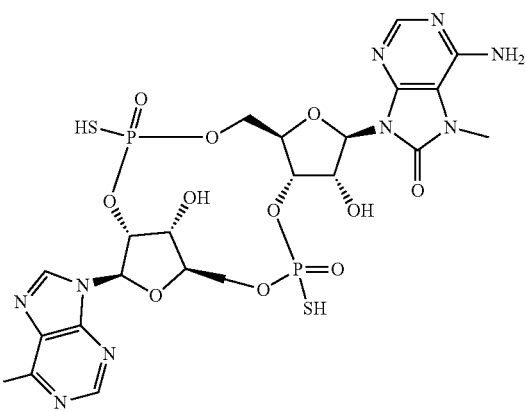

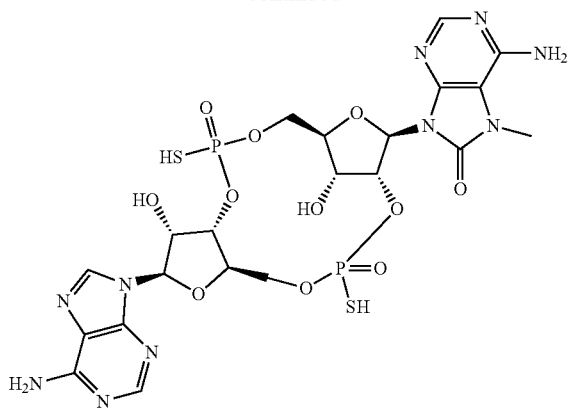
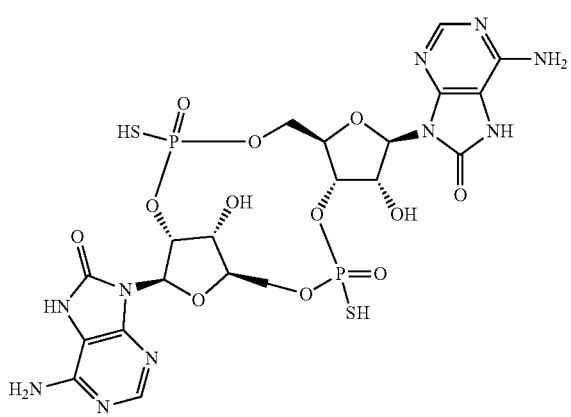
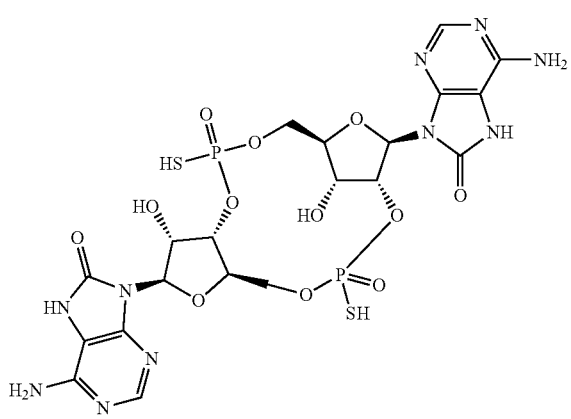
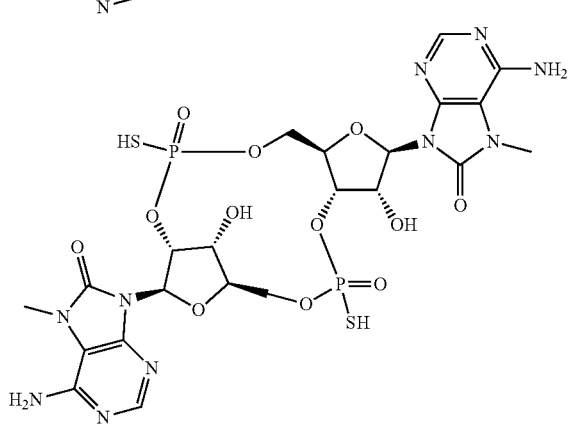
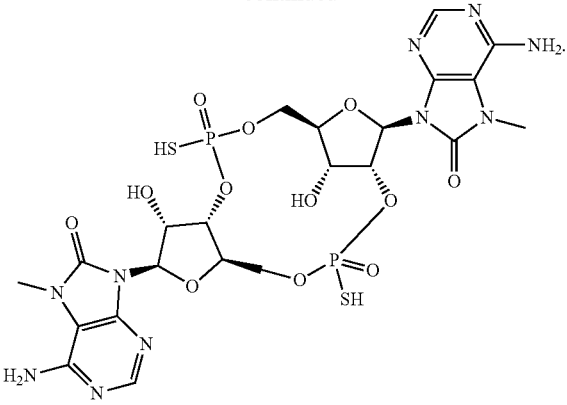
In some embodiments, the compound of Formula I, the isomer, prodrug, stable isotope derivative or pharmaceutically acceptable salt is any of the following structures:
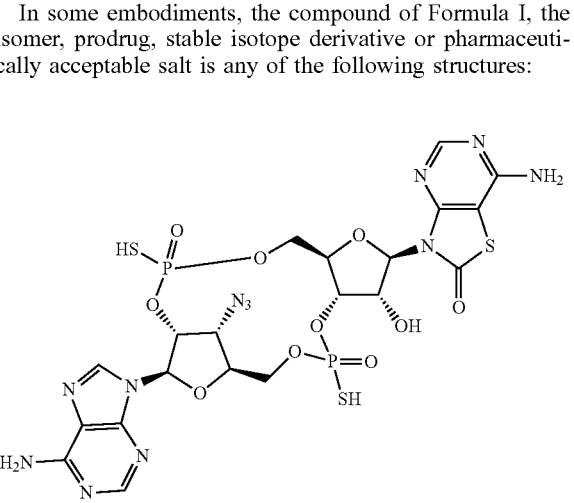
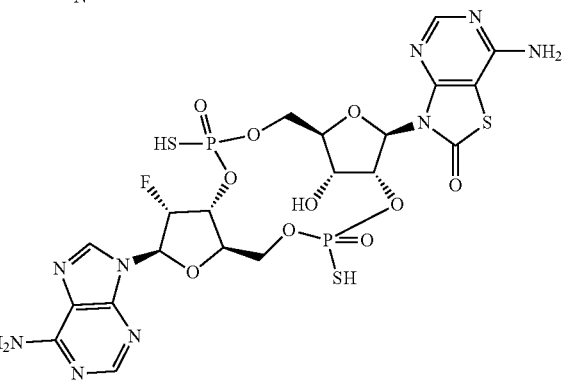
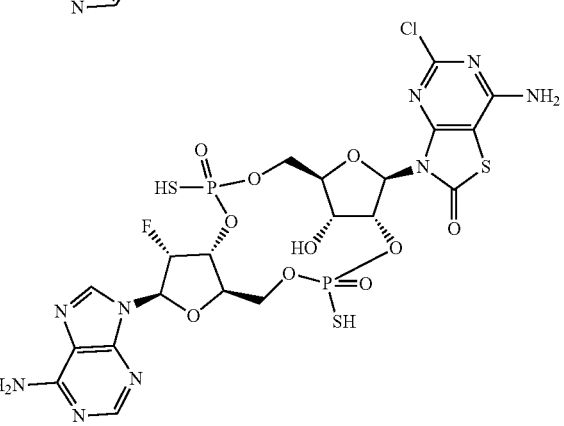

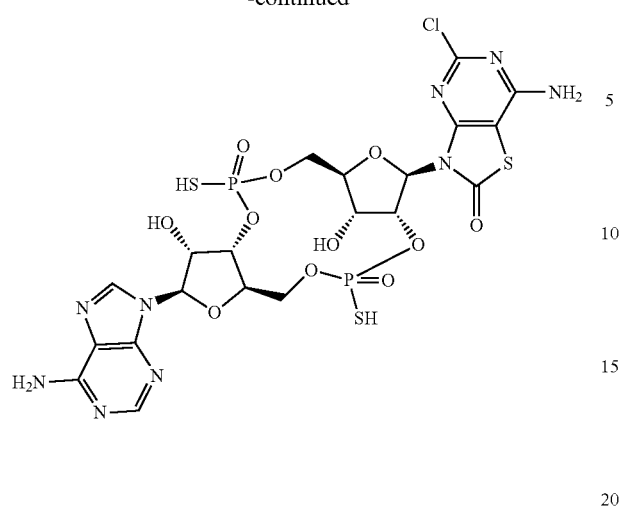
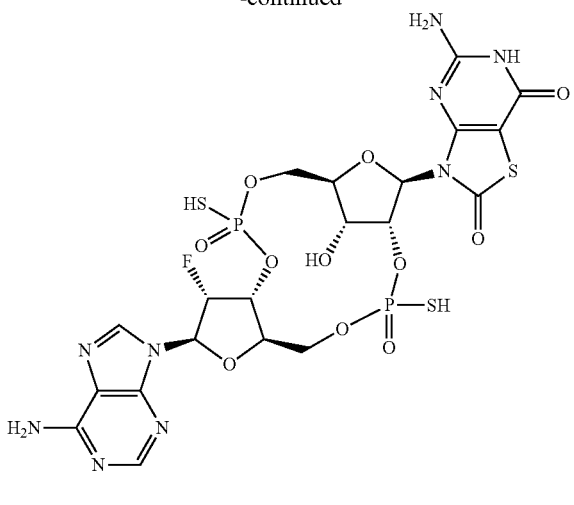
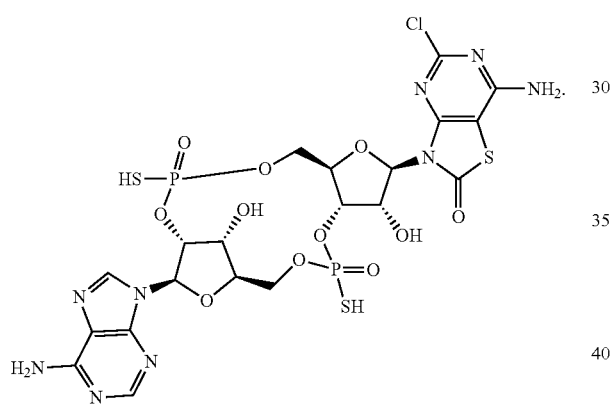
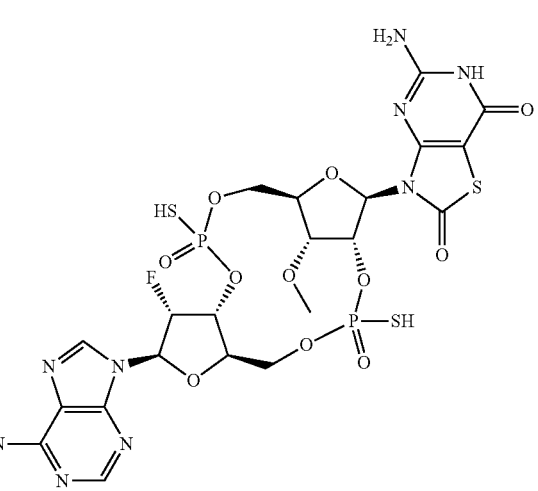
In some embodiments, the compound of Formula I, the isomer, prodrug, stable isotope derivative or pharmaceutically acceptable salt is any of the following structures:
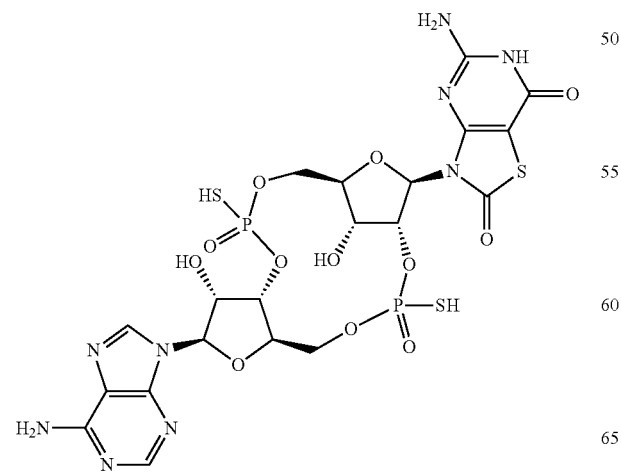
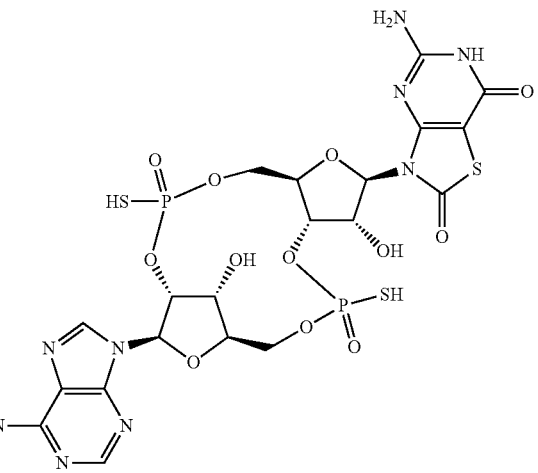

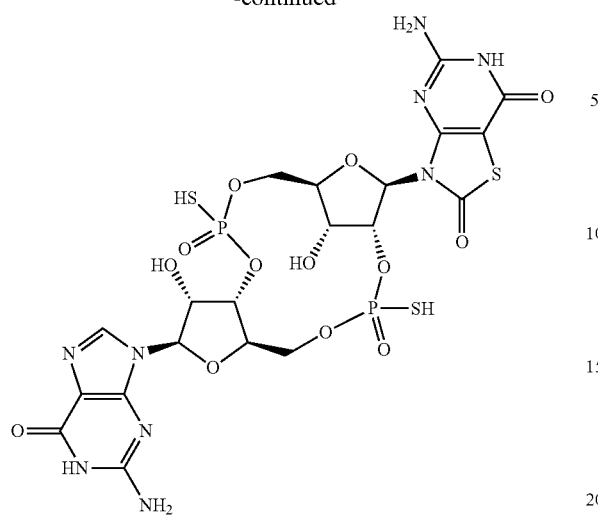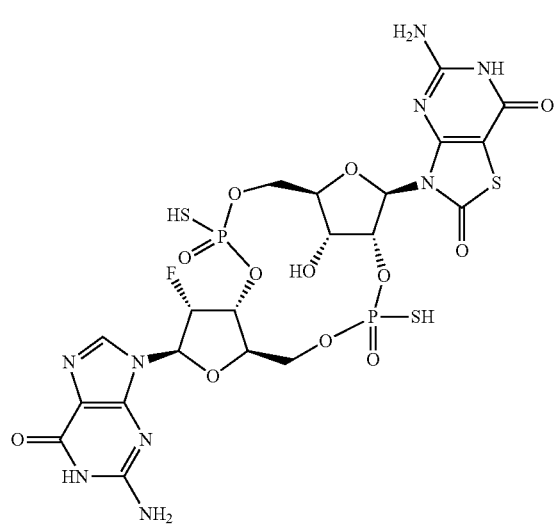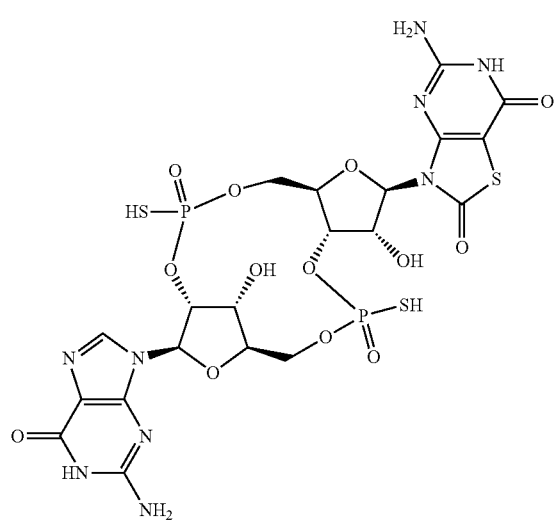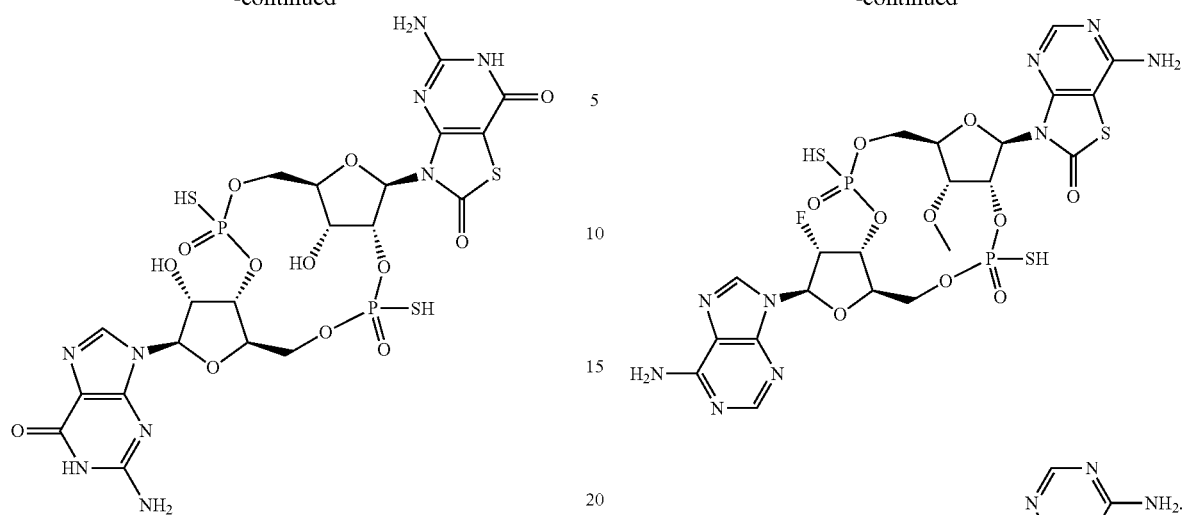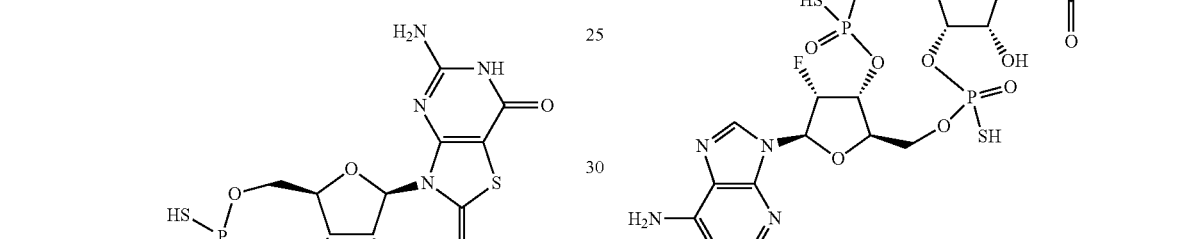
In some embodiments, the compound of Formula I, the isomer, prodrug, stable isotope derivative or pharmaceutically acceptable salt is most preferably any of the following structures:
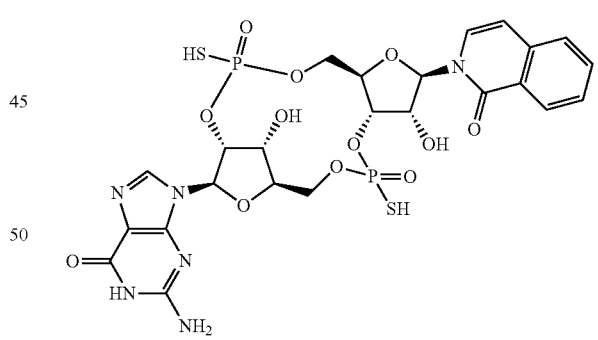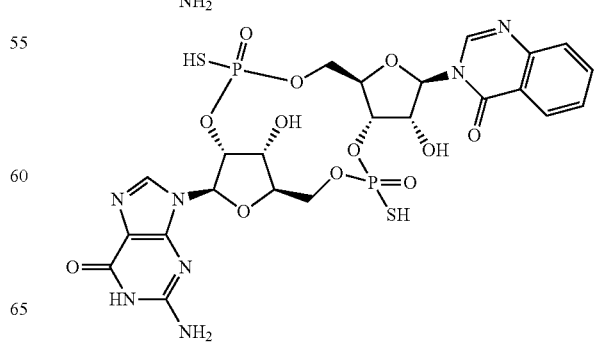

57
-continued
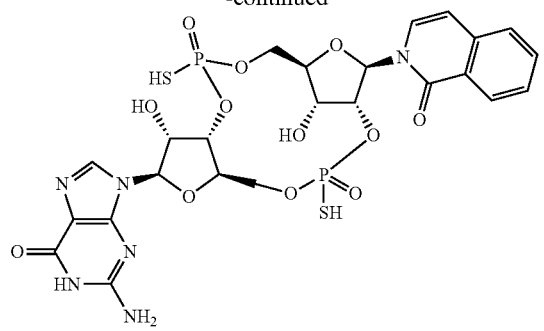
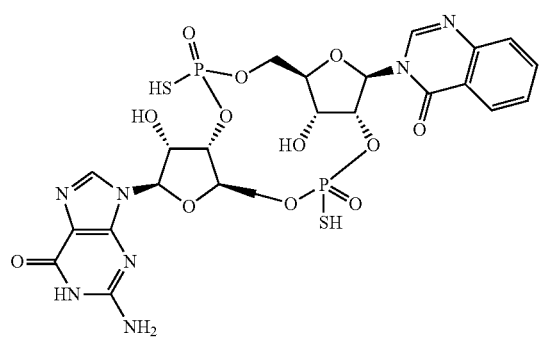
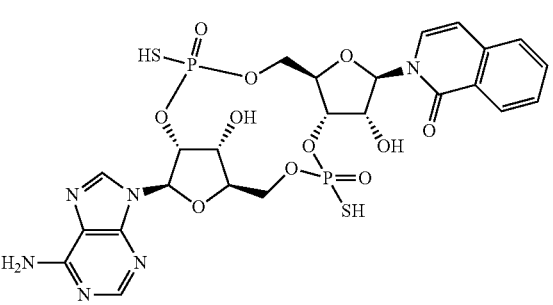
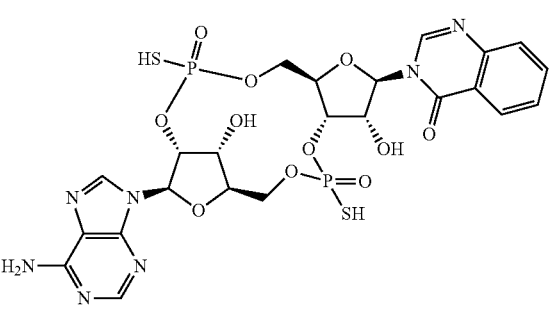
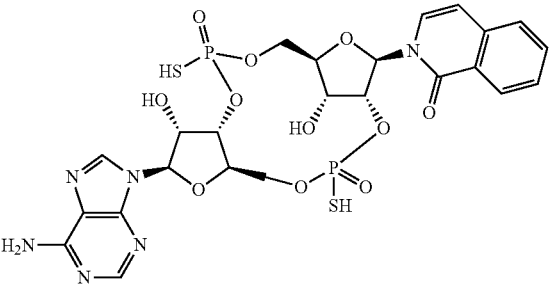
58
-continued
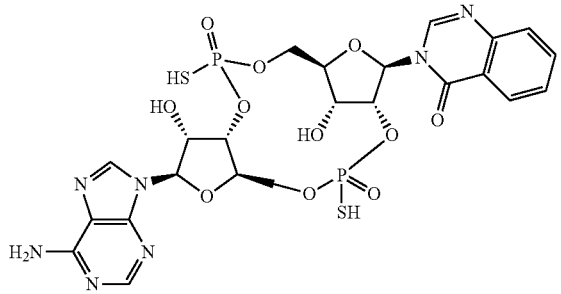
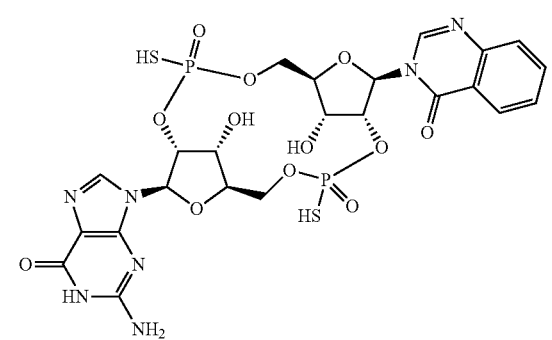
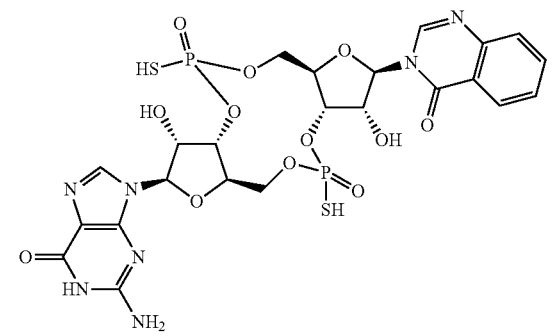
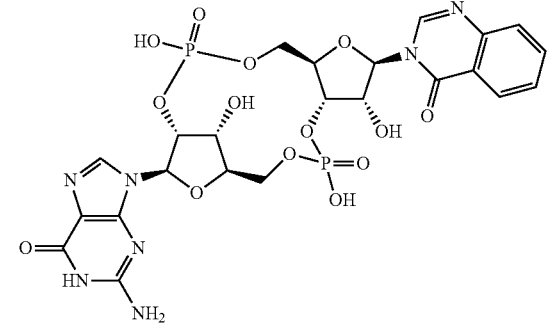
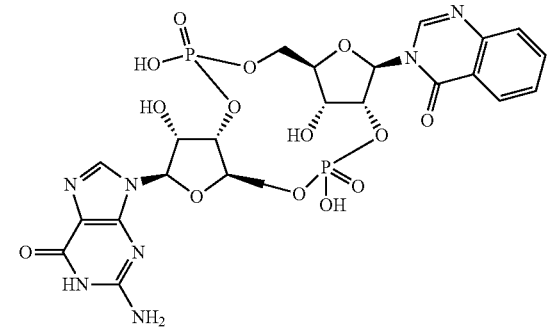

59
-continued
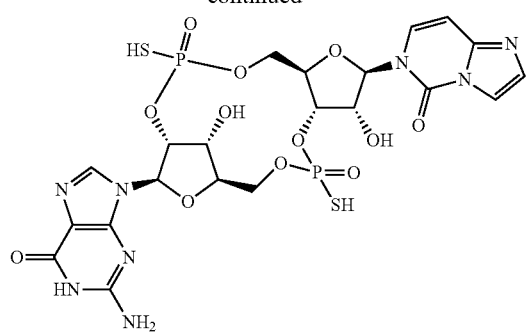
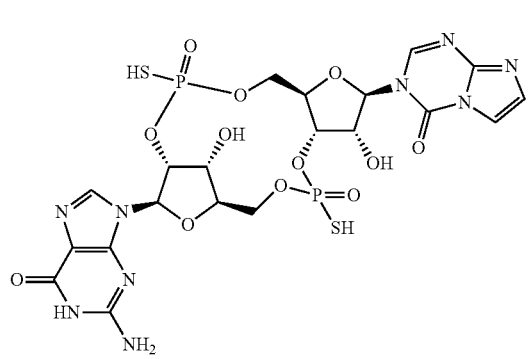
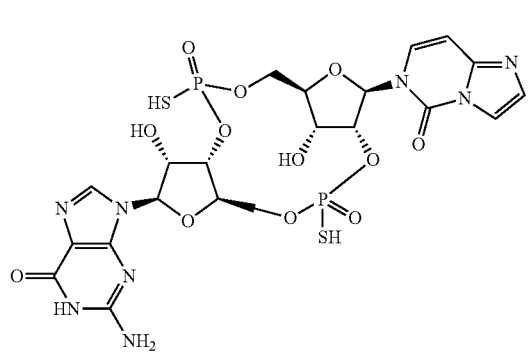
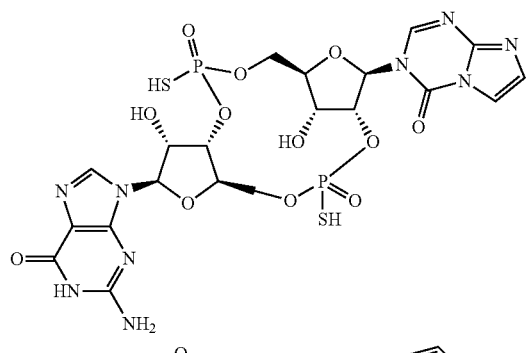
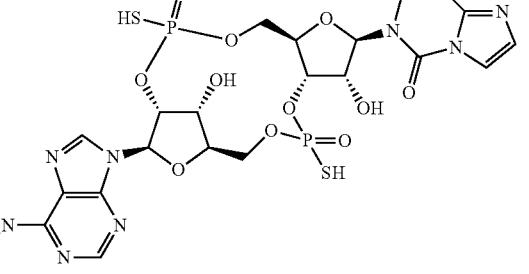
60
-continued
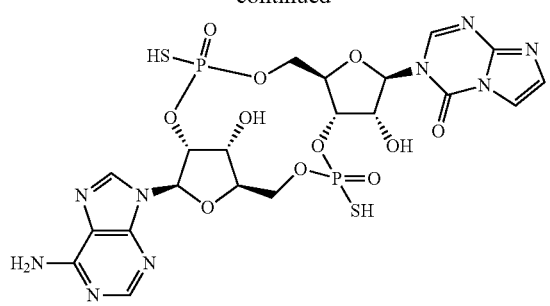
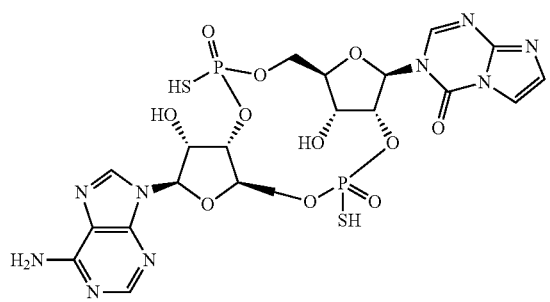
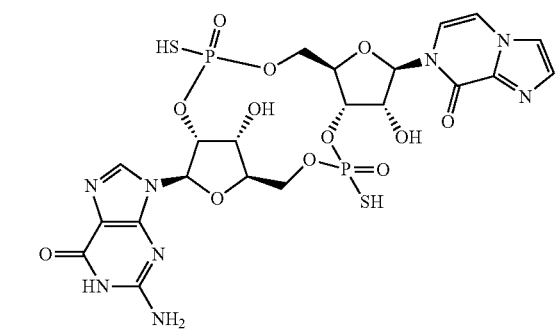
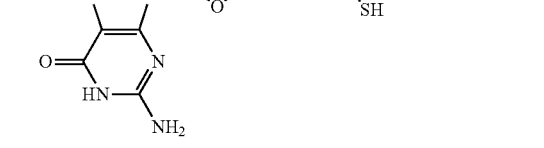

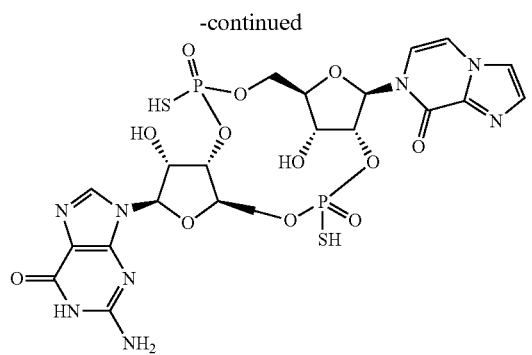
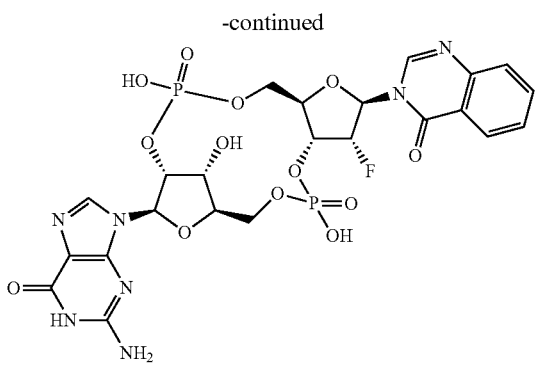

63
-continued
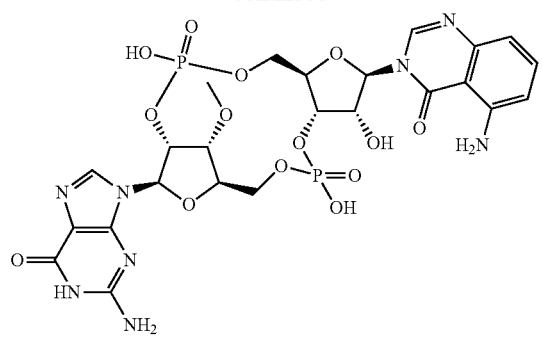
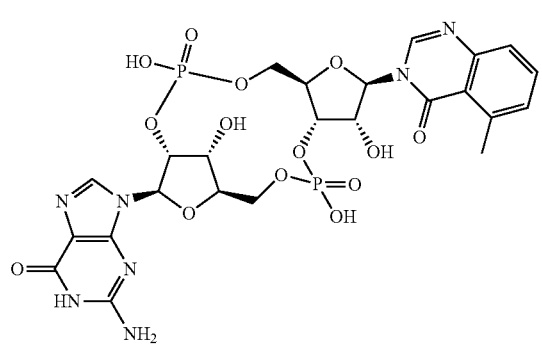
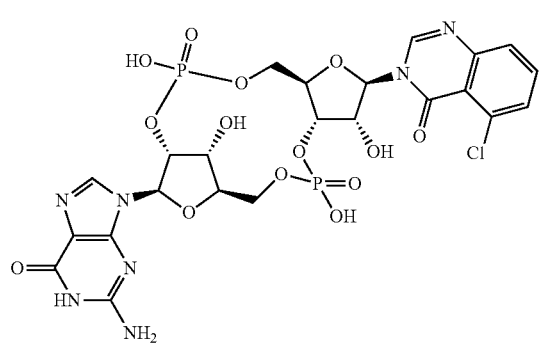
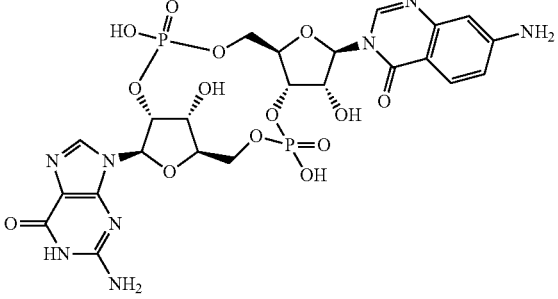
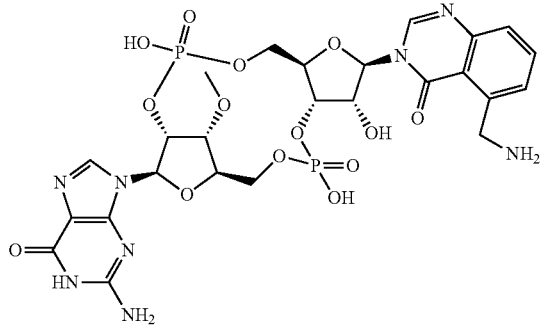
64
-continued
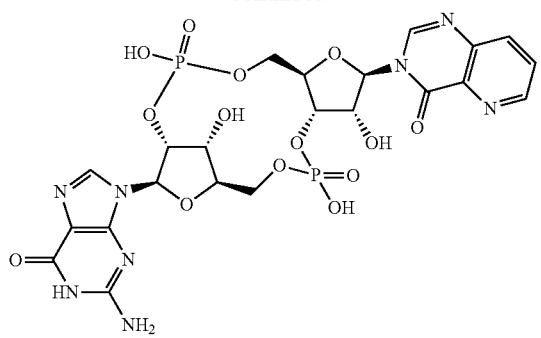
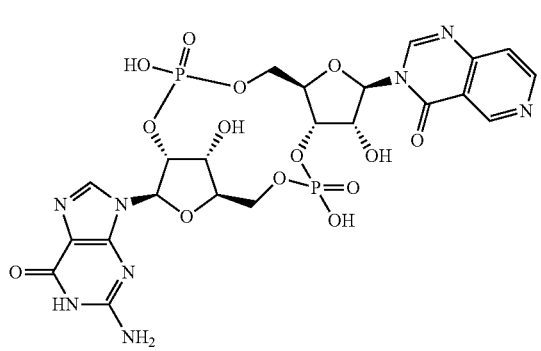
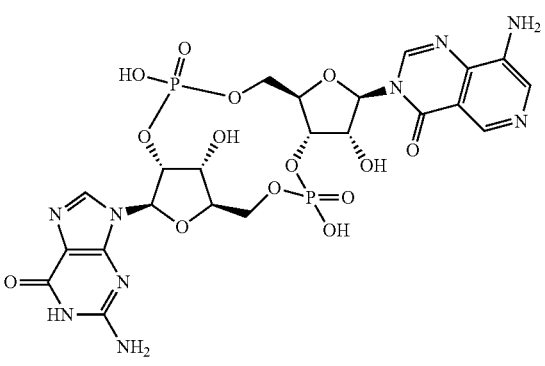
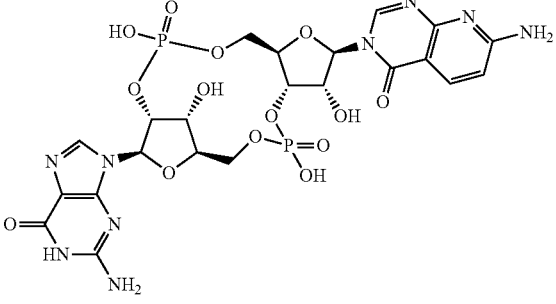
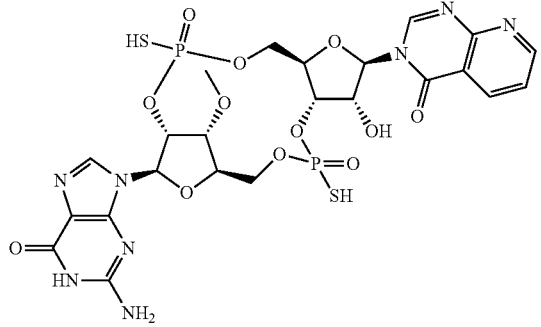

65
-continued
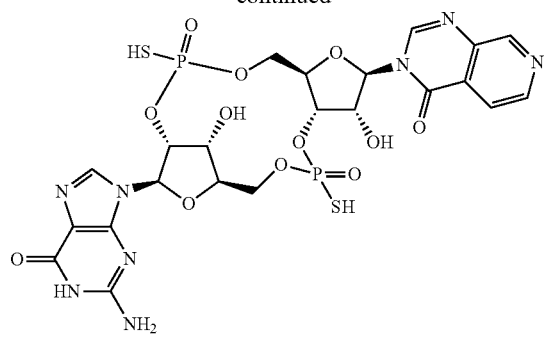
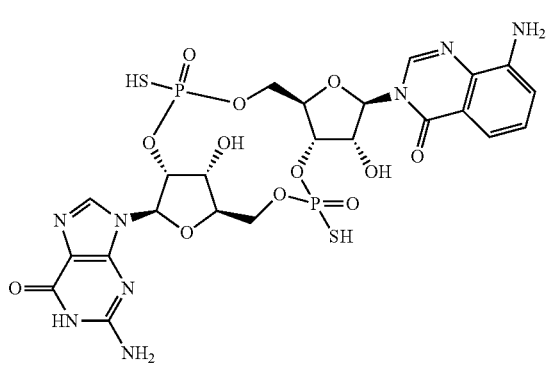
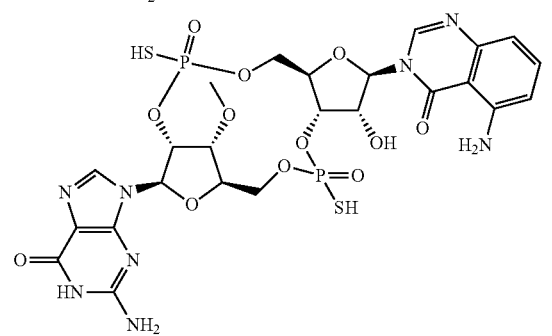
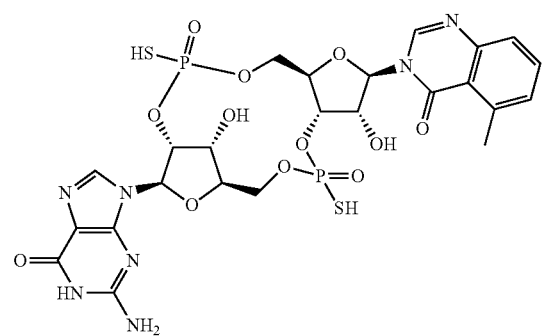
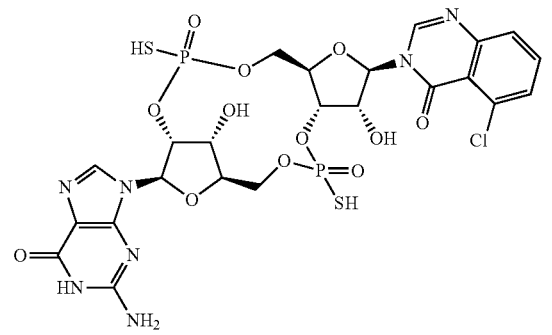
66
-continued
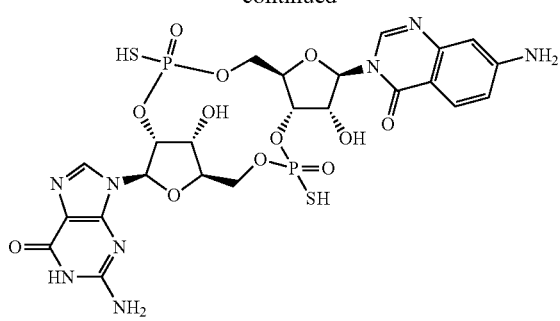
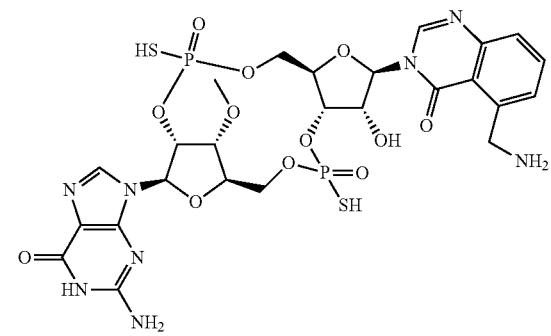
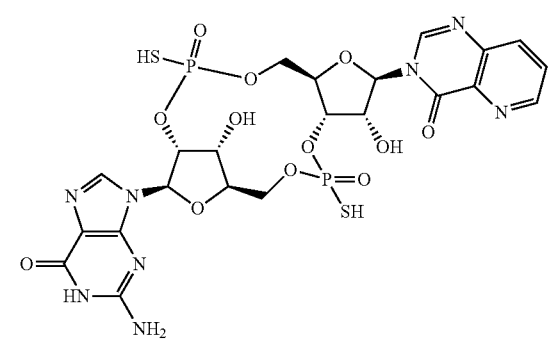
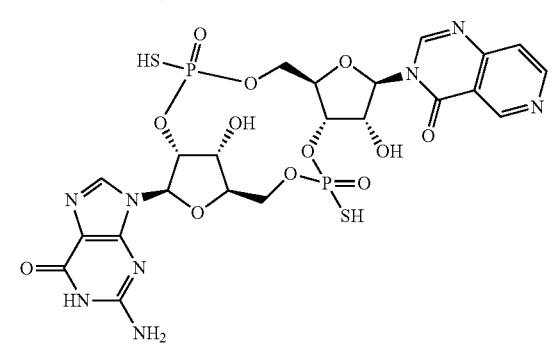
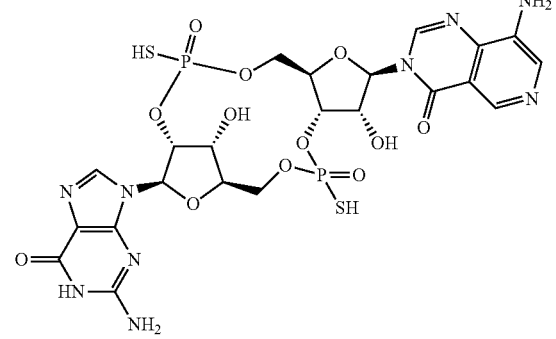

-continued
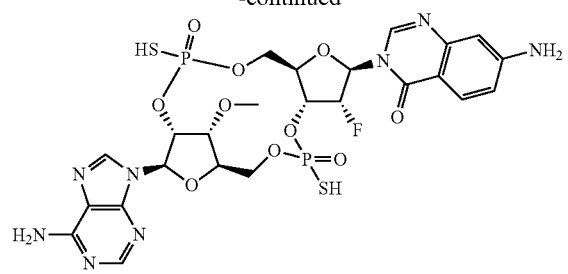
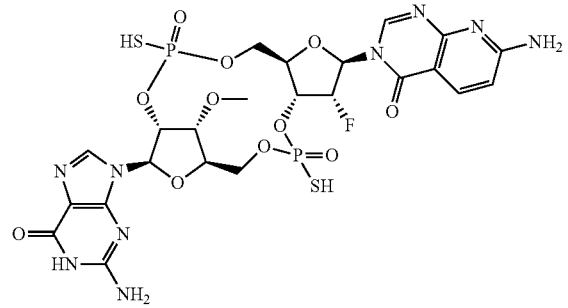
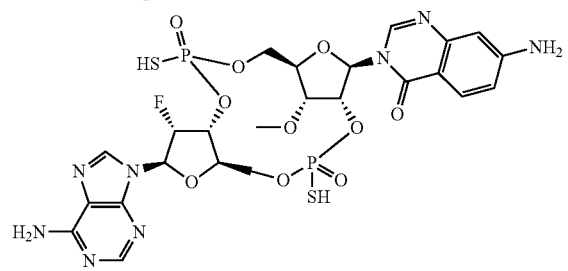
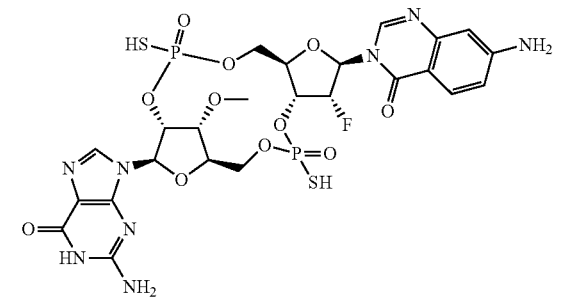
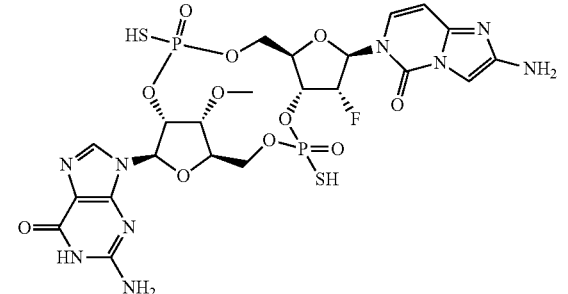
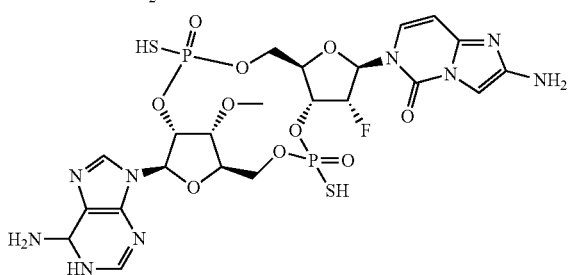
-continued
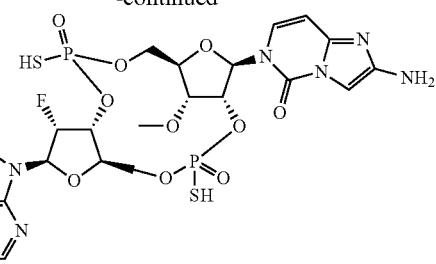
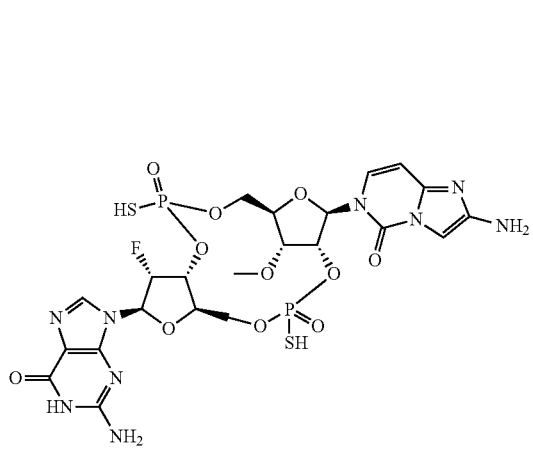
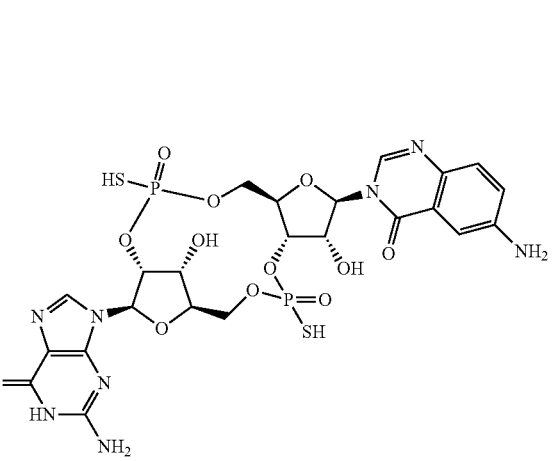
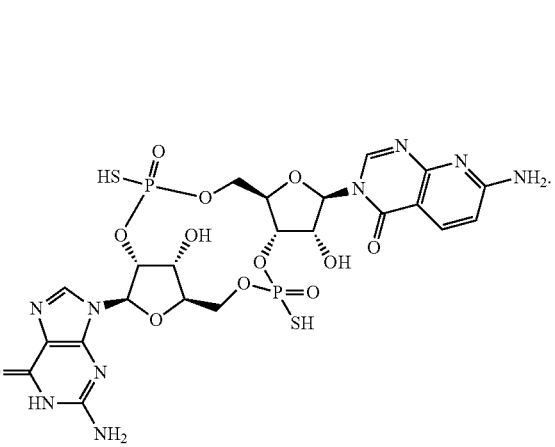
In some embodiments, the compound of Formula I, the isomer, prodrug, stable isotope derivative or pharmaceutically acceptable salt is any of the following structures:

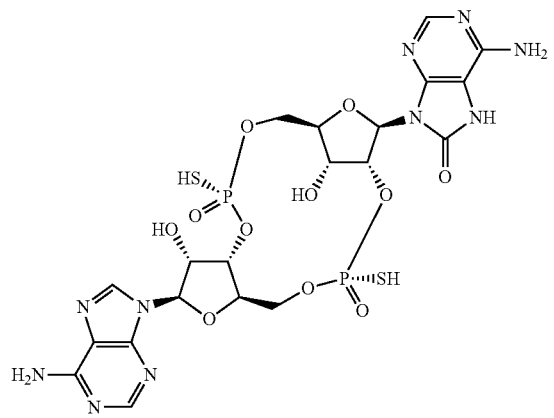
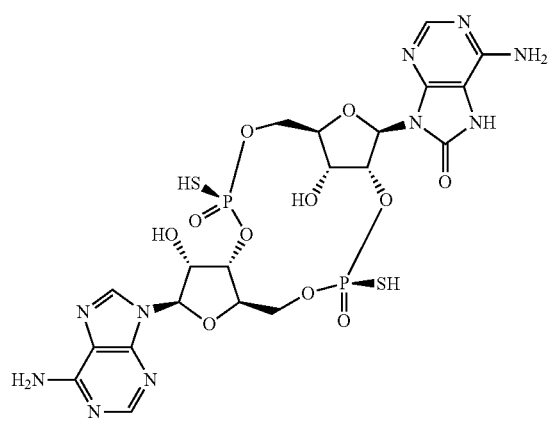
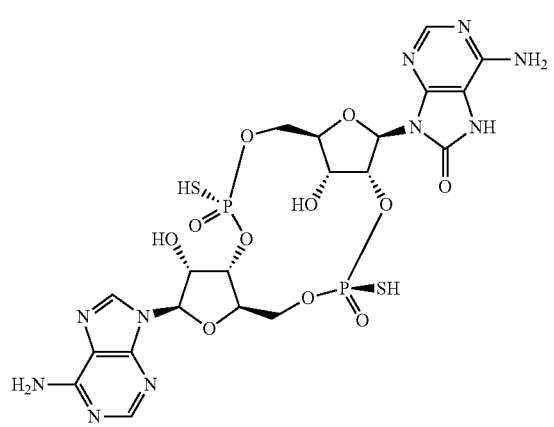
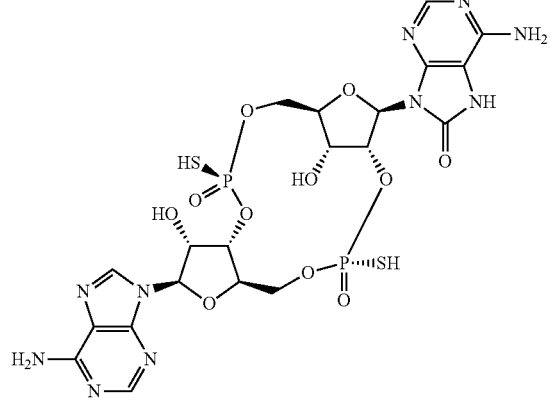
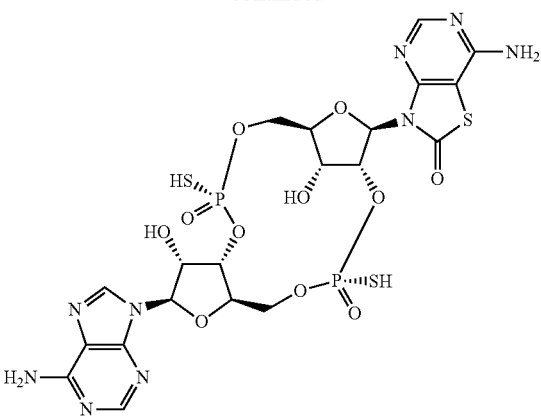
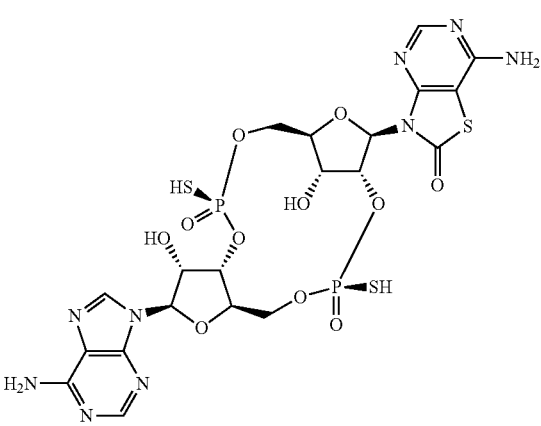
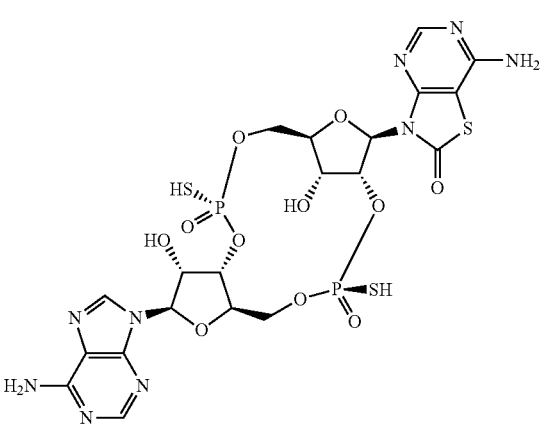
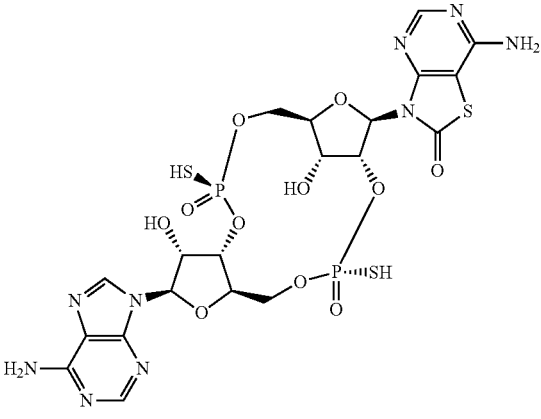

71
-continued
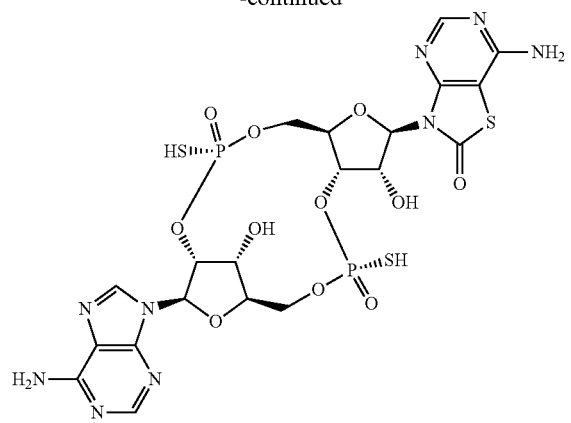
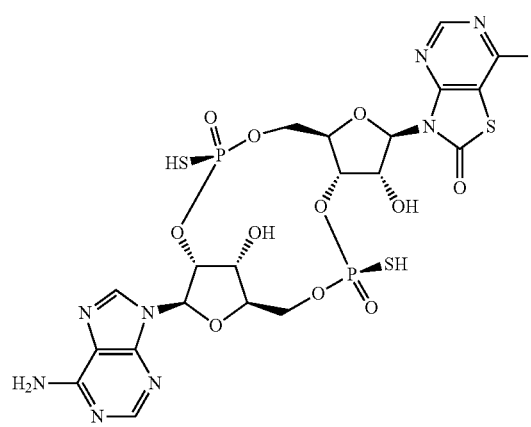
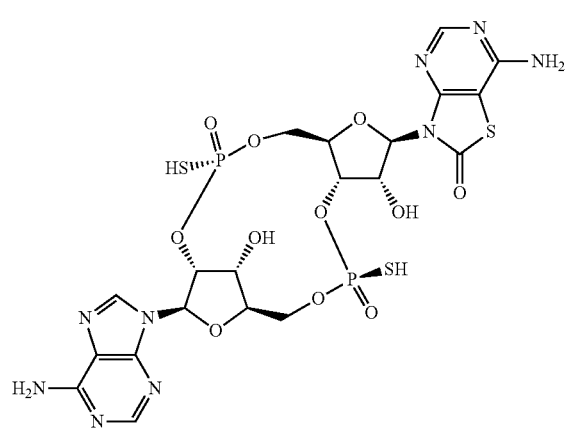
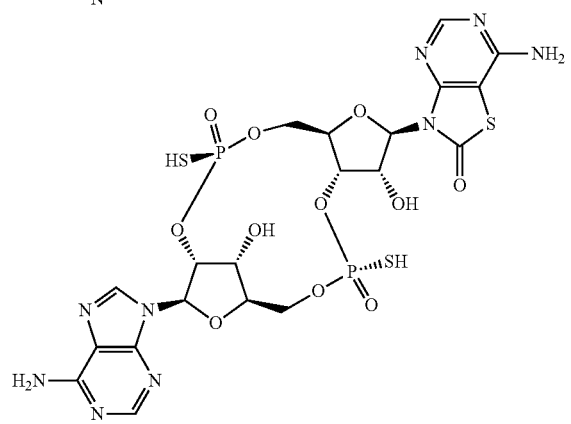
72
-continued
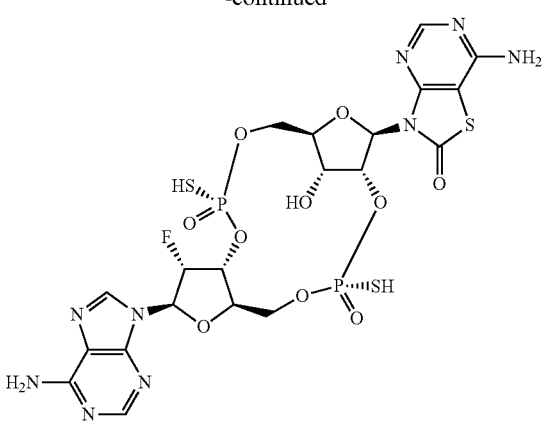
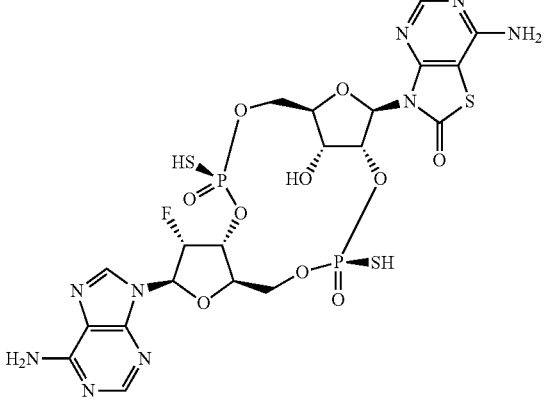
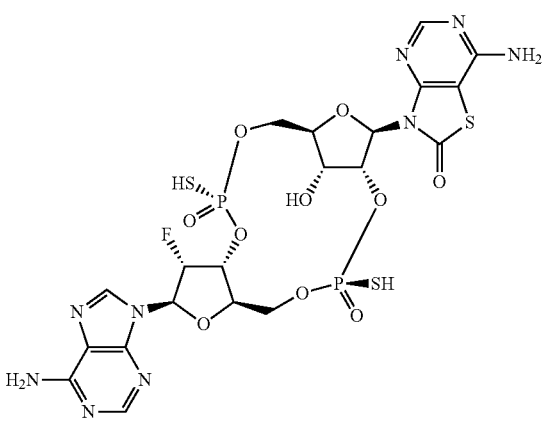
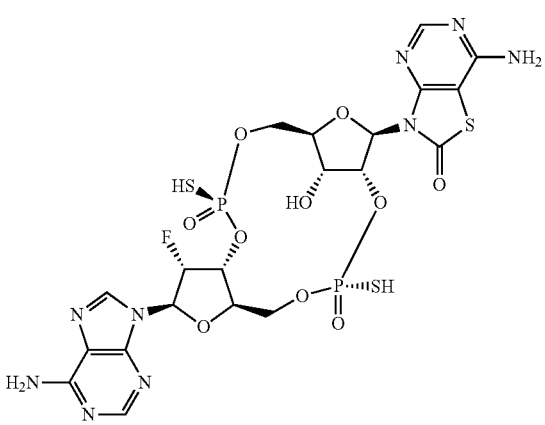

73
-continued
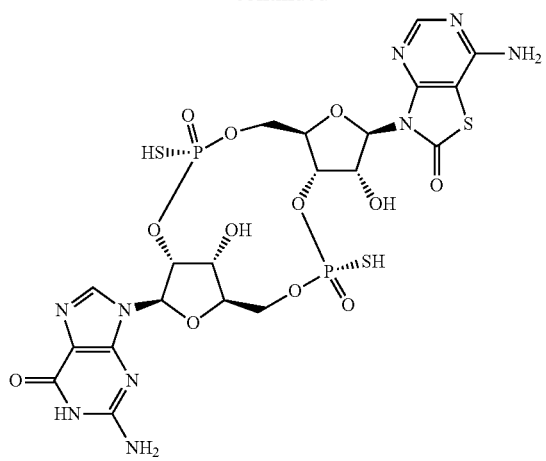
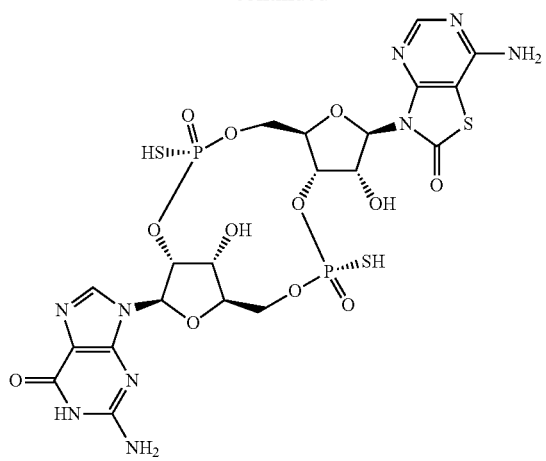
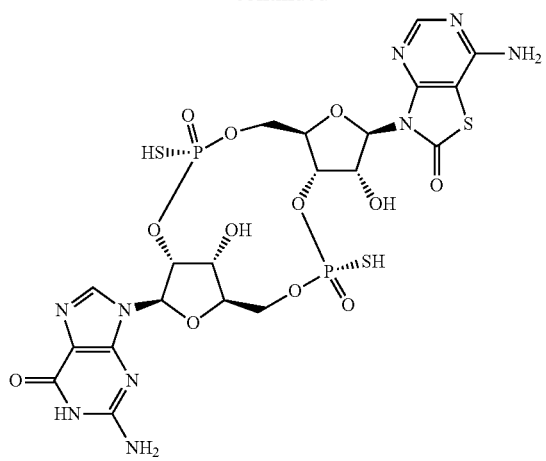
74
-continued
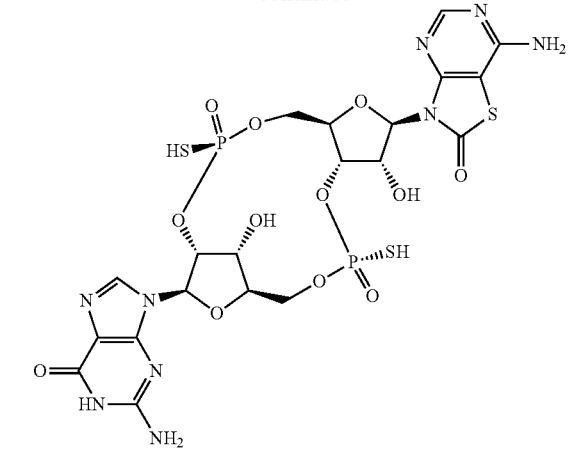
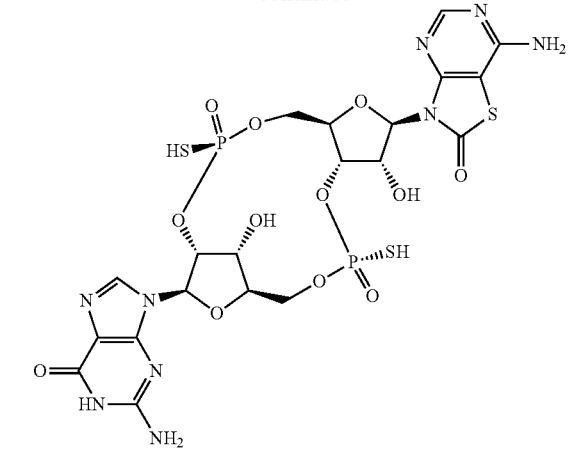
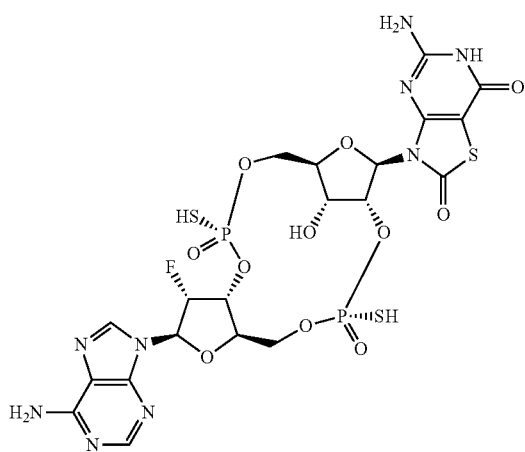

75
-continued
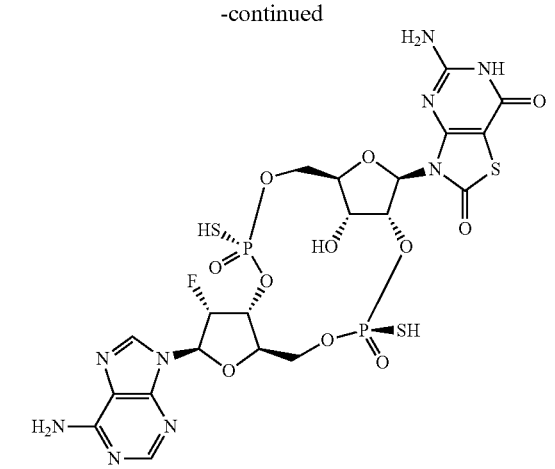
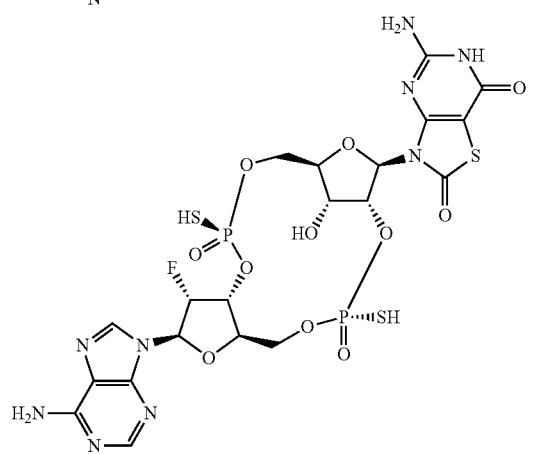
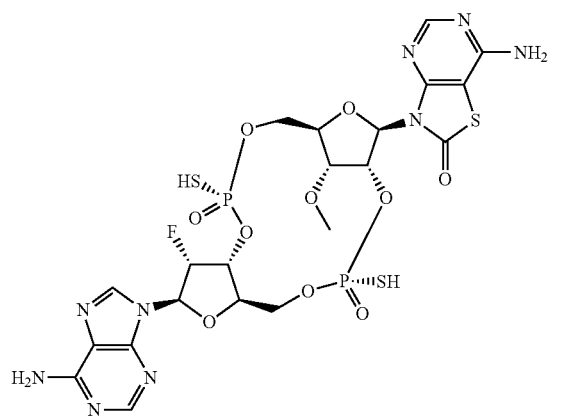
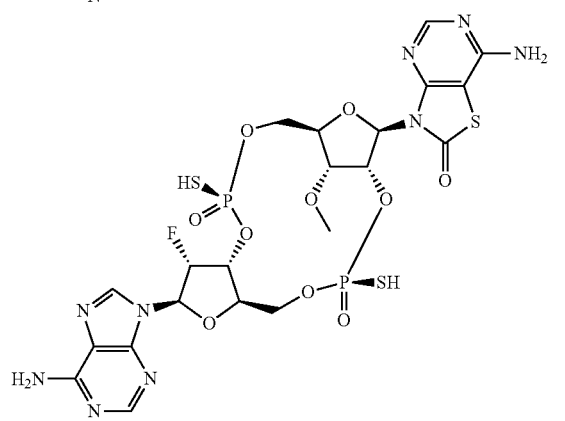
76
-continued
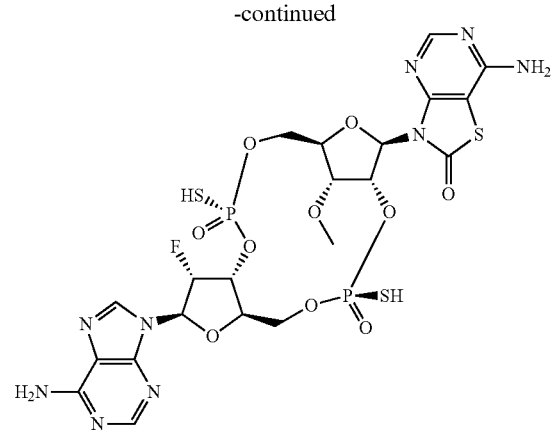
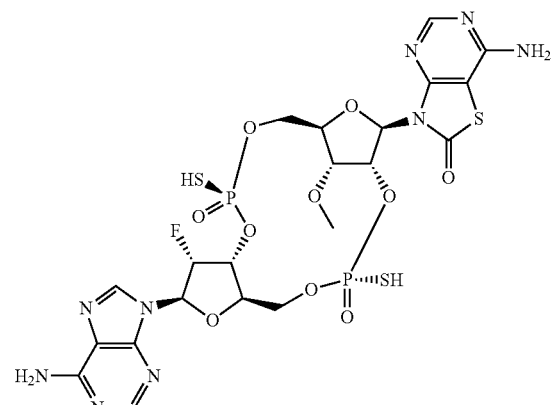
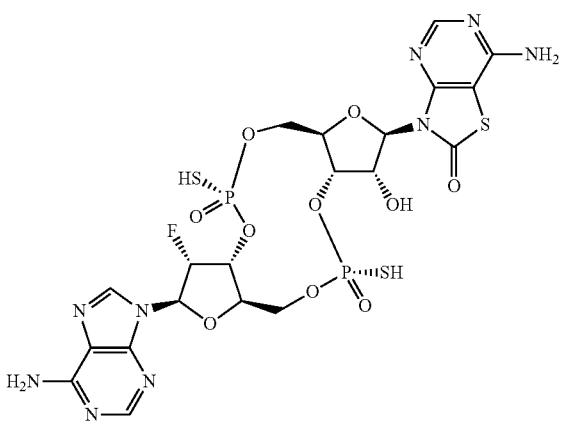
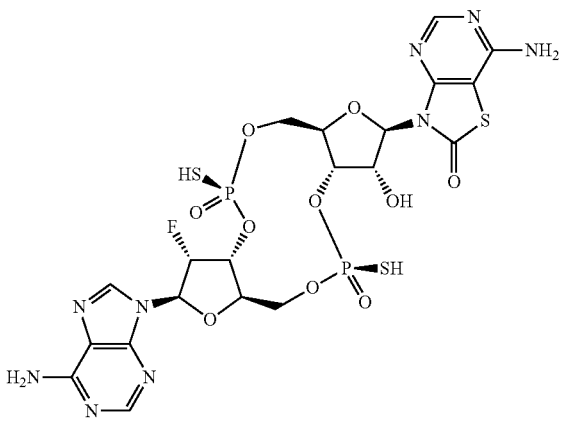

77
-continued
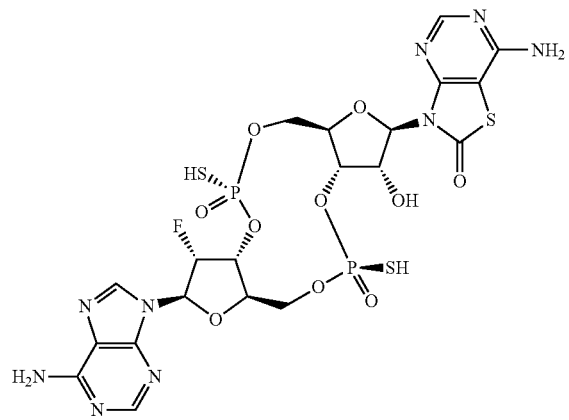
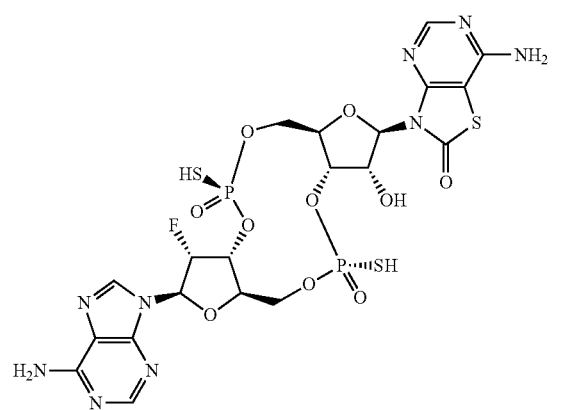
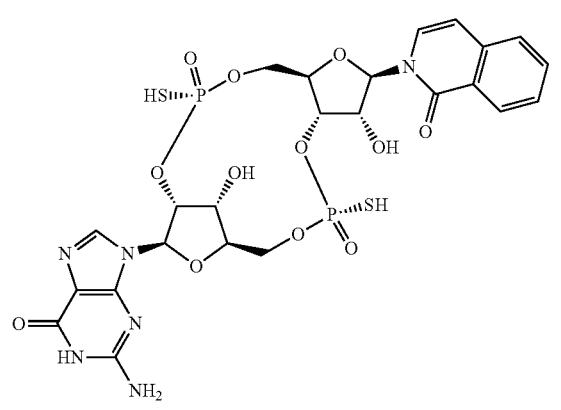
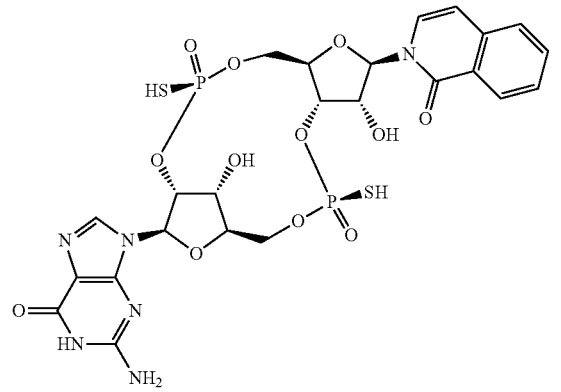
78
-continued
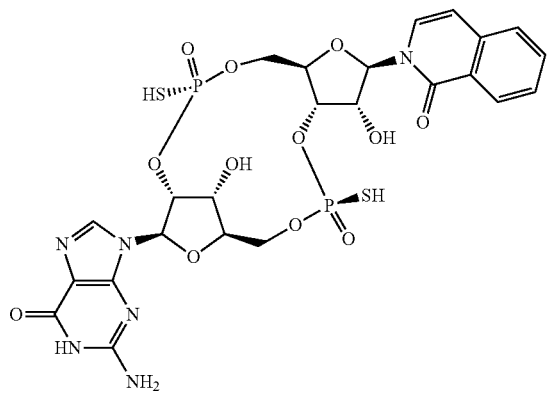
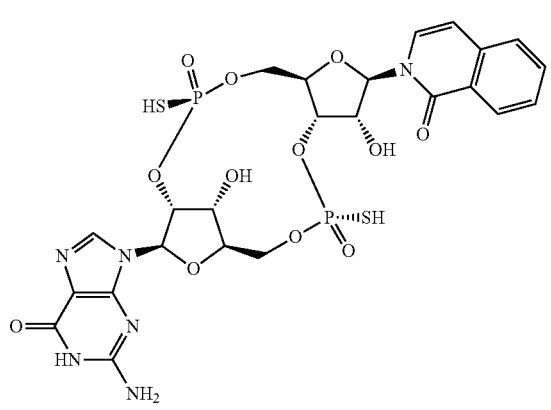
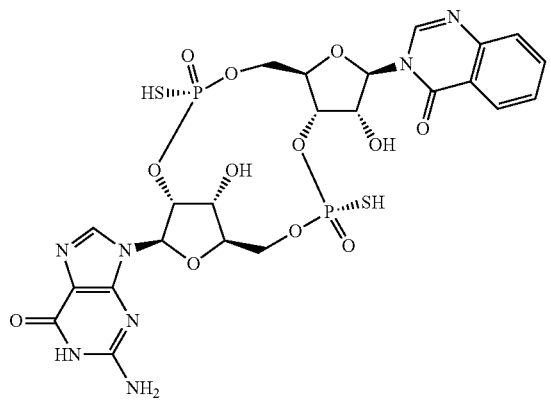
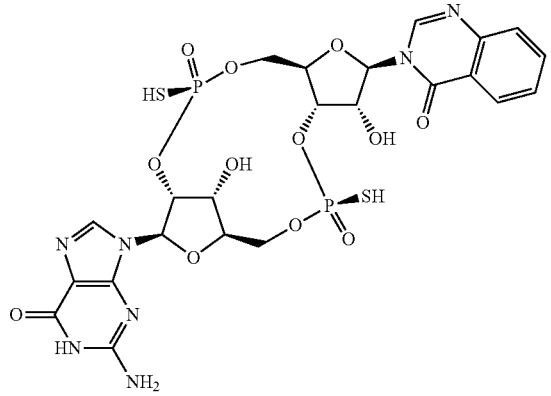

-continued
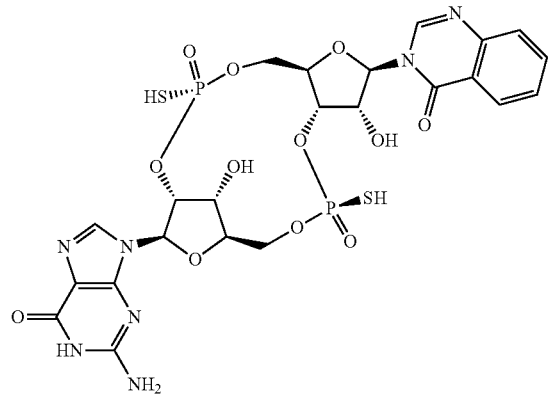
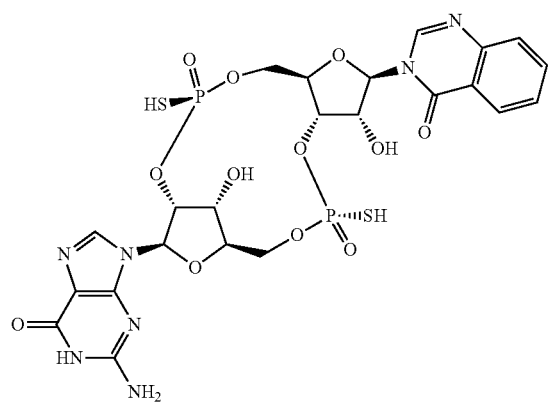
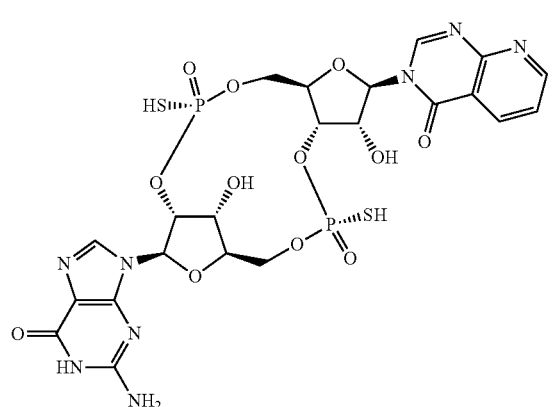
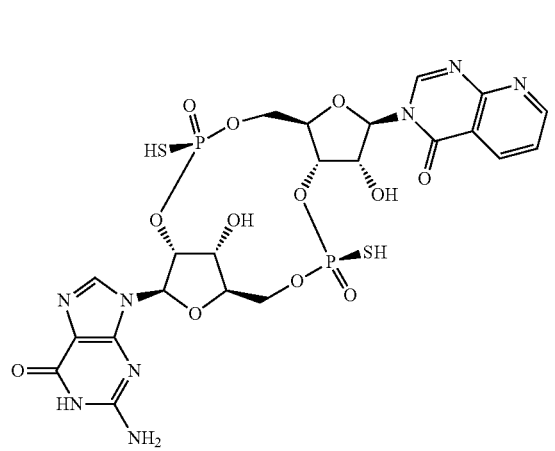
-continued
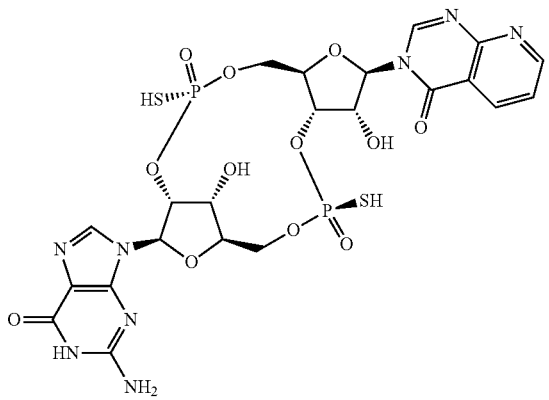
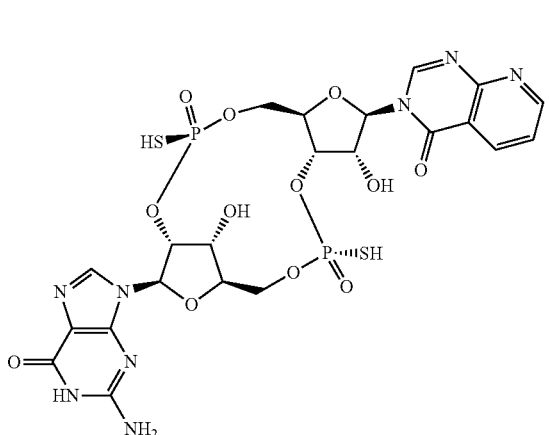
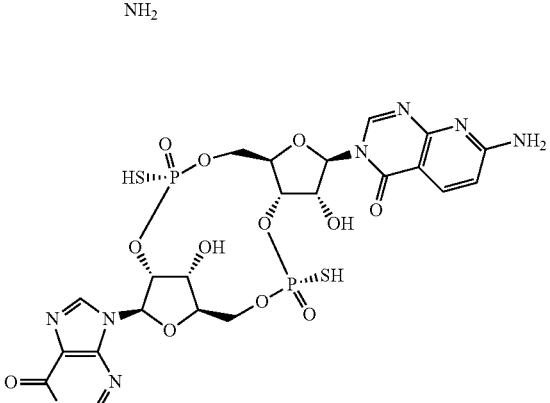
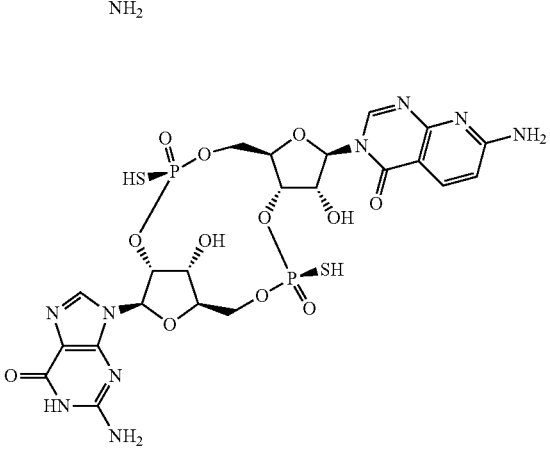

81
-continued
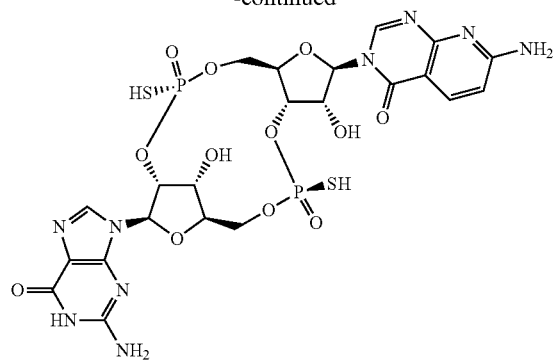
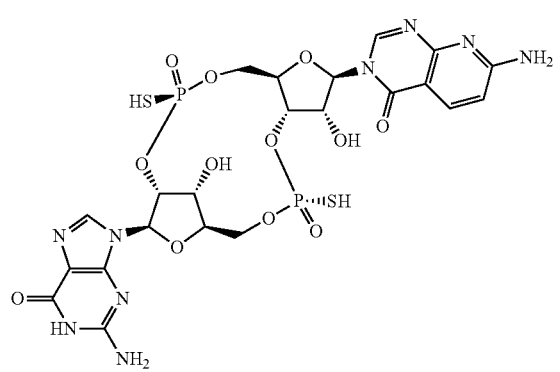
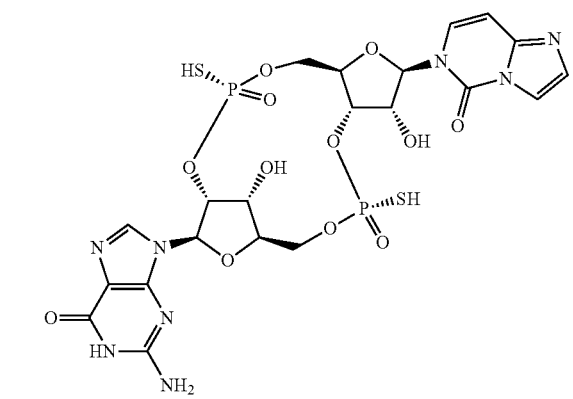
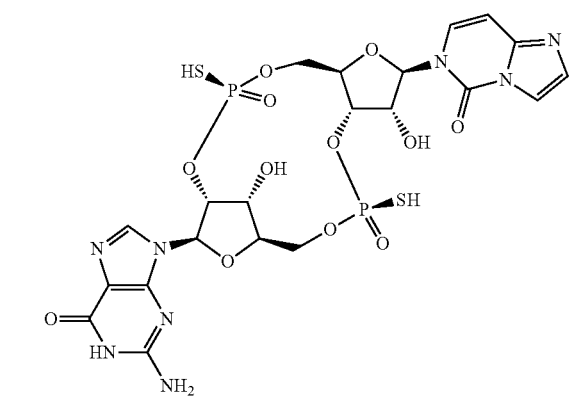
82
-continued
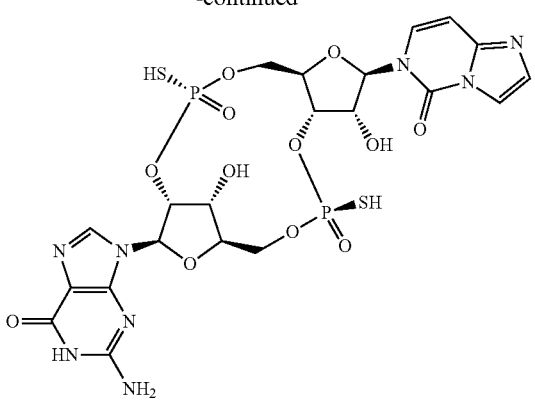
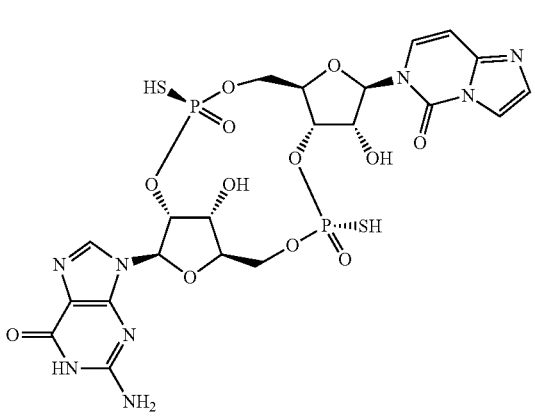
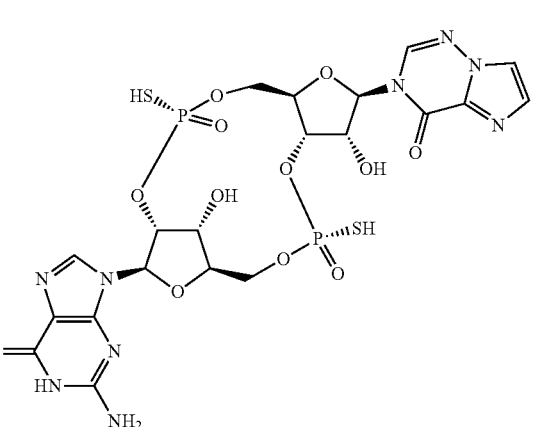
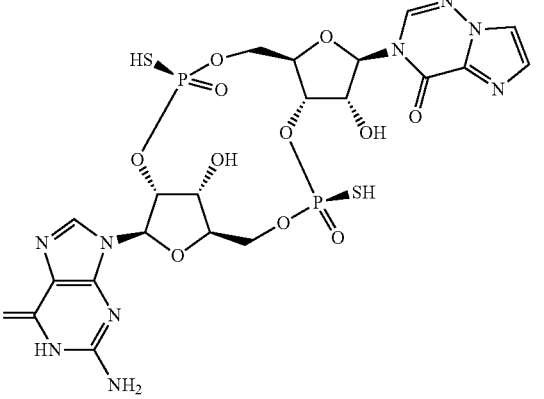

-continued

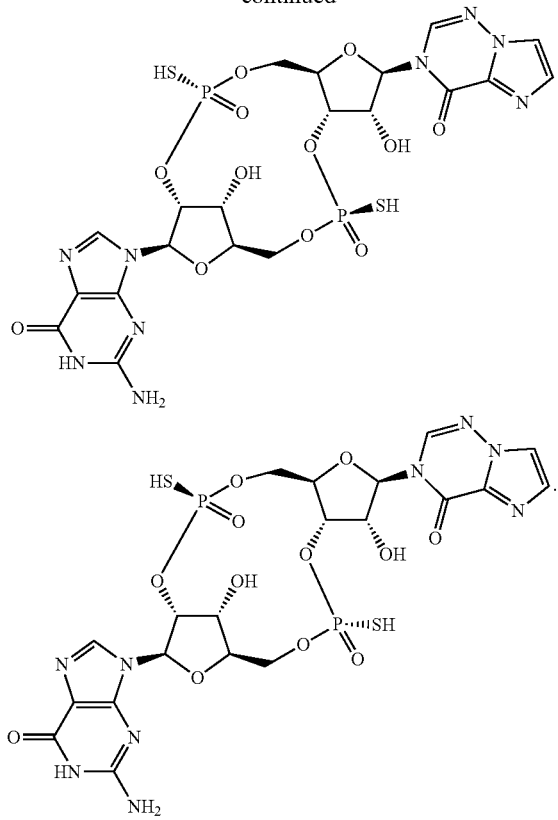

The compound of formula (I), the pharmaceutically acceptable salt thereof can be synthesized by a general chemical method.

In general, the preparation of the salt can be carried out by reacting the free base or acid with an equivalent chemical equivalent or an excess of an acid (inorganic or organic acid) or a base (inorganic or organic base) in a suitable solvent or solvent composition.

The present disclosure also provides a pharmaceutical composition comprising a therapeutically effective amount of an active component and a pharmaceutically acceptable excipient; the active component comprises one or more of the cyclic di-nucleotide analogue (I), the isomer thereof, prodrug, stable isotope derivative and pharmaceutically acceptable salt thereof.

The active component in the pharmaceutical composition can also include other therapeutic agents for viral infections or other infectious diseases (e.g., HIV, HBV, HCV infection, etc.), autoimmune diseases (e.g., rheumatoid arthritis, lupus erythematosus, psoriasis, etc.) or malignancies.

In the pharmaceutical composition, the pharmaceutically acceptable excipient can include a pharmaceutically acceptable carrier, diluent, and/or excipient.

According to the purpose of the treatment, the pharmaceutical composition can be formulated into various types of unit dosage forms, such as tablets, pills, powders, liquids, suspensions, emulsions, granules, capsules, suppositories, and injections (solutions and suspensions) and the like, and preferably liquids, suspensions, emulsions, suppositories and injections (solutions and suspensions), etc.

In order to shape the pharmaceutical composition in the form of a tablet, any excipient known and widely used in the art can be used. For example, carriers such as lactose, white sugar, sodium chloride, glucose, urea, starch, calcium carbonate, kaolin, crystalline cellulose, and silicic acid; binders such as water, ethanol, propanol, common syrup, dextrose solution, starch solution, gelatin solution, carboxymethyl cellulose, shellac, methyl cellulose and potassium phosphate, polyvinylpyrrolidone, etc.; disintegrating agents, such as dry starch, sodium alginate, agar powder, kelp powder, sodium bicarbonate, calcium carbonate, fatty acid esters of polyethylene dehydrated sorbitol, sodium dodecyl sulfate, monoglyceryl stearate, starch and lactose; disintegration inhibitors such as white sugar, glyceryl tristearate, coconut oil and hydrogenated oil; adsorption promoters such as quaternary ammonium bases and sodium dodecyl sulfate; wetting agents such as glycerin, starch, etc.; adsorbents such as starch, lactose, kaolin, bentonite and colloidal silicic acid; and lubricating agents such as pure talc, stearate, boric acid powder and polyethylene glycol. It is also possible to use a usual coating material to formulate a sugar-coated tablet, a gelatin film tablet, a casing tablet, a film-coated tablet, a two-layer film tablet, and a multilayer tablet.

In order to shape the pharmaceutical composition in the form of a pill, any excipient known and widely used in the art may be used, for example, carriers such as lactose, starch, coconut oil, hardened vegetable oil, kaolin and talc, etc.; binders such as gum arabic powder, tragacanth powder, gelatin and ethanol, etc.; disintegrating agents such as agar and kelp powder.

In order to shape the pharmaceutical composition in the form of a suppository, any excipient known and widely used in the art can be used, for example, polyethylene glycol, coconut oil, higher alcohols, esters of higher alcohols, gelatin and semi-synthetic glycerides, etc.

For the preparation of a pharmaceutical composition in the form of an injection, the solution or suspension may be sterilized (preferably by adding an appropriate amount of sodium chloride, glucose or glycerin, etc.) to prepare an injection which is isotonic with blood. Any of the commonly used carriers in the art can also be used. For example, water, ethanol, propylene glycol, ethoxylated isostearyl alcohol, polyoxylated isostearyl alcohol, and fatty acid esters of polyethylene dehydrated sorbitol. In addition, usual solubilizers, buffers, analgesics can be added.

In the present disclosure, the content of the composition in the pharmaceutical composition is not particularly limited and can be selected in a wide range, usually 5-95% by mass, preferably 30-80% by mass.

In the present disclosure, the administration method of the pharmaceutical composition is not particularly limited. Formulations of various dosage forms can be selected depending on the age, sex and other conditions and symptoms of the patient. For example, tablets, pills, solutions, suspensions, emulsions, granules or capsules are administered orally; injections can be administered alone or in combination with solutions for injection (e.g., glucose solution and amino acid solution); suppositories are given to the rectum.

The present disclosure also provides a use of the cyclic di-nucleotide analogue (I), the isomer thereof, prodrug, stable isotope derivative or pharmaceutically acceptable salt, or the pharmaceutical composition in the preparation of interferon gene stimulating factor STING modulators. The interferon gene stimulating factor STING modulator is preferably interferon gene stimulating factor STING agonist. The STING agonist refers to the compound of formula (I), the isomer, prodrug, stable isotope derivative or pharmaceutically acceptable salt thereof, or the pharmaceutical composition capable of activating STING signaling.

The present disclosure also provides a use of the cyclic di-nucleotide analogue (I), the isomer thereof, prodrug, stable isotope derivative or pharmaceutically acceptable salt, or the pharmaceutical composition in the preparation of a medicament for modulation of the proliferation of T cells or other immune cells.

The present disclosure also provide a use of the cyclic di-nucleotide analogue (I), the isomer thereof, prodrug, stable isotope derivative or pharmaceutically acceptable salt, or the pharmaceutical composition in the preparation of a vaccine adjuvant.

The present disclosure also provide a use of the cyclic di-nucleotide analogue (I), the isomer thereof, prodrug, stable isotope derivative or pharmaceutically acceptable salt, or the pharmaceutical composition in the preparation of a medicament for the treatment and/or alleviation of a STING-mediated neoplastic disease and non-neoplastic disease. The STING-mediated diseases refer to diseases caused by immunosuppression or hyperactivation due to STING signaling. The types of related diseases include, but are not limited to: viral infections or other infectious diseases, autoimmune diseases, and malignancies.

The present disclosure preferably provides a use of the cyclic di-nucleotide analogue (I), the isomer thereof, prodrug, stable isotope derivative or pharmaceutically acceptable salt, or the pharmaceutical composition in the preparation of a medicament for the treatment and/or alleviation of malignancies caused by immunosuppression.

The present disclosure further provides a method of treating viral infections or other infectious diseases, malignancies, autoimmune diseases with the cyclic di-nucleotide analogue (I), the isomer thereof, prodrug, stable isotope derivative or pharmaceutically acceptable salt, or the pharmaceutical composition, comprising: administering to a mammal a required dose of the cyclic di-nucleotide analogue (I), the isomer thereof, prodrug, stable isotope derivative or pharmaceutically acceptable salt, or the pharmaceutical composition.

The mammal is preferably human.

The present disclosure preferably provides the compound represented by formula (I), the isomer thereof, prodrug, stable isotope derivative or pharmaceutically acceptable salt, or the pharmaceutical composition in the preparation of a medicament for the treatment and/or alleviation of a STING-mediated disease; the STING-mediated disease is those caused by STING mediated immunosuppression, the diseases can include: viral infections or other infectious diseases (e.g., HIV, HBV, HCV infection, etc.), autoimmune diseases (e.g., rheumatoid arthritis, lupus erythematosus, psoriasis, etc.), or malignancies.

The present disclosure further provides a use of the compound represented by formula (I), the isomer thereof, prodrug, stable isotope derivative or pharmaceutically acceptable salt, or the pharmaceutical composition in the preparation of a medicament for the treatment and/or alleviation of malignancies.

The present disclosure further provides a use of the compound represented by formula (I), the isomer thereof, prodrug, stable isotope derivative or pharmaceutically acceptable salt, or the pharmaceutical composition in the preparation of a medicament for the treatment and/or alleviation of viral or other infections.

The present disclosure further provides a use of the compound represented by formula (I), the isomer thereof, prodrug, stable isotope derivative or pharmaceutically acceptable salt, or the pharmaceutical composition in the preparation of a medicament for the treatment and/or alleviation of autoimmune diseases.

The present disclosure further provides the cyclic di-nucleotide analogue (I), the isomer thereof, prodrug, stable isotope derivative or pharmaceutically acceptable salt, or the pharmaceutical composition in combination with one or more other kinds of therapeutic agents and/or therapeutic methods for use in the treatment, alleviation and/or prevention of STING-mediated diseases. The STING-mediated diseases are those caused by STING-mediated immunosuppression, and the diseases can include: viral or other infections (e.g., HIV, HBV, HCV infections, etc.), autoimmune diseases (e.g., rheumatoid arthritis, lupus erythematosus, psoriasis, etc.), or cancer.

The present disclosure preferably provides the cyclic di-nucleotide analogue (I), the isomer thereof, prodrug, stable isotope derivative or pharmaceutically acceptable salt, or the pharmaceutical composition in combination with one or more other kinds of therapeutic agents and/or therapeutic methods for use in the treatment and/or alleviation of cancer.

The present disclosure preferably provides the cyclic di-nucleotide analogue (I), the isomer thereof, prodrug, stable isotope derivative or pharmaceutically acceptable salt, or the pharmaceutical composition in combination with one or more other kinds of therapeutic agents and/or therapeutic methods for use in the treatment and/or alleviation of STING-mediated cancer.

In the present disclosure, the other kinds of therapeutic agents (e.g., other kinds of therapeutic agents for the treatment of cancer) can be made into a therapeutic dosage form with the cyclic di-nucleotide analogue (I) for a single dosage form, or separate therapeutic dosage forms for sequential administration.

The present disclosure further provides a combination formulation comprising the compound of formula (I), the isomer thereof, prodrug, stable isotope derivative or pharmaceutically acceptable salt, or the pharmaceutical composition and other kinds of therapeutic agents and/or therapeutic methods for the treatment of cancer.

In the present disclosure, the other kinds of therapeutic agents for the treatment of cancer can include, but are not limited to one or more of: microtubule protein inhibitors, alkylating agents, topozyme I/II inhibitors, platinum compounds, antimetabolites, hormones and hormone analogs, signal transduction pathway inhibitors, angiogenesis inhibitors, targeted therapeutic agents (e.g., specific kinase inhibitors), immunotherapeutic agents, pro-apoptotic agents, and cell cycle signaling pathway inhibitors.

In the present disclosure, the other kinds of therapeutic methods for the treatment of cancer can include, but are not limited to, one or more of: tumor immunotherapy and radiotherapy.

In the present disclosure, the other kinds of therapeutic agents for the treatment of cancer are preferably immunotherapeutic agents.

In the present disclosure, the microtubulin inhibitor may be selected from, but is not limited to, one or more of: the vincristine family (e.g., vinblastine, vincristine, vinorelbine, vindesine sulfate), the taxane family (docetaxel, paclitaxel), and eribulin mesylate.

In the present disclosure, the alkylating agent may be selected from, but is not limited to: nitrogen mustard, N-oxo-nitrogen mustard hydrochloride, cyclobutoic nitrogen mustard, uracil mustard, cyclophosphamide, ifosfamide, thiotepa, carboquone, trisethyleneiminoquinone, improsulfan tosylate, mannosesufan, treosulfan, busulfan, nimustine hydrochloride, dibromomannitol, melphalan, dacarbazine, ranimustine, carmustine, lomustine, streptozotocin, temozolomide, procarbazine, ethyleneimine derivatives, methanesulfonates, nitrosoureas, triazenes.

In the present disclosure, the topozyme I/II inhibitors may be selected from, but not limited to, one or more of doxorubicin, daunorubicin, epirubicin, idarubicin, irinotecan, topotecan, rubitecan, belotecan, etoposide, teniposide, adriamycin, and dexrazoxane, camptothecin.

In the present disclosure, the platinum compound may be selected from, but not limited to, one or more of: cisplatin, carboplatin, oxaliplatin, and nedaplatin.

In the present disclosure, the antimetabolites may be selected from, but not limited to, one or more of: folate antagonists, pyrimidine analogs, purine analogs, adenosine deaminase inhibitors, such as: methotrexate, 5-fluorouracil, floxuridine, cytarabine, 6-mercaptopurine, 6-thioguanine, fludarabine phosphate, pentostatin, and gemcitabine.

In the present disclosure, the immunotherapeutic agent may be selected from, but not limited to one or more of: immunomodulators, tumor microenvironment modulators, and anti-angiogenic factors. The immunomodulators may include, but are not limited to: 1) protein antagonists (e.g., immune checkpoint inhibitors) that inhibit T-cell activity: one or more of CTLA4 (e.g., one or more of ipilimumab, tremelimumab, abatacept, belatacept, BMS-986249, BMS-986218, AGEN-1884 and KN-046), PD-1 (e.g., one or more of camrelizumab, toripalimab, sintilimab, cemiplimab, pembrolizumab, nivolumab, tislelizumab, spartalizumab, dostarlimab, genolimzumab, cetrelimab, HLX-10, BCD-100, AK-105, MEDI-0680, CS-1003, BAT-1306, HX-008, sasanlimab, AGEN-2034, BI-754091, GLS-010, MGA-012, AK-104 and AK-103), PD-L1 (e.g., one or more of durvalumab, avelumab, atezolizumab, envafolimab, cosibelimab, CS1001, SHR-1316, lazertinib, bintrafusp alfa, TQB-2450, CA-170, CX-072, BGB-A333, BMS-936559, GEN-1046, KL-A167 and IO-103), LAG3, and TIM3; 2) protein agonists that stimulate T-cell activity: one or more of GITR, OX40, OX40L, 4-1BB (CD137), CD27 and CD40; 3) one or more of TLR2 agonists, TLR4 agonists, TLR5 agonists, TLR7 agonists, TLR8 agonists and TLR9 agonists; (4) IDO inhibitors, CD73 inhibitors.

In the present disclosure, the signal transduction pathway inhibitors (STI) may be selected from, but not limited to, one or more of: BCR/ABL kinase inhibitors, epidermal growth factor receptor inhibitors, her-2/neu receptor inhibitors, AKT family kinase inhibitors, PI3K signaling pathway inhibitors, and cell cycle checkpoint inhibitors.

In the present disclosure, the angiogenesis inhibitors may be selected from, but not limited to, one or more of: VEGF/VEGFR signaling pathway inhibitors, Src family kinase inhibitors, Src signaling pathway inhibitors, and c-Fes kinase inhibitors.

In the present disclosure, the targeted therapeutic agents may be selected from, but not limited to: one or more of erlotinib, imatinib, apatinib, nilotinib, crizotinib, dasatinib, pazopanib, regorafenib, ruxolitinib, sorafenib, sunitinib, vandetanib, vemurafenib, bosutinib, gefitinib, afatinib, axitinib, dabrafenib, dacomitinib, nintedanib, levatinib, masitinib, midostaurin, neratinib, ponatinib, radotinib, trametinib, brivanib alaninate, cediranib, cabozantinib malate, ibrutinib, icotinib, lapatinib, cobimetinib, idelalisib, ponatinib, alisertib, dinaciclib, linsitinib, orantinib, rigosertib, tipifarnib, tivozanib, pimasertib, buparlisib, and fedratinib.

In the present disclosure, the tumor immunotherapy may be selected from, but not limited to, one or more of: antitumor vaccines (e.g., synthetic peptides, DNA vaccines, and recombinant viruses), oncolytic viruses, cytokine therapies (e.g., TL2 and GM-CSF), and chimeric antigen receptor T-cell therapies (CAR-T).

In the present disclosure, the viral and other infections may include: the infections caused by viruses such as influenza viruses, hepatitis B virus (HBV), hepatitis C virus (HCV), human papillomavirus (HPV), cytomegalovirus (CMV), Epstein-Barr virus (EBV), poliovirus, varicella-zoster virus, coxsackievirus, or human immunodeficiency virus (HIV).

In the present disclosure, the malignant tumors include metastatic and non-metastatic cancers, also include familial hereditary and sporadic cancers, and may also include solid and non-solid tumors.

In the present disclosure, specific examples of the solid tumors may include, but not limited to: eye, bone, lung, stomach, pancreas, breast, prostate, brain (including glioblastoma and medulloblastoma), ovary (including those stromal cells, germ cells and mesenchymal cells arising from epithelial cells), bladder, testis, spinal cord, kidney (including adenocarcinoma, nephroblastoma), mouth, lip, throat, oral cavity (including squamous cell carcinoma), nasal cavity, small intestine, colon, rectum, parathyroid gland, gallbladder, bile duct, cervix, heart, subpharyngeal gland, bronchus, liver, ureter, vagina, anus, laryngeal gland, thyroid gland (including thyroid cancer and medullary carcinoma), esophagus, nasopharyngeal gland pituitary, salivary gland, adrenal gland, intraepithelial neoplasia of head and neck (including Bowen's disease and Paget's disease), sarcoma (including smooth muscle sarcoma, rhabdomyosarcoma, liposarcoma, fibrosarcoma, osteosarcoma), skin (including melanoma, Kaposi's sarcoma, basocellular carcinoma and squamous cell carcinoma) and other related tumors.

In the present disclosure, the solid tumor is preferably one or more of eye cancer, bone cancer, lung cancer, stomach cancer, pancreatic cancer, breast cancer, prostate cancer, brain cancer (including but not limited to glioblastoma, adult neural tube cell tumor), ovarian cancer, bladder cancer, cervical cancer, testicular cancer, kidney cancer (including but not limited to adenocarcinoma, nephroblastoma), oral cancer (including squamous cell carcinoma), tongue cancer, laryngeal cancer, nasopharyngeal cancer, head and neck cancer, colon cancer, small intestine cancer, rectal cancer, parathyroid cancer, thyroid cancer, esophageal cancer, gallbladder cancer, bile duct cancer, cervical cancer, liver cancer, lung cancer (including but not limited to small cell lung cancer, non-small cell lung cancer), chorionic epithelioma, osteosarcoma, ewing tumor, soft tissue sarcoma and skin cancer.

In the present disclosure, specific examples of the non-solid tumors (including hematological tumors) may include, but not limited to: lymphoid leukemia (including acute lymphoblastic leukemia, lymphoma, myeloma, chronic lymphocytic leukemia, Hodgkin's lymphoma, non-Hodgkin's lymphoma, T-cell chronic lymphatic leukemia, B-cell chronic lymphatic leukemia), myeloid-associated leukemia (including acute myeloid leukemia, chronic myeloid leukemia) and AIDs-associated leukemia.

In the present disclosure, the autoimmune diseases may include, but not limited to: one or more of rheumatoid arthritis, systemic lupus erythematosus, mixed connective tissue disease (MCTD), systemic scleroderma (including: CREST syndrome), dermatomyositis, nodular vasculitis, renal diseases (including: pulmonary hemorrhagic nephritis syndrome, acute glomerulonephritis, primary membrano-proliferative glomerulonephritis, etc.), endocrine-related diseases (including: type I diabetes, gonadal insufficiency, pernicious anemia, hyperthyroidism, etc.), liver disease (including: primary biliary cirrhosis, autoimmune cholangitis, autoimmune hepatitis, primary sclerosing cholangitis, etc.) and autoimmune reactions caused by infections (e.g., AIDS, malaria, etc.).

Unless otherwise stated, the following terms appearing in the specification and claims of the disclosure have the following meanings:

The term "alkyl" refers to a saturated straight or branched-chain hydrocarbon group comprising 1 to 20 carbon atoms, preferably 1 to 10 carbon atoms, more preferably 1 to 8, 1 to 6, 1 to 4, 1 to 3 carbon atoms, representative examples of alkyl groups include, but are not limited to: methyl, ethyl, n-propyl, isopropyl, n-butyl, sec-butyl, tert-butyl, isobutyl, n-pentyl, n-hexyl, n-heptyl, octyl, nonyl, decyl, 1,1-dimethylpropyl, 1,2-dimethylpropyl, 2,2-dimethylpropyl, 1-ethylpropyl, 2-methylbutyl, 3-methylbutyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2,3-dimethylbutyl, 2-ethylbutyl, 2-methylpentyl, 3-methylpentyl, 4-methylpentyl, 4,4-dimethylpentyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, 2,2,4-trimethylpentyl, undecyl, dodecyl, and their various isomers, etc.

The term "cycloalkyl" refers to a saturated or partially unsaturated (containing 1 or 2 double bonds) monocyclic or polycyclic group containing 3 to 20 carbon atoms. The term "monocyclic cycloalkyl" is preferably a 3 to 10 membered monocyclic alkyl, more preferably a 3 to 8 membered monocyclic alkyl, such as: cyclopropyl, cyclobutyl, cyclopentyl, cyclohexyl, cycloheptyl, cyclooctyl, cyclodecyl, cyclohexenyl. The term "polycyclic cycloalkyl" includes "bridged cycloalkyl", "fused cycloalkyl" and "spiro cycloalkyl". Monocyclic cycloalkyl or polycyclic cycloalkyl can be linked to the parent molecule by any carbon atom on the ring.

The term "heterocycloalkyl" refers to a saturated or partially unsaturated (containing 1 or 2 double bonds) non-aromatic cyclic group consisting of carbon atom(s) and heteroatom(s) selected from nitrogen, oxygen or sulfur, which may be monocyclic or polycyclic, in the present disclosure the number of heteroatom(s) in the heterocycloalkyl group is preferably 1, 2, 3 or 4, the nitrogen, carbon or sulfur atom in the heterocycloalkyl group may optionally be oxidized.

The nitrogen atom may optionally be further substituted with other groups to form tertiary amines or quaternary ammonium salts. The "monocyclic heterocycloalkyl" is preferably a 3 to 10 membered monocyclic heterocycloalkyl, more preferably a 3 to 8 membered monocyclic heterocycloalkyl. For example: aziridinyl, tetrahydrofuran-2-yl, morpholin-4-yl, thiomorpholin-4-yl, thiomorpholine-S-oxide-4-yl, piperidin-1-yl, N-alkylpiperidin-4-yl, pyrrolidin-1-yl, N-alkylpyrrolidin-2-yl, piperazin-1-yl, 4-alkylpiperazin-1-yl, etc. "Polycyclic heterocycloalkyl" includes "fused heterocycloalkyl", "spiro heterocycloalkyl" and "bridged heterocycloalkyl". Monocyclic heterocycloalkyl and polycyclic heterocycloalkyl can be linked to the parent molecule by any ring atom on the ring. The above ring atoms refer specifically to the carbon and/or nitrogen atoms that constitute the ring skeleton.

The term "cycloalkyl alkyl" refers to a cycloalkyl group connected to the parent nucleus structure through an alkyl group. Thus, the term "cycloalkyl alkyl" encompasses the above definitions of alkyl and cycloalkyl.

The term "heterocycloalkyl alkyl" refers to a heterocycloalkyl group connected to the parent nucleus structure through an alkyl group. Thus, the term "heterocycloalkyl" encompasses the above definitions of alkyl and heterocycloalkyl.

The term "alkoxy" refers to a cyclic or non-cyclic alkyl group having indicated carbon atoms attached through an oxygen bridge, and includes alkyloxy, cycloalkyloxy and heterocycloalkyloxy. Thus, "alkoxy" includes the above definitions of alkyl, heterocycloalkyl, and cycloalkyl.

The term "alkenyl" refers to a straight, branched or cyclic non-aromatic hydrocarbon group containing at least 1 carbon-carbon double bond. There may be 1 to 3 carbon-carbon double bonds present, preferably 1 carbon-carbon double bond present. The term "$C_{2-4}$ alkenyl" refers to an alkenyl group having 2 to 4 carbon atoms, and the term "$C_{2-6}$ alkenyl" refers to an alkenyl group having 2 to 6 carbon atoms, including vinyl, propylenyl, butenyl, 2-methylbutenyl, and cyclohexenyl. The alkenyl groups can be substituted.

The term "alkynyl" refers to a straight, branched or cyclic hydrocarbon group containing at least 1 carbon-carbon triple bond. There may be 1 to 3 carbon-carbon triple bonds present, preferably 1 carbon-carbon triple bond present. The term "$C_{2-6}$ alkynyl" refers to an alkynyl group having 2 to 6 carbon atoms, including ethynyl, propinyl, butynyl and 3-methylbutynyl.

The term "aryl" refers to any stable 6 to 10 monocyclic or bicyclic aromatic group, such as: phenyl, naphthyl, tetrahydronaphthyl, 2,3-dihydroindenyl, or biphenyl.

The term "heteroaryl" refers to an aromatic cyclic group formed by replacing at least 1 carbon atom on the ring by a heteroatom selected from nitrogen, oxygen or sulfur, which may be a 5 to 7 membered monocyclic structure or a 7 to 12 membered bicyclic structure, preferably 5 to 6 membered heteroaryl. In the present disclosure, the number of the heteroatom is preferably 1, 2 or 3, and includes: pyridyl, pyrimidinyl, pyridazin-3 (2H)-one group, furanyl, thienyl, thiazolyl, pyrrolyl, imidazolyl, pyrazolyl, oxazolyl, isoxazolyl, 1,2,5-oxadiazolyl, 1,2,4-oxadiazolyl, 1,2,4-triazolyl, 1,2,3-triazolyl, tetrazolyl, indazolyl, isoindazolyl, indolyl, isoindolyl, benzofuranyl, benzothienyl, benzo[d][1,3]dioxolyl, benzothiazolyl, benzoxazolyl, quinolinyl, isoquinolinyl, quinazolinyl, etc.

The term "arylalkyl" refers to an aryl group connected to the parent nucleus structure through an alkyl group. Thus, the term "arylalkyl" encompasses the above definitions of the alkyl and aryl.

The term "heteroaryl-alkyl" refers to a heterocycloalkyl group connected to the parent nucleus structure through an alkyl group. Thus, the term "heteroarylalkyl" encompasses the above definitions of the alkyl and heteroaryl.

The term "halogen" indicates fluorine, chlorine, bromine or iodine.

The term "halo-alkyl" refers to an alkyl group arbitrarily substituted with halogen.

Thus, "halo-alkyl" includes the definitions of the halogen and alkyl above.

The term "halo-alkoxy" refers to an alkoxy group arbitrarily substituted with halogen.

Thus, the term "halo-alkoxy" encompasses the above definitions of the halogen and alkoxy.

The term "amino" refers to —NH$_2$ and the term "alkylamino" refers to that at least one hydrogen atom on the amino group is the substituted by an alkyl group, including but not limited to: —NHCH$_3$, —N(CH$_3$)$_2$, —NHCH$_2$CH$_3$, —N(CH$_2$CH$_3$)$_2$.

The term "nitro" refers to —NO$_2$.

The term "cyano" refers to —CN.

The term "azido" refers to —N$_3$.

The term "room temperature" in the present disclosure refers to 15-30° C.

The isotope-substituted derivative includes an isotope-substituted derivative that any hydrogen atom of the compound of formula (I) is replaced by 1 to 5 deuterium atoms, or any carbon atom of the compound of formula (I) is replaced by 1-3 C$^{14}$ atom, or any oxygen atom of the compound of formula I is replaced by 1 to 3 O$^{18}$ atom.

The term "prodrug" refers to a compound capable of converting to its original active compound after metabolism in vivo. Representatively, a prodrug is an inactive substance or less active than the active parent compound, but may provide convenient handling, administration, or improved metabolic properties.

The "pharmaceutically acceptable salts" described in the present disclosure are discussed in Berge, et al., "pharmaceutically acceptable salts", *J. Pharm. Sci.*, 66, 1-19 (1977), and it is apparent to pharmaceutical chemists that the salts are substantially non-toxic and provide the desired pharmacokinetic properties, palatability, absorption, distribution, metabolism or excretion, etc. The compounds described herein may have acidic groups, basic groups, or amphoteric groups, and typical pharmaceutically acceptable salts include those obtained by reaction of compounds of the present disclosure with acids, such as: hydrochloride, hydrobromide, sulfate, pyrosulfate, bisulfate, sulfite, bisulfite, phosphate, monohydrogen phosphate, dihydrogen phosphate, metaphosphate, pyrophosphate, nitrate, acetate, propionate, decanoate, octanoate, formate, acrylate, isobutyrate, caproate, heptanoate, oxalate, malonate, succinate, octanedioate, benzoate, methylbenzoate, phthalate, maleate, methanesulfonate, p-toluenesulfonate, (D,L)-tartaric acid, citric acid, maleic acid, (D,L)-malic acid, fumaric acid, succinate, lactate, trifluoromethanesulfonate, naphthalene-1-sulfonate, mandelate, pyruvate, stearate, ascorbate, salicylate. When the compounds of the disclosure contain acidic groups, pharmaceutically acceptable salts thereof may also include: alkali metal salts, such as lithium, sodium or potassium salts; alkaline earth metal salts, such as zinc, calcium or magnesium salts; organic alkali salts, such as salts formed with ammonia, alkylamines (including but not limited to: methylamine, triethylamine), hydroxyalkylamines, amino acids (including but not limited to: lysine, arginine), N-methylglucosamine, etc.

The term "isomer" in the present disclosure means that the compound of formula (I) of the present disclosure may have asymmetric centers and racemates, racemic mixtures and individual diastereoisomers, all of which are included in the present disclosure, including stereoisomers and geometric isomers. In the present disclosure, the individual stereoisomers (enantiomers and diastereoisomers), as well as mixtures thereof, are included within the scope of the present disclosure when the compound of formula (I) or its salt can be present in stereoisomeric form (e.g., it contains one or more asymmetric carbon atoms and/or phosphorus atoms). The present disclosure also includes the individual isomers of the compounds represented by formula (I) or salts, as well as mixtures of isomers with one or more of the chiral centers reversed. The scope of the present disclosure includes mixtures of stereoisomers, and purified enantiomeric or enantiomeric/diastereoisomeric enriched mixtures. The present disclosure includes stereoisomeric mixtures formed by all enantiomers and diastereoisomers in all possible different combinations. The present disclosure includes all combinations and subsets of stereoisomers of all specific groups as defined above. The compound of formula (I) in the present disclosure contains chiral P-atoms with Rp or Sp conformation, so that compounds with individual stereo-configuration of (Sp, Sp), (Sp, Rp), (Rp, Rp) or (Rp, Sp) and any mixture thereof are included in the scope of the present disclosure.

The above preferred conditions of the present disclosure may be arbitrarily combined without departing from the general knowledge in the art to obtain the preferred embodiments of the present disclosure.

The reagents and raw materials used in the present disclosure are commercially available.

BRIEF DESCRIPTION OF THE DRAWINGS

FIG. 1 is the tumor volume change curves of compounds 6-p3 (1 mg/kg, 2 mg/kg, i.t.) and Ref.1 (2 mg/kg, i.t.) in the colon cancer CT26 subcutaneously implanted tumor in mouse.

DETAILED DESCRIPTION OF THE EMBODIMENT

The following Embodiments serve to illustrate the present disclosure, but the Embodiments should not be considered as limiting the scope of the disclosure. Some of the experimental methods of the following Embodiments that are not indicated the specific conditions, can in according with the commonly used reaction conditions and procedures, or in accordance with the product specifications.

All the structures of the compounds in the present disclosure were confirmed by Nuclear Magnetic Resonance (H NMR) and/or Mass Spectra (MS).

$^1$H NMR chemical shifts (6) were recorded in ppm (10$^{-6}$). NMR Spectra were recorded on Bruker AVANCE-400 spectrometer. The proper solvents were Chloroform-d (CDCl$_3$), Methanol-d$_4$ (CD$_3$OD), and Dimethyl sulfoxide-d$_6$ (DMSO-d$_6$), tetramethylsilane as internal standard (TMS).

The analytical low-resolution mass spectra (LCMS) were recorded on Agilent 1200 HPLC/6120 using an XBridge C18, 3.0×50 mm, 3 µm, column temperature: 35° C.; or recorded on ThermoUltiMate 3000HIPLC/MSQPLUS using an XBridge C18, 3.0×50 mm, 3.5 m, column temperature: 30° C. The gradient elution method 1 of Agilent: 95-5% solvent A$_1$ and 5-95% solvent B$_1$ (0-2.0 min), and then 95% solvent B$_1$ and 5% solvent A$_1$ (for 1.1 min). Percentage as used herein is volume percentage of the volume of a solvent in the total solvent volume. Solvent A$_1$: 0.01% aqueous solution of trifluoroacetic acid (TFA); Solvent B$_1$: 0.01% trifluoroacetic acid acetonitrile solution. Percentage is the volume of a solvent in the total solvent volume. The gradient elution method 2 of Thermo: 95-5% solvent A$_2$ and 5-95% solvent B$_2$ (0-2 min), and then 95% solvent B$_2$ and 5% solvent A$_2$ (for 1.8 min), Percentage is the volume of a solvent in the total solvent volume. Solvent A$_2$: 10 mM aqueous solution of ammonium bicarbonate; Solvent B$_2$: acetonitrile.

All the compounds in the present disclosure were separated by preparative high-performance liquid chromatography or flash column chromatography.

Preparative high-performance liquid chromatography purification (prep-HPLC) was performed on Shimadzu LC-20 HPLC, chromatographic column: waters xbridge Pre C18, 10 um, 19 mm×250 mm. Separation method 1 (acidic condition): mobile phase A: 0.05% aqueous solution of trifluoroacetic acid, mobile phase B: acetonitrile; elution B was 40%, elution time: 20 min. Separation method 2 (alkali condition): mobile phase A: 10 mmol/L aqueous solution of ammonium bicarbonate, mobile phase B: acetonitrile; the gradient elution B was from 10% to 80%, elution time: 30 min. Separation method 3 (alkali condition): mobile phase A: 10 mmol/L aqueous solution of ammonium bicarbonate, mobile phase B: acetonitrile; the gradient elution B was from 0% to 15%, elution time: 30 min. Separation method 4 (alkali condition): mobile phase A: 10 mmol/L aqueous solution of ammonium bicarbonate, mobile phase B: acetonitrile; the gradient elution B was from 0% to 4%, elution time: 10 min; the gradient elution B was from 4% to 8%, elution time: 15 min. Separation method 5 (alkali condition): mobile phase A: 10 mmol/L aqueous solution of ammonium bicarbonate, mobile phase B: acetonitrile; the gradient elution B was from 0% to 5%, elution time: 10 min; the gradient elution B was from 5% to 10%, elution time: 15 min. Separation method 6 (alkali condition): mobile phase A: 10 mmol/L aqueous solution of ammonium bicarbonate, mobile phase B: acetonitrile; the gradient elution B was from 10% to 30%, elution time: 5 min; the gradient elution B was from 30% to 75%, elution time: 20 min. Separation method 7 (alkali condition): mobile phase A: 10 mmol/L aqueous solution of ammonium bicarbonate, mobile phase B: acetonitrile; the gradient elution B was from 0% to 10%, elution time: 7 min; the gradient elution B was from 10% to 40%, elution time: 18 min. Detection wavelength: 214 nm&254 nm; the flow rate: 15.0 mL/min.

Flash column chromatography (flash system/Cheetah™) was performed on Agela Technologies MP200. Normal-phase chromatography column was Flash column Silica-CS (25 g, 40 g, 80 g, 120 g or 330 g), Agela Technologies, Tianjing. Ethyl acetate/petroleum ether or dichloromethane/methanol was chosen as elution system. Reversed-phase chromatography column was C18 column (12 g, 20 g or 40 g), Santai Technologies, Changzhou. Acetonitrile/aqueous solution of ammonium bicarbonate (10 mmol/L) were chosen as elution system.

All the compounds in the present disclosure were analyzed by high-performance liquid chromatography. High-performance liquid chromatography (HPLC) was performed on Waters e2695, 2498 UV/VIS Detector, chromatography column: Waters Xselect CHS C18 (4.6*150 mm) 5 m, mobile phase A: acetonitrile, mobile phase B: acetic acid triethylamine buffer solution which was adjusted pH to 5.0 with acetic acid. Gradient elution of mobile phase B from 95% to 15%, elution time: 30 min. Detection wavelength: 214 nm&254 nm; column temperature: 35° C.

Embodiment 1: Synthesis of Intermediate 1-8

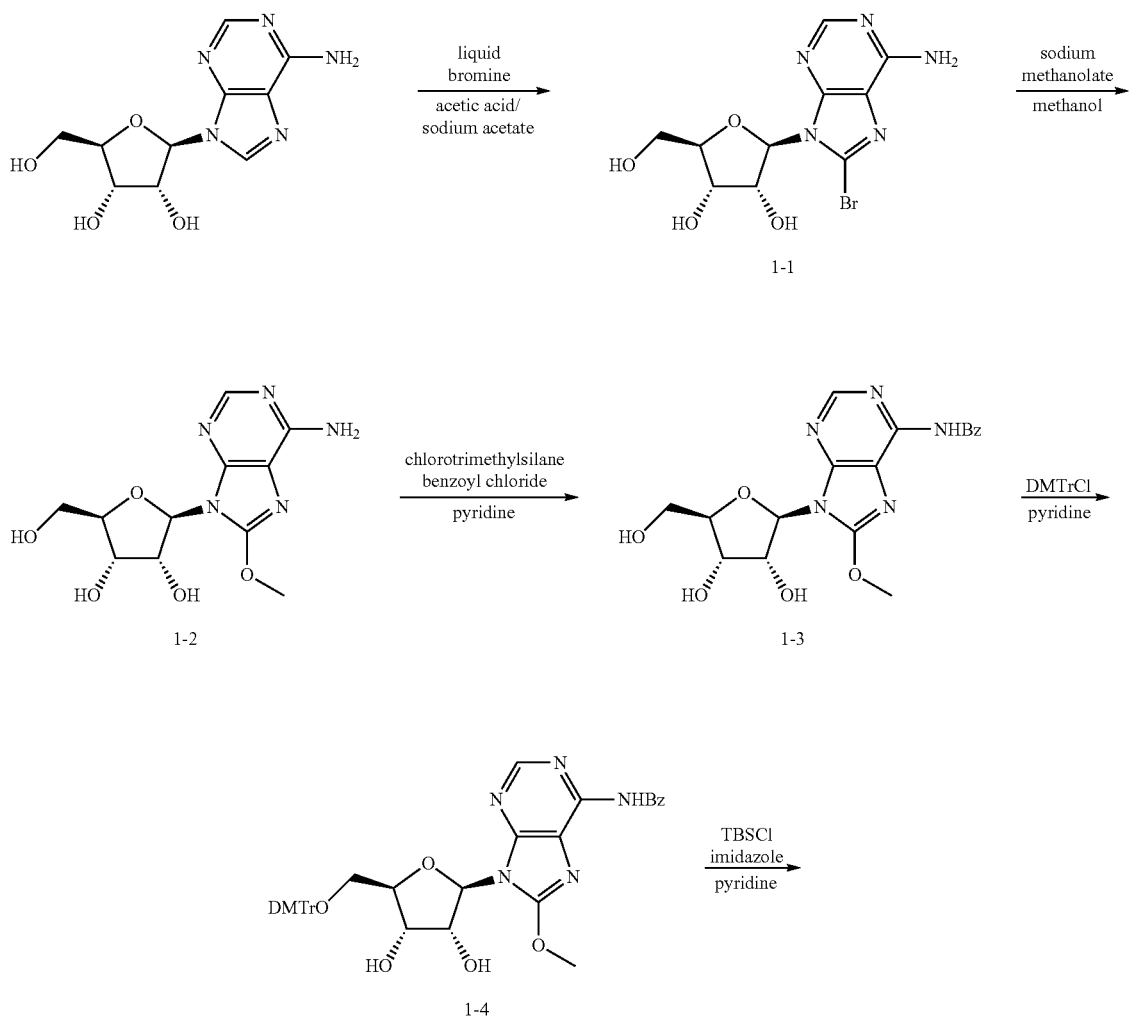

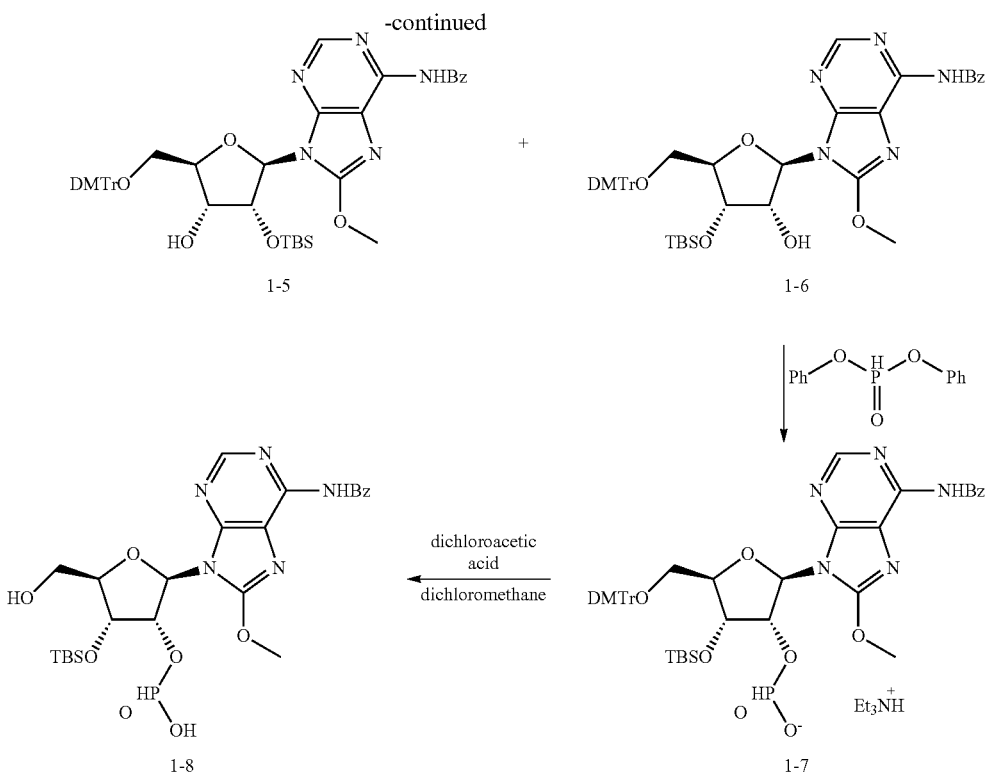

Step 1: To a suspension of adenosine (50 g, 187 mmol) in acetic acid/sodium acetate buffer solution (pH=4.0, 0.5M, 1 L) was added liquid bromine (60 g, 374 mmol), keep the system temperature below 10° C. After addition, the reaction system was stirred at room temperature for 48 h. The saturated aqueous solution of sodium bisulfate was added into the reaction solution to remove the excess bromine, and then adjusted pH to neutral with an aqueous solution of sodium hydroxide (1M), the reaction solution was stirred for 2 h under ice-water bath. The precipitate was formed and collected by filtration, dried under vacuum to afford intermediate 1-1 (29 g). m/z: [M+H]$^+$ 346.0/348.0.

Step 2: To a suspension of intermediate 1-1 (10 g, 28.9 mmol) in methanol (100 mL) was added sodium methanolate (9.36 g, 173 mmol), the reaction system was stirred at reflux for 5 h, methanol was concentrated under reduced pressure. The residue was dissolved in a mixed solvent of methanol/dichloromethane (1/10). The solution was filtered through a Büchner funnel which was covered with a layer of silica gel. The filtrate was concentrated under reduced pressure to afford intermediate 1-2 (3.8 g). m/z: [M+H]$^+$298.2.

Step 3: To a solution of intermediate 1-2 (10 g, 336 mmol) in pyridine (40 mL) was added chlorotrimethylsilane (16 mL, 121 mmol) under nitrogen at 0° C. The reaction system was stirred at room temperature for 2 h, benzoyl chloride (9.4 mL, 80.7 mmol) was slowly added to the above reaction system. The resulting solution was stirred at room temperature for overnight, and then ammonium hydroxide solution (25-28%) was added thereto and stirred for 30 min. The solvent was concentrate under reduced pressure. The residue was purified by Flash column chromatography (0-10% methanol/dichloromethane) to afford intermediate 1-3 (7.3 g) as a white solid. m/z: [M+H]$^+$402.2.

Step 4: To a solution of intermediate 1-3 (7 g, 17.4 mmol) in anhydrous pyridine (40 mL) was added 4,4'-dimethoxytrityl chloride (DMTrCl, 5.9 g, 17.4 mmol) at 0° C. under nitrogen. The reaction system was stirred at room temperature for 3 h and then quenched by addition of water (1 mL). The solvent was concentrated under reduced pressure. The residue was purified by Flash column chromatography (0-10% methanol/dichloromethane) to afford intermediate 1-4 (7.4 g) as a yellow solid. m/z: [M+H]$^+$704.2.

Step 5: To a solution of intermediate 1-4 (1.2 g, 1.70 mmol) in pyridine (5 mL) was added tert-butyldimethylsilyl chloride (TBSCl, 0.31 g, 2.05 mmol) and imidazole (0.29 g, 4.30 mmol) at 0° C. under nitrogen. The reaction system was stirred at room temperature for 16 h, and then cooled with ice-water, diluted with water (10 mL) and ethyl acetate (50 mL), the organic layer washed with brine (50 mL×2), the organic layer was separated and dried over anhydrous sodium sulfate, filtered, and concentrated under reduced pressure. The residue was purified by Flash column chromatography (0-60% ethyl acetate/petroleum ether) to afford intermediate 1-5 (less polar, 276 mg, white solid) and 1-6 (more polar, 670 mg, off-white solid). Intermediate 1-5: m/z: [M+H]$^+$818.3; TLC R$_f$=0.42 (DCM/MeOH=15/1); $^1$H NMR (400 MHz, DMSO-d$_6$): δ 11.00 (s, 1H), 8.48 (s, 1H), 8.02 (d, J=7.8 Hz, 2H), 7.62 (t, J=7.4 Hz, 1H), 7.53 (t, J=7.6 Hz, 2H), 7.39 (d, J=7.8 Hz, 2H), 7.29-7.16 (m, 7H), 6.83 (d, J=8.6 Hz, 4H), 5.90 (d, J=5.8 Hz, 1H), 5.13 (d, J=6.0 Hz, 1H), 5.08 (t, J=5.5 Hz, 1H), 4.27 (dd, J=9.6, 5.2 Hz, 1H), 4.07 (d, J=4.0 Hz, 1H), 4.00 (s, 3H), 3.71 (s, 6H), 3.27-2.23 (m, 1H), 3.14-3.10 (m, 1H), 0.74 (s, 9H), 0.10 (d, J=6.6 Hz, 6H).

Intermediate 1-6: m/z: [M+H]⁺818.3; TLC R$_f$=0.23 (DCM/MeOH=10/1); ¹H NMR (400 MHz, DMSO-d$_6$): δ 11.00 (s, 1H), 8.50 (s, 1H), 8.01 (d, J=7.6 Hz, 2H), 7.62 (m, 1H), 7.52 (m, 2H), 7.32 (d, J=7.5 Hz, 2H), 7.26-7.16 (m, 7H), 6.82 (dd, J=8.8, 2.3 Hz, 4H), 5.83 (d, J=5.2 Hz, 1H), 5.40 (d, J=6.1 Hz, 1H), 5.06 (m, 1H), 4.59 (t, J=4.5 Hz, 1H), 4.06 (s, 3H), 3.71 (s, 6H), 3.35-3.33 (m, 1H), 3.31-3.26 (m, 1H), 3.09-3.01 (m, 1H), 0.85 (s, 9H), 0.08 (d, J=7.8 Hz, 6H).

Step 6: To a solution of intermediate 1-6 (400 mg, 0.48 mmol) in pyridine (4 mL) was added diphenyl phosphite (460 mg, 1.92 mmol) and then stirred at room temperature for 30 min. Triethylamine (0.4 mL) and water (0.4 mL) was successively added to the above reaction system and stirred for 30 min. Dicholormethane (5 mL) and aqueous solution of sodium bicarbonate (5 mL, 5%) was successively added to the above reaction system. The organic layer washed with water, and then the separated organic layer was dried over anhydrous sodium sulfate, filtered and concentrated. The residue was purified by Flash column chromatography (0-10% methanol/dichloromethane) to afford intermediate 1-7 (triethylamine salt, 600 mg) as a white solid. m/z: [M+H]⁺882.3.

Step 7: To a solution of intermediate 1-7 (2.8 g, 2.85 mmol) in a mixed solvent of dichloromethane (20 mL) and water (0.3 mL) was added a dichloromethane solution of dichloroacetic acid (DCA) (0.6M, 23.7 mL), and then stirred at room temperature for 1 h. To the reaction solution was added pyridine (20 mL), the resulting mixture was stirred at room temperature for 10 min. The solvent was concentrate under reduced pressure to afford intermediate 1-8 (pyridinium salt, curd product). m/z: [M+H]⁺580.1.

Embodiment 2: Synthesis of Compounds 1-p1, 1-p2, 1-p3 and 1-p4

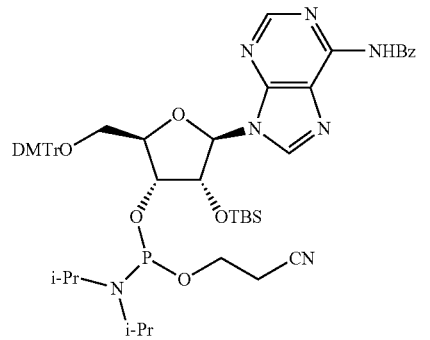

1-9

intermediate 1-8
DDTT
―――――――→
acetonitrile

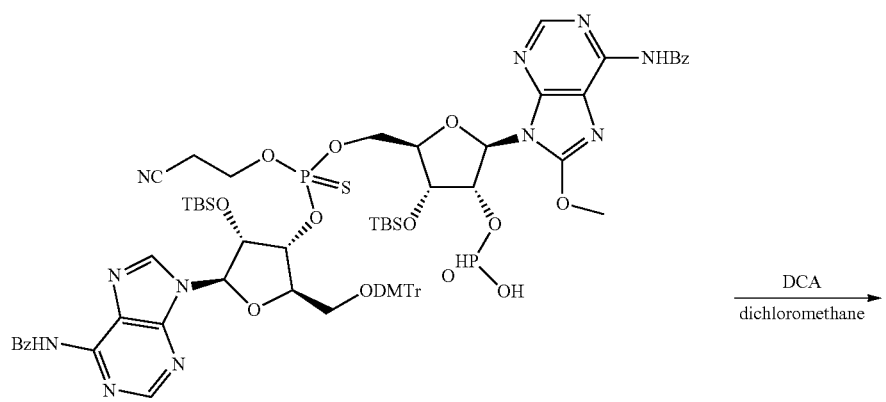

1-10

-continued
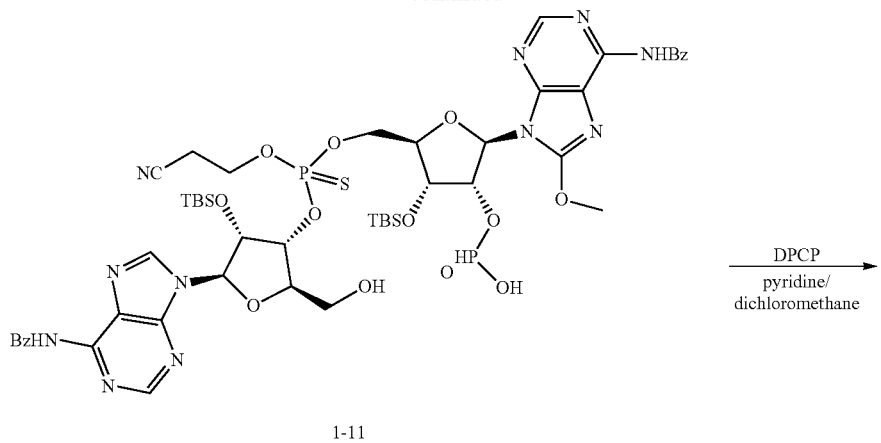
1-11
DPCP
pyridine/
dichloromethane
→
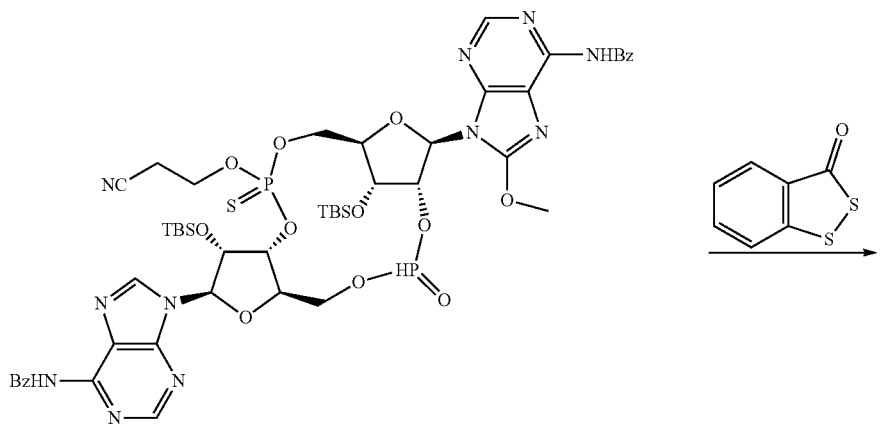
1-12
→
1) tert-butylamine/acetonitrile
2) 2.0M hydrochloric acid/acetonitrile
→
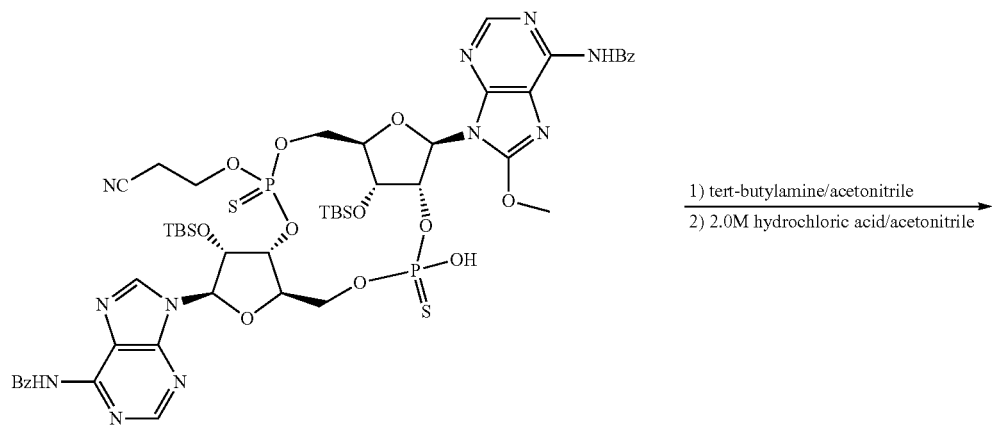
1-13-p1
1-13-p2
1-13-p3

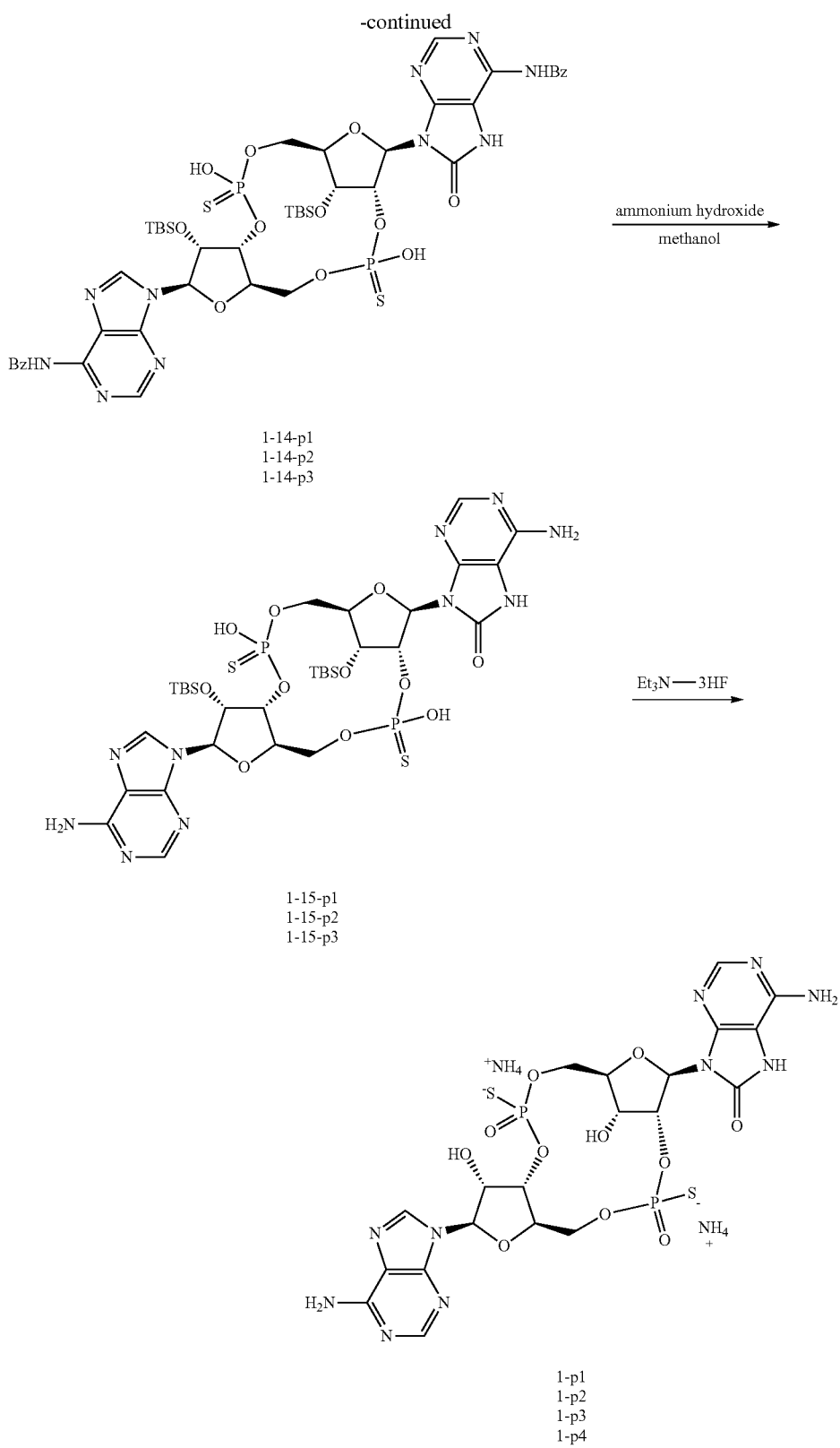

1-14-p1
1-14-p2
1-14-p3

1-15-p1
1-15-p2
1-15-p3

1-p1
1-p2
1-p3
1-p4

Step 1: Intermediate 1-8 (2.85 mmol) was dissolved in anhydrous acetonitrile (15 mL) and then the solvent was concentrated under reduced pressure, repeated twice and left 10 mL acetonitrile at last time, 4 Å molecular sieve (0.8 g) was added thereto. Compound 1-9 (CASNo: 104992-55-4, 3.3 g, 3.42 mmol) was dissolved in anhydrous acetonitrile (15 mL) and then the solvent was concentrated under reduced pressure, repeated twice and left 5 mL acetonitrile at last time. To the solution of 1-8 in acetonitrile was slowly added the acetonitrile solution of compound 1-9 at 0° C., the reaction system was stirred at room temperature for 0.5 h, ((Dimethylaminomethylidene)amino)-3H-1,2,4-dithiazoline-3-thione (DDTT, 697 mg, 3.42 mmol) was added thereto, and stirred for additional 40 min. The molecular sieve was removed by filtration, and the filtrate was concentrated under reduced pressure to afford compound 1-10 (7.5 g). m/z: [M+H]$^+$1499.3.

Step 2: Compound 1-10 (3.7 g, 2.35 mmol) was dissolved in dichloromethane (35 mL) and water (0.7 mL); dichloromethane solution of DCA (0.6 M, 31 mL, 18.8 mmol) was dropped thereto at room temperature. The reaction system was stirred at room temperature for 2 h. Triethylsilane (20 mL) was dropped thereto, and the reaction solution was stirred at room for additional 1 h. Pyridine (10 mL) was dropped thereto, the the reaction solution was concentrated under reduced pressure. The residue was purified by prep-HPLC to afford compound 1-11 (400 mg) as a white solid. m/z: [M+H]$^+$1196.2.

Step 3& 4: To pyridine (5 mL) was slowly added diphenyl chlorophosphate (DPCP, 1 g, 3.8 mmol) dropwise at −40° C., to the above solution was slowly added anhydrous dichloromenthane solution (5 mL) of compound 1-11 (230 mg, 0.19 mmol) dropwise at −40° C., and then stirred at this temperature for 30 min, and obtained the reaction solution of compound 1-12. To the solution of compound 1-12 was directly added 3H-1,2-benzodithiol-3-one (64 mg, 0.38 mmol) and stirred for 1 h. Water (68 mg, 0.38 mmol) was added thereto and stirred for additional 1 h. The reaction solution was diluted with ethyl acetate and washed with aqueous solution of sodium bicarbonate (2.7%, 30 mL), the organic layer was separated and concentrated to afford compound 1-13. Compound 1-13 was separated by prep-HPLC (separation method 2) to afford 3 isomers: 1-13-p1 (60 mg) as a yellow solid, 1-13-p2 (30 mg) as a white solid, and 1-13-p3 (40 mg) as a white solid.

Step 5: To a solution of compound 1-13-p1 (80 mg, 0.066 mmol) in acetonitrile (2 mL) was added tert-butylamine (2 mL). The reaction system was stirred at room temperature for 0.5 h. The solvent was concentrate under reduced pressure. The residue was dissolved in methanol (4 mL), methanolic hydrochloric acid solution (2M, 4 mL) was added thereto, the reaction solution was stirred at 45° C. for 1 h, and the solvent was concentrate under reduced pressure to afford compound 1-14-p1 (100 mg) as a yellow solid. m/z: [M+H]$^+$ 1143.1.

Step 6: To a solution of compound 1-14-p1 (100 mg) in methanol (6 mL) was added ammonium hydroxide solution (6 mL). The reaction system was stirred at 45° C. for overnight.

The solvent was concentrate under reduced pressure. The residual liquid was lyophilized to afford compound 1-15-p1 (100 mg, crude compound) as a yellow solid. m/z: [M+H]$^+$ 935.2.

Step 7: Compound 1-15-p1 (45 mg) was subjected to azeotropic dehydration three times with anhydrous pyridine (10 mL) and then dissolved in pyridine (2 mL), and then triethylamine (0.66 mL) and triethylamine trihydrofluoride (387 mg) was added thereto under nitrogen. The resulting solution was stirred at 45° C. for 3 h. The solvent was concentrate under reduced pressure. The residue was purified by prep-HPLC (separation method 3) to afford compound 1-p1 (0.34 mg, m/z: [M+H]$^+$ 706.8, HPLC-RT: 8.584 min) and 1-p2 (0.30 mg, m/z: [M+H]$^+$ 706.8, HPLC-RT: 8.662 min), as white solids.

Synthesis of Compound 1-p3

In a same way, to a solution of compound 1-13-p2 (50 mg, 0.041 mmol) in acetonitrile (2.0 mL) was added tert-butylamine (2 mL), and stirred at room temperature for 0.5 h, the solvent was concentrate under reduced pressure. The residue was dissolved in methanol (1 mL), methanolic hydrochloric acid solution (2 mL, 2M) was added thereto, the reaction solution was stirred at 40° C. for 4 h, and then the solvent was concentrate under reduced pressure. The residue was dissolved in methanol (1 mL), ammonium hydroxide solution (1 mL) was added thereto and stirred at 50° C. for 16 h, and then the reaction solution was purged with nitrogen to remove most of the ammonia. The solvent was concentrate under reduced pressure. The residual liquid was lyophilized. The crude compound was subjected to azeotropic dehydration three times with anhydrous pyridine (10 mL) and then dissolved in pyridine (2 mL), triethylamine (0.66 mL) and triethylamine trihydrofluoride (0.36 mL) was added thereto under nitrogen. The resulting solution was stirred at 50° C. for 2 h. The solvent was concentrate under reduced pressure. The residue was purified by prep-HPLC (separation method 3) to afford compound 1-p3 (0.40 mg, m/z: [M+H]$^+$ 706.8, HPLC-RT: 9.789 min) as an off-white solid.

Synthesis of Compound 1-p4

Compound 1-p4 (2.4 mg, m/z: [M+H]$^+$ 706.8, HPLC-RT: 9.960 min) was obtained as a white solid in the same manner as compound 1-p3, by using compound 1-13-p3 (40 mg, 0.033 mmol) as a starting material. $^1$H NMR (400 MHz, DMSO-$d_6$+$D_2O$): δ 8.37 (s, 1H), 8.16 (s, 1H), 7.97 (s, 1H), 5.93 (d, J=7.8 Hz, 1H), 5.74 (d, J=8.0, 1H), 5.35 (m, 1H), 5.14 (m, 1H), 4.70 (m, 1H), 4.59 (s, 1H), 4.18 (s, 1H), 4.15 (m, 1H), 3.85 (m, 2H), 3.53 (m, 1H), 3.06 (m, 1H); $^{31}$P NMR (161 MHz, DMSO-$d_6$+$D_2O$): δ 58.47, 46.58.

Embodiment 3: Synthesis of Intermediates 2-8 and 2-9
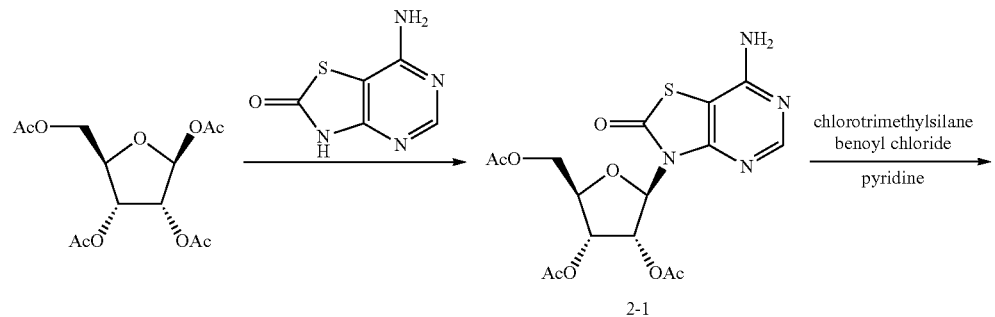
2-1
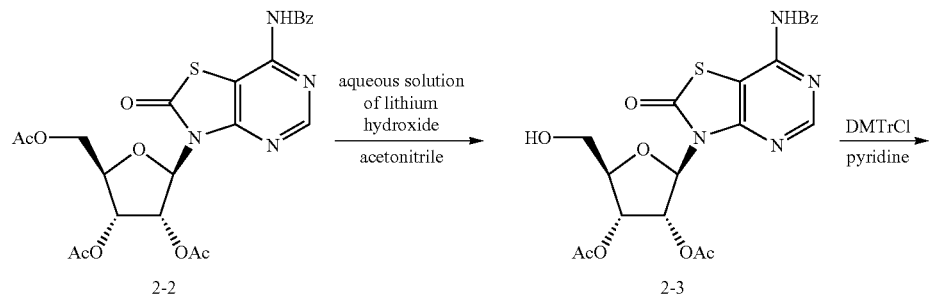
2-2    2-3
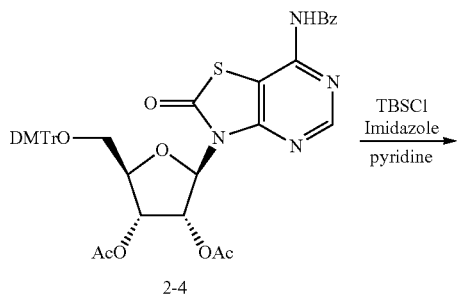
2-4
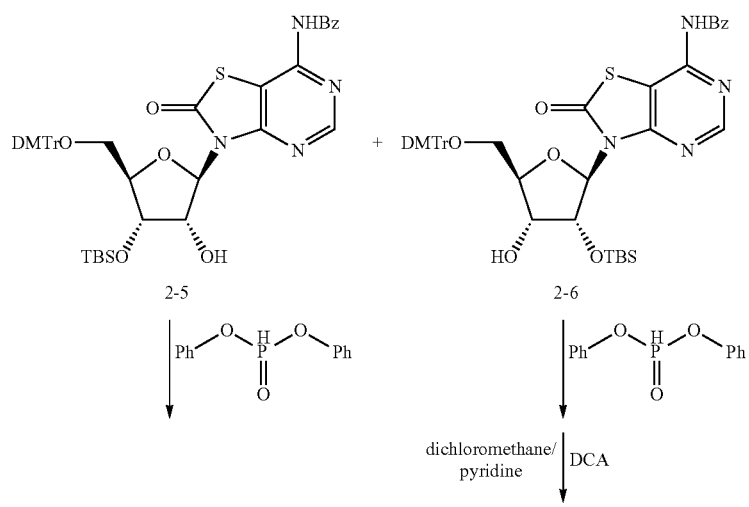
2-5    2-6

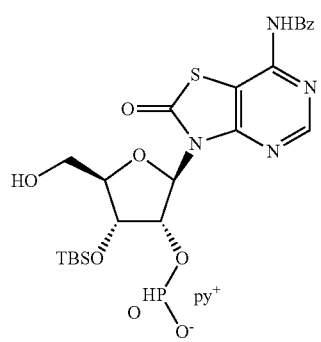 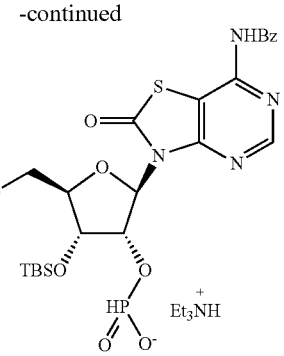 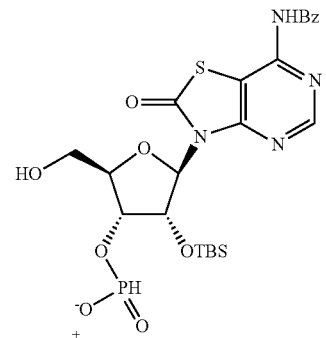

2-8  2-7  2-9

Step 1: To a solution of 7-aminothiazolo[4,5-d]pyrimidin-2 (3H)-one (refer to J. Med. Chem. 1990, 33, 407-415, compound 28) (6.5 g, 38.7 mmol) and tetraacetylribose (1 g, 46.4 mmol) in acetonitrile (120 mL) was added N,O-bis(trimethylsilyl)acetamide (BSA, 13.6 g, 116 mmol), and then stirred at reflux for 1 h. To the above reaction solution was added trimethylsilyl trifluoromethylsulphonate (TMSOTf, 17.2 g, 77.4 mmol) after cooling to room temperature, and stirred at reflux for additional 48 h. The reaction solution was cooled to room temperature, and saturated aqueous solution of sodium bicarbonate was slowly added thereto, the mixture was extracted with ethyl acetate (150 mL×3), the combined organic layers were washed with water, the separated organic layer was dried over anhydrous sodium sulfate, filtered and concentrated. The residue was purified by Flash column chromatography (ethyl acetate/petroleum ether=3/4) to afford intermediate 2-1 (4.3 g) as a light yellow solid. m/z: [M+H]$^+$ 427.0.

Step 2: To a solution of intermediate 2-1 (0.5 g, 1.17 mmol) in pyridine (5 mL) was added chlorotrimethylsilane (0.07 mL, 0.58 mmol) at 0° C. under nitrogen, and stirred at for 5 min, to the above reaction solution was added benzoyl chloride (0.32 mL, 2.81 mmol), the reaction system was stirred at room temperature for overnight, and then quenched by addition of water (50 mL). The aqueous layer was extracted with ethyl acetate (50 mL×2), the combined organic layers were washed with water, and the separated organic layer was dried over anhydrous sodium sulfate, filtered and concentrated. The residue was purified by Flash column chromatography (ethyl acetate/petroleum ether=9/10) to afford intermediate 2-2 (0.45 g) as a light yellow solid. m/z: [M+H]$^+$ 34.8.

Step 3: To a solution of intermediate 2-2 (3 g, 4.7 mmol) in acetonitrile (150 mL) was added aqueous solution of lithium hydroxide (47 mL, 1M), the reaction system was stirred at room temperature for 15 min and then neutralized pH to 6 with hydrochloric acid (2M). The reaction solution was concentrated to ⅓ of the total volume, the solid was precipitated, filtered, the filter cake washed with water for 3 times, and then dried under vacuum to afford intermediate 2-3 (1 g) as a yellow solid. m/z: [M+H]$^+$405.0.

Step 4: To a solution of intermediate 2-3 (7.6 g, 18.8 mmol) in pyridine (95 mL) was added DMTrCl (9.5 g, 28.5 mmol) under nitrogen. The reaction system was stirred at room temperature for overnight. The solvent was concentrate under reduced pressure. The residue was purified by Flash column chromatography (methanol/dichloromethane=1/25) to afford intermediate 2-4 (8.3 g) as an off-white solid. m/z: [M+H]$^+$706.8.

Step 5: To a solution of intermediate 2-4 (8.3 g, 11.7 mmol) and imidazole (2 g, 29.3 mmol) in pyridine (60 mL) was added TBSCl (2.1 g, 14 mmol) at 0° C. under nitrogen. The reaction system was stirred at room temperature for overnight, and then quenched by addition of water (1 mL) and saturated aqueous solution of sodium bicarbonate (100 mL), the aqueous layer was extracted with ethyl acetate (200 mL×2), the combined organic layers were washed with water, the organic layer was dried over anhydrous sodium sulfate, filtered and concentrated, the residue was purified by Flash column chromatography (methanol/dichloromethane=1/50-1/20) to afford intermediate 2-5 (4 g, off-white solid, LCMS-RT (Thermo): 2.813 min) and 2-6 (2 g, off-white solid, LCMS-RT (Thermo): 2.763 min. Intermediate 2-5: m/z: [M+H]$^+$ 821.1; $^1$H NMR (400 MHz, DMSO-d$_6$): δ 11.71 (s, 1H), 8.66 (s, 1H), 8.05-8.03 (m, 2H), 7.68-7.64 (m, 1H), 7.56-7.52 (m, 2H), 7.43-7.32 (m, 2H), 7.27-7.17 (m, 7H), 6.84-6.82 (m, 4H), 6.05-6.04 (m, 1H), 5.29-5.28 (m, 1H), 4.88-4.84 (m, 1H), 4.53-4.50 (m, 1H), 4.05-3.98 (m, 1H), 3.71 (s, 6H), 3.35-3.27 (m, 1H), 3.08-3.04 (m, 1H), 0.82 (s, 9H), 0.05 (s, 3H), 0.01 (s, 3H); Intermediate 2-6: m/z: [M+H]$^+$ 821.1; $^1$H NMR (400 MHz, DMSO-d$_6$): δ 11.73 (s, 1H), 8.62 (s, 1H), 8.06-8.04 (m, 2H), 7.68-7.65 (m, 1H), 7.57-7.53 (m, 2H), 7.41-7.36 (m, 2H), 7.27-7.17 (m, 7H), 6.85-6.82 (m, 4H), 6.09-6.08 (m, 1H), 5.00-4.95 (m, 2H), 4.31-4.27 (m, 1H), 4.05-4.03 (m, 1H), 3.72 (s, 6H), 3.23-3.16 (m, 2H), 0.95 (s, 9H), 0.05 (s, 6H).

Step 6: To a solution of intermediate 2-5 (0.5 g, 0.61 mmol) in pyridine (5 mL) was added diphenyl phosphite (0.57 g, 1.43 mmol) at 0° C. under nitrogen, the reaction system was stirred for 1 h, and then triethylamine (0.6 mL) and water (0.6 mL) was added thereto. The resulting mixture was stirred at room temperature for 5 min and then diluted with water (50 mL), the aqueous layer was extracted with dicholormethane (30 mL×2), the combined organic layers were washed with water, and the separated organic layer was dried over anhydrous sodium sulfate, filtered and concentrated. The residue was purified by Flash column chromatography (methanol/dichloromethane=1/10) to afford intermediate 2-7 (triethylamine salt, 0.6 g) as an off-white solid. m/z: [M+H]$^+$ 884.5.

Step 7: To a solution of intermediate 2-7 (0.6 g, 0.61 mmol) in a mixed solvent of dichloromethane (10 mL) and water (1 mL) was added a dichloromethane solution of DCA (0.6 M, 9.1 mL). The reaction mixture was stirred for 0.5 h, and then pyridine (20 mL) was added thereto, the resulting mixture was concentrate under reduced pressure to afford intermediate 2-8 (pyridinium salt, curd product). m/z: [M+H]$^+$ 582.9.

Synthesis of intermediate 2-9: intermediate 2-9 (pyridinium salt) was obtained in the same manner as intermediate 2-8, by using intermediate 2-6 as a starting material. m/z: [M+H]$^+$ 583.0.

Embodiment 4: Synthesis of Compounds 2-p1, 2-p2, 2-p3 and 2-p4

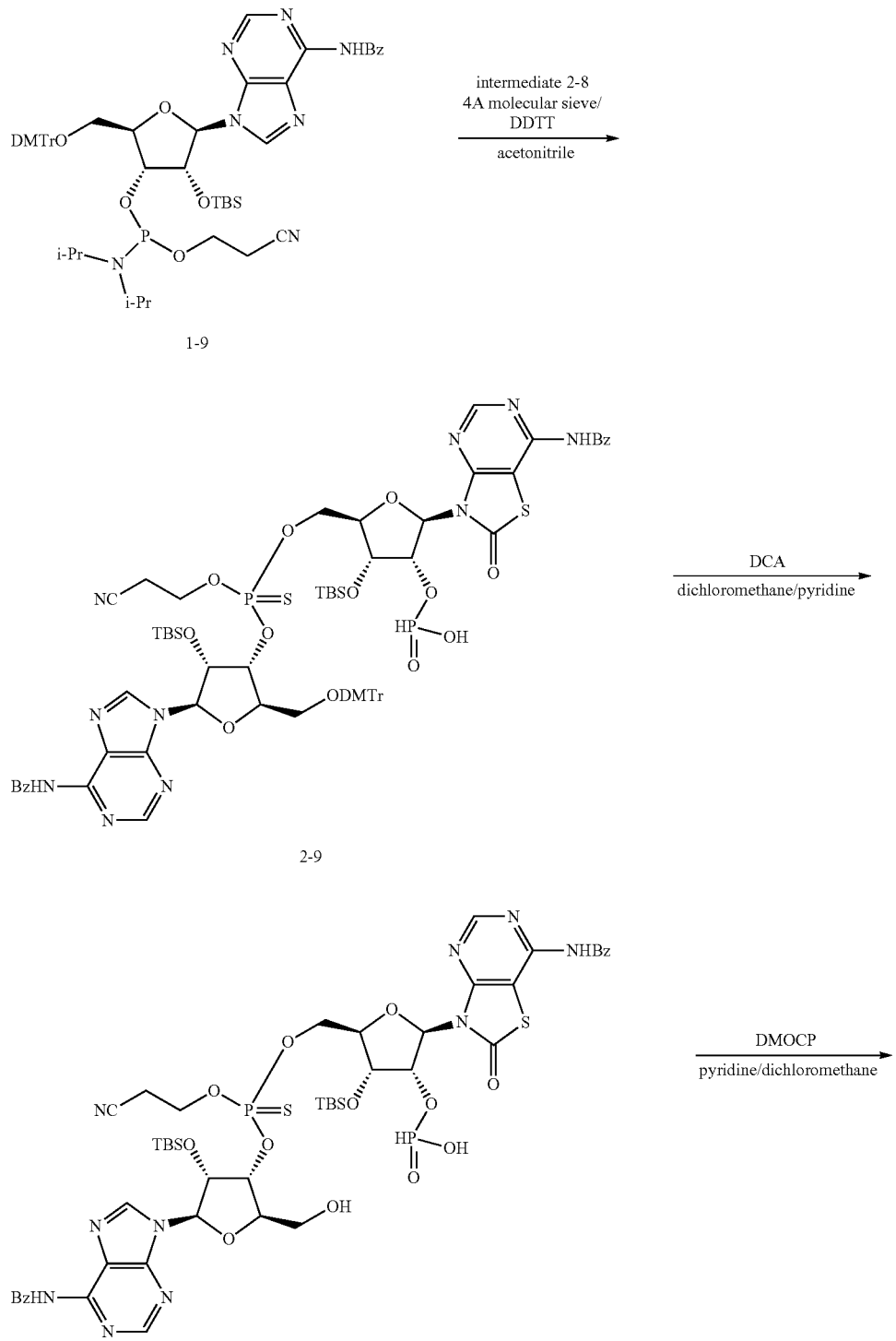

-continued
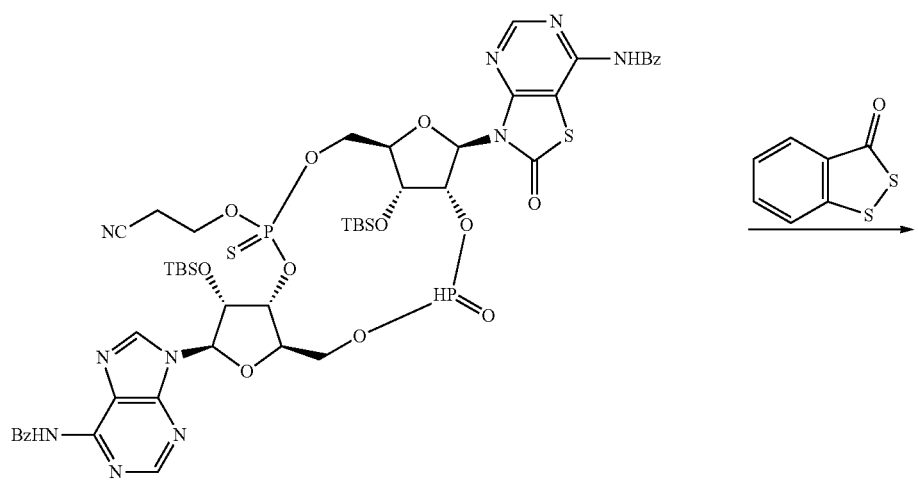
2-11
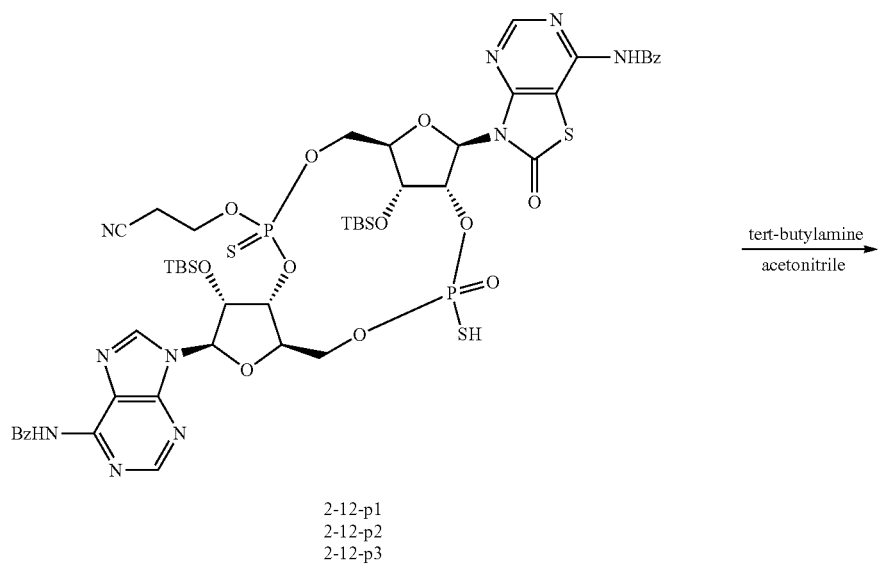
2-12-p1
2-12-p2
2-12-p3
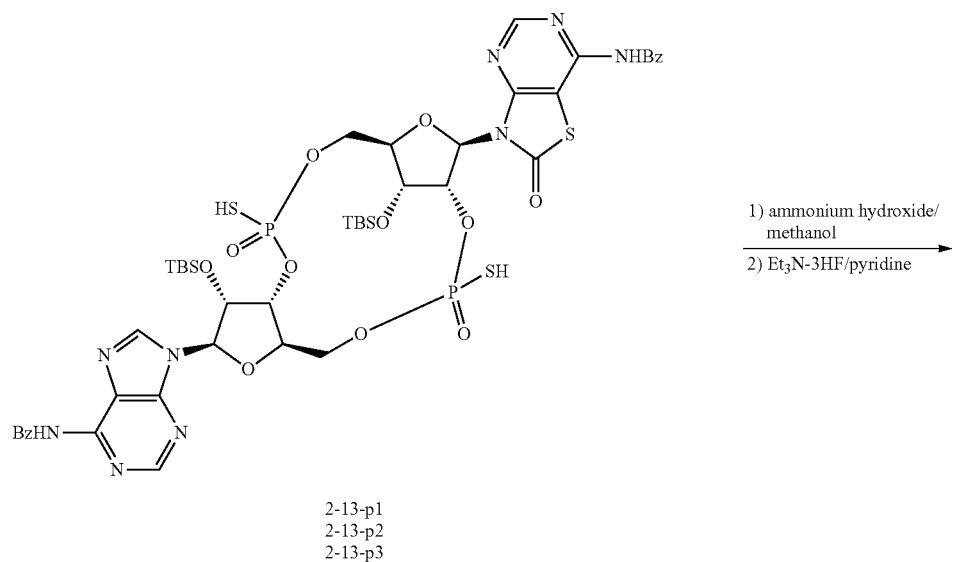
2-13-p1
2-13-p2
2-13-p3

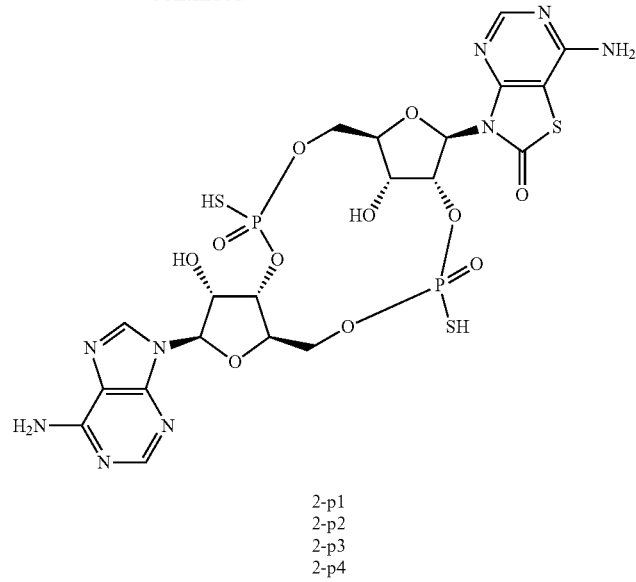 [SMILES: Nc1ncnc2c1ncn2[C@@H]1O[C@@H]2COP(=O)(S)O[C@@H]3[C@H](O)[C@@H](COP(=O)(S)O[C@H]2[C@H]1O)O[C@H]3n1c(=O)sc2c(N)ncnc21]

2-p1
2-p2
2-p3
2-p4

Step 1: Intermediate 2-8 (0.68 mmol) and 1-9 (0.81 g, 0.82 mmol) were subjected to azeotropic dehydration twice with anhydrous acetonitrile (10 mL) respectively, and then dissolved in acetonitrile (5 mL) respectively for use. To the solution of intermediate 2-8 in acetonitrile, which contained 4 A molecular sieve, was slowly added the acetonitrile solution of intermediate 1-9 at 0° C. under nitrogen, the resulting mixture was stirred for 1 h. To the above reaction system was added DDTT (0.16 g, 0.79 mmol) and stirred for additional 1 h. The molecular sieve was removed by filtration, and the filtrate was concentrated under reduced pressure to afford compound 2-9 (1 g). m/z: [M+H]$^+$1501.5.

Step 2: To the solution of compound 2-9 (0.33 g, 0.22 mmol) in a mixed solvent of dichloromethane (3 mL) and water (0.3 mL) was added dichloromethane solution of DCA (0.6 M, 2.93 mL) under nitrogen. The reaction system was stirred for 0.5 h, and then pyridine (1 mL) was added thereto and concentrated under reduced pressure, and the residue was purified by Flash column chromatography (acetonitrile/aqueous solution of ammonium bicarbonate (10 mmol/L)=60%) to afford compound 2-10 (0.25 g, pyridinium salt) as a white solid. m/z: [M+H]$^+$ 1199.6.

Step 3&4: Compound 2-10 (250 mg, 0.21 mmol) was subjected to azeotropic dehydration three times with pyridine (1 mL) and then dissolved in a mixed solvent of pyridine (2 mL) and dichloromethane (2 mL). 2-chloro-5,5-dimethyl-1,3,2-dioxaphosphorinane 2-oxide (DMOPC) (775 mg, 4.2 mmol) was added thereto, the mixture was stirred at room temperature for 10 min to obtain the reaction solution of compound 2-11. To the above reaction solution of compound 2-11 was directly added water (756 mg, 42 mmol) and 3H-1,2-benzodithiol-3-one (71 mg, 0.42 mmol), and stirred at room temperature for 20 min, aqueous solution of sodium bicarbonate (2.7%, 50 mL) was added thereto. The aqueous layer was extracted with ethyl acetate, and the separated organic layer was concentrated. The residue was purified by Flash column chromatography (acetonitrile/aqueous solution of ammonium bicarbonate (10 mmol/L)=10-80%) to afford compound 2-12-p1 (30 mg, LCMS-RT(Thermo): 2.147 min), 2-12-p2 (35 mg, LCMS-RT(Thermo): 2.247 min), and 2-12-p3 (50 mg, LCMS-RT(Thermo): 2.327 min), as white solids.

Step 5: To a solution of compound 2-12-p1 (30 mg, 0.01 mmol) in acetonitrile (2 mL) was added tert-butylamine (2 mL), the reaction system was stirred at room temperature for 0.5 h, and then directly concentrated to afford compound 2-13-p1 (30 mg, crude product). m/z: [M+H]$^+$ 1159.9.

Step 6: To a solution of compound 2-13-p1 (30 mg, crude) in methanol (2 mL) was added ammonium hydroxide solution (2 mL), the reaction system was stirred at 45° C. for overnight in a sealed tube, and then the reaction solution was concentrated in reduced pressure. The residue was subjected to azeotropic dehydration three times with pyridine (2 mL) and then dissolved in pyridine (2 mL). To the above reaction system was added triethylamine (0.35 g, 3.5 mmol) and triethylamine trihydrofluoride (0.28 g, 1.75 mmol) under nitrogen. The resulting mixture was stirred at 45° C. for 6 h. The solvent was concentrate under reduced pressure. The residue was adjust pH to 8 with aqueous solution of ammonium bicarbonate (1M), and then purified by prep-HPLC (separation method 3) to afford compound 2-p1 (di-ammonium salt, 2 mg, m/z: [M+H]$^+$ 723.8, HPLC-RT: 8.116 min) and 2-p2 (di-ammonium salt, 2 mg, m/z: [M+H]$^+$ 723.8, HPLC-RT: 10.121 min), as white solids.

Synthesis of Compound 2-p3

To a solution of compound 2-12-p2 (30 mg, 0.01 mmol) in acetonitrile (2 mL) was added tert-butylamine (2 mL). The mixture was stirred at room temperature for 0.5 h, and then concentrated under reduced pressure to afford compound 2-13-p2. To a solution of compound 2-13-p2 in methanol (2 mL) was added ammonium hydroxide solution (2 mL), the reaction system was stirred in a sealed tube at 45° C. for overnight, and then the reaction solution was directly concentrated under reduced pressure. The residue was subjected to azeotropic dehydration three times with pyridine (2 mL) and then dissolved in pyridine (2 mL). To the above reaction system was added triethylamine (0.35 g, 3.5 mmol) and triethylamine trihydrofluoride (0.28 g, 1.75 mmol) under nitrogen. The resulting mixture was stirred at 45° C. for 6 h. The solvent was concentrate under reduced pressure. The residue was adjust pH to 8 with aqueous solution of ammonium bicarbonate (1M), and then purified by prep-HPLC (separation method 3) to afford compound 2-p3 (di-ammonium salt, 0.3 mg, m/z: [M+H]$^+$723.7, HPLC-RT: 10.121 min) as a white solid.

Synthesis of Compound 2-p4

Compound 2-p4 (di-ammonium salt, 0.4 mg, m/z: [M+H]$^+$723.7, HPLC-RT: 9.632 min) was obtained as a white solid in the same manner as compound 2-p3, by using compound 2-12-p3 (17 mg, 0.01 mmol) as a starting material.

Embodiment 5: Synthesis of Compounds 3-p1, 3-p1/3-p2 and 3-p3

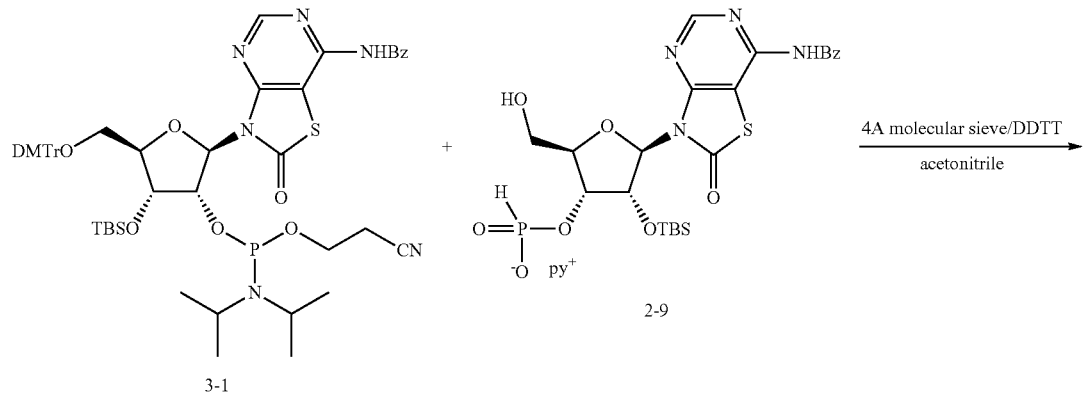

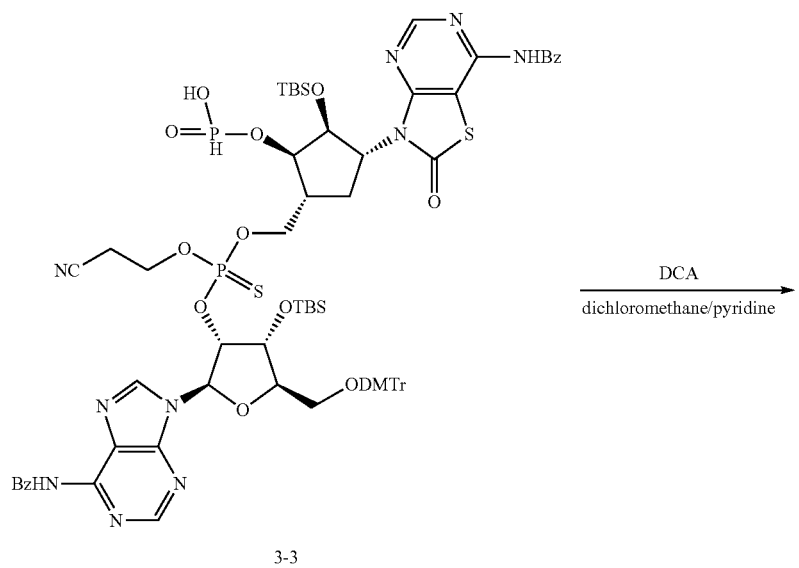

-continued
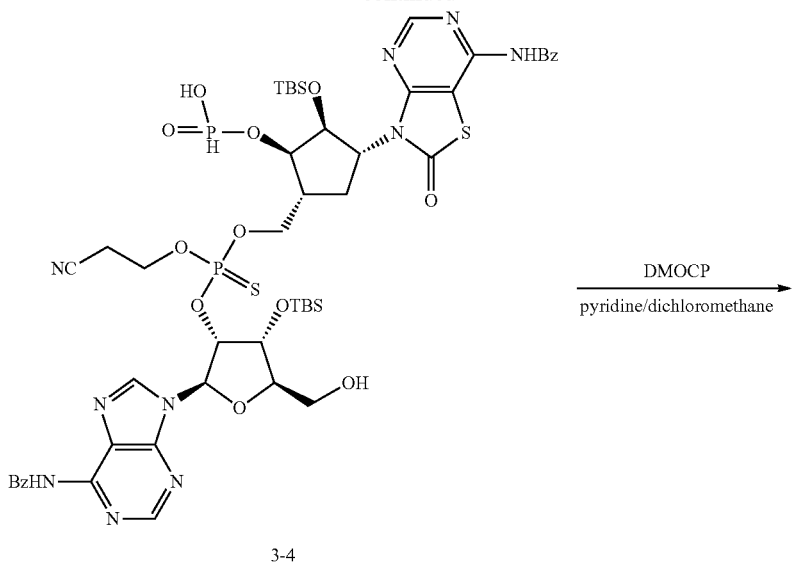
3-4
DMOCP
pyridine/dichloromethane
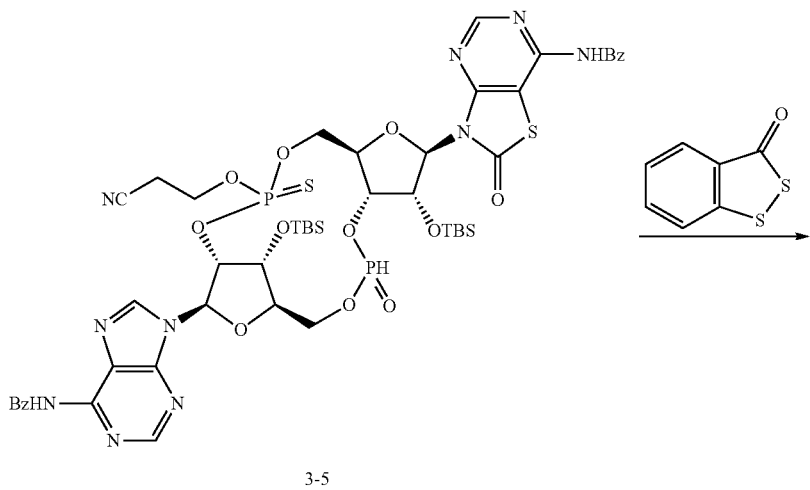
3-5
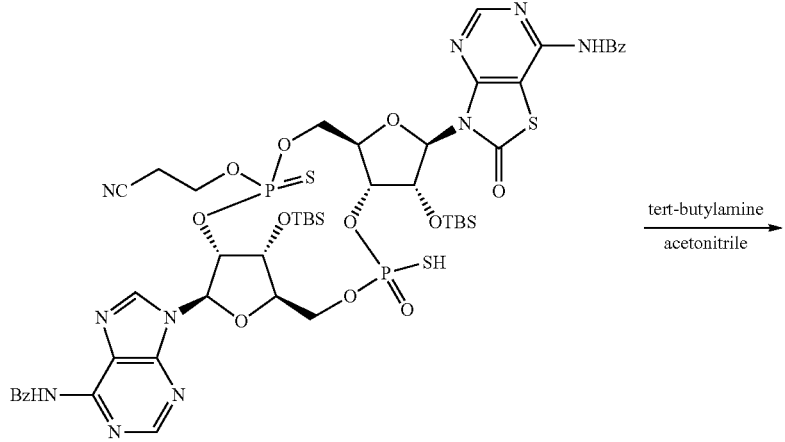
3-6-p1
3-6-p2
3-6-p3
tert-butylamine
acetonitrile -continued

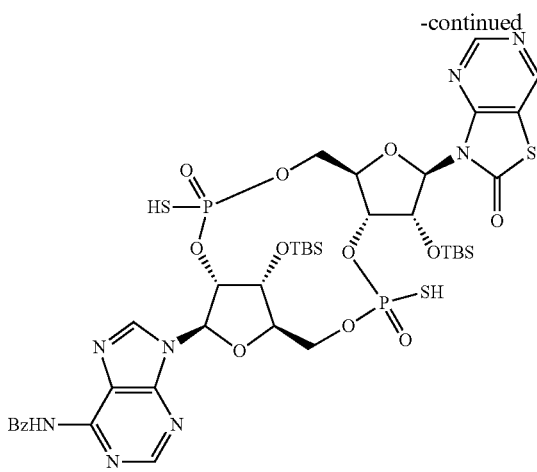

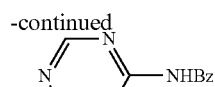
1) ammonium hydroxide/methanol
2) Et₃N-3HF/pyridine 3-7-p1
3-7-p3

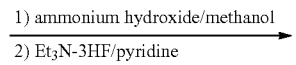

3-p1
3-p1/3-p2
3-p3

Step 1: Compound 3-1 (CAS No.: 129451-95-8) (2.36 g, 2.4 mmol) and Intermediate 2-9 (1.05 g, 2 mmol) were subjected to azeotropic dehydration twice with anhydrous acetonitrile (10 mL) respectively, and then dissolved in acetonitrile (5 mL) respectively for use. To the solution of intermediate 2-9 in acetonitrile, which contained 4 A molecular sieve, was slowly added the acetonitrile solution of compound 3-1 at 0° C. under nitrogen, the resulting mixture was stirred for 1 h, To the above reaction system was added DDTT (0.49 g, 2.4 mmol), and stirred for additional 1 h. The molecular sieve was removed by filtration, and the filtrate was concentrated under reduced pressure to afford compound 3-3 (1.3 g). m/z: [M+H]⁺1501.5.

Step 2: To the solution of compound 3-3 (1 g, 0.66 mmol) in a mixed solvent of dichloromethane (3 mL) and water (0.3 mL) was added dichloromethane solution of DCA (0.6 M, 10 mL). The reaction system was stirred for 0.5 h. Pyridine (3 mL) was added thereto, the mixture was concentrated under reduced pressure. The residue was purified by Flash column chromatography (acetonitrile/aqueous solution of ammonium bicarbonate (10 mmol/L)=60%) to afford compound 3-4 (390 mg, pyridinium salt) as a white solid. m/z: [M+H]⁺ 1199.6.

Step 3&4: Compound 3-4 (250 mg, 0.21 mmol) was subjected to azeotropic dehydration three times with pyridine (1 mL) and then dissolved in a mixed solvent of pyridine (2 mL) and dichloromethane (2 mL). To the above reaction system was added DMOPC (775 mg, 4.2 mmol), the mixture was stirred at room temperature for 10 min to obtain the reaction solution of compound 3-5. To the reaction solution of compound 3-5 was added water (756 mg, 42 mmol) and 3H-1,2-benzodithiol-3-one (71 mg, 0.42 mmol) and stirred at room temperature for 20 min, and then aqueous solution of sodium bicarbonate (2.7%, 50 mL) was added thereto, the aqueous layer was extracted with ethyl acetate, and the separated organic layer was concentrated. The residue was purified by Flash column chromatography (acetonitrile/aqueous solution of ammonium bicarbonate (10 mmol/L)=10-80%) to afford compound 3-6-p1 (50 mg, LCMS-RT(Thermo): 2.143 min), 3-6-p2 (15 mg, LCMS-RT(Thermo): 2.230 min), and 3-6-p3 (18 mg, LCMS-RT(Thermo): 2.320), as white solids.

Step 5: To a solution of compound 3-6-p1 (20 mg, 0.02 mmol) in acetonitrile (2 mL) was added tert-butylamine (2 mL), the reaction system was stirred at room temperature for 0.5 h, and then directly concentrated to afford compound 3-7-p1 (25 mg, crude product). m/z: [M+H]$^+$1159.9.

Step 6: To a solution of compound 3-7-p1 (25 mg, crude) in methanol (2 mL) was added ammonium hydroxide solution (2 mL), the reaction system was stirred in a sealed tube at 45° C. for overnight, and then the reaction solution was concentrated in reduced pressure. The residue was subjected to azeotropic dehydration three times with pyridine (2 mL) and then dissolved in pyridine (2 mL). To the above reaction system was added triethylamine (0.35 g, 3.5 mmol) and triethylamine trihydrofluoride (0.28 g, 1.75 mmol) under nitrogen. The resulting mixture was stirred at 50° C. for 6 h. The solvent was concentrate under reduced pressure. The residue was adjust pH to 8 with aqueous solution of ammonium bicarbonate (1M), and then purified by prep-HPLC (separation method 3) to afford compound 3-p1 (di-ammonium salt, 0.7 mg, m/z: [M+H]$^+$ 723.8, HPLC-RT: 9.726 min) and a mixture of 3-p1/3-p2 (di-ammonium salt, 1.1 mg, m/z: [M+H]$^+$ 723.8, HPLC-RT: 9.726 min and 11.161 min).

Synthesis of Compound 3-p3

To a solution of compound 3-6-p3 (50 mg, 0.04 mmol) in acetonitrile (2 mL) was added tert-butylamine (2 mL). The mixture was stirred at room temperature for 0.5 h, and then concentrated under reduced pressure to afford compound 3-7-p3. To a solution of compound 3-7-p3 in methanol (2 mL) was added ammonium hydroxide solution (2 mL), the reaction system was stirred in a sealed tube at 45° C. for overnight, and then the reaction solution was directly concentrated under reduced pressure. The residue was subjected to azeotropic dehydration three times with pyridine (2 mL) and then dissolved in pyridine (2 mL). To the above reaction system was added triethylamine (0.35 g, 3.5 mmol) and triethylamine trihydrofluoride (0.28 g, 1.75 mmol) under nitrogen. The resulting mixture was stirred at 45° C. for 6 h. The solvent was concentrate under reduced pressure. The residue was adjust pH to 8 with aqueous solution of ammonium bicarbonate (1M), and then purified by prep-HPLC (separation method 3) to afford compound 3-p3 (di-ammonium salt, 2.2 mg, m/z: [M+H]$^+$ 723.7, HPLC-RT: 11.76 min) as a white solid.

Embodiment 6: Synthesis of Intermediate 4-3

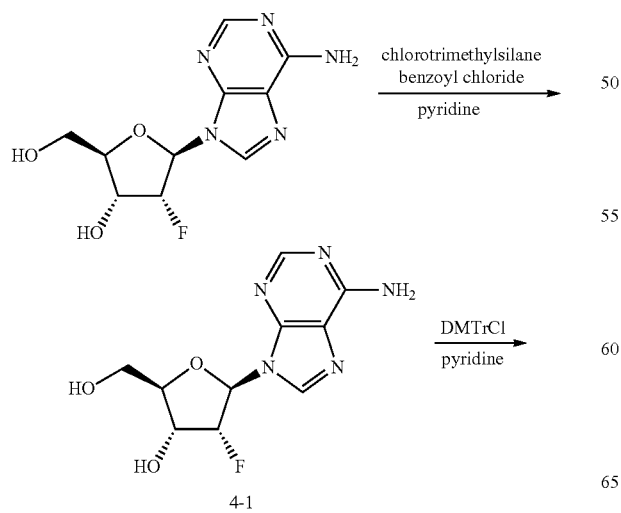

4-1

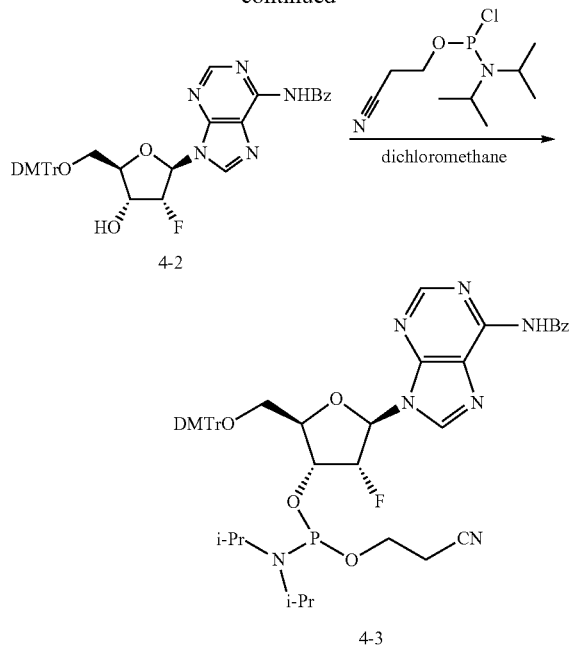

4-2

4-3

Step 1: To a solution of 2'-fluoro-2'-deoxyadenosine (CAS No.: 64183-27-3) (9.7 g, 36.0 mmol) in pyridine (110 mL) was added chlorotrimethylsilane (23.5 g, 216 mmol) at 0° C. under nitrogen. The mixture was stirred at room temperature for 2 h, and then benzoyl chloride (7.6 g, 54 mmol) was added thereto. The resulting mixture was stirred at room temperature for overnight. To the reaction solution was added water (40 mL) and stirred for 1 h, and then ammonium hydroxide solution (40 mL) was added thereto and stirred for additional 2 h. Additional water (40 mL) was added thereto, the mixture was extracted with ethyl acetate (500 mL×2), and the combined organic layers were dried over anhydrous sodium sulfate, and then concentrated to ⅕ of the total volume, filtered, the filter cake was dried under vacuum to afford intermediate 4-1 (10 g) as a white solid. m/z: [M+H]$^+$374.0.

Step 2: To a solution of intermediate 4-1 (1.2 g, 3.2 mmol) in pyridine (15 mL) was added DMTrCl (1.6 g, 4.8 mmol) under nitrogen. The reaction system was stirred at room temperature for overnight. To the reaction solution was added water (50 mL), the mixture was extracted with ethyl acetate (40 mL×3), and the combined organic layers were dried over anhydrous sodium sulfate and concentrated under reduced pressure. The residue was purified by Flash column chromatography (2% methanol/dichloromethane) to afford intermediate 4-2 (1.9 g) as a light yellow solid. m/z: [M+H]$^+$676.0.

Step 3: To a solution of intermediate 4-2 (1.35 g, 2 mmol) in dichloromethane (10 mL) was added N,N-diisopropylethylamine (1.1 mL, 6 mmol) and 2-cyanoethyl N,N-diisopropylchloro-phosphoramidite (947 mg, 4 mmol) at 0° C. under nitrogen. The resulting mixture was stirred at room temperature for 2 h. To the reaction solution was added water (50 mL) and saturated aqueous solution of sodium bicarbonate (20 mL). The resulting mixture was extracted with ethyl acetate (50 mL×3), and the combined organic layers were dried over anhydrous sodium sulfate, filtered and concentrated under reduced pressure. The residue was purified by Flash column chromatography (3% methanol/dichloromethane) to afford intermediate 4-3 (1.2 g) as a yellow solid. m/z: [M+H]$^+$876.1.

Embodiment 7: Synthesis of Compounds 4-p1, 4-p2 and 4-p3

Step 1: To a solution of intermediate 4-4 (4-4 was obtained as a mixture of stereoisomers in the same manner as Embodiment 4 steps 1-4, by using intermediates 4-3 and 2-8 as starting materials) (50 mg, 0.05 mmol) in acetonitrile (2 mL) was added tert-butylamine (2 mL). The resulting mixture was stirred at room

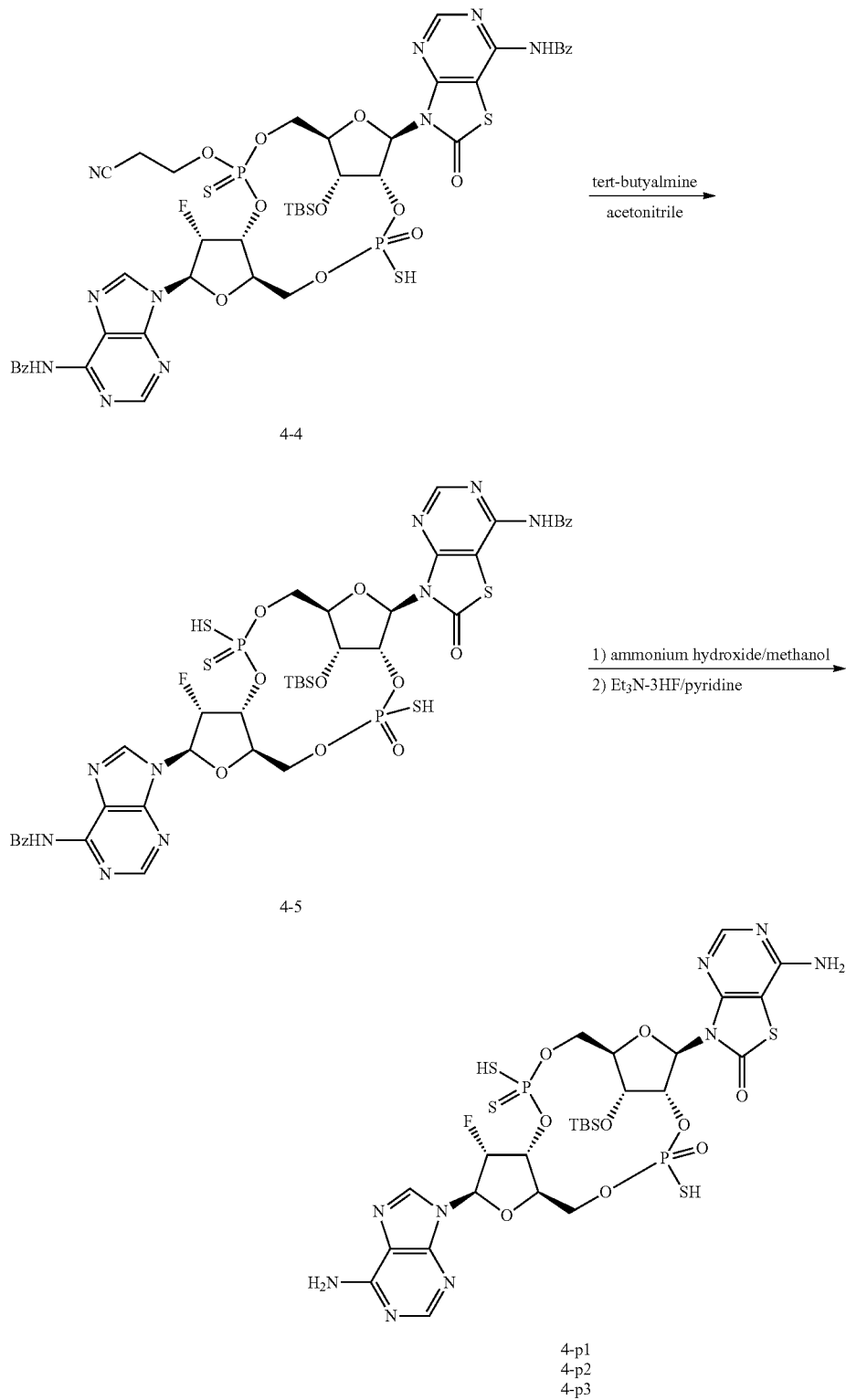

temperature for 0.5 h, and then concentrated under reduced pressure. The residue was purified by Flash column chromatography (acetonitrile/aqueous solution of ammonium bicarbonate (10 mmol/L)=10-80%) to afford compound 4-5 (15 mg) as a white solid. m/z: [M+H]$^+$1047.8.

Step 2: To the solution of compound 4-5 (30 mg, 0.03 mmol) in methanol (2 mL) was added ammonium hydroxide solution (2 mL), the reaction solution was stirred in a sealed tube at 45° C. for overnight, and then the solvent was concentrated in reduced pressure. The residue was subjected to azeotropic dehydration three times with anhydrous pyridine (2 mL) and then dissolved in pyridine (1 mL), and then triethylamine (0.91 g, 9 mmol) and triethylamine trihydrofluoride (0.58 g, 3.6 mmol) was added thereto under nitrogen. The resulting mixture was stirred at 50° C. for 6 h. The solvent was concentrate under reduced pressure. The residue was adjusted pH to 8 with ammonium hydroxide solution, and then directly purified by prep-HPLC (separation method 3) to afford compound 4-p1 (di-ammonium salt, 0.76 mg, m/z: [M+H]$^+$725.8, HPLC-RT: 9.04 min), 4-p2 (di-ammonium salt, 0.82 mg, m/z: [M+H]$^+$725.8, HPLC-RT: 10.45 min), and 4-p3 (di-ammonium salt, 0.97 mg, m/z: [M+H]$^+$725.8, HPLC-RT: 10.35 min), as white solids.

Embodiment 8: Synthesis of Compounds 5-p1, 5-p2, 5-p3 and 5-p4

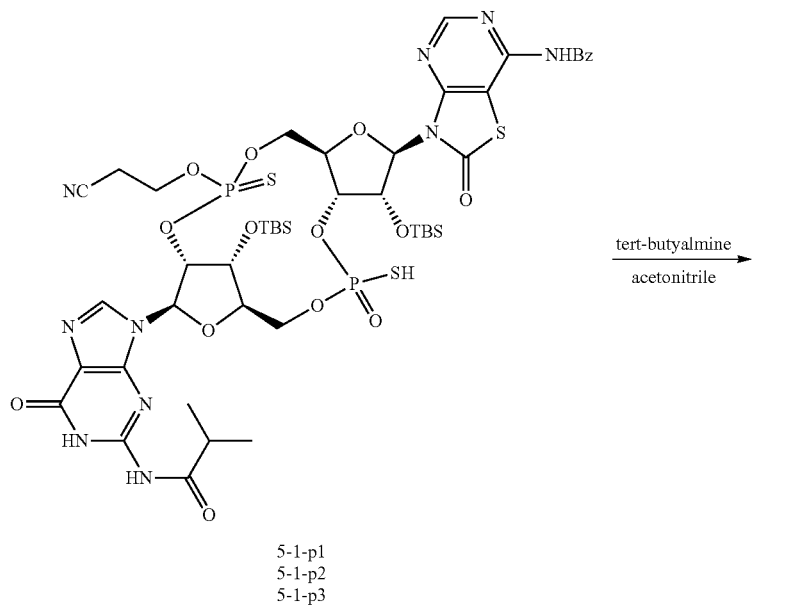

5-1-p1
5-1-p2
5-1-p3

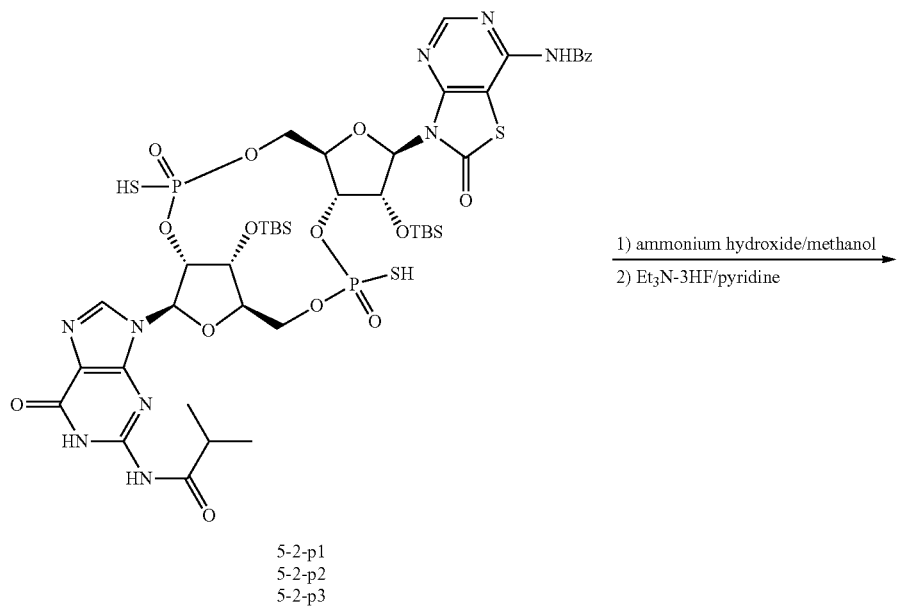

5-2-p1
5-2-p2
5-2-p3

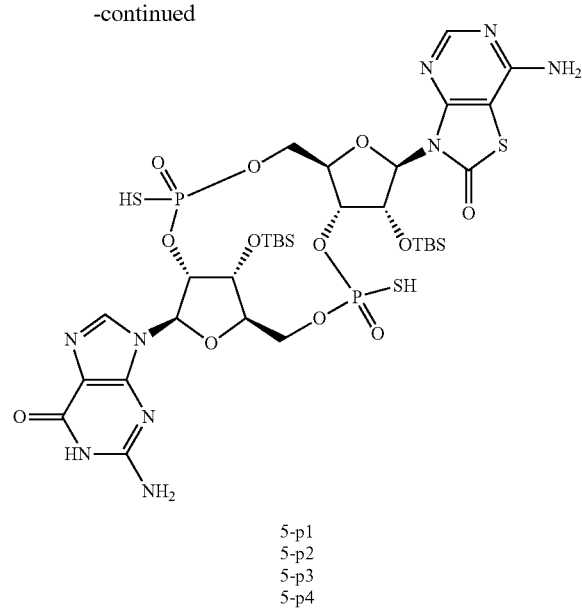

5-p1
5-p2
5-p3
5-p4

Step 1: To a solution of compound 5-1-p1 (5-1-p1, 5-2-p2 and 5-3-p3 were obtained in the same manner as Embodiment 4 steps 1-4, by using intermediates 3-2 and 3'-TBDMS—IBU-RG phosphoramidite (CAS No: 1445905-51-0) as starting materials, LCMS-RT (Thermo) of 5-1-p1, 5-2-p2 and 5-3-p3 were 2.11 min, 2.14 min and 2.31 min, respectively) (30 mg, 0.03 mmol) in acetonitrile (2 mL) was added tert-butylamine (2 mL). The resulting mixture was stirred at room temperature for 0.5 h, and then concentrated to afford compound 5-2-p1 (30 mg, crude product). m/z: [M+H]$^+$1141.6.

Step 2: To the solution of compound 5-2-p1 (30 mg, crude) in methanol (2 mL) was added ammonium hydroxide solution (2 mL), the reaction solution was stirred in a sealed tube at 45° C. for overnight, and then the solvent was concentrated in reduced pressure. The residue was subjected to azeotropic dehydration three times with anhydrous pyridine (2 mL) and then dissolved in pyridine (1 mL), and then triethylamine (0.35 g, 3.5 mmol) and triethylamine trihydrofluoride (0.28 g, 1.75 mmol) was added thereto under nitrogen. The resulting mixture was stirred at 50° C. for 6 h. The solvent was concentrate under reduced pressure. The residue was adjusted pH to 8 with ammonium hydroxide solution, and then directly purified by prep-HPLC (separation method 3) to afford compound 5-p1 (di-ammonium salt, 0.89 mg, m/z: [M+H]$^+$ 739.8, HPLC-RT: 6.495 min) as a white solid.

Synthesis of Compounds 5-p2 and 5-p3

Compounds 5-p2 (di-ammonium salt, 13 mg, m/z: [M+H]$^+$ 739.8, HPLC-RT: 10.666 min, $^1$H NMR (400 MHz, DMSO-d$_6$+D$_2$O): δ 8.22 (s, 1H), 8.10 (s, 1H), 5.99 (d, J=7.7 Hz, 1H), 5.85 (d, J=8.5 Hz, 1H), 5.34-5.28 (m, 1H), 5.21-5.25 (m, 1H), 5.12-5.16 (m, 1H), 4.43-4.31 (m, 1H), 4.16-4.12 (m, 1H), 4.08-4.06 (m, 1H), 4.01-3.97 (m, 2H), 3.66 (d, J=11.8 Hz, 1H), 3.59-3.55 (m, 1H); $^{31}$P NMR (162 MHz, DMSO-d$_6$): δ 59.36, 57.52) and 5-p3 (di-ammonium salt, 0.7 mg, m/z: [M+H]$^+$ 739.9, HPLC-RT: 10.663 min) were obtained as white solids in the same manner as compound 5-p1, by using compound 5-1-p2 (76.5 mg, crdue) as a starting material.

Synthesis of Compound 5-p4

Compounds 5-p4 (di-ammonium salt, 1.41 mg, m/z: [M+H]$^+$ 739.9, HPLC-RT: 11.973 min) was obtained as a white solid in the same manner as compound 5-p1, by using compound 5-1-p3 (100 mg, crude) as a starting material.

Embodiment 9: Synthesis of Intermediate 6-14

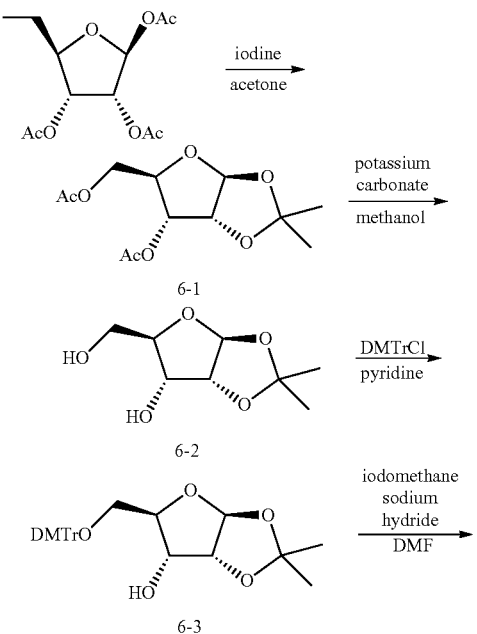

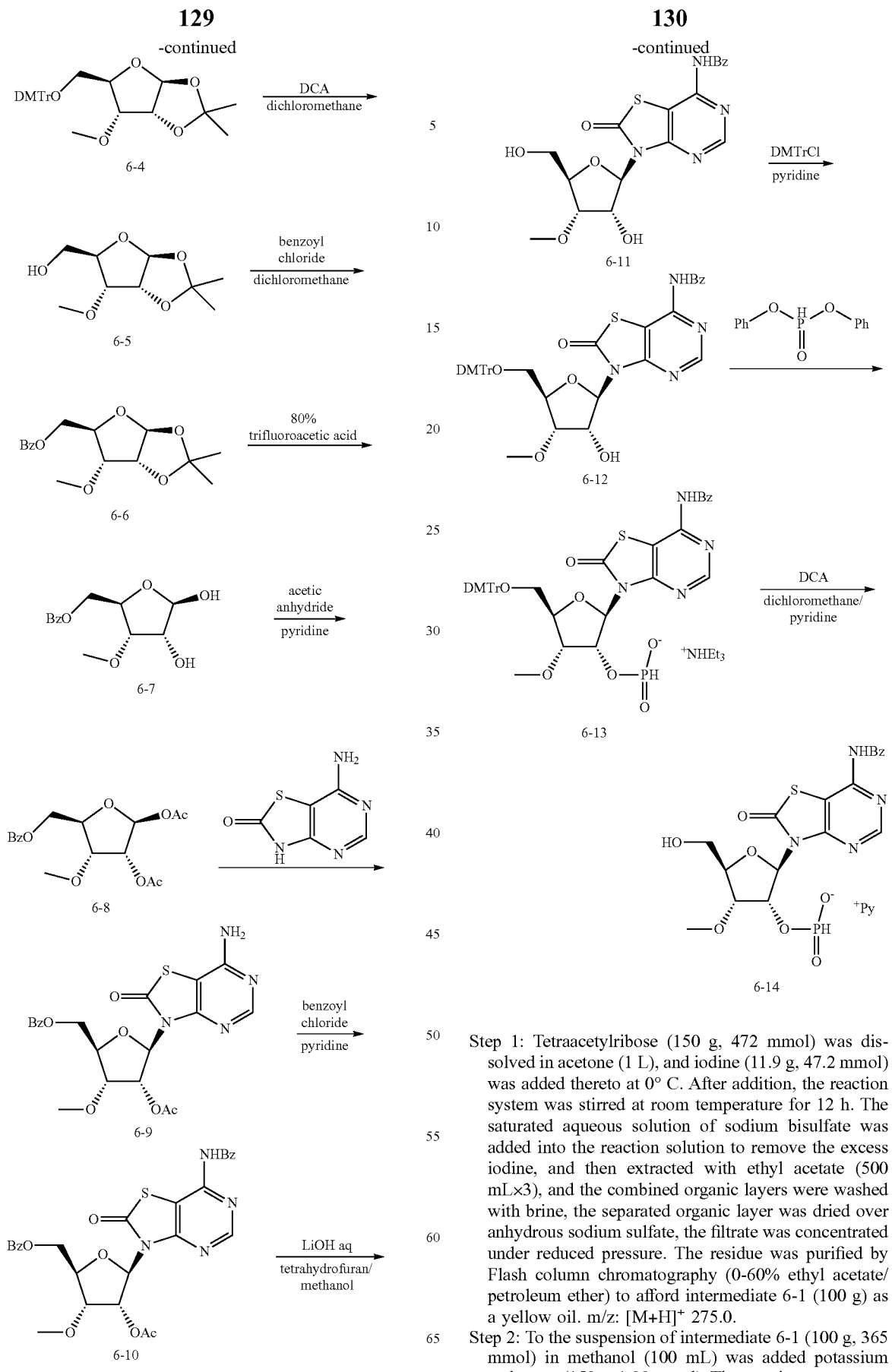

Step 1: Tetraacetylribose (150 g, 472 mmol) was dissolved in acetone (1 L), and iodine (11.9 g, 47.2 mmol) was added thereto at 0° C. After addition, the reaction system was stirred at room temperature for 12 h. The saturated aqueous solution of sodium bisulfate was added into the reaction solution to remove the excess iodine, and then extracted with ethyl acetate (500 mL×3), and the combined organic layers were washed with brine, the separated organic layer was dried over anhydrous sodium sulfate, the filtrate was concentrated under reduced pressure. The residue was purified by Flash column chromatography (0-60% ethyl acetate/petroleum ether) to afford intermediate 6-1 (100 g) as a yellow oil. m/z: [M+H]+ 275.0.

Step 2: To the suspension of intermediate 6-1 (100 g, 365 mmol) in methanol (100 mL) was added potassium carbonate (150 g, 1.09 mmol). The reaction system was stirred at room temperature for 12 h, and then filtered, the filtrate was concentrated under reduced pressure. The residue was purified by Flash column chromatography (0-10% methanol/dichloromethane) to afford intermediate 6-2 (60.3 g) as a white solid. m/z: [M+H]$^+$ 191.0.

Step 3: To a solution of intermediate 6-2 (60 g, 316 mmol) in pyridine (300 mL) was added DMTrCl (128 g, 379 mmol) in small portions at 0° C. under nitrogen. The reaction system was stirred at room temperature for 12 h and then quenched by addition of water (100 mL). The solvent was concentrate under reduced pressure. The residue was purified by Flash column chromatography (0-50% petroleum ether/ethyl acetate) to afford intermediate 6-3 (150.3 g) as a white solid.

Step 4: To a solution of intermediate 6-3 (150 g, 305 mmol) in DMF (500 mL) was added sodium hydride (18.3 g, 458 mmol, 60%) under nitrogen at 0° C. The reaction system was stirred at 0° C. for 0.5 h. To the reaction system was added iodomethane (56.3 g, 396 mmol) and stirred at room temperature for 3 h. The mixture was diluted with water (100 mL) and ethyl acetate (300 mL×3). The organic layer washed with brine, and then separated and dried over anhydrous sodium sulfate, the filtrate was concentrated under reduced pressure to afford intermediate 6-4 (150 g) as a white solid. m/z: [M+H]$^+$ 507.1.

Step 5: To a solution of intermediate 6-4 (150 g, 296 mmol) in dichloromethane (500 mL) was added DCA (344 g, 2.67 mol) at 0° C. The reaction system was stirred at 0° C. for 3 h, and then quenched by addition of saturated aqueous solution of sodium carbonate, the aqueous layer was extracted with dichloromethane (300 mL×3), the combined organic layers were washed with brine (150 mL×2), the separated organic layer was dried over anhydrous sodium sulfate, and then concentrated under reduced pressure. The residue was purified by Flash column chromatography (0-10% methanol/dichloromethane) to afford intermediate 6-5 (50.2 g) as a white solid. m/z: [M+H]$^+$205.0.

Step 6: To a solution of intermediate 6-5 (50 g, 245 mmol) in dichloromethane (500 mL) was added benzoyl chloride (41.2 g, 294 mmol) at 0° C. The reaction system was stirred at room temperature for 12 h, and then the reaction was quenched by addition of water, the aqueous layer was extracted with dichloromethane (150 mL×3), the combined organic layers were washed with brine (150 mL×2), the separated organic layer was dried over anhydrous sodium sulfate, filtered and concentrated under reduced pressure. The residue was purified by Flash column chromatography (0-70% petroleum ether/ethyl acetate) to afford intermediate 6-6 (65.3 g) as a white solid. m/z: [M+H]$^+$ 309.0.

Step 7: Intermediate 6-6 (65 g, 211 mmol) was dissolved in an aqueous solution of trifluoroacetic acid (150 mL, 80%), the reaction system was stirred at room temperature for 5 h. Most of the solvent was removed under reduced pressure, and then the reaction solution washed with saturated aqueous solution of sodium bicarbonate, the aqueous layer was extracted with dichloromethane (100 mL×3), the organic layer washed with brine (150 mL×2), the separated organic layer was dried over anhydrous sodium sulfate and concentrated under reduced pressure to afford intermediate 6-7 (50.2 g) as an off-white solid.

Step 8: To a solution of intermediate 6-7 (50 g, 187 mmol) in pyridine (150 mL) was slowly added acetic anhydride (114 g, 1.11 mol), the reaction system was stirred at room temperature for 12 h. Most of the solvent was removed under reduced pressure, and then the reaction solution washed with saturated aqueous solution of sodium bicarbonate, the aqueous layer was extracted with ethyl acetate (100 mL×3), the combined organic layers were washed with brine (100 mL×2), the separated organic layer was dried over anhydrous sodium sulfate, filtered, the filtrate was concentrated under reduced pressure. The residue was purified by Flash column chromatography (0-70% petroleum ether/ethyl acetate) to afford intermediate 6-8 (60.2 g) as an off-white solid.

Step 9: To a solution of 7-aminothiazolo[4,5-d]pyrimidin-2 (3H)-one (6.5 g, 38.7 mmol) and intermediate 6-8 (16.3 g, 46.4 mmol) in acetonitrile (120 mL) was added BSA (13.6 g, 116 mmol), the reaction system was stirred at reflux for 1 h. To the reaction solution was added TMSOTf (17.2 g, 77.4 mmol) after the reaction solution was cooled to room temperature and stirred at reflux for additional 72 h, and then to the reaction solution was slowly added saturated aqueous solution of sodium bicarbonate after the reaction solution was cooled to room temperature, and then the aqueous layer was extracted with ethyl acetate (150 mL×3), the combined organic layers were washed with water, the separated organic layer was dried over anhydrous sodium sulfate, filtered and concentrated. The residue was purified by Flash column chromatography (ethyl acetate/petroleum ether=3/4) to afford intermediate 6-9 (5 g) as a light yellow solid. m/z: [M+H]$^+$ 461.0.

Step 10: To a solution of intermediate 6-9 (5 g, 10.9 mmol) in pyridine (5 mL) was added benzoyl chloride (5.3 g, 38 mmol) at 0° C. The reaction system was stirred at room temperature for overnight, and then quenched by addition of water (50 mL), the aqueous layer was extracted with dichloromethane (150 mL×3), the combined organic layers were washed with water, the separated organic layer was dried over anhydrous sodium sulfate, filtered and concentrated. The residue was purified by Flash column chromatography (petroleum ether/ethyl acetate=1/1) to afford intermediate 6-10 (6.8 g) as a white solid. m/z: [M+H]$^+$ 669.1.

Step 11: To a solution of intermediate 6-10 (6.8 g, 10.1 mmol) in a mixed solvent of tetrahydrofuran and methanol (60/20 mL) was added aqueous solution of lithium hydroxide (36 mL, 1M) at 0° C., the reaction system was stirred at 0° C. for 2 h and then neutralized pH to 6 with acetic acid. The reaction solution was concentrated to ⅓ of the total volume, the solid was precipitated, filtered, the filter cake washed with water for 3 times, and then dried under vacuum to afford intermediate 6-11 (3.8 g) as a yellow solid. m/z: [M+H]$^+$419.0.

Step 12: To a solution of intermediate 6-11 (3.8 g, 9.09 mmol) in pyridine (60 mL) was added DMTrCl (3.6 g, 10.9 mmol) under nitrogen. The reaction system was stirred at room temperature for overnight. The solvent was concentrate under reduced pressure. The residue was purified by Flash column chromatography (petroleum ether/ethyl acetate=1/1) to afford intermediate 6-12 (6 g) as a light yellow solid.

Step 13: To a solution of intermediate 6-12 (5 g, 6.94 mmol) in pyridine (5 mL) was added diphenyl phosphite (4.9 g, 20.8 mmol), the reaction solution was stirred at room temperature for 1 h. Triethylamine (2 mL) and water (1 mL) was successively added thereto.

The reaction solution was stirred at room temperature for 5 min, and then diluted with water (50 mL) and extracted with dicholormethane (60 mL×3), the combined organic layers were washed with aqueous solution of sodium bicarbonate (5%), the separated organic layer was dried over anhydrous sodium sulfate, filtered and concentrated. The residue was purified by Flash column chromatography (methanol/dichloromethane=1/10) to afford intermediate 6-13 (5.1 g, triethylamine salt) as an off-white solid. m/z: [M+H]⁺886.3.

Step 14: To a solution of intermediate 6-13 (3 g, 3.39 mmol) in dichloromethane (20 mL) was added a dichloromethane solution of DCA (0.6M, 50 mL) at 0° C. The reaction mixture was stirred at room temperature for 1 h and then triethylsilane (1 mL) and pyridine (3 mL) were added thereto, the resulting mixture was stirred at room temperature for additional 10 min, the solvent was concentrated under reduced pressure to afford intermediate 6-14 (2.5 g, pyridinium salt).

Embodiment 10: Synthesis of Compounds 6-p1, 6-p2, 6-p3 and 6-p4

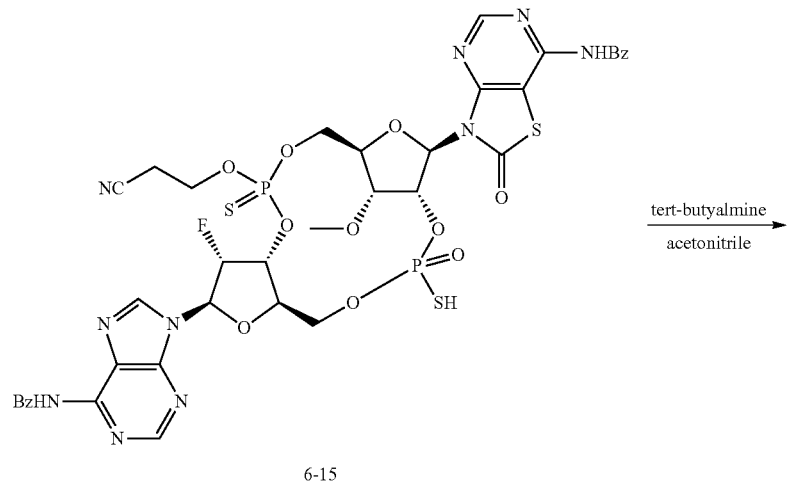

6-15

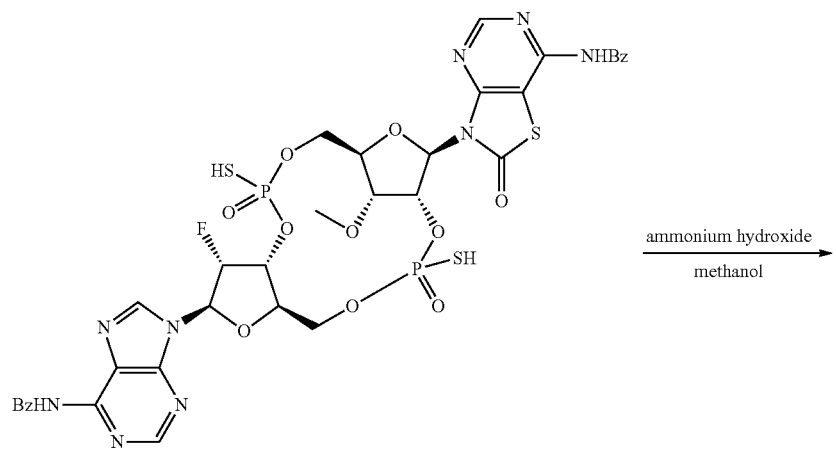

6-16

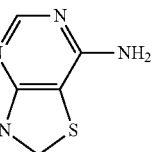
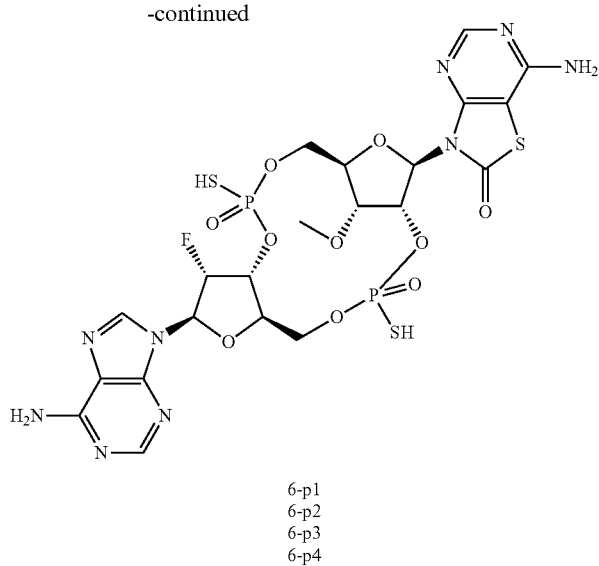

6-p1
6-p2
6-p3
6-p4

Step 1: To a solution of compound 6-15 (6-15 was obtained as a mixture of stereoisomers in the same manner as Embodiment 4 steps 1-4, by using intermediates 6-14 and 4-3 as starting materials) (50 mg, 0.05 mmol) in acetonitrile (2 mL) was added tert-butylamine (2 mL). The resulting mixture was stirred at room temperature for 0.5 h, and then concentrated under reduced pressure to afford compound 6-16 (40 mg). m/z: [M+H]$^+$948.0.

Step 2: To a solution of compound 6-16 (40 mg, crude) in methanol (1 mL) was added ammonium hydroxide solution (1 mL), the mixture was stirred in a sealed tube at 50° C. for 5 h, and then cooled to room temperature and quenched by addition of acetic acid, the mixture was lyophilized. The residue was purified by prep-HPLC (separation method 4) to afford compound 6-p1 (di-ammonium salt, 3.6 mg, m/z: [M+H]$^+$740.0, HPLC-RT: 10.814 min), 6-p2 (di-ammonium salt, 3.2 mg, m/z: [M+H]$^+$740.0, HPLC-RT: 11.380 min), 6-p3 (di-ammonium salt, 3.9 mg, m/z: [M+H]$^+$740.0, HPLC-RT: 10.370 min; $^1$H NMR (400 MHz, D$_2$O): δ 8.36 (s, 2H), 8.12 (s, 1H), 6.61 (s, 1H), 6.11 (s, 1H), 5.79 (s, 1H), 5.39 (d, J=51.6 Hz, 1H), 4.93-5.02 (m, 1H), 4.36-4.48 (m, 3H), 3.84-4.03 (m, 4H), 3.51 (s, 3H); $^{31}$P NMR (162 MHz, D$_2$O): δ 56.49, 51.13; $^{19}$F NMR (162 MHz, D$_2$O): δ–202.92) and 6-p4 (di-ammonium salt, 2.3 mg, m/z: [M+H]$^+$740.0, HPLC-RT: 11.650 min), as white solids.

Embodiment 11: Synthesis of Intermediate 7-1

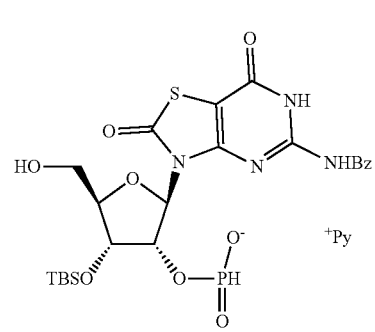

7-1

Intermediate 7-1 was obtained as a yellow solid in the same manner as Embodiment 3 intermediate 2-8, by using tetraacetylribose and 5-aminothiazolo[4,5-d]pyrimidine-2,7 (3H,6H)-dione (refer to J. Med. Chem. 1990, 33, 407-415, compound 4) as starting materials. m/z: [M+H]$^+$599.1.

Embodiment 12: Synthesis of Compounds 7-p1, 7-p2, 7-p3 and 7-p4
Step 1: To a solution of compound 7-2 (7-2 was obtained as a mixture of stereoisomers in the same manner as
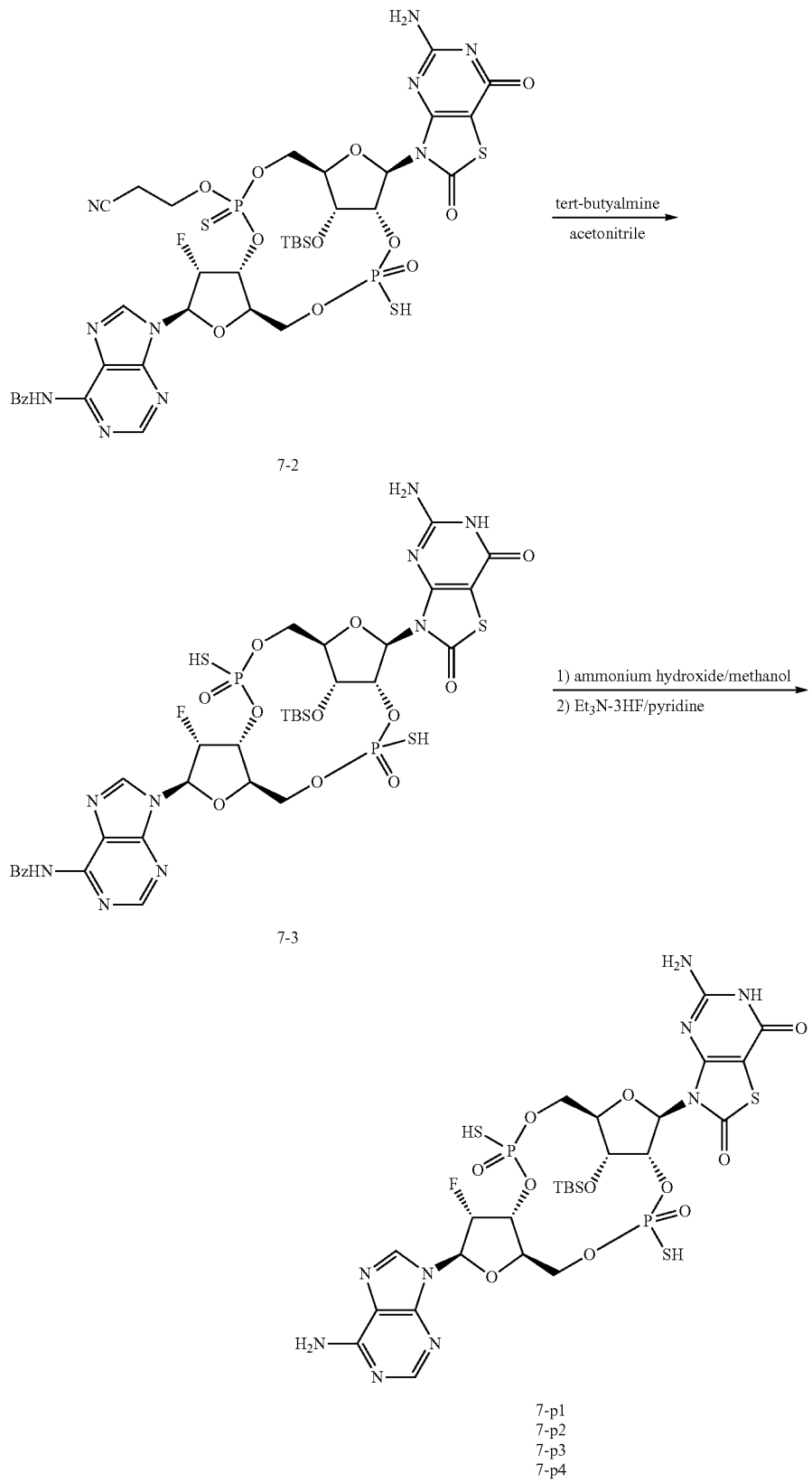

Embodiment 4 steps 1-4, by using intermediates 7-1 and 4-3 as starting materials) (330 mg, 0.3 mmol) in acetonitrile (2 mL) was added tert-butylamine (2 mL). The resulting mixture was stirred at room temperature for 1 h, and then concentrated under reduced pressure. The residue was purified by Flash column chromatography (acetonitrile/aqueous solution of ammonium bicarbonate (10 mmol/L)=0~60%) to afford compound 7-3 (100 mg) as a white solid. m/z: [M+H]$^+$1063.8.

Step 2: To the solution of compound 7-3 (100 mg, 94 mol) in methanol (2 mL) was added ammonium hydroxide solution (2 mL), the reaction solution was stirred in a sealed tube at 55° C. for 5 h, and then the solvent was concentrated in reduced pressure. The residue was subjected to azeotropic dehydration three times with anhydrous pyridine (2 mL) and then dissolved in pyridine (1 mL) and then triethylamine (1 mL) and triethylamine trihydrofluoride (0.5 mL) was added thereto under nitrogen. The resulting mixture was stirred at 50° C. for 3 h. The solvent was concentrate under reduced pressure. The residue was neutralized with ammonium hydroxide solution, and then directly purified by prep-HPLC (separation method 5) to afford compound 7-p1 (di-ammonium salt, 1.29 mg, m/z: [M+H]$^+$741.3, HPLC-RT: 9.058 min), 7-p2 (di-ammonium salt, 4.41 mg, m/z: [M+H]$^+$741.3, HPLC-RT: 9.590 min), 7-p3 (di-ammonium salt, 2.3 mg, m/z: [M+H]$^+$ 741.3, HPLC-RT: 10.438 min) and 7-p4 (di-ammonium salt, 24 mg, m/z: [M+H]$^+$741.7, HPLC-RT: 10.929 min), as white solids.

Embodiment 13: Synthesis of Compounds 8-p1, 8-p2, 8-p3 and 8-p4

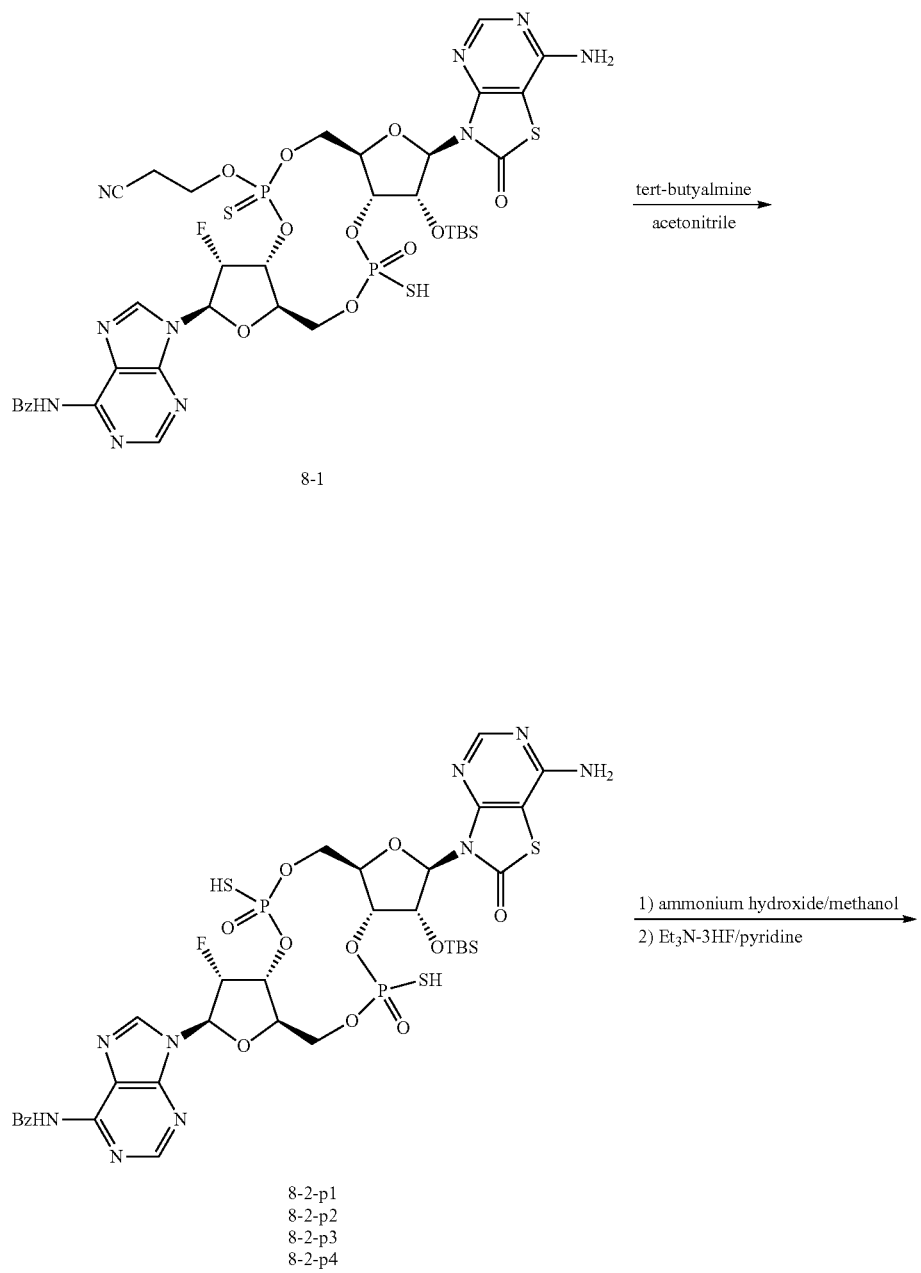

-continued

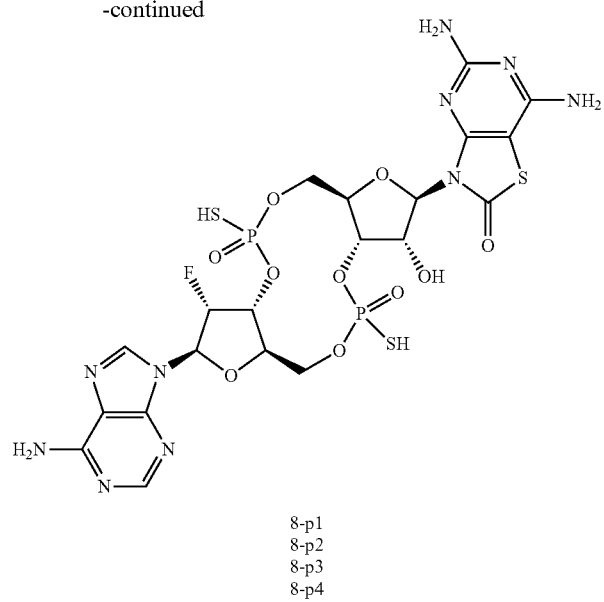

8-p1
8-p2
8-p3
8-p4

Step 1: To a solution of compound 8-1 (8-1 was obtained as a mixture of stereoisomers in the same manner as Embodiment 4 steps 1-4, by using intermediates 2-9 and 4-3 as starting materials) (618 mg, 0.61 mmol) in acetonitrile (3 mL) was added tert-butylamine (3 mL). The resulting mixture was stirred at room temperature for 1 h, and then concentrated under reduced pressure. The residue was purified by Flash column chromatography (acetonitrile/aqueous solution of ammonium bicarbonate (10 mmol/L)=10~80%) to afford compounds 8-2-p1 (67 mg), 8-2-p2 (40 mg), 8-2-p3 (40 mg), and 8-2-p4 (87 mg), as white solids. m/z: [M+H]$^+$ 1047.7.

Step 2: To a solution of compound 8-2-p1 (50 mg, 52 mol) in methanol (1 mL) was added ammonium hydroxide solution (1 mL), the reaction solution was stirred in a sealed tube at 50° C. for 4 h, and then the solvent was concentrated in reduced pressure. The residue was subjected to azeotropic dehydration three times with anhydrous pyridine (1 mL) and then dissolved in pyridine (1 mL) and then triethylamine (1 mL) and triethylamine trihydrofluoride (0.5 mL) was added thereto under nitrogen. The resulting mixture was stirred at 55° C. for 4 h. The solvent was concentrate under reduced pressure. The residue was neutralized with ammonium hydroxide solution, and then directly purified by prep-HPLC (separation method 5) to afford compound 8-p1 (di-ammonium salt, 7 mg, m/z: [M+H]$^+$725.5, HPLC-RT: 11.702 min) as a white solid.

Synthesis of Compound 8-p2

Compound 8-p2 (di-ammonium salt, 1.98 mg, m/z: [M+H]$^+$ 725.6, HPLC-RT: 10.602 min) was obtained as a white solid in the same manner as compound 8-p1, by using compound 8-2-p2 (40 mg, 0.04 mmol) as a starting material.

Synthesis of Compound 8-p3

Compound 8-p3 (di-ammonium salt, 1.1 mg, m/z: [M+H]$^+$726.1, HPLC-RT: 10.556 min) was obtained as a white solid in the same manner as compound 8-p1, by using compound 8-2-p3 (40 mg, 0.04 mmol) as a starting material.

Synthesis of Compound 8-p4

Compound 8-p4 (di-ammonium salt, 7.5 mg, m/z: [M+H]$^+$725.6, HPLC-RT: 12.102 min) was obtained as a white solid in the same manner as compound 8-p1, by using compound 8-2-p4 (80 mg, 0.08 mmol) as a starting material.

Embodiment 14: Synthesis of Intermediates 9-4 and 9-5

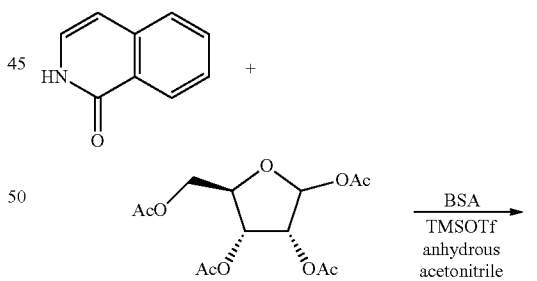

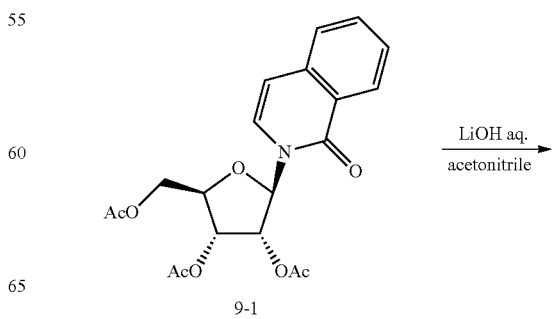

9-1

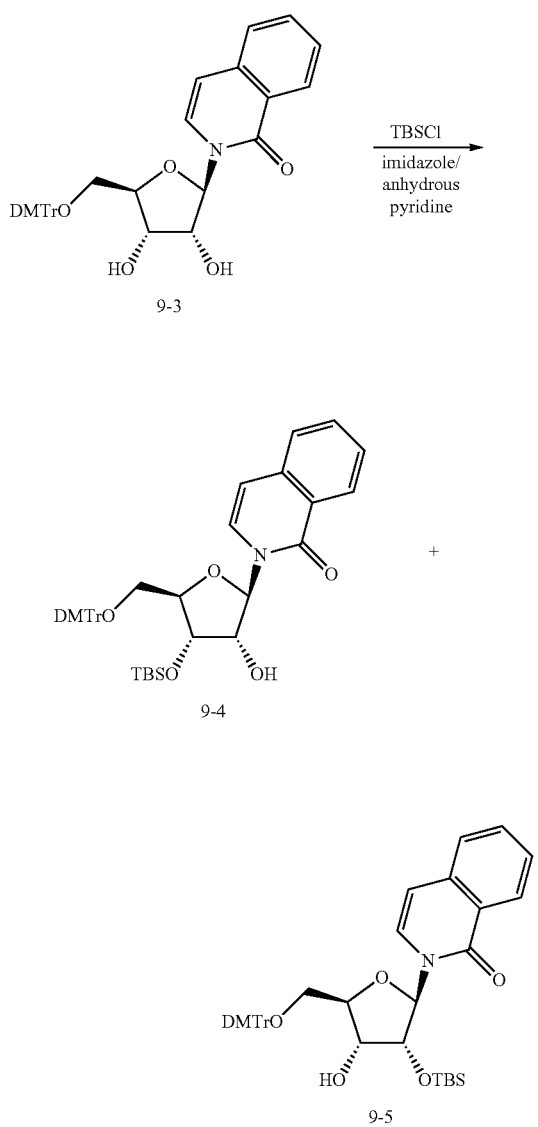

Step 1: The solution of isocarbostyril (25 g, 172 mmol), tetraacetylribose (137 g, 431 mmol) and BSA (105 g, 517 mmol) in anhydrous acetonitrile was stirred at reflux for 1 h, and then TMSOTf (62 mL, 344 mmol) was added thereto after the reaction solution was cooled to room temperature, the mixture was stirred at reflux for additional 5 h, saturated aqueous solution of sodium bicarbonate was slowly added thereto to adjusted pH to about 7 after the reaction solution was cooled to room temperature, the aqueous layer was extracted with ethyl acetate (150 mL×3), the combined organic layers were washed with water, the separated organic layer was dried over anhydrous sodium sulfate, filtered and concentrated. The residue was purified by Flash column chromatography (petroleum ether/ethyl acetate=2/1) to afford intermediate 9-1 (41.1 g) as an orange oil. m/z: $[M+H]^+$ 404.0.

Step 2: To a solution of intermediate 9-1 (41.1 g, 102 mmol) in acetonitrile (300 mL) was added aqueous solution of lithium hydroxide (510 mL, 1M), and then the reaction system was stirred at room temperature for 1.5 h. An amount of white solid was precipitated, filtered, the filter cake washed with water for 3 times, and then dried under vacuum to afford intermediate 9-2 (18.5 g) as a white solid. m/z: $[M+H]^+$ 278.0.

Step 3: Intermediate 9-2 (17.5 g, 63.1 mmol) was subjected to azeotropic dehydration three times with anhydrous pyridine and then dissolved in pyridine (100 mL) under nitrogen. To the above reaction solution was added pyridine solution of DMTrCl (22.5 g, 66.3 mmol, 50 mL) at 0° C. The resulting mixture was stirred at this temperature for 3 h. The reaction was quenched by addition of water (50 mL), the aqueous layer was extracted with ethyl acetate (100 mL×2), and the combined organic layers were concentrated under reduced pressure. The residue was purified by Flash column chromatography (petroleum ether/ethyl acetate=1/1) to afford intermediate 9-3 (32.6 g) as an off-white solid. m/z: $[M+Na]^+$ 602.0.

Step 4: Intermediate 9-3 (12 g, 20.7 mmol) and imidazole (4.9 g, 72.5 mmol) were subjected to azeotropic dehydration three times with anhydrous pyridine and then dissolved in pyridine (50 mL) under nitrogen, TBSCl (3.4 g, 22.8 mmol) was added thereto at 0° C. The reaction system was stirred at room temperature for overnight, and water (50 mL) was added thereto, the aqueous layer was extracted with ethyl acetate (100 mL×2), the combined organic layers were washed with water, dried over anhydrous sodium sulfate, filtered and concentrated, the residue was purified by Flash column chromatography (petroleum ether/ethyl acetate=10/1-6/1) to afford intermediates 9-4 (4.3 g, off-white solid, less polar) 9-5 (3.5 g, off-white solid, more polar). 9-4: m/z: $[M+Na]^+$ 716.0; $^1$H NMR (400 MHz, DMSO-$d_6$): δ 8.28 (d, J=8.4 Hz, 1H), 7.71 (t, J=8.0 Hz, 2H), 7.65 (d, J=8.0 Hz, 1H), 7.53-7.45 (m, 3H), 7.36-7.32 (m, 6H), 7.26 (t, J=8.0 Hz, 1H), 6.93 (d, J=8.4 Hz, 4H), 6.46 (d, J=8.0 Hz, 1H), 6.29 (d, J=4.0 Hz, 1H), 5.14 (d, J=6.0 Hz, 1H), 4.28-4.26 (m, 1H), 4.20-4.16 (m, 1H), 4.14-4.20 (m, 1H), 4.05-4.00 (m, 1H), 3.74 (s, 6H), 3.37-3.35 (m, 1H), 0.82 (m, 9H), 0.03 (s, 3H), 0.01 (s, 3H); 9-5: m/z: $[M+Na]^+$ 716.0; $^1$H NMR (400 MHz, DMSO-$d_6$): δ 8.27 (d, J=8.0 Hz, 1H), 7.75-7.70 (m, 2H), 7.66-7.64 (m, 1H), 7.52 (t, J=8.0 Hz, 1H), 7.45-7.43 (m, 2H), 7.35-7.25 (m, 7H), 6.92 (d, J=8.4 Hz, 4H), 6.50 (d, J=7.6 Hz, 1H), 6.27 (d, J=3.6 Hz, 1H), 5.39 (d, J=6.0 Hz, 1H), 4.28-4.26 (m, 1H), 4.05-4.00 (m, 2H), 3.74 (s, 6H), 3.46-3.44 (m, 1H), 3.22-3.18 (m, 1H), 0.78 (m, 9H), 0.03 (s, 3H), 0.01 (s, 3H).

Embodiment 15: Synthesis of Compounds 9-p1, 9-p2 and 9-p3
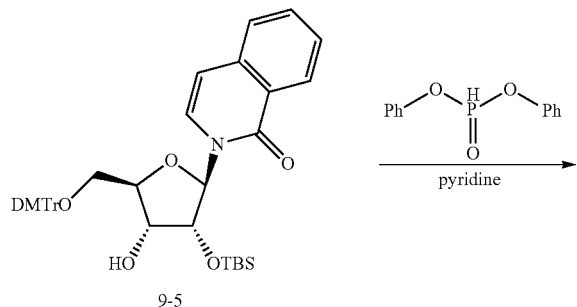
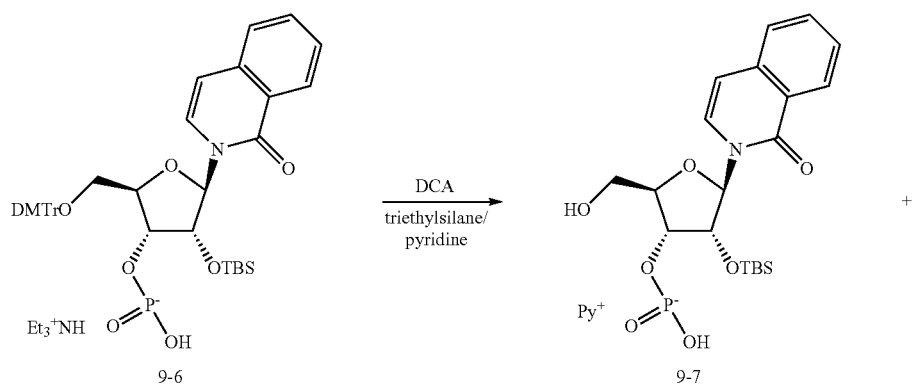
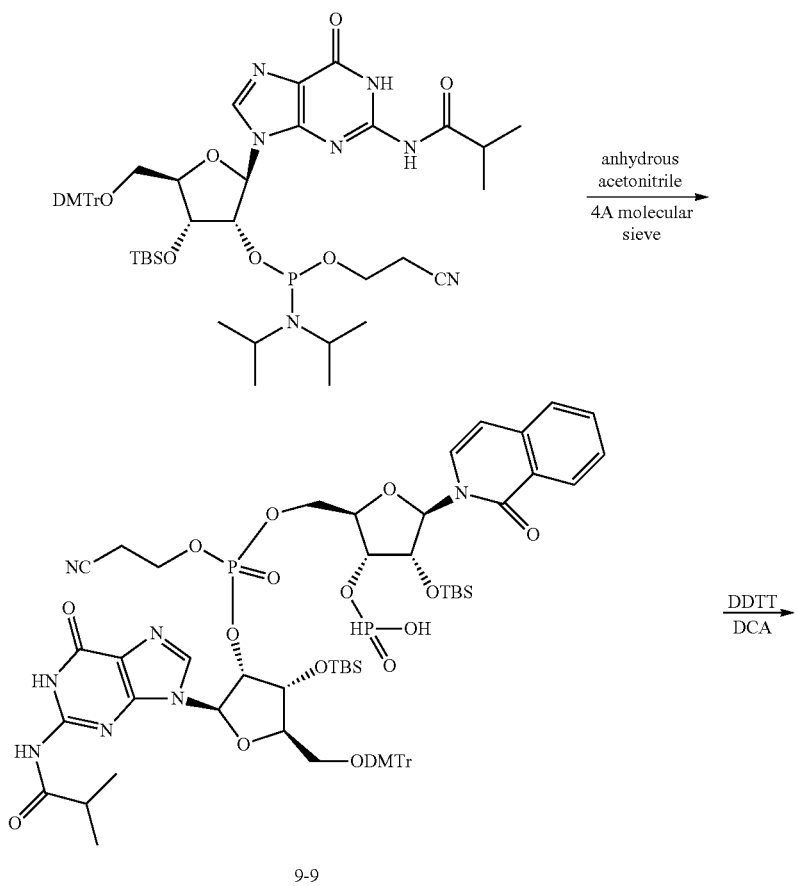

147 148

-continued

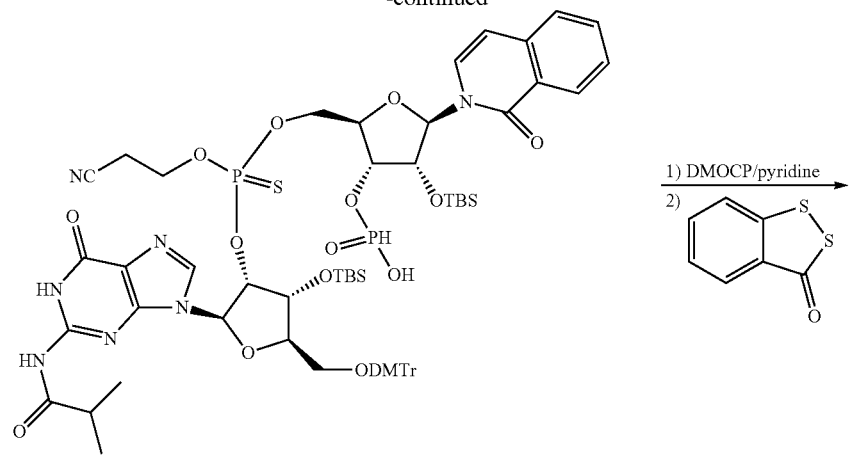

9-10

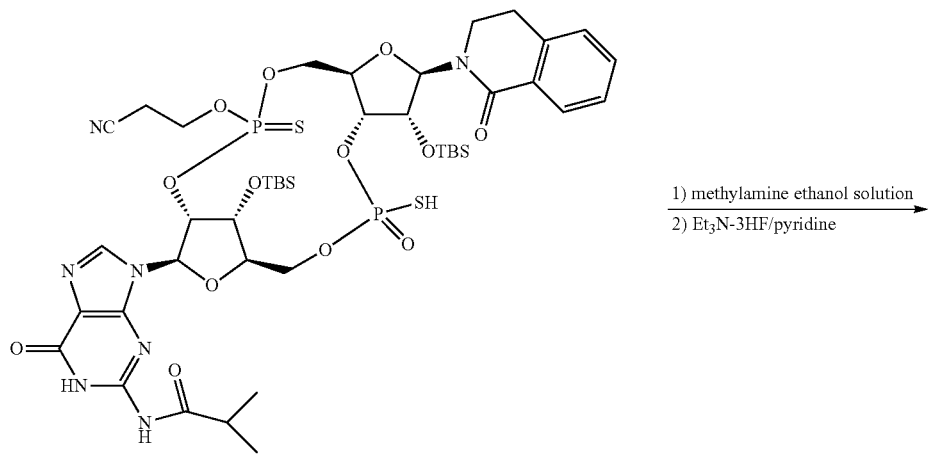

9-11-p1
9-11-p2
9-11-p3

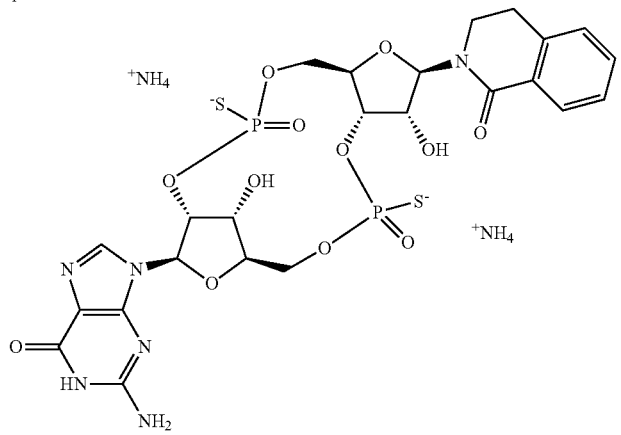

9-p1
9-p2
9-p3

Step 1: To a solution of intermediate 9-5 (3.1 g, 4.47 mmol) in pyridine (20 mL) was added diphenyl phosphite (3.1 g, 13.4 mmol) at 0° C. under nitrogen, the reaction system was stirred for 0.5 h, and then triethylamine (3 mL) and water (3 mL) was added thereto. The resulting mixture was stirred at room temperature for 5 min and then diluted with water (50 mL), extracted with propan-2-ol/chloroform (30 mL×2), the combined organic layers were washed with water, the separated organic layer was dried over anhydrous sodium sulfate, filtered and concentrated. The residue was purified by Flash column chromatography (dichloromethane/methanol/triethylamine=100/5/1) to afford compound 9-6 (4.5 g, triethylamine salt) as an off-white solid. m/z: [M−H]⁻756.0.

Step 2: To a solution of compound 9-6 (3 g, 3.49 mmol) in a mixed solvent of dichloromethane (28 mL) and water (1 mL) was added dichloromethane solution of DCA (0.6 M, 46.5 mL). The mixture was stirred at room temperature for 30 min, to the the reaction solution was added triethylsilane (28 mL) and stirred for additional 1 h. When the color of the reaction solution changes from brown to colorless, pyridine (28 mL) was added thereto, the solvent was concentrated under reduced pressure to afford compound 9-7 (3 g, pyridinium salt, curd product). m/z: [M+H]⁺445.0.

Step 3&4: Compound 9-7 (3 g, crude) was dissolved in anhydrous acetonitrile (15 mL) and then concentrated under reduced pressure, repeated three times. The residue was dissolved in acetonitrile (50 mL), and 4 Å molecular sieve (1 g) was added thereto. 3'-TBDMS-ibu-rG Phosphoramidite (CAS No.: 1445905-51-0, 3.4 g, 3.49 mmol) was dissolved in anhydrous acetonitrile (15 mL) and concentrated under reduced pressure, repeated three times. The residue was dissolved in acetonitrile (20 mL), and 4 Å molecular sieve (2 g) was added thereto. To a solution of 9-7 in acetonitrile was slowly added the acetonitrile solution of 3'-TBDMS-ibu-rG Phosphoramidite at 0° C., the resulting mixture was stirred at room temperature for 0.5 h, and then DDTT (697 mg, 3.42 mmol) was added thereto and stirred at room temperature for additional 3 h. The molecular sieve was removed by filtration. To the mixtue was added water (1 mL) and then slowly added DCA (3.6 g, 27.9 mmol) dropwise, the resulting mixture was stirred at room temperature for 2 h, triethylsilane (28 mL) was added thereto and stirred for additional 1 h, pyridine (28 mL) was added thereto, and the reaction solution was concentrated under reduced pressure. The residue was purified by Flash column chromatography (acetonitrile/aqueous solution of ammonium bicarbonate (10 mmol/L)=50%) to afford compound 9-10 (680 mg) as a white solid. m/z: [M+H]⁺1053.9.

Step 5: To a solution of compound 9-10 (200 mg, 0.19 mmol) in anhydrous pyridine (8 mL) was added DMOPC (0.7 g, 3.8 mmol) for one charge, the mixture was stirred at room temperature for 0.5 h, to the above reaction solution was added 3H-1,2-benzodithiol-3-one (38 mg, 0.23 mmol), and then stirred at room temperature for 0.5 h, the reaction was quenched by addition of aqueous solution of sodium bicarbonate (2.7%). The mixture was extracted with ethyl acetate (50 mL×2), and the combined organic layers were washed with brine, dried over anhydrous sodium sulfate, filtered and concentrated under reduced pressure. The residue was purified by prep-HPLC (separation method 5) to afford compound 9-11-p1 (13.5 mg, LCMS-RT (Thermo): 2.023 min), 9-11-p2 (30.2 mg, LCMS-RT (Thermo): 2.157 min), and 9-11-p3 (38.0 mg, LCMS-RT (Thermo): 2.300 min), as white solids. m/z: [M+H]⁺ 1067.9.

Step 6: Compound 9-11-p1 (10 mg, 0.094 mmol) was dissolved in methylamine ethanol solution (1 mL, 30%) and stirred at room temperature for 1 h, and then concentrated under reduced pressure, the residue was dissolved in pyridine (0.5 mL), triethylamine (0.5 mL) and triethylamine trihydrofluoride (0.25 mL) was added thereto, the reaction system was stirred at 50° C. for 5 h and then concentrated under reduced pressure. The residue was diluted with methanol, and then ammonium hydroxide solution was slowly dropped to adjusted pH to 8-9. The resulting mixture was purified by prep-HPLC (separation method 5) to afford compound 9-p1 (4.07 mg, HPLC-RT: 11.311 min; m/z: [M+H]⁺716.8; ¹H NMR (400 MHz, DMSO-d₆): δ 8.26 (d, J=6.0 Hz, 1H), 8.19 (s, 1H), 7.73 (t, J=7.6 Hz, 1H), 7.68 (d, J=8.0 Hz, 1H), 7.53 (t, J=8.0 Hz, 1H), 7.42 (d, J=7.6 Hz, 1H), 6.69 (d, J=7.6 Hz, 1H), 6.51-6.47 (m, 2H), 6.22 (d, J=4.0 Hz, 1H), 5.90-5.82 (m, 2H), 5.52-5.51 (m, 1H), 5.08-5.06 (m, 1H), 4.95-4.90 (m, 1H), 4.88-4.86 (m, 1H), 4.65-4.61 (m, 1H), 4.57-4.55 (m, 1H), 4.40-4.36 (m, 2H), 4.25-4.19 (m, 2H), 4.10-3.99 (m, 2H), 3.94-3.87 (m, 2H); ³¹P NMR (162 MHz, DMSO-d₆): δ 56.49, 54.10) a as white solid.

Synthesis of Compounds 9-p2

Compound 9-p2 (4.45 mg, HPLC-RT: 11.389 min; m/z: [M+H]⁺706.8; ¹H NMR (400 MHz, DMSO-d₆): δ 8.26 (d, J=8.0 Hz, 1H), 8.02 (s, 1H), 7.74 (t, J=7.2 Hz, 1H), 7.67 (d, J=7.6 Hz, 1H), 7.53 (t, J=7.6 Hz, 1H), 7.37 (d, J=7.6 Hz, 1H), 6.91-6.34 (m, 4H), 5.87-5.85 (m, 1H), 5.37-5.19 (m, 2H), 4.38-4.37 (m, 1H), 4.21-4.19 (m, 1H), 4.11-4.05 (m, 2H), 3.74-3.70 (m, 1H), 3.01-2.99 (m, 8H); ³¹P NMR (162 MHz, DMSO-d₆): δ 59.18, 56.65, 54.32, 47.74) was obtained as a white solid in the same manner as compound 9-p1, by using compound 9-11-p2 as a starting material and purified by prep-HPLC (separation method 5).

Synthesis of Compounds 9-p3

Compound 9-p3 (7.0 mg, HPLC-RT: 10.912 min; m/z: [M+H]⁺ 716.8; ¹H NMR (400 MHz, DMSO-d₆): δ 8.26 (d, J=8.0 Hz, 1H), 7.97 (s, 1H), 7.73 (t, J=7.6 Hz, 1H), 7.65 (d, J=7.6 Hz, 1H), 7.53 (t, J=7.6 Hz, 1H), 7.44 (d, J=7.6 Hz, 1H), 6.62 (d, J=8.0 Hz, 1H), 6.56-6.52 (m, 1H), 6.33 (d, J=6.8 Hz, 1H), 5.86 (d, J=8.4 Hz, 1H), 5.27-5.23 (m, 1H), 5.06-5.04 (m, 2H), 4.46-4.40 (m, 2H), 4.22-4.18 (m, 1H), 4.12-4.08 (m, 2H), 3.96-3.92 (m, 2H), 3.78-3.75 (m, 1H), 3.01-2.95 (m, 4H); ³¹P NMR (162 MHz, DMSO-d₆): δ 57.77, 50.27) was obtained as a white solid in the same manner as compound 9-p1, by using compound 9-11-p3 as a starting material, and purified by prep-HPLC (separation method 5).

Embodiment 16: Synthesis of Compounds 10-p1, 10-p2 and 10-p3

Synthesis of Intermediates 10-4 and 10-5

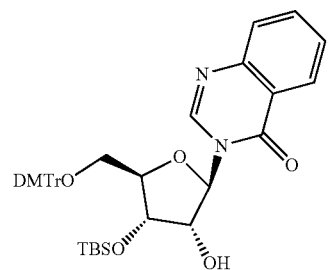

10-4

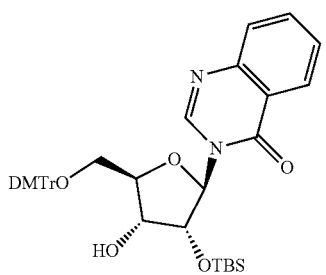
Intermediates 10-4 (2.0 g, more polar) and 10-5 (3.4 g, less polar) were obtained as white solids in the same manner as compounds 9-4 and 9-5, by using quinazolin-4 (3H)-one as a starting material. m/z: [M+H]$^+$ 695.0; 10-4: $^1$H NMR (400 MHz, DMSO-d$_6$): δ 8.50 (s, 1H), 8.16 (d, J=8.0 Hz, 2H), 7.86-7.82 (m, 1H), 7.67 (d, J=8.0 Hz, 2H), 7.58-7.54 (m, 1H), 7.40 (d, J=8.0 Hz, 2H), 7.31-7.22 (m, 7H), 6.89-6.87 (m, 4H), 6.09 (d, J=4.0 Hz, 1H), 5.10 (d, J=8.0 Hz, 1H), 4.38-4.36 (m, 1H), 4.13-4.09 (m, 2H), 3.72 (s, 6H), 0.81 (s, 9H), 0.01-0.00 (s, 6H); 10-5: $^1$H NMR (400 MHz, DMSO-d$_6$): δ 8.53 (s, 1H), 8.15 (d, J=8.0 Hz, 1H), 7.86-7.82 (m, 1H), 7.67 (d, J=8.0 Hz, 1H), 7.58-7.54 (m, 1H), 7.41-7.39 (m, 2H), 7.30-7.19 (m, 7H), 6.85 (d, J=8.0 Hz, 4H), 6.06-6.05 (m, 1H), 5.36 (d, J=8.0 Hz, 1H), 4.31-4.26 (m, 2H), 4.02-4.00 (m, 1H), 3.71 (s, 6H), 0.79 (s, 9H), 0.02-0.00 (s, 6H).
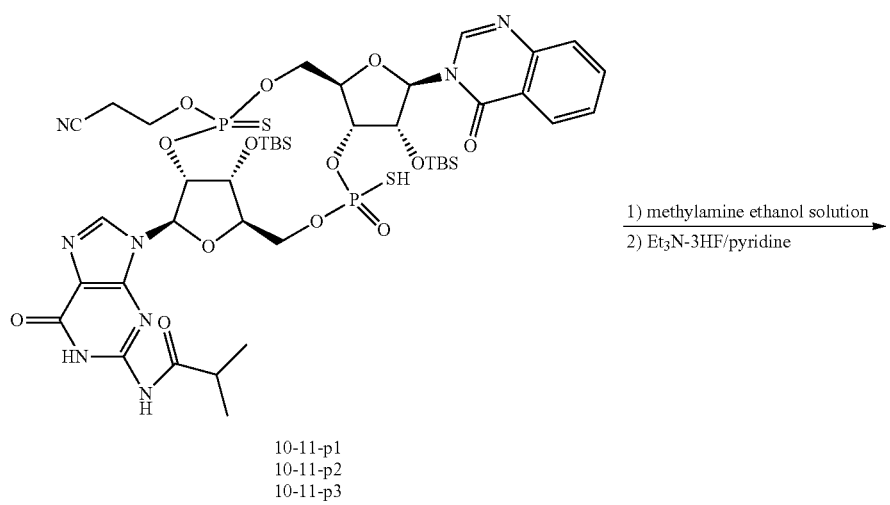
10-11-p1
10-11-p2
10-11-p3
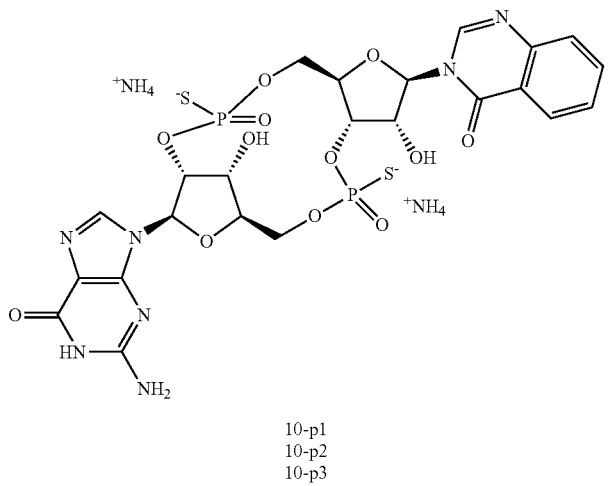
10-p1
10-p2
10-p3

Synthesis of compounds 10-11-p1, 10-11-p2 and 10-11-p3: compounds 10-11-p1 (7.0 mg, LCMS-RT (Thermo): 2.020 min), 10-11-p2 (26 mg, LCMS-RT (Thermo): 2.170 min) and 10-11-p3 (19 mg, LCMS-RT (Thermo): 2.350 min) were obtained as white solids in the same manner as Embodiment 15 steps 1-5, by using compound 10-5 as a starting material, and purified by prep-HPLC (separation method 6). m/z: [M+H]$^+$1068.9.

Synthesis of Compound 10-p1

To compound 10-11-p1 (7.0 mg, 0.006 mmol) was added methylamine ethanol solution (1 mL, 30%), the reaction system was stirred at room temperature for 1 h and then concentrated under reduced pressure, the residue was dissolved in anhydrous pyridine (0.5 mL), triethylamine (0.5 mL) and triethylamine trihydrofluoride (0.25 mL) was added thereto under nitrogen, the reaction solution was stirred at 50° C. for 1 h. The solvent was concentrated under reduced pressure, the residue was diluted with methanol, and then ammonium hydroxide solution was slowly dropped to adjusted pH to 8-9. The mixture was purified by prep-HPLC (separation method 4) to afford compound 10-p1 (0.73 mg, HPLC-RT: 10.671 min, m/z: [M+H]$^+$ 717.8) as a white solid.

Synthesis of Compound 10-p2

Compound 10-p2 (7.10 mg, HPLC-RT: 10.826 min; m/z: [M+H]$^+$ 717.8; $^1$H NMR (400 MHz, DMSO-$d_6$): δ 8.41 (s, 1H), 8.25-8.20 (m, 1H), 8.03 (s, 1H), 7.89-7.85 (m, 1H), 7.72-6.69 (m, 1H), 7.61-7.57 (m, 1H), 7.61-7.57 (m, 1H), 6.52-6.48 (m, 2H), 6.07-6.00 (m, 1H), 5.91-5.79 (m, 1H), 0.56 (s, 1H), 5.34-5.30 (m, 1H), 5.20-5.19 (m, 1H), 5.09-5.01 (m, 1H), 4.70-4.64 (m, 1H), 4.36-4.33 (m, 1H), 4.27-4.18 (m, 1H), 4.14-4.05 (m, 2H), 3.95-3.70 (m, 3H), 1.24 (s, 2H)) was obtained as a white solid in the same manner as compound 10-p1, by using compound 10-11-p2 as a starting material, and purified by prep-HPLC (separation method 4).

Synthesis of Compound 10-p3

Compound 10-p3 (5.46 mg, HPLC-RT: 10.925 min; m/z: [M+H]$^+$ 717.8; $^1$H NMR (400 MHz, DMSO-$d_6$): δ 8.44 (s, 1H), 8.22-8.20 (m, 1H), 7.99 (s, 1H), 7.89-7.85 (m, 1H), 7.68 (d, J=8.0 Hz, 1H), 7.61-7.57 (m, 1H), 6.56 (s, 2H), 6.09 (d, J=4.0 Hz, 2H), 5.83 (d, J=8.0 Hz, 1H), 5.34-5.32 (m, 1H), 5.26 (s, 1H), 5.08 (m, 1H), 4.71-4.68 (m, 1H), 4.46-4.45 (m, 1H), 4.25 (m, 1H), 4.14-3.95 (m, 5H), 3.79-3.76 (m, 1H), 1.24 (s, 2H).) was obtained as a white solid in the same manner as compound 10-p1, by using compound 10-11-p3 as a starting material, and purified by prep-HPLC (separation method 4).

Embodiment 17: Synthesis of Compounds 11-p1, 11-p2, 11-p3 and 11-p4

Synthesis of Intermediates 11-4 and 11-5

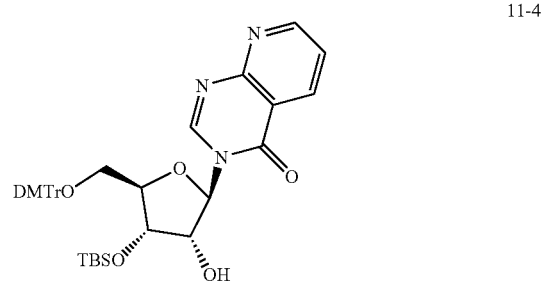

11-4

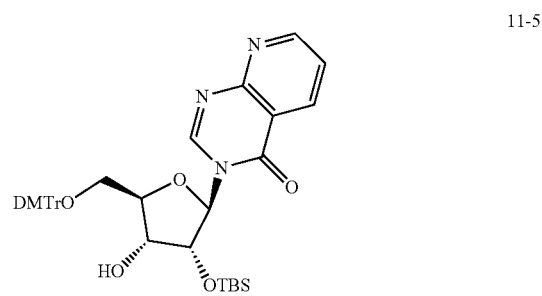

11-5

Synthesis of compounds 11-4 and 11-5: compounds 11-4 (650 mg, more polar) and 11-5 (610 mg, less polar) were obtained as white solids in the same manner as compounds 9-4 and 9-5, by using pyrido[2,3-d]pyrimidin-4-one as a starting material. m/z: [M+H]$^+$696.0; 11-4: $^1$H NMR (400 MHz, DMSO-$d_6$): δ 8.97 (d, J=4.0 Hz, 1H), 8.74 (s, 1H), 8.56 (d, J=8.0 Hz, 1H), 7.60-7.57 (m, 1H), 7.42 (d, J=8.0 Hz, 2H), 7.31-7.20 (m, 1H), 6.88 (d, J=12.0 Hz, 4H), 6.02 (s, 1H), 5.40 (d, J=4.0 Hz, 1H), 4.30-4.29 (m, 2H), 4.01-3.98 (m, 1H), 3.71 (s, 6H), 3.40-3.37 (m, 1H), 3.21-3.18 (m, 1H), 0.74 (s, 9H), 0.00 (s, 6H); 11-5: $^1$H NMR (400 MHz, DMSO-$d_6$): δ 8.94 (d, J=4.0 Hz, 1H), 8.67 (s, 1H), 8.55 (d, J=8.0 Hz, 1H), 7.56-7.53 (m, 1H), 7.41 (d, J=8.0 Hz, 2H), 7.29-7.25 (m, 1H), 6.86 (d, J=8.0 Hz, 4H), 6.00 (s, 1H), 5.13 (d, J=4.0 Hz, 1H), 4.13-4.08 (m, 2H), 4.00-3.98 (m, 1H), 3.39 (s, 6H), 3.36-3.32 (m, 1H), 3.27-3.25 (m, 1H), 0.79 (s, 9H), 0.00 (s, 6H).

Synthesis of compounds 11-11-p1, 11-11-p2, 11-11-p3 and 11-11-p4: compounds 11-11-p1 (27 mg), 11-11-p2 (15 mg), 11-11-p3 (19 mg) and 11-11-p4 (36 mg) were obtained as white solids in the same manner as Embodiment 15 steps 1-5, by using compound 11-5 as a starting material, and purified by prep-HPLC (separation method 6).

Synthesis of Compound 11-p1

To compound 11-11-p1 (20 mg, 0.019 mmol) was added methylamine ethanol solution (2 mL, 30%), the reaction system was stirred at room temperature for 10 h and then concentrated under reduced pressure, the residue was dissolved in anhydrous pyridine (0.5 mL), and triethylamine (0.5 mL) and triethylamine trihydrofluoride (0.25 mL) were added thereto under nitrogen, the reaction solution was stirred at 50° C. for 1 h. The solvent was concentrated under reduced pressure. The residue was diluted with methanol, and then ammonium hydroxide solution was slowly added to dropped pH to 8-9. The mixture was purified by prep-HPLC (separation method 7) to afford compound 11-p1 (2.45 mg, HPLC-RT: 8.963 min, m/z: [M+H]$^+$ 718.8) as a white solid.

Synthesis of Compound 11-p2

Compound 11-p2 (3.07 mg, HPLC-RT: 8.527 min, m/z: [M+H]$^+$ 718.7) was obtained as a white solid in the same manner as compound 11-p1, by using compound 11-11-p2 as a starting material, and purified by prep-HPLC (separation method 5).

Synthesis of Compound 11-p3

Compound 11-p3 (1.28 mg, HPLC-RT: 9.103 min, m/z: [M+H]$^+$ 719.1) was obtained as a white solid in the same manner as compound 11-p1, by using compound 11-11-p3 as a starting material, and purified by prep-HPLC (separation method 5).

Synthesis of Compound 11-p4

Compound 11-p4 (3.03 mg, HPLC-RT: 9.403 min, m/z: [M+H]$^+$ 718.6) was obtained as a white solid in the same manner as compound 11-p1, by using compound 11-11-p4 as a starting material, and purified by prep-HPLC (separation method 5).

Embodiment 18: Synthesis of Intermediate 12-1

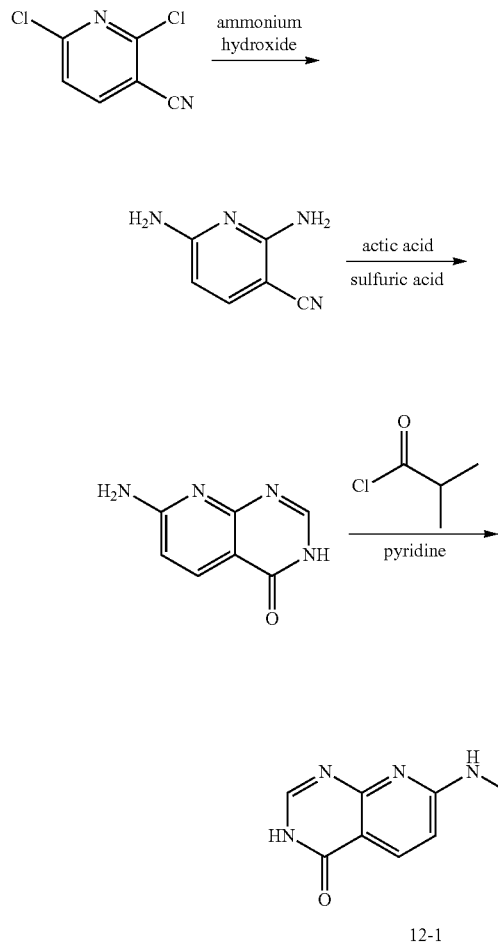

12-1

Step 1: 2,6-dichloronicotinonitrile (25 g, 145 mmol) and ammonium hydroxide solution (250 mL) was charged into a sealed tube. The reaction system was stirred at 120° C. for 48 h and then cooled to 10° C., the solid was filtered and washed with cold water, the the filter cake was dried under vacuum to afford 2,6-diaminonicotinonitrile (12.5 g) as a light yellow solid. m/z: [M+H]⁺ 135.0.

Step 2: To a solution of 2,6-diaminonicotinonitrile (12.5 g, 93.2 mmol) in acetic acid (120 mL) was slowly added concentrated sulfuric acid (3 mL), the reaction system was stirred at reflux for 9 h, and then cooled to room temperature and concentrated under reduced pressure. The residue was triturated with ammonium hydroxide solution, the solid was filtered, the filter cake washed with cold water, and dried under vacuum to afford 7-aminopyrido[2,3-d]pyrimidin-4 (3H)-one (15.1 g) as a light yellow solid. m/z: [M+H]⁺163.0.

Step 3: 7-aminopyrido[2,3-d]pyrimidin-4 (3H)-one (15.1 g, 93.1 mmol) was dissolved in pyridine (1.5 L), isobutyryl chloride (29.7 g, 279 mmol) was slowly added thereto, the reaction system was stirred at room temperature for 18 h and then water (1.5 L) was added thereto, the reaction solution was extracted with chloroform/propan-2-ol (1.5 L), the organic layer was concentrated under reduced pressure. The residue was purified by Flash column chromatography (0-6.2% methanol/dichloromethane) to afford compound 12-1 (11.9 g) as a white solid. m/z: [M+H]⁺233.1.

Embodiment 19: Synthesis of Compounds 12-p1, 12-p2, 12-p3 and 12-p4

Synthesis of intermediates 12-4 and 12-5

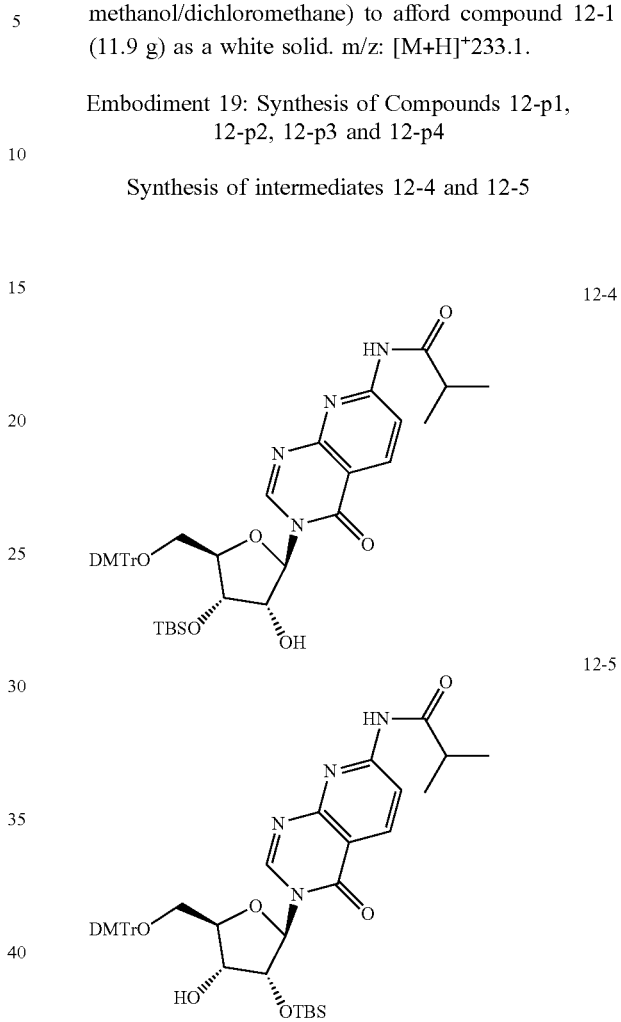

Intermediates 12-4 (1.73 g, more polar) and 12-5 (1.1 g, less polar) were obtained as white solids in the same manner as compounds 9-4 and 9-5, by using compound 12-1 as a starting material. m/z: [M+H]⁺ 781.0; 12-4: ¹H NMR (400 MHz, DMSO-d₆): δ 11.15 (s, 1H), 8.70 (s, 1H), 8.52 (d, J=8.8 Hz, 1H), 8.33 (d, J=8.8 Hz, 1H), 7.43 (d, J=7.6 Hz, 2H), 7.32 (d, J=7.6 Hz, 2H), 7.29 (d, J=8.4 Hz, 4H), 6.89 (d, J=8.4 Hz, 4H), 6.03 (d, J=2.8 Hz, 1H), 5.40 (d, J=6.0 Hz, 1H), 4.30 (t, J=3.2 Hz, 1H), 4.05-4.02 (m, 2H), 3.73 (s, 6H), 3.40-3.36 (m, 1H), 3.25-3.22 (m, 1H), 2.83-2.79 (m, 1H), 1.12 (s, 3H), 1.11 (s, 3H), 0.77 (s, 9H), 0.03 (s, 3H), −0.04 (s, 3H); 12-5: ¹H NMR (400 MHz, DMSO-d₆): δ 11.13 (s, 1H), 8.67 (s, 1H), 8.54 (d, J=8.8 Hz, 1H), 8.31 (d, J=8.8 Hz, 1H), 7.45 (d, J=7.6 Hz, 2H), 7.33 (d, J=7.6 Hz, 2H), 7.31 (d, J=8.4 Hz, 4H), 6.90 (d, J=8.4 Hz, 4H), 6.04 (d, J=2.8 Hz, 1H), 5.16 (d, J=6.0 Hz, 1H), 4.40 (t, J=3.2 Hz, 1H), 4.17-4.12 (m, 2H), 3.74 (s, 6H), 3.43-3.40 (m, 1H), 3.30-3.27 (m, 1H), 2.82-2.79 (m, 1H), 1.13 (s, 3H), 1.11 (s, 3H), 0.85 (s, 9H), 0.05 (s, 6H).

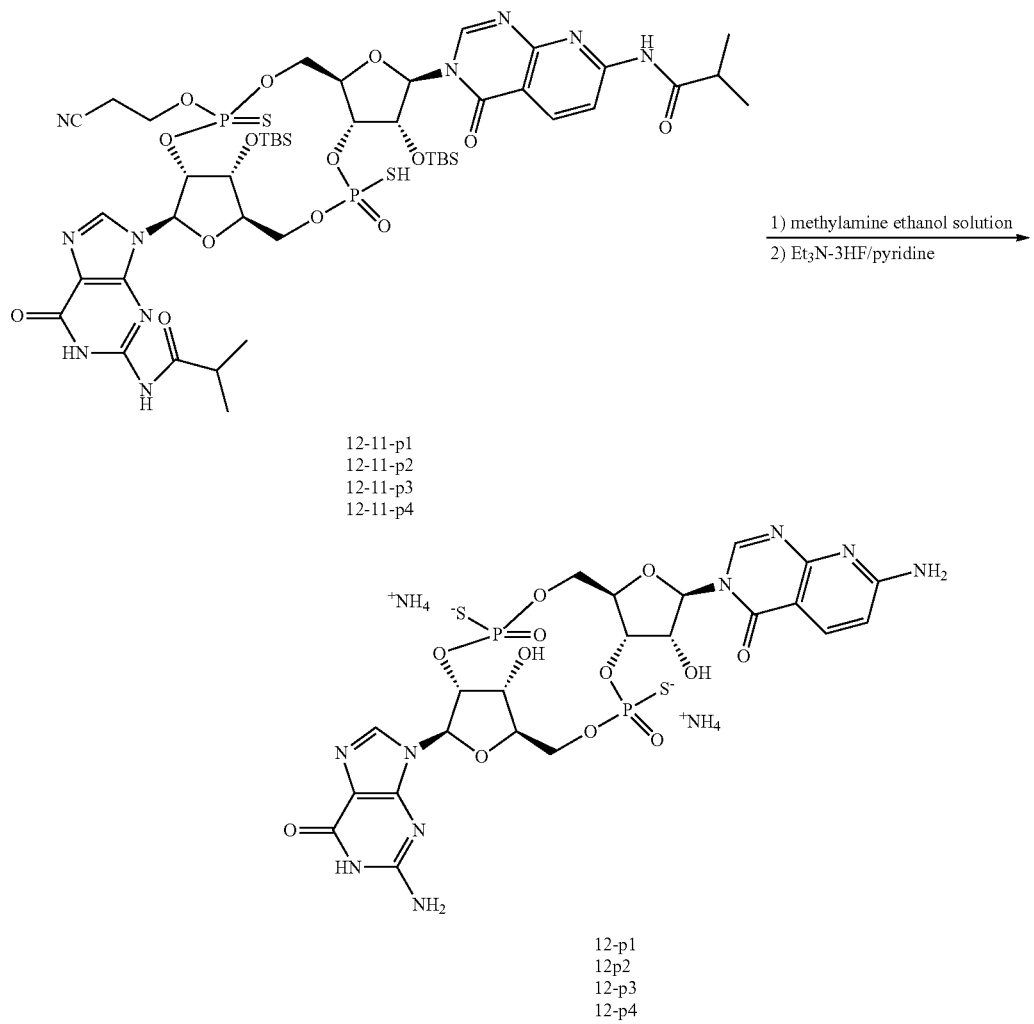

12-11-p1
12-11-p2
12-11-p3
12-11-p4

1) methylamine ethanol solution
2) Et₃N-3HF/pyridine 12-p1
12p2
12-p3
12-p4

Synthesis of compounds 12-11-p1, 12-11-p2, 12-11-p3 and 12-11-p4: compounds 12-11-p1 (25 mg), 12-11-p2 (7 mg), 12-11-p3 (40 mg) and 12-11-p4 (32 mg) were obtained as white solids in the same manner as Embodiment 15 steps 1-5, by using compound 12-5 as a starting material, and purified by prep-HPLC (separation method 6).

Synthesis of Compound 12-p1

To compound 12-11-p1 (25 mg, 19 μmol) was added methylamine ethanol solution (2 mL, 30%), the reaction system was stirred at room temperature for 3 h and then concentrated under reduced pressure, the residue was dissolved in anhydrous pyridine (0.5 mL), triethylamine (0.5 mL) and triethylamine trihydrofluoride (0.25 mL) was added thereto under nitrogen, the reaction solution was stirred at 50° C. for 1 h. The solvent was concentrated under reduced pressure. The residue was diluted with methanol, and then ammonium hydroxide solution was slowly dropped to adjusted pH to 8-9. The mixture was purified by prep-HPLC (separation method 4) to afford compound 12-p1 (0.9 mg, HPLC-RT: 8.891 min, m/z: [M+H]⁺ 733.7) as a white solid.

Synthesis of Compound 12-p2

Compound 12-p2 (0.5 mg, HPLC-RT: 8.571 min, m/z: [M+H]⁺ 733.7) was obtained as a white solid in the same manner as compound 12-p1, by using compound 12-11-p2 as a starting material, and purified by prep-HPLC (separation method 4).

Synthesis of Compound 12-p3

Compound 12-p3 (1.5 mg, HPLC-RT: 10.020 min, m/z: [M+H]⁺ 733.8) was obtained as a white solid in the same manner as compound 12-p1, by using compound 12-11-p3 as a starting material, and purified by prep-HPLC (separation method 4).

Synthesis of Compound 12-p4

Compound 12-p4 (3.07 mg, HPLC-RT: 9.468 min, m/z: [M+H]⁺ 733.8) was obtained as a white solid in the same manner as compound 12-p1, by using compound 12-11-p4 as a starting material, and purified by prep-HPLC (separation method 4)

Embodiment 20: Synthesis of Intermediates 13-4 and 13-5

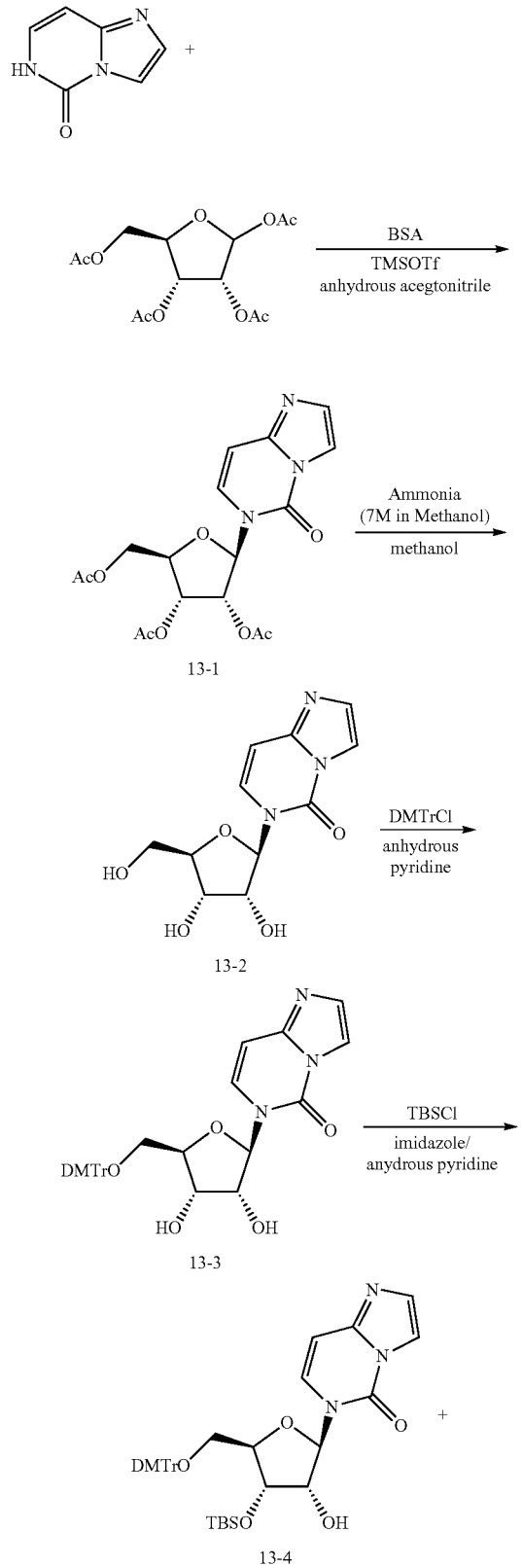

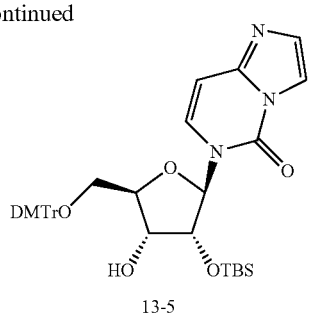

13-5

Synthesis of imidazo[1,2-c]pyrimidin-5 (6H)-one: The suspension of cytosine (18 g, 0.16 mol), aqueous solution of chloroacetaldehyde (63.6 g, 0.32 mol, 40%) and sodium acetate (32.8 g, 0.40 mol) in water (180 mL) was stirred at 80° C. for 3 h, and then the reaction system was cooled to 10° C., the solid was filtered and washed with cold water, the filter cake was dried under vacuum to afford imidazo[1,2-c]pyrimidin-5 (6H)-one (17.8 g) as a brown solid. m/z: [M+H]$^+$ 136.0.

Step 1: To a suspension of imidazo[1,2-c]pyrimidin-5 (6H)-one (17.8 g, 0.13 mmol), tetraacetylribose (46.1 g, 0.14 mmol) and BSA (39.7 g, 0.19 mmol) in acetonitrile (200 mL) was added TMSOTf (43.3 g, 0.19 mol) dropwise at 0° C., the reaction system was stirred at 60° C. for 3 h and then concentrated under reduced pressure to afford compound 13-1 (100 g, crude product) as a brown oil. m/z: [M+H]$^+$ 394.0.

Step 2: Compound 13-1 (45 g, crude) was dissolved in methanol (100 mL), ammonia in methanol (81.7 mL, 7M) was slowly added thereto, the reaction system was stirred at room temperature for overnight, the solid was filtered and washed with methanol, the filter cake was dried under vacuum to afford compound 13-2 (8 g) as a brown solid. m/z: [M+H]$^+$ 268.0.

Step 3: Compound 13-2 (12.5 g, 5.76 mmol) was subjected to azeotropic dehydration three times with anhydrous pyridine (20 mL) and then dissolved in pyridine (100 mL). To the above reaction solution was added DMTrCl (19.52 g, 5.76 mmol) in small portions at 0-5° C. under nitrogen. The reaction system was stirred at room temperature for overnight, the solvent was concentrated under reduced pressure, and the residue was diluted with chloroform (100 mL). The organic layer washed with saturated aqueous solution of sodium bicarbonate (30 mL×2), the organic layer was separated and dried over anhydrous sodium sulfate, filtered and concentrated. The residue was purified by Flash column chromatography (methanol/dichloromethane=0-3%) to afford compound 13-3 (16.65 g) as a brown solid. m/z: [M+Na]$^+$570.0.

Step 4: Compound 13-3 (5.38 g, 9.44 mmol) was subjected to azeotropic dehydration three times with anhydrous pyridine (20 mL) and then dissolved in pyridine (60 mL). To the mixture was added TBSCl (2.13 g, 14.2 mmol) and imidazole (2.25 g, 33.1 mmol) at 0° C. under nitrogen. The reaction system was stirred at room temperature for overnight, the solvent was concentrated under reduced pressure, and the residue was diluted with chloroform (100 mL). The organic layer washed with saturated aqueous solution of sodium bicarbonate (30 mL×2), the separated organic layer was dried over anhydrous sodium sulfate, filtered and the filtrate was concentrated under reduced pressure. The residue was purified by Flash column chromatography (0-3% methanol/dichloromethane) to afford compounds 13-4 (1.32 g, less polar) and 13-5 (3.68 g, more polar), as white foam solids. m/z: [M+H]$^+$684.0; 13-4: $^1$H NMR (400 MHz, DMSO-d$_6$): δ 7.88 (d, J=5.6 Hz, 1H), 7.82 (s, 1H), 7.76 (s, 1H), 7.40-7.26 (m, 9H), 6.92-6.90 (m, 4H), 6.68 (d, J=6.0 Hz, 1H), 5.90 (d, J=9.2 Hz, 1H), 5.33 (d, J=4.8 Hz, 1H), 4.50 (t, J=4.4 Hz, 1H), 4.15-4.14 (m, 2H), 3.74 (s, 6H), 3.28-3.26 (m, 2H), 0.77 (s, 9H), 0.02 (s, 3H), −0.12 (s, 3H). 13-5: $^1$H NMR (400 MHz, DMSO-d$_6$): δ 7.92 (d, J=6.0 Hz, 1H), 7.78 (s, 2H), 7.36-7.21 (m, 9H), 6.88-6.86 (m, 4H), 6.68 (d, J=8.8 Hz, 1H), 5.81 (d, J=4.8 Hz, 1H), 5.63 (d, J=6.0 Hz, 1H), 4.40-4.35 (m, 2H), 4.27 (t, J=4.8 Hz, 1H), 4.06-4.04 (m, 1H), 3.74 (s, 6H), 3.20-3.16 (m, 1H), 0.80 (s, 9H), 0.06 (s, 3H), −0.01 (s, 3H).

Embodiment 21: Synthesis of Compounds 13-p1, 13-p2, 13-p3 and 13-p4

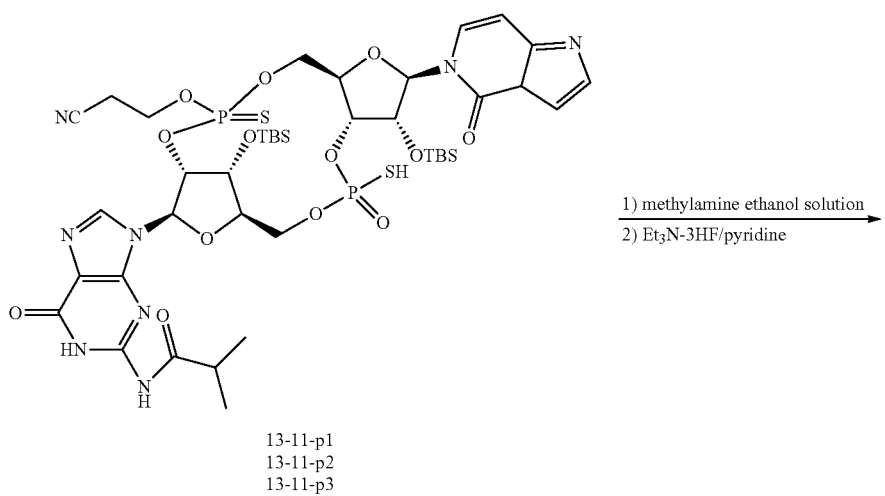

13-11-p1
13-11-p2
13-11-p3

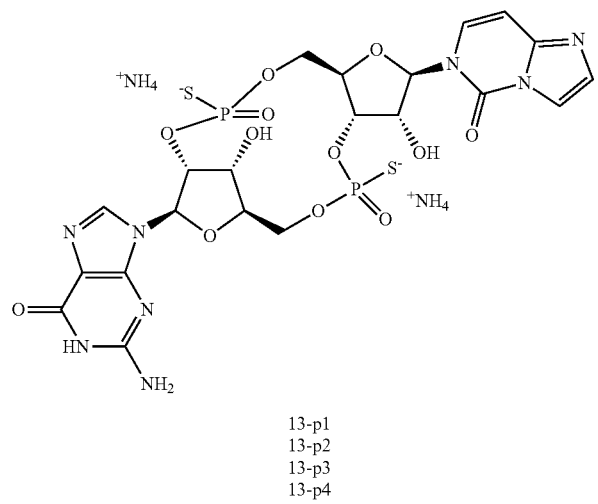

13-p1
13-p2
13-p3
13-p4

Synthesis of compounds 1$^3$-11-p1, 13-11-p2, 13-11-p3 and 13-11-p4: compounds 13-11-p1 (55 mg, LCMS-RT (Thermo): 1.874, 1.944 min), 13-11-p2 (25 mg, LCMS-RT (Thermo): 2.030 min), and 13-11-p3 (11 mg, LCMS-RT (Thermo): 2.170 min) were obtained as white solids in the same manner as Embodiment 15 steps 1-5, by using compound 13-5 as a starting material, and purified by Flash column chromatography (acetonitrile/aqueous solution of ammonium bicarbonate (10 mmol/L)=40%). m/z: [M+H]$^+$ 1057.9.

Synthesis of Compounds 13-p1 and 13-p2

Compound 13-11-p1 (43 mg, 0.04 mmol) was dissolved in methylamine ethanol solution (3 mL, 30%) and stirred at room temperature for 3 h, and then concentrated under reduced pressure, the residue was dissolved in anhydrous pyridine (0.5 mL), triethylamine (0.5 mL) and triethylamine trihydrofluoride (0.25 mL) was added thereto under nitrogen, the reaction solution was stirred at 50° C. for 3 h and then concentrated under reduced pressure. The residue was diluted with methanol and ammonium hydroxide solution was slowly dropped to adjusted pH to 8-9. The mixture was purified by prep-HPLC (separation method 5) to afford compounds 13-p1 (2.28 mg, HPLC-RT: 6.048 min, m/z: [M+H]$^+$706.8) and 13-p2 (0.68 mg, HPLC-RT: 7.781 min, m/z: [M+H]$^+$706.8), as white solids.

Synthesis of Compound 13-p3

Compound 13-p3 (3.82 mg, HPLC-RT: 6.445 min, m/z: [M+H]⁺706.8) was obtained as a white solid in the same manner as compounds 13-p1/13-p2, by using compound 13-11-p2 as a starting material, and purified by prep-HPLC (separation method 4).

Synthesis of Compound 13-p4

Compound 13-p4 (4.03 mg, HPLC-RT: 10.395 min, m/z: [M+H]⁺706.8) was obtained as a white solid in the same manner as compounds 13-p1/13-p2, by using compound 13-11-p3 as a starting material, and purified by prep-HPLC (separation method 5).

Embodiment 22: Synthesis of Compounds 14-p1, 14-p2, 14-p3 and 14-p4

Synthesis of intermediates 14-4 and 14-5

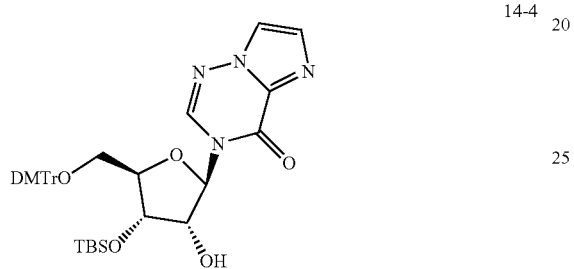

14-4

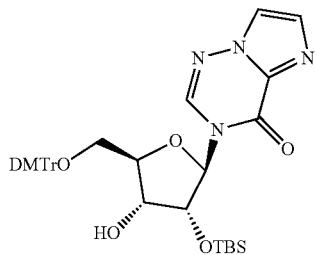

14-5

Intermediates 14-4 (1.3 g, more polar) and 14-5 (0.56 g, less polar) were obtained as white solids in the same manner as compounds 13-4 and 13-5, by using imidazo[5,1-f][1,2,4]triazin-4(3H)-one (CAS No.: 865444-76-4) as a starting material. m/z: [M+H]⁺685.0.

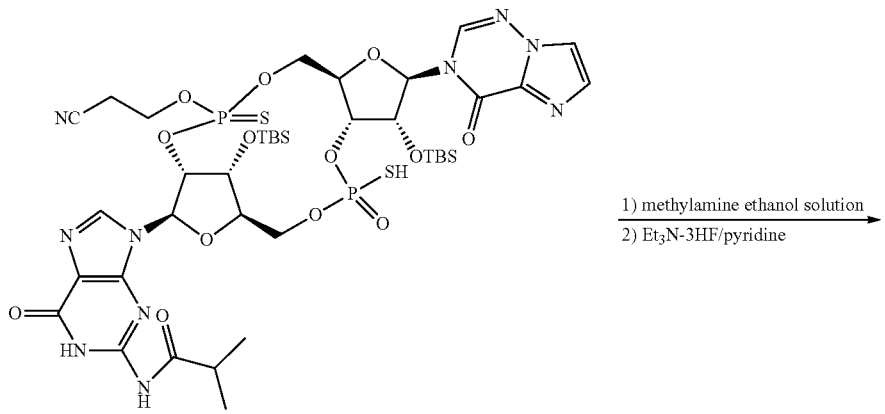

14-11-p1
14-11-p2
14-11-p3
14-11-p4

1) methylamine ethanol solution
2) Et₃N-3HF/pyridine

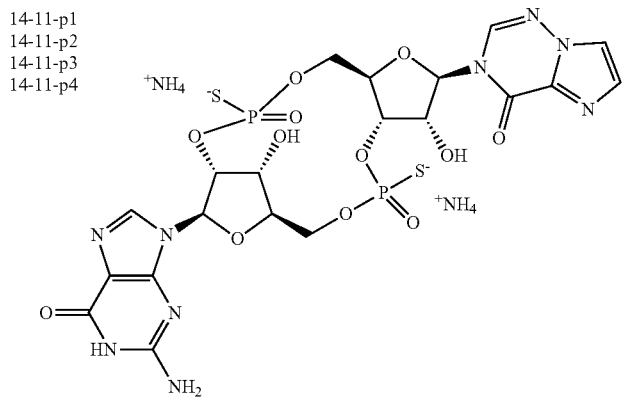

14-p1
14-p2
14-p3
14-p4

Synthesis of compounds 14-11-p1, 14-11-p2, 14-11-p3 and 14-11-p4: compounds 14-11-p1 (5 mg, LCMS-RT (Thermo): 1.850 min), 14-11-p2 (17 mg, LCMS-RT (Thermo): 1.880 min), 14-11-p3 (22 mg, LCMS-RT (Thermo): 2.020 min) and 14-11-p4 (18 mg, LCMS-RT (Thermo): 2.140 min) were obtained as white solids in the same manner as Embodiment 15 steps 1-5, by using compound 14-5 as a starting material, and purified by prep-HPLC (separation method 7). m/z: $[M+H]^+$ 1059.0.

Synthesis of Compound 14-p1

Compound 14-11-p1 (5.0 mg, 0.05 mmol) was dissolved in methylamine ethanol solution (3.0 mL, 30%), the mixture was stirred at room temperature for 3 h and then concentrated under reduced pressure, the residue was dissolved in anhydrous pyridine (0.5 mL), triethylamine (0.5 mL) and triethylamine trihydrofluoride (0.3 mL) was added thereto under nitrogen, the reaction solution was stirred at 50° C. for 2 h. The solvent was concentrated under reduced pressure. The residue was diluted with methanol and then ammonium hydroxide solution was slowly dropped to adjusted pH to 8-9. The mixture was purified by prep-HPLC (separation method 5) to afford compound 14-p1 (3.65 mg, HPLC-RT: 1.914 min, m/z: $[M+H]^+$ 707.5) as a white solid.

Synthesis of Compound 14-p2

Compound 14-p2 (17.5 mg, HPLC-RT: 3.123 min, m/z: $[M+H]^+$ 707.5) was obtained as a white solid in the same manner as compound 14-p1, by using compound 14-11-p2 as a starting material, and purified by prep-HPLC (separation method 4).

Synthesis of Compound 14-p3

Compound 14-p3 (1.04 mg, HPLC-RT: 3.193 min, m/z: $[M+H]^+$ 707.5) was obtained as a white solid in the same manner as compound 14-p1, by using compound 14-11-p3 as a starting material, and purified by prep-HPLC (separation method 4).

Synthesis of Compound 14-p4

Compound 14-p4 (1.04 mg, HPLC-RT: 36.036 min, m/z: $[M+H]^+$ 707.5) was obtained as a white solid in the same manner as compound 14-p1, by using compound 14-11-p4 as a starting material, and purified by prep-HPLC (separation method 4).

EMBODIMENTS OF BIOASSAYS

Embodiment 1: Type 1 IFN Activation Assay

Plated THP-1 dual cells (Invivogen) as 100000 cells/well in a 96 well-plate, and then phorbol 12-myristate 13-acetate (PMA) was added and the final concentration of PMA was 30 ng/mL. After 24 h incubation, cells were washed with fresh medium for twice, and 3-folds dilution compounds were added to appropriate wells. The compounds were diluted by PB buffer (50 mM HEPES, 100 mM KCl, 3 mM $MgCl_2$, 0.1 mM DTT, 85 mM sucrose, 1 mM ATP, 0.1 mM GTP, 0.2% o bovine serum albumin and 5 μg/ml digitonin) and the top dose was 10 μM, minimum dose was 0.0015 μM. The cells were incubated for 30 min, and then washed with fresh medium for twice again. Add fresh medium, and the cells were incubated for additional 24 h. After incubation, 10 ul supernant and 50 μL QUANTI-Luc (Invivogen) was add to a 96 well-plate, fluorescence was read with TECAN. The express level of IFN was proportional to the fluorescence intensity. Drew the curve with Graphpad Prism and analyse $EC_{50}$ of the compounds.

| Compound No. | $EC_{50}$ (μM) |
| --- | --- |
| 1-p1 | >10 |
| 1-p2 | >10 |
| 1-p3 | >10 |
| 1-p4 | 25.615 |
| 2-p1 | 45.755 |
| 2-p2 | >100 |
| 2-p3 | 97.411 |
| 2-p4 | 2.077 |
| 4-p1 | 6.834 |
| 4-p2 | 0.625 |
| 4-p3 | 0.417 |
| 5-p1 | >10 |
| 5-p2 | 51.981 |
| 5-p3 | 58.238 |
| 5-p4 | 3.223 |
| 6-p1 | 2.273 |
| 6-p2 | 1.063 |
| 6-p3 | 0.429 |
| 6-p4 | 0.311 |
| 7-p1 | 3.464 |
| 7-p2 | 40.62 |
| 7-p3 | 0.275 |
| 7-p4 | 2.307 |
| 8-p1 | >100 |
| 8-p2 | >100 |
| 8-p3 | 99.53 |
| 8-p4 | 38.80 |
| 9-p1 | >100 |
| 9-p2 | >100 |
| 9-p3 | 4.865 |
| 10-p1 | 70.69 |
| 10-p2 | 118.8 |
| 10-p3 | 0.494 |
| 11-p1 | 60.81 |
| 11-p2 | 9.805 |
| 11-p3 | 17.50 |
| 11-p4 | 0.421 |
| 12-p1 | >100 |
| 12-p2 | 19.01 |
| 12-p3 | 8.628 |
| 12-p4 | 0.565 |
| 13-p1 | 188.1 |
| 13-p2 | 351.6 |
| 13-p3 | 176.0 |
| 13-p4 | 4.991 |
| 14-p1 | >100 |
| 14-p2 | >100 |
| 14-p3 | 40.35 |
| 14-p4 | 21.52 |
| Ref. 1 | 2.942 |

Embodiment 2: STING IFNβ Secretion Assay

Plated 40 uL THP-1 cells (ATCC) as 16000 cells/well in a 96 well-plate (Corning, 3596). 3-folds dilution compounds were added to appropriate wells. The compounds were diluted with buffer (RPMI1640+2 mM L-glutamine+1× non-essential amino acids+1 mM sodium pyruvate+0.5% Fetal bovine serum), and the top dose of the compound was 100 μM, minimum dose was 1.23 μM. After 5 h incubation, 2 L supernant was added to 384-well plate (Greiner, Cat: 784075) and the secretion of IFN-β was detected with AllphaLISA IFN-β kit(PerkinElmer, Cat:AL577C). 1× buffer was prepared to dilute the receptor and donor, and then 4 μL 20 μg/mL Anti-pIFNβ AlphaLISA receptor was added to every well. After 30 mins incubation at room temperature, 4 μL 2 nM biotinylated Anti-pIFNβ antibody was added to a 384 well-plate, incubated overnight at 4° C. 10 μL 40 g/mL Streptavidin (SA) donor which was diluted with 1×buffer was added, and then incubated at room temperature for 30 min. Fluorescence was read with TECAN. The expressed level of IFN-β was proportional to the fluorescence intensity. Drew the curve with Graphpad Prism and analysed $EC_{50}$ of the compounds.

| Compound No. | $EC_{50}$ (μM) |
|---|---|
| 2-p4 | 47.64 |
| 4-p2 | 36.22 |
| 4-p3 | 94.39 |
| 6-p2 | 58.09 |
| 6-p3 | 9.84 |
| 6-p4 | 9.40 |

Embodiment 3: Efficacy Study in a CT-26 Colon Tumor Xenograft Model in Mice

Cell Culture: The CT26 colon tumor cells (ATCC) were maintained in vitro as a monolayer culture in RPMI1640 medium supplemented with 10% fetal bovine serum at 37° C. in an atmosphere of 5% $CO_2$ in air. The tumor cells were routinely passaged twice per week by trypsin-EDTA treatment. The cells growing in an exponential growth phase were harvested and counted for tumor inoculation.

Animals: BALB/c nude mice, 6-8 weeks, 19-22 g, animal supplier: Beijing Vital River Laboratory Animal Technology Co., Ltd.

4 groups were set up as follows:

| Group | No. | Treatment | Dose | Dosing Route | Actual Schedule |
|---|---|---|---|---|---|
| 1 | 8 | Vehicle | — | i.t. | Q3D × 3 doses |
| 2 | 8 | Ref. 1 | 2 mg/kg | i.t. | Q3D × 3 doses |
| 3 | 8 | Compound 6-p3 | 1 mg/kg | i.t. | Q3D × 3 doses |
| 4 | 8 | Compound 6-p3 | 2 mg/kg | i.t. | Q3D × 3 doses |

Note: i.t.: intra-tumor injection, Q3D: once every 3 days

Experiment method: Each mouse was inoculated subcutaneously with CT-26 tumor cells ($1 \times 10^5$) in 0.1 mL over right flank region. The growth of tumor was observed regularly, when the tumor volume reached 150 $mm^3$, mice were randomized based on tumor volume and body weight, and treated with schedule. The weight and tumor size of mice were measured 2-3 times a week during the whole experiment.

Tumor volumes($mm^3$)=0.5×(long diameters of the tumor×short diameters of the $tumor^2$). Tumor size formula:

The tumor growth curves of different 4 groups are shown in FIG. 1. The result indicated that compared with the positive control Ref. 1, the compound of the disclosure can show better efficacy on the subcutaneous CT-26 colon tumor model in mice.

Note: Ref. 1 used in embodiments of bioassays 1 and 3 was MLRR-CDA (ammonia salt), CASNo: 1638750-96-5, the synthesis method could refer to PCT patent application WO2014/189805A1 compound 22.

What is claimed is:
1. A cyclic di-nucleotide analogue (I), an isomer, stable isotope derivative or pharmaceutically acceptable salt thereof; wherein the cyclic di-nucleotide analogue (I) is a compound of formula (VI) or (VII), a stereoisomer, or pharmaceutically acceptable salt thereof:

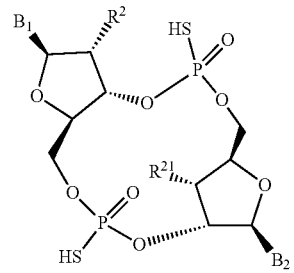

(VI)

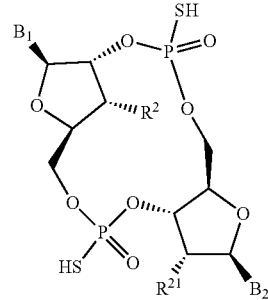

(VII)

$B_1$ is,

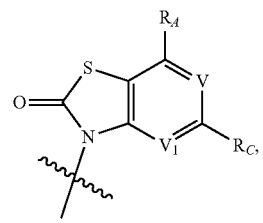

B-2

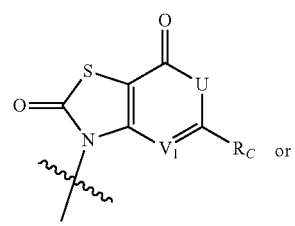

B-17

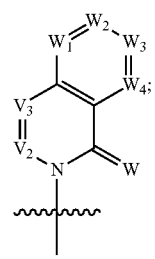

B-18

B₂ is

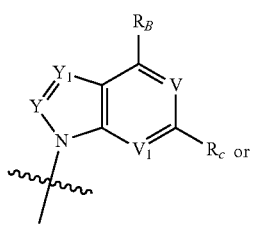

R² is hydrogen, halogen, cyano, hydroxyl, thiol, amino, azido, C₂₋₆ alkenyl, C₂₋₆ alkynyl, C₁₋₆ alkyl, halo-C₁₋₆ alkyl, halo-C₁₋₆ alkoxy, halo-C₁₋₆ alkylthio, C₁₋₆ alkylamino, OC(O)Rᵃ or ORᵃ; the C₂₋₆ alkenyl, C₂₋₆ alkynyl, or C₁₋₆ alkyl is unsubstituted or selectively substituted at any position by 1 to 3 substituents selected from halogen, hydroxyl, amino, azido, and cyano;

R²¹ is hydrogen, halogen, cyano, hydroxyl, thiol, amino, azido, C₂₋₆ alkenyl, C₂₋₆ alkynyl, C₁₋₆ alkyl, halo-C₁₋₆ alkyl, halo-C₁₋₆ alkoxy, halo-C₁₋₆ alkylthio, C₁₋₆ alkylamino, OC(O)Rᵃ, or ORᵃ; the C₂₋₆ alkenyl, C₂₋₆ alkynyl, or C₁₋₆ alkyl is unsubstituted or selectively substituted at any position by 1 to 3 substituents selected from halogen, hydroxyl, amino, azido, and cyano;

Y and Y₁ are independently $CR_E$ or N;

U is $CHR_E{'}$ or $NR_D{'}$;

V and V₁ are each independently $CRE''$ or N, V₂ and Vs are each independently N or CH;

W is O or S;

W₁ is N or CH, W₂ is $CR_F{'}$, W₃ and W₄ are each independently CH;

each of $R_A$, $R_B$, $R_C$, $R_E$, $R_E{'}$, $R_E{''}$ and $R_F{'}$ are independently H, halogen, —CN, —NO₂, —N₃, Rᶜ, —SRᶜ, —ORᶜ, —OC(O)Rᶜ, —OC(O)ORᶜ, —OC(O)NRᵇRᶜ, —C(O)ORᶜ, —C(O)Rᶜ, —C(O)NRᵇRᶜ, —NRᵇRᶜ, —NRᵇC(O)Rᶜ, —N(Rᵇ)C(O)ORᶜ, —N(Rᵃ)C(O)NRᵇRᶜ, —NRᵇS(O)₂Rᶜ, —NRᵇC(=NH)Rᶜ, —NRᵇC(=NRᶜ)NH₂, —S(O)₁₋₂Rᶜ, —S(O)₂NRᵇRᶜ or —NRᵃS(O)₂NRᵇRᶜ;

RD' is independently H or Rᶜ;

each of Rᵃ and Rᵇ is independently H, C₂₋₆ alkenyl, C₂₋₆ alkynyl, C₁₋₁₀ alkyl or halo- C₁₋₆ alkyl;

each Rᶜ is independently H, substituted or unsubstituted C₁₋₁₀ alkyl, substituted or unsubstituted C₂₋₈ alkenyl, substituted or unsubstituted C₂₋₈ alkynyl, substituted or unsubstituted C₃₋₁₀ cycloalkyl, substituted or unsubstituted C₆₋₁₀ aryl, substituted or unsubstituted 3-10 membered heterocycloalkyl, substituted or unsubstituted 5-10 membered heteroaryl, substituted or unsubstituted C₆₋₁₀ aryl-C₁₋₆ alkyl, substituted or unsubstituted C₃₋₁₀ cycloalkyl-C₁₋₆ alkyl, substituted or unsubstituted 3-10 membered heterocycloalkyl-C₁₋₆ alkyl, substituted or unsubstituted 5-10 membered heteroaryl-C₁₋₆ alkyl; the C₁₋₁₀ alkyl, C₂₋₈ alkenyl, C₂₋₈ alkynyl, C₃₋₁₀ cycloalkyl, C₆₋₁₀ aryl, 3-10 membered heterocycloalkyl, 5-10 membered heteroaryl, C₆₋₁₀ aryl-C₁₋₆ alkyl, C₃₋₁₀ cycloalkyl-C₁₋₆ alkyl, 3-10 membered heterocycloalkyl-C₁₋₆ alkyl, or 5-10 membered heteroaryl-C₁₋₆ alkyl is unsubstituted or selectively substituted at any position by one or more Rᵈ;

each Rᵈ is independently halogen, halo-C₁₋₆ alkyl, halo-C₁₋₆ alkoxy, C₁₋₆ alkyl, —CN, —N₃, —SRᵉ, —ORᵉ, —C(O)Rᵉ, —NRᵉRᵉ', substituted or unsubstituted C₆₋₁₀ aryl, substituted or unsubstituted 5-10 membered heteroaryl, substituted or unsubstituted C₃₋₁₀ cycloalkyl, or substituted or unsubstituted 3-10 membered heterocycloalkyl; the C₆₋₁₀ aryl, 5-10 membered heteroaryl, C₃₋₁₀ cycloalkyl or 3-10 membered heterocycloalkyl is unsubstituted or selectively substituted at any position by one or more substituents selected from halogen, hydroxyl, cyano, amino, C₁₋₄ alkyl, halo-C₁₋₄ alkyl, C₁₋₄ alkoxy, C₁₋₄ alkylamino and halo-C₁₋₄ alkoxy;

each of Rᵉ and Rᵉ' is independently C₂₋₆ alkenyl, C₂₋₆ alkynyl, C₁₋₁₀ alkyl or halo- C₁₋₆ alkyl.

2. The cyclic di-nucleotide analogue of formula (I), the isomer, stable isotope derivative or pharmaceutically acceptable salt thereof according to claim 1, wherein B₁ is any of the following structures:

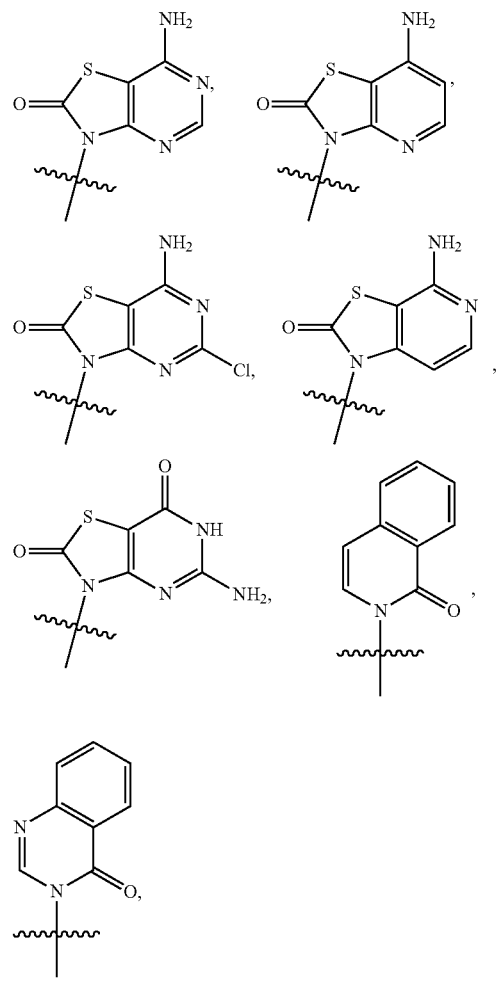

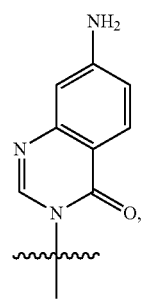
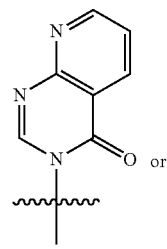 or
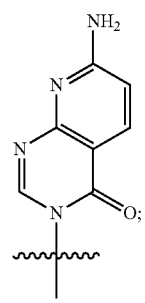
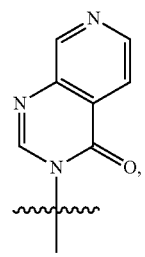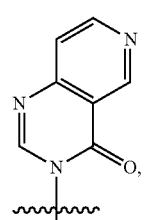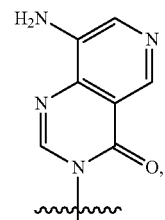
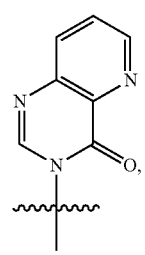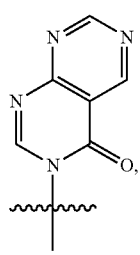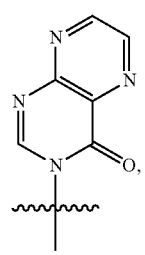
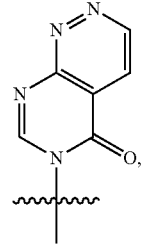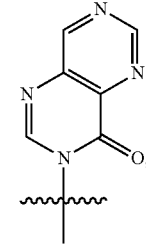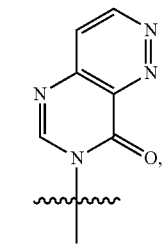
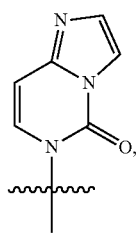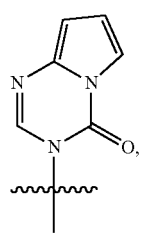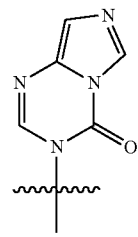
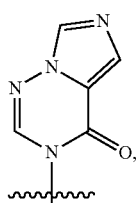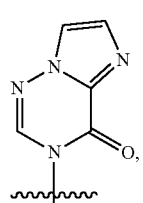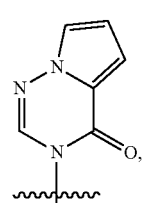
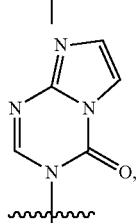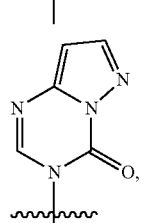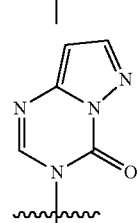
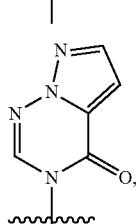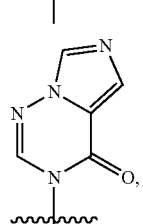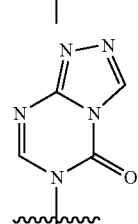
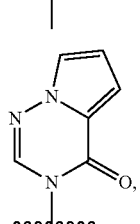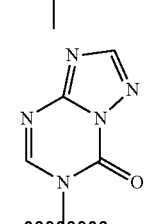 or
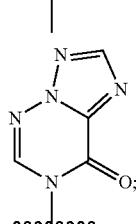
and/or, $B_2$ is any of the following structures:
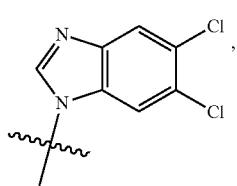

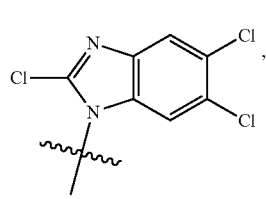
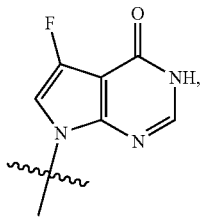
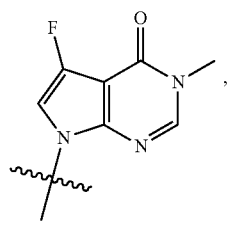
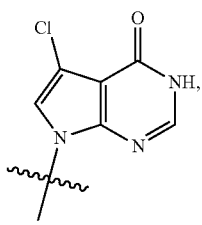
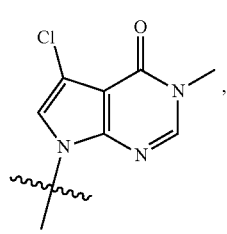
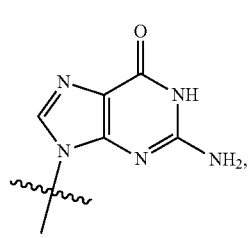
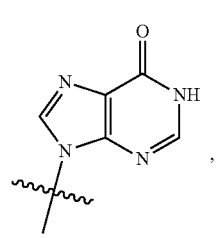
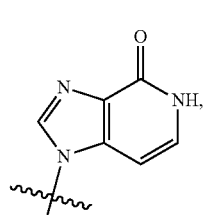
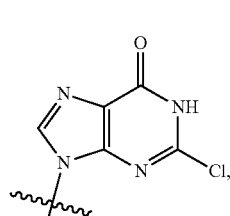
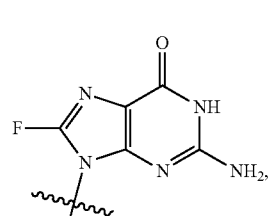
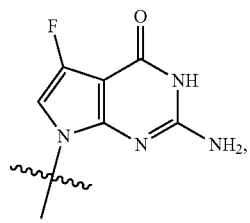
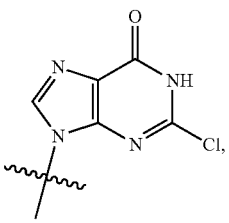
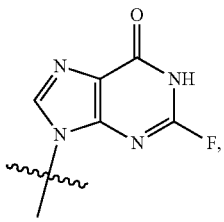
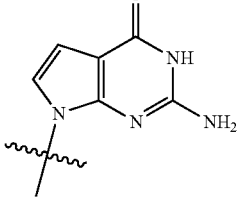
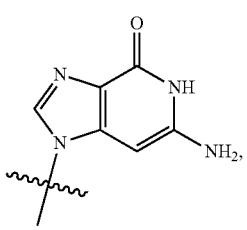
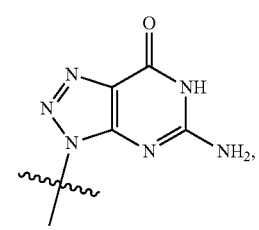
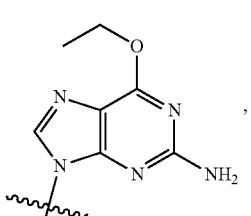
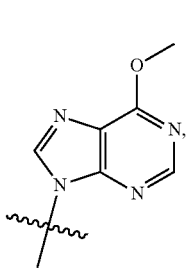
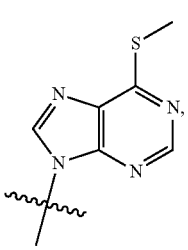
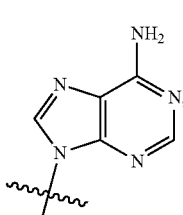
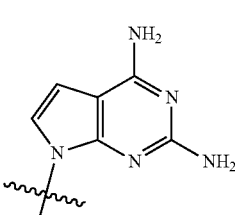
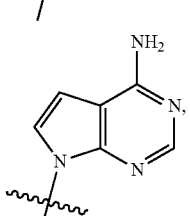
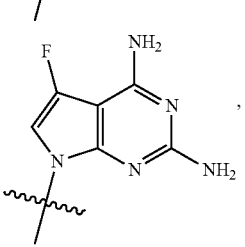
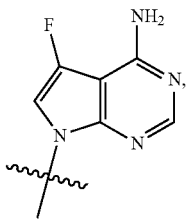

-continued

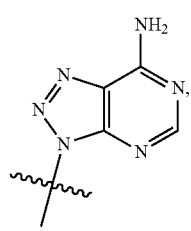
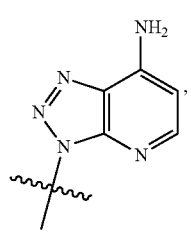
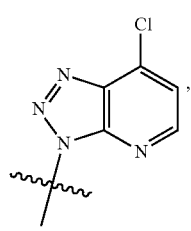
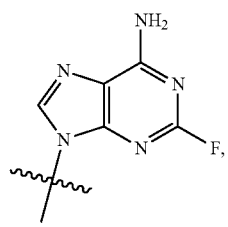 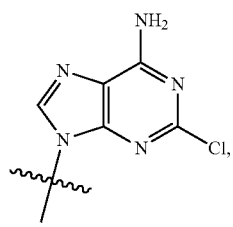
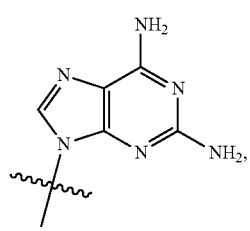 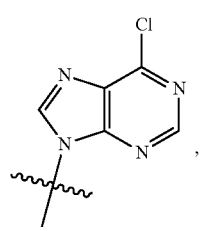
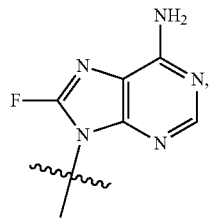 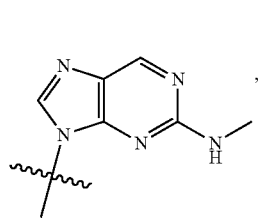
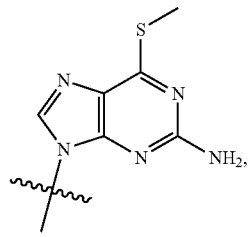 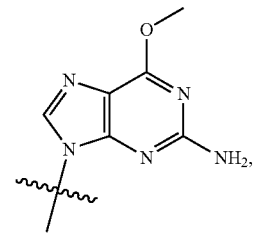

-continued

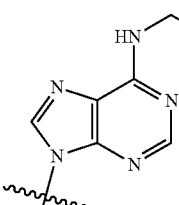 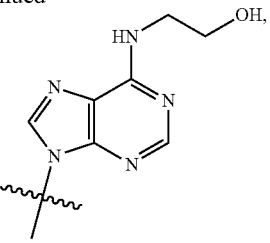
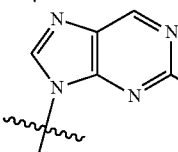
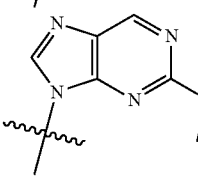 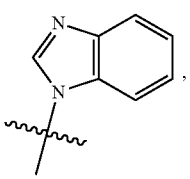
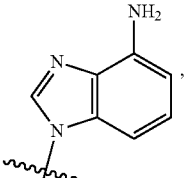 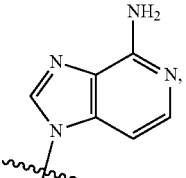
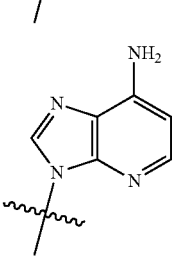 or 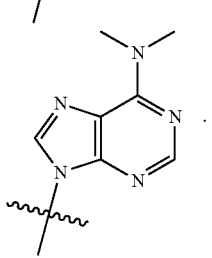 .

3. The cyclic di-nucleotide analogue of formula (I), the isomer, stable isotope derivative or pharmaceutically acceptable salt thereof according to claim 1, wherein $R^2$ is each independently hydrogen, halogen, hydroxyl, or $OR^a$;

and/or, $R^{21}$ is each independently hydrogen, halogen, hydroxyl, or $OR^a$;

and/or, each $R^a$ is independently $C_{1-4}$ alkyl or halo-$C_{1-4}$ alkyl.

4. The cyclic di-nucleotide analogue of formula (I), the isomer, stable isotope derivative or pharmaceutically acceptable salt thereof according to claim 1, wherein $B_1$ is

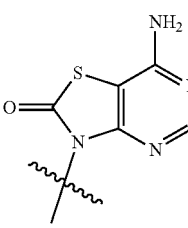 or 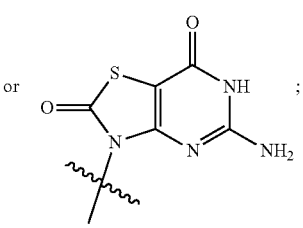 ;

B₂ is

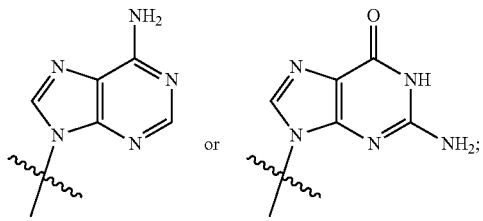 [SMILES: *n1cnc2c(N)ncnc21 ; *n1cnc2c(=O)[nH]c(N)nc21]

R² is each independently hydrogen, halogen, hydroxyl or ORᵃ;

R²¹ is each independently hydrogen, halogen, hydroxyl or ORᵃ;

each Rᵃ is independently $C_{1-4}$ alkyl or halo-$C_{1-4}$ alkyl.

5. The cyclic di-nucleotide analogue of formula (I), the isomer, stable isotope derivative or pharmaceutically acceptable salt thereof according to claim 1, wherein B₁ is

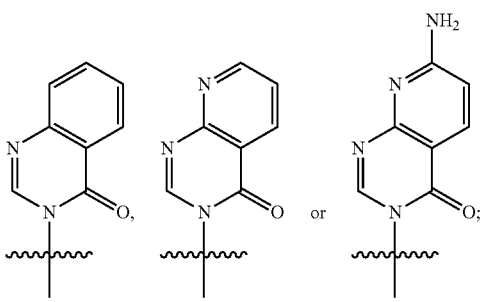

B₂ is

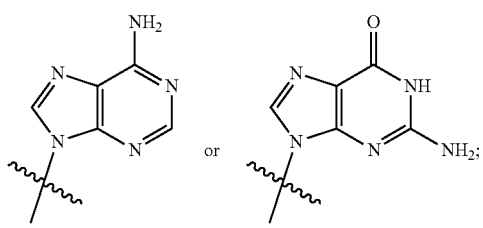 [SMILES: *n1cnc2c(N)ncnc21 ; *n1cnc2c(=O)[nH]c(N)nc21]

R² is each independently hydrogen, halogen, hydroxyl or ORᵃ;

R²¹ is each independently hydrogen, halogen, hydroxyl or ORᵃ;

each Rᵃ is independently $C_{1-4}$ alkyl or halo-$C_{1-4}$ alkyl.

6. The cyclic di-nucleotide analogue of formula (I), the isomer, stable isotope derivative or pharmaceutically acceptable salt thereof according to claim 1, wherein the stereoconfiguration of P is (Sp, Sp), (Sp, Rp), (Rp, Rp) or (Rp, Sp).

7. The cyclic di-nucleotide analogue of formula (I), the isomer, stable isotope derivative or pharmaceutically acceptable salt thereof according to claim 1, wherein B₁ is

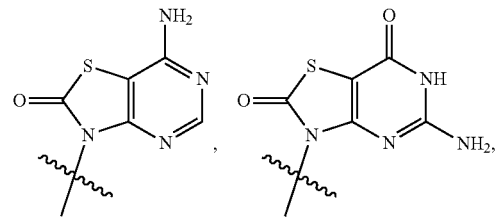

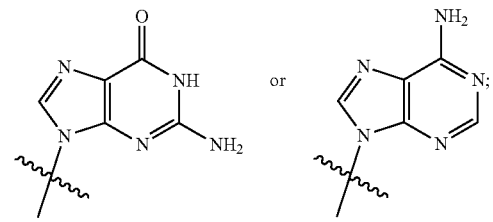 [SMILES: *n1cnc2c(=O)[nH]c(N)nc21 ; *n1cnc2c(N)ncnc21]

and/or, B₂ is in Formula VI, R² is —OH; R²¹ is —OH;

in Formula VII, R² is —OH or —OCH₃; R²¹ is —OH or F.

8. The cyclic di-nucleotide analogue of formula (I), the isomer, stable isotope derivative or pharmaceutically acceptable salt thereof according to claim 1, which is any of the following structures:

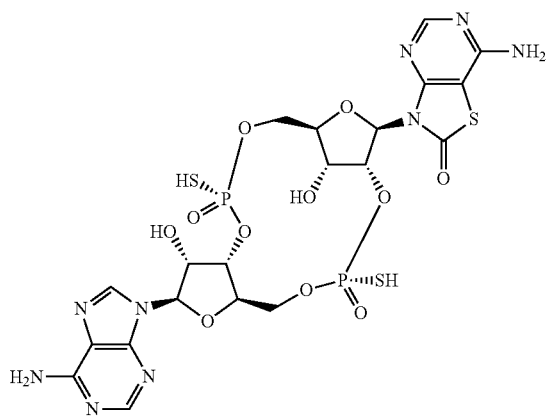

-continued

183
-continued
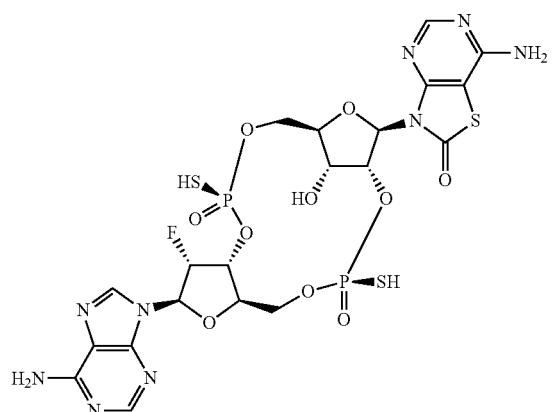
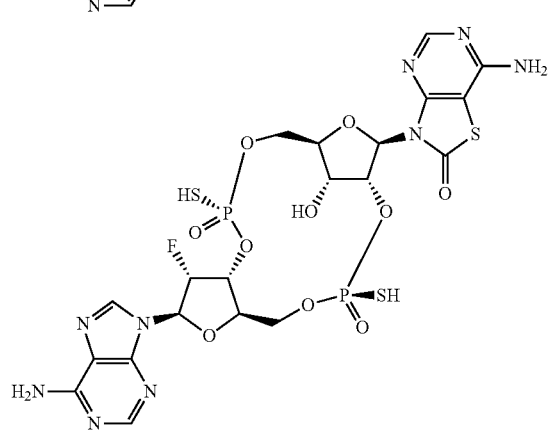
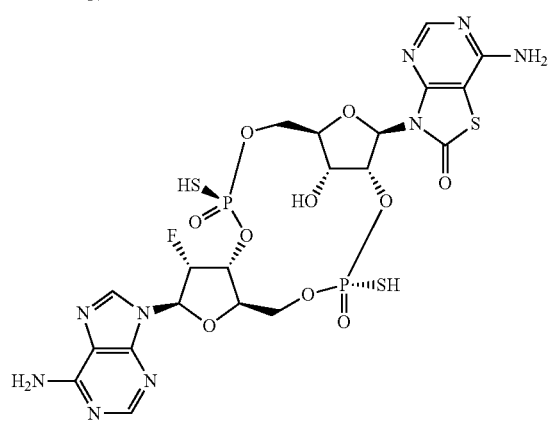
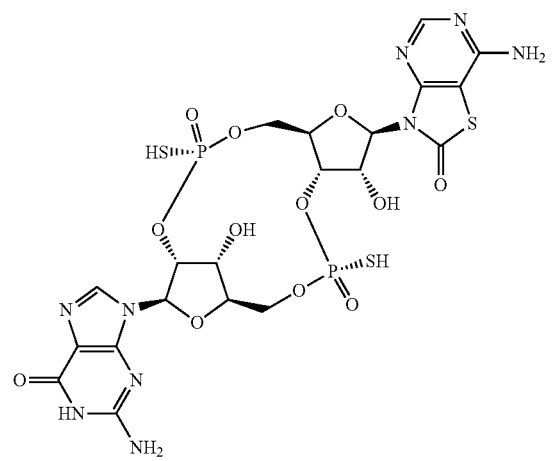
184
-continued
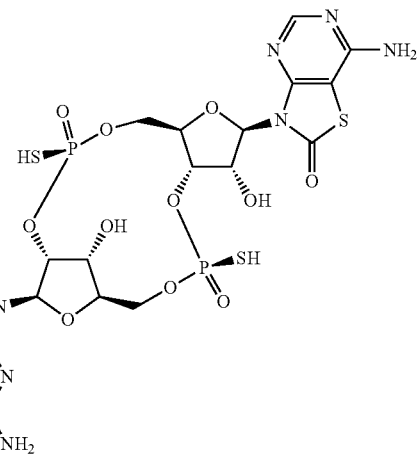
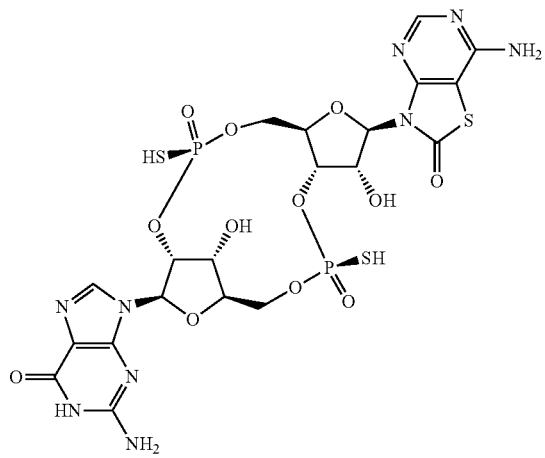

185
-continued

186
-continued

187
-continued
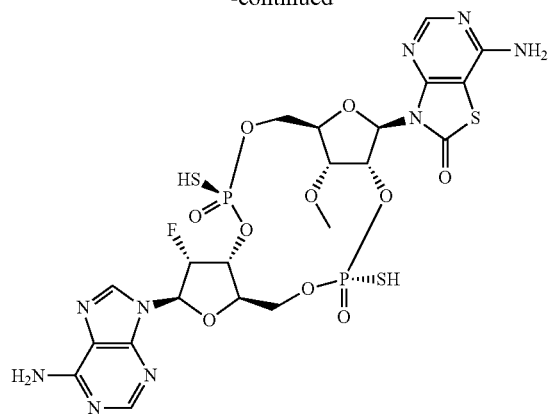
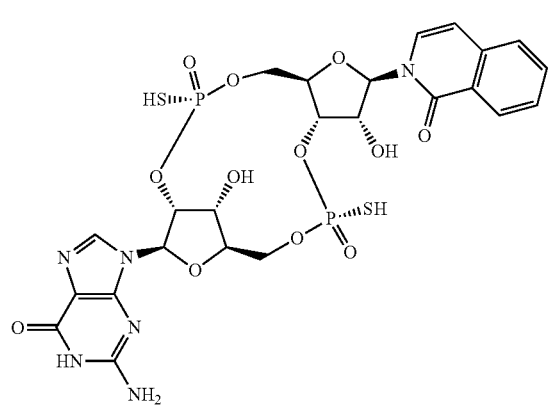
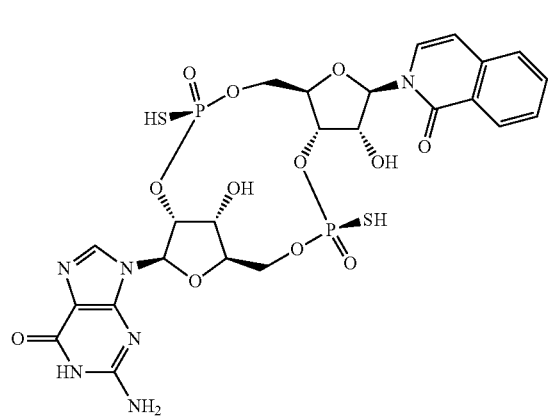
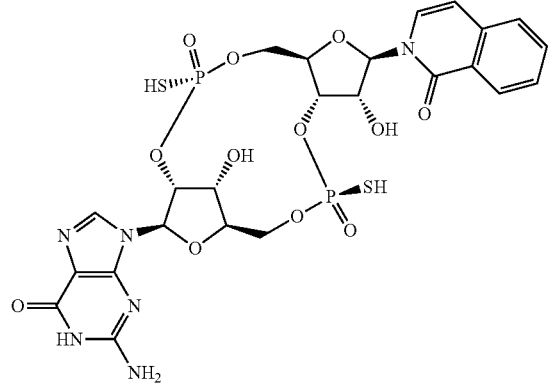
188
-continued
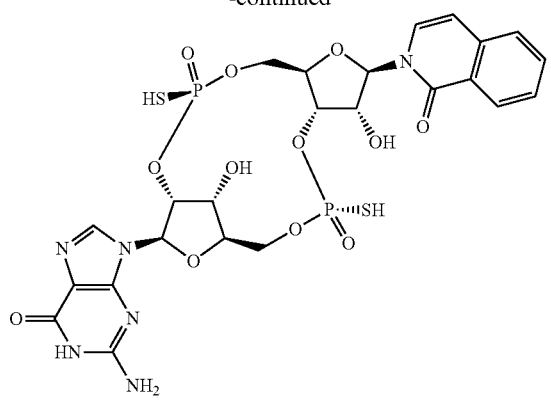
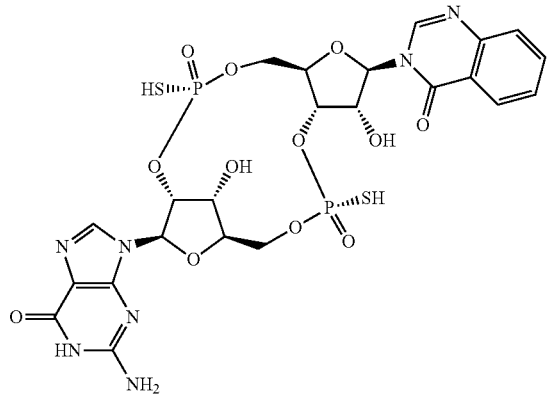
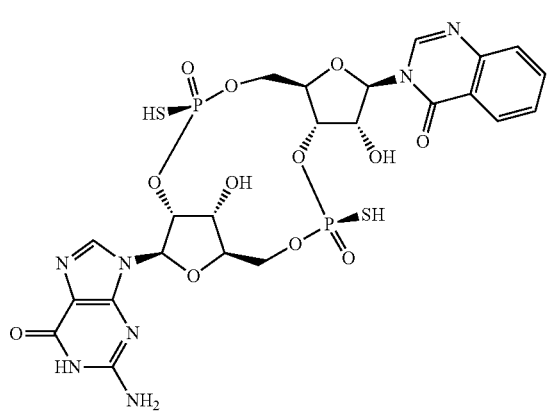
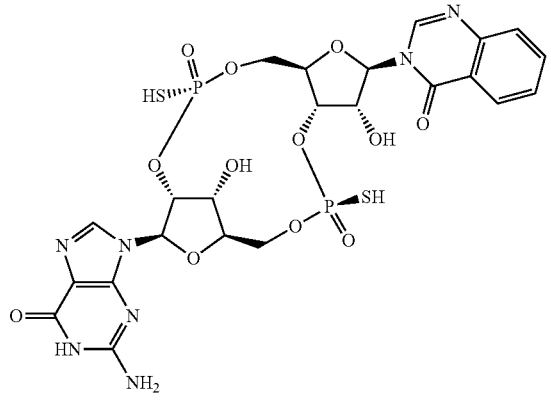

189
-continued
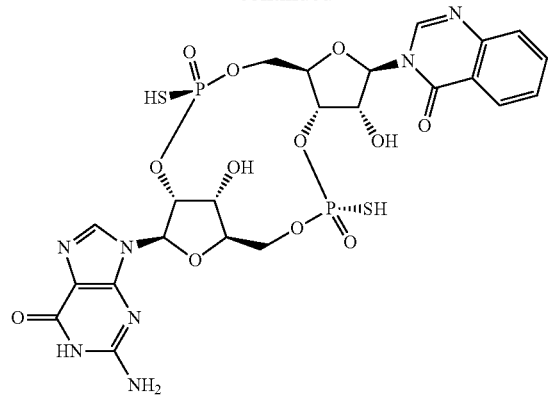
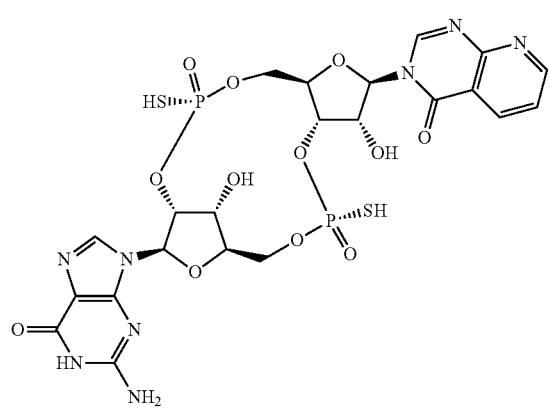
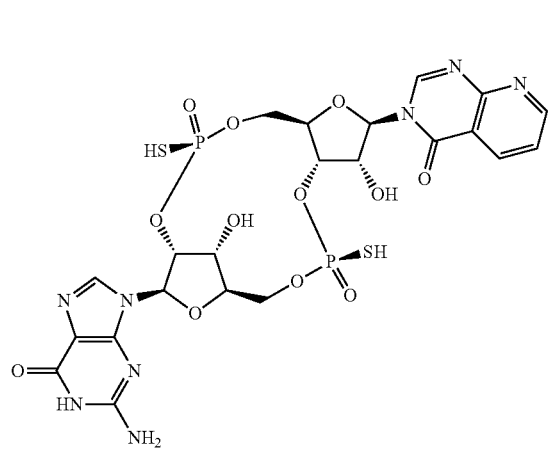
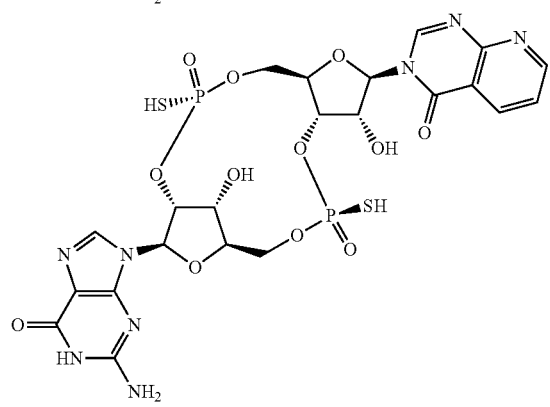
190
-continued
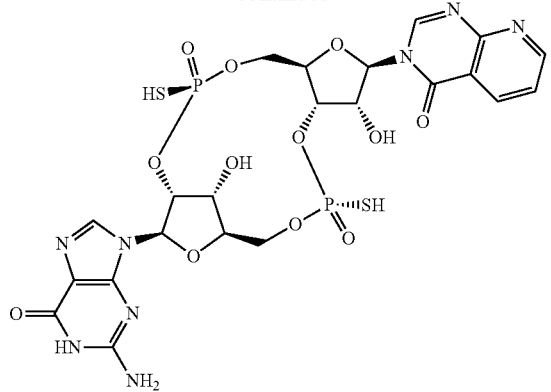
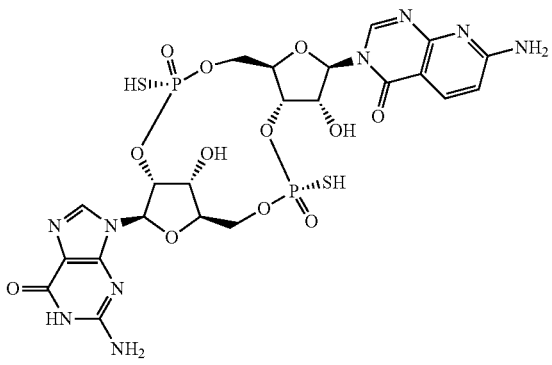
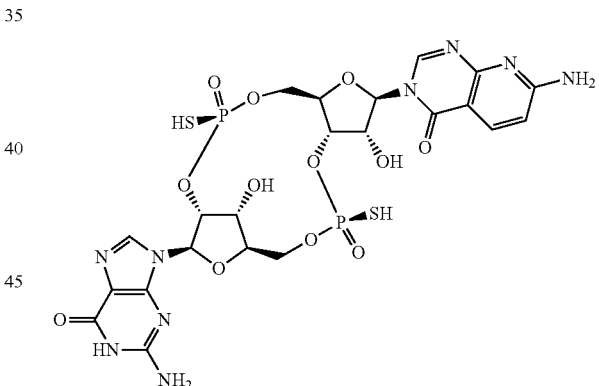
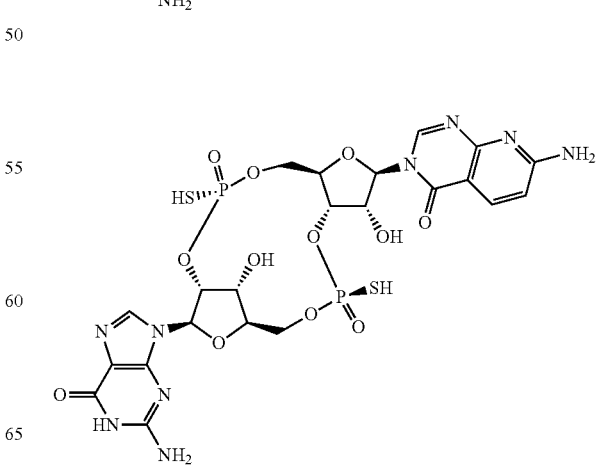

191
-continued
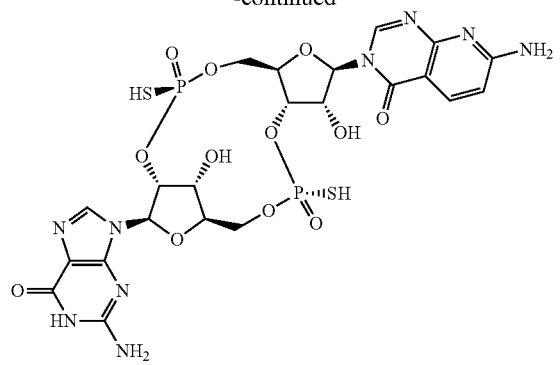
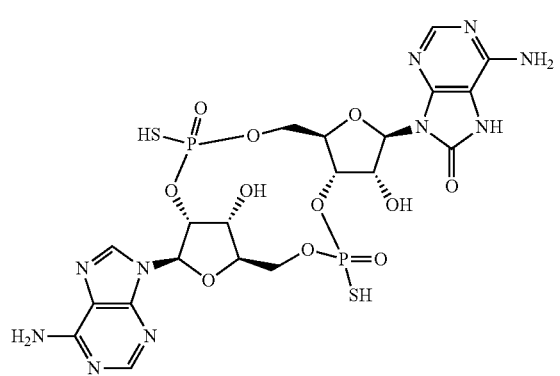
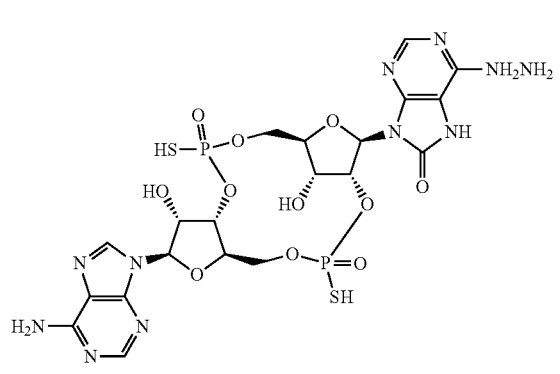
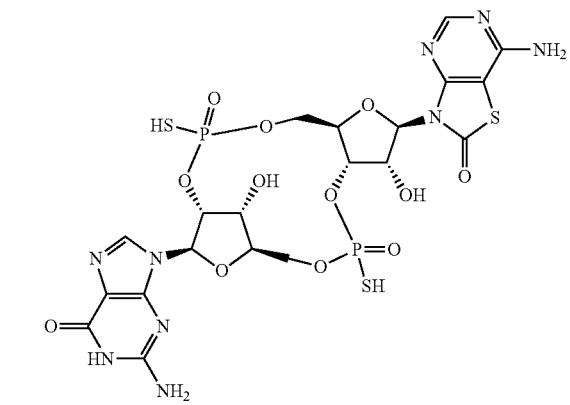 [SMILES: Nc1nc2c(ncn2[C@@H]2O[C@@H]3COP(=O)(S)O[C@H]4[C@@H](O)[C@H](n5c(=O)sc6c(N)ncnc65)O[C@@H]4COP(=O)(S)O[C@@H]2[C@@H]3O)c(=O)[nH]1]
192
-continued
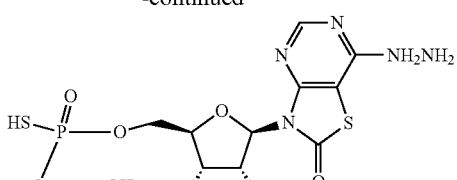
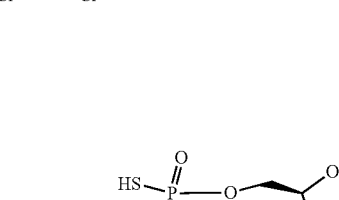
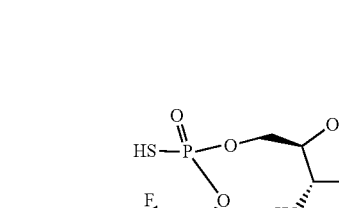
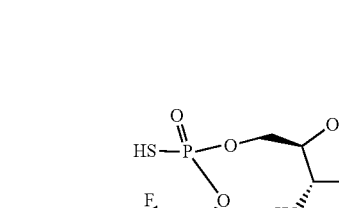

193
-continued
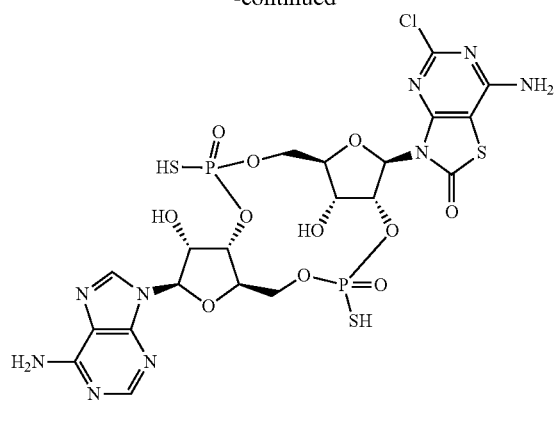
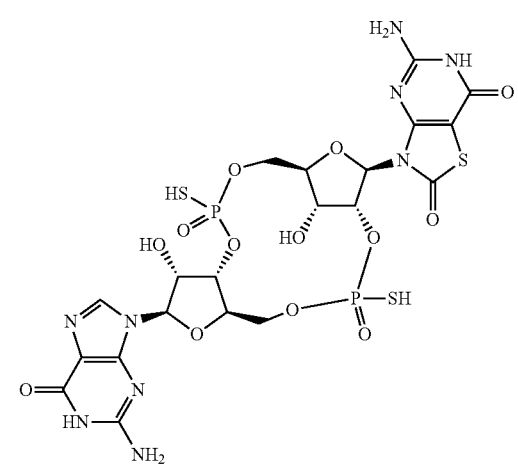
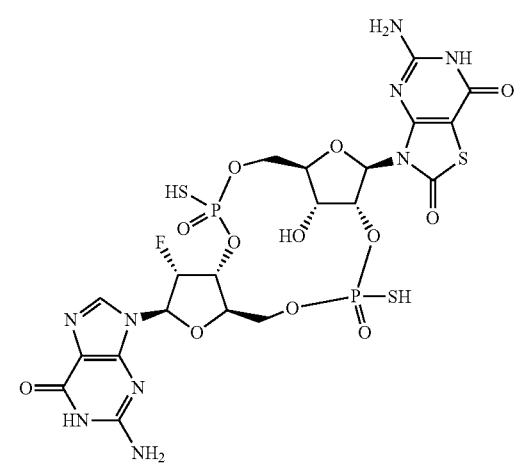
194
-continued
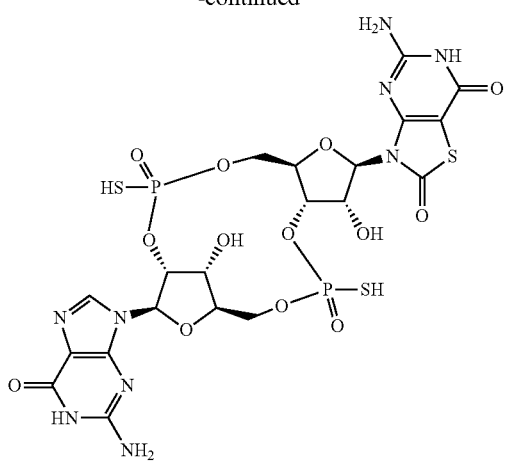
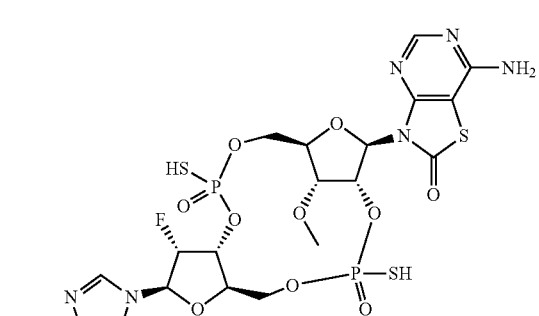
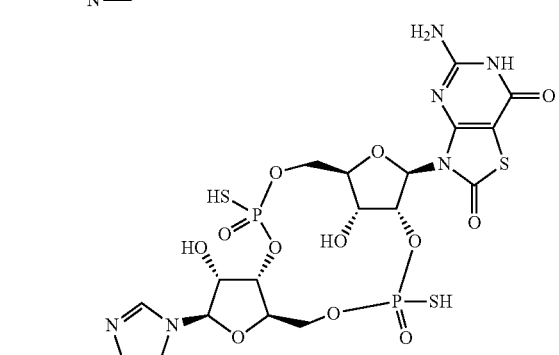
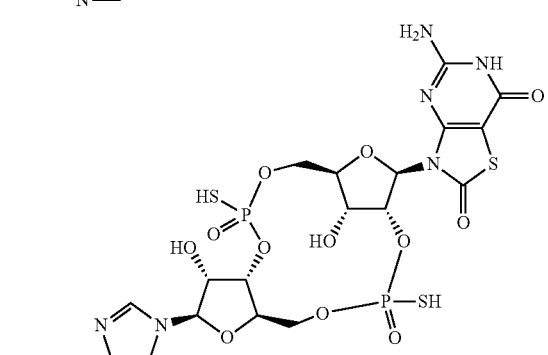
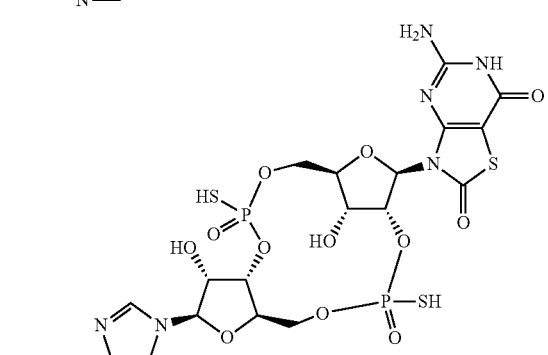

-continued
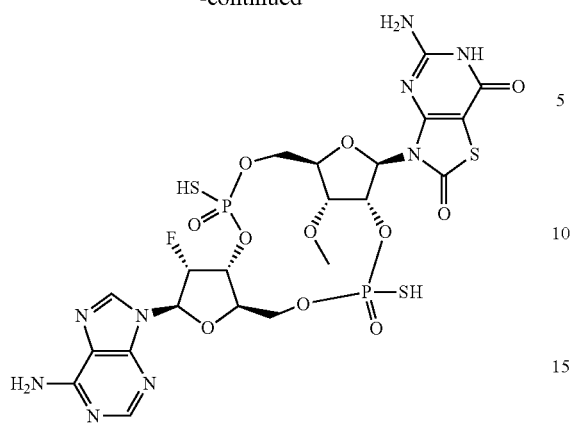
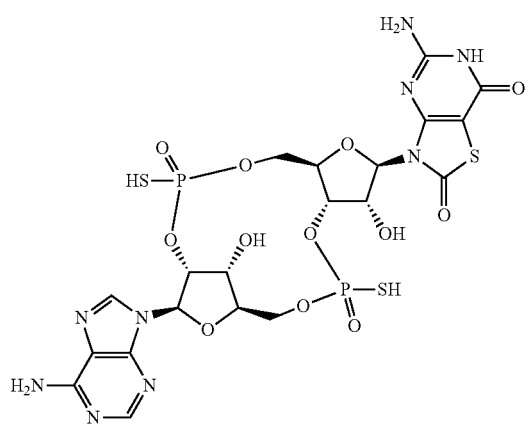
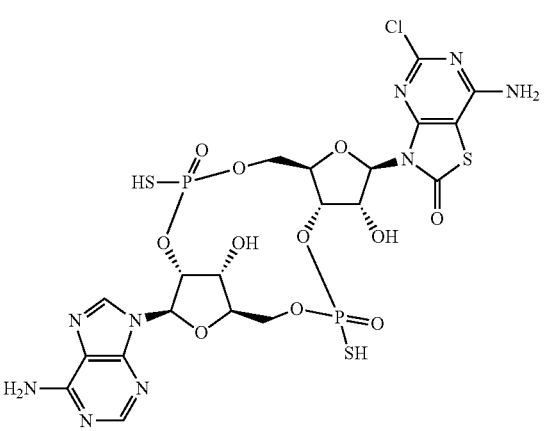 [SMILES: Nc1ncnc2c1ncn2[C@@H]1O[C@@H]2COP(=O)(S)O[C@H]3[C@@H](O)[C@H](n4c(=O)sc5c(N)nc(Cl)nc54)O[C@@H]3COP(=O)(S)O[C@@H]1[C@@H]2O]
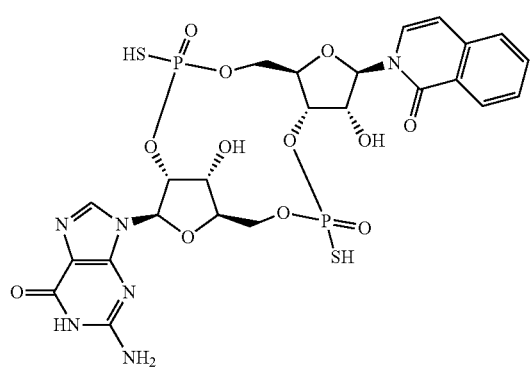
-continued
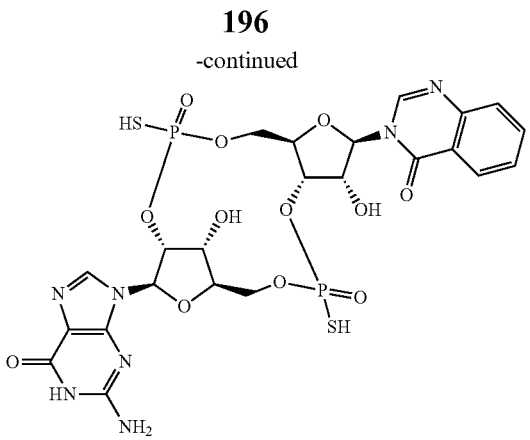
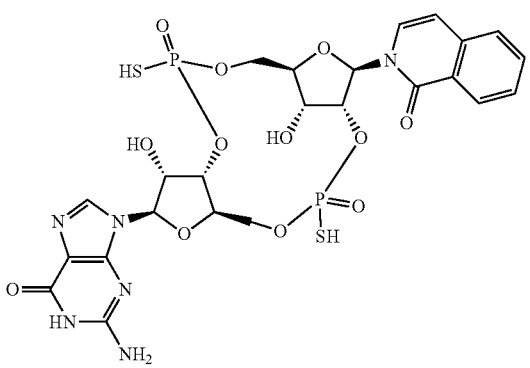
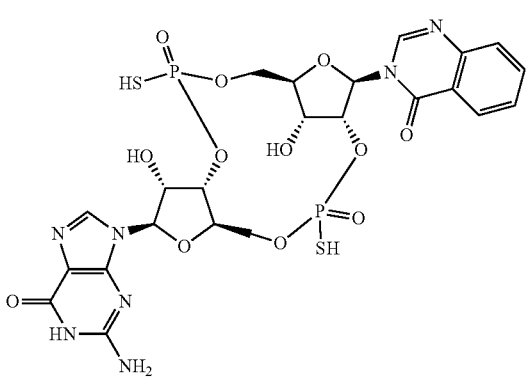
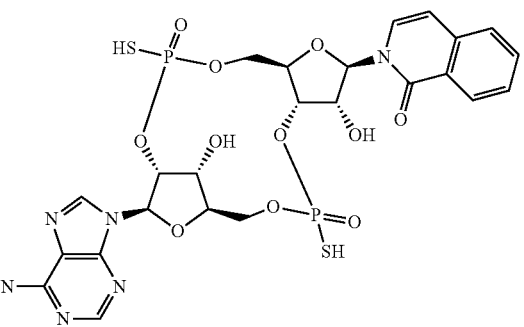

197
-continued
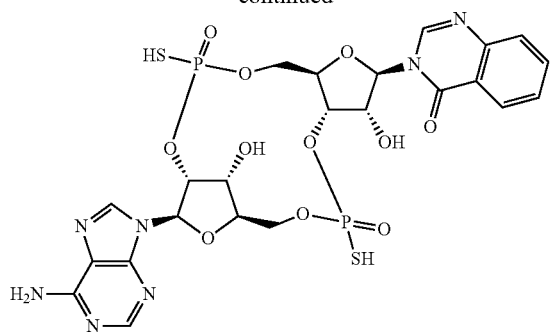
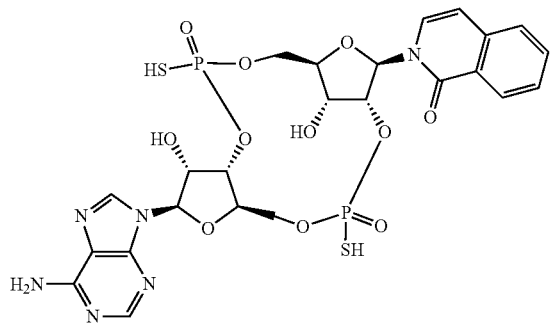
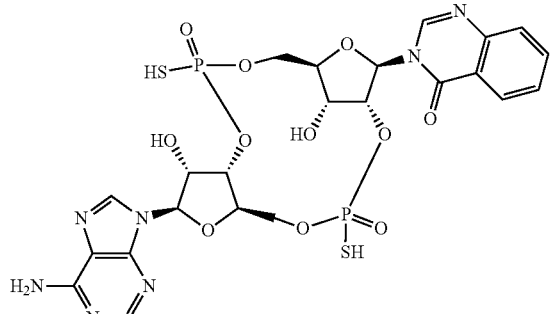
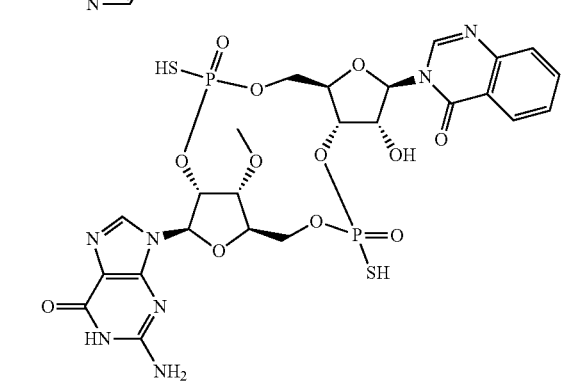
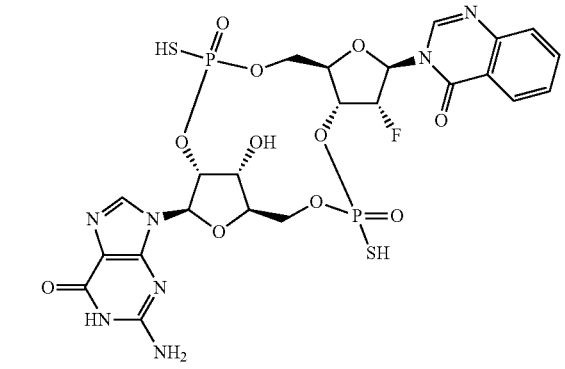
198
-continued
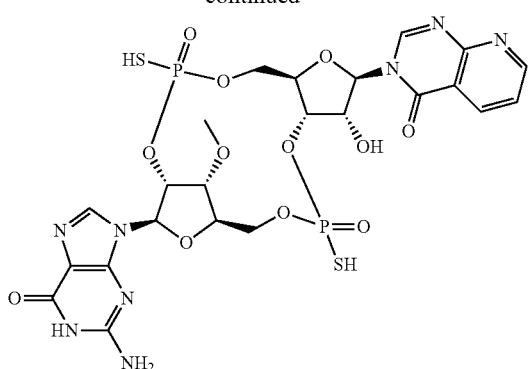
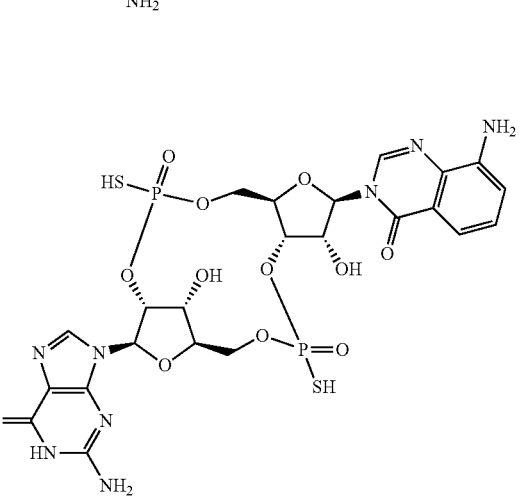
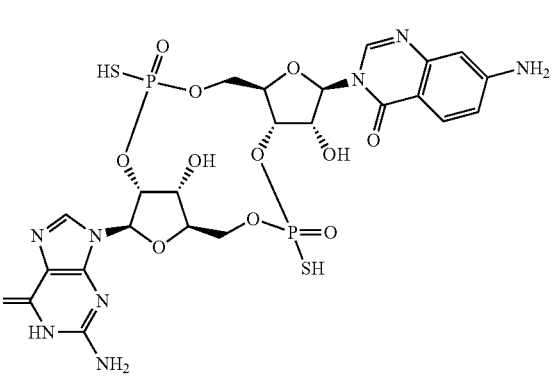
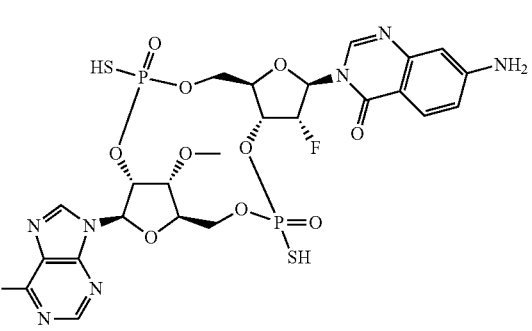

-continued

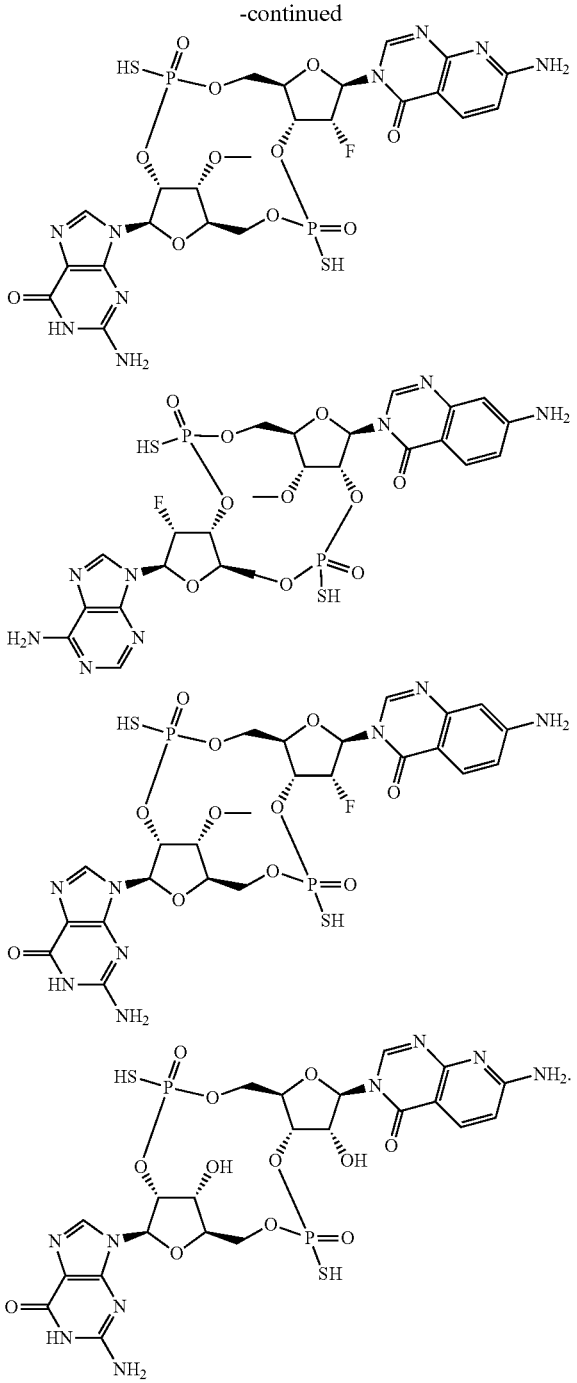

9. A pharmaceutical composition comprising a therapeutically effective amount of the cyclic di-nucleotide analogue of formula (I), the isomer, stable isotope derivative or pharmaceutically acceptable salt thereof according to claim 1, and a pharmaceutically acceptable excipient.

10. A method of modulating STING in a subject in need thereof, comprising administering the cyclic di-nucleotide analogue of formula (I), the isomer, stable isotope derivative or pharmaceutically acceptable salt thereof according to claim 1 to the subject.

11. The method according to claim 10, wherein the modulating is activating.

12. A method of treating and/or alleviating a STING-mediated disease in a subject in need thereof, comprising administering the cyclic di-nucleotide analogue of formula (I), the isomer, stable isotope derivative or pharmaceutically acceptable salt thereof according to claim 1 to the subject.

13. The method according to claim 12, wherein the STING-mediated disease is viral infection or other infectious diseases, autoimmune diseases, or malignancies.

14. A method of regulating the proliferation of T cells or other immune cells in a subject in need thereof, comprising administering the cyclic di-nucleotide analogue of formula (I), the isomer, stable isotope derivative or pharmaceutically acceptable salt thereof according to claim 1 to the subject.

15. A method of treating and/or alleviating malignancies in a subject in need thereof, comprising administering the cyclic di-nucleotide analogue of formula (I), the isomer, stable isotope derivative or pharmaceutically acceptable salt thereof according to claim 1 to the subject.

16. A method of improving the effectiveness of vaccine in a subject in need thereof, comprising administering the cyclic di-nucleotide analogue of formula (I), the isomer, stable isotope derivative or pharmaceutically acceptable salt thereof according to claim 1 to the subject.

17. A combination formulation, comprising the cyclic di-nucleotide analogue of formula (I), the isomer, stable isotope derivative or pharmaceutically acceptable salt thereof according to claim 1 and other kinds of therapeutic agents for the treatment of cancer.

* * * * *